US012590977B2

(12) United States Patent
Potter et al.

(10) Patent No.: US 12,590,977 B2
(45) Date of Patent: Mar. 31, 2026

(54) ANTI-CERULOPLASMIN ANTIBODIES AND USES THEREOF

(71) Applicant: Alexion Pharmaceuticals, Inc., Boston, MA (US)

(72) Inventors: David George Potter, The Woodlands, TX (US); Jennifer Ann Dzielawa, Montgomery, TX (US); Brenda Sue Carter, Montgomery, TX (US); Mark Ma, Madison, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 54 days.

(21) Appl. No.: 18/024,474

(22) PCT Filed: Sep. 10, 2021

(86) PCT No.: PCT/US2021/049890
§ 371 (c)(1),
(2) Date: Mar. 2, 2023

(87) PCT Pub. No.: WO2022/056278
PCT Pub. Date: Mar. 17, 2022

(65) Prior Publication Data

US 2024/0044920 A1 Feb. 8, 2024

Related U.S. Application Data

(60) Provisional application No. 63/077,155, filed on Sep. 11, 2020.

(51) Int. Cl.

*G01N 33/84* (2006.01)
*C07K 16/40* (2006.01)
*G01N 33/573* (2006.01)

(52) U.S. Cl.

CPC ............. *G01N 33/84* (2013.01); *C07K 16/40* (2013.01); *G01N 33/573* (2013.01); *G01N 2333/90287* (2013.01); *G01N 2800/52* (2013.01)

(58) Field of Classification Search

CPC ................. G01N 33/84; G01N 33/573; G01N 2333/90287; G01N 2800/52; G01N 33/6893; C07K 16/40; C07K 2317/565; C07K 2317/94; A61K 31/132; A61K 31/198; A61K 33/24; A61K 33/30
See application file for complete search history.

(56) References Cited

U.S. PATENT DOCUMENTS

| | | | |
|---|---|---|---|
| 4,376,110 A | 3/1983 | David et al. | |
| 4,816,567 A | 3/1989 | Cabilly et al. | |
| 5,223,409 A | 6/1993 | Ladner et al. | |
| 5,225,539 A | 7/1993 | Winter | |
| 5,403,484 A | 4/1995 | Ladner et al. | |
| 5,427,908 A | 6/1995 | Dower et al. | |
| 5,508,717 A | 4/1996 | Miller | |
| 5,571,698 A | 11/1996 | Ladner et al. | |
| 5,780,279 A | 7/1998 | Matthews et al. | |
| 6,001,329 A | 12/1999 | Buchsbaum et al. | |
| 6,010,903 A | 1/2000 | Hiyamuta et al. | |
| 6,040,136 A | 3/2000 | Bass et al. | |
| 6,090,382 A | 7/2000 | Salfeld et al. | |
| 6,258,562 B1 | 7/2001 | Salfeld et al. | |
| 6,806,044 B2 | 10/2004 | Hahn et al. | |
| 6,933,368 B2 | 8/2005 | Co et al. | |
| 7,393,648 B2 | 7/2008 | Rother et al. | |
| 7,408,041 B2 | 8/2008 | Bowdish et al. | |
| 7,427,665 B2 | 9/2008 | Bowdish et al. | |
| 7,435,412 B2 | 10/2008 | Bowdish et al. | |
| 7,704,497 B2 | 4/2010 | Dall et al. | |
| 9,593,161 B2 | 3/2017 | Borras et al. | |
| 2009/0104187 A1 | 4/2009 | Kovacevich et al. | |
| 2010/0312139 A1 | 12/2010 | Dash et al. | |
| 2016/0347864 A1 | 12/2016 | Escher | |
| 2017/0252458 A1* | 9/2017 | Albone | C07K 16/32 |
| 2018/0127493 A1 | 5/2018 | Borras et al. | |
| 2018/0327803 A1* | 11/2018 | Kumada | C12N 15/09 |
| 2018/0340026 A1* | 11/2018 | Rader | C07K 16/2803 |

FOREIGN PATENT DOCUMENTS

| | | |
|---|---|---|
| CN | 108802360 A | 11/2018 |
| JP | 06-265545 A | 9/1994 |
| JP | 08-075743 A | 3/1996 |
| WO | 88/06630 A1 | 9/1988 |
| WO | 92/15679 A1 | 9/1992 |
| WO | 97/08320 A1 | 3/1997 |

(Continued)

OTHER PUBLICATIONS

Chiu ML et al. Antibody Structure and Function: The Basis for Engineering Therapeutics. Antibodies 2019 8, 55, 1-80 (Year: 2019).*

Altschul et al., Basic local alignment search tool, Journal of Molecular Biology, 215(3):403-410 (Oct. 1990).

Altschul et al., Gapped BLAST and PSI-BLAST: a new generation of protein database search programs, Nucleic Acids Research, 25(17):3389-3402 (Sep. 1997).

(Continued)

*Primary Examiner* — Julie Wu
*Assistant Examiner* — John J Skoko, III
(74) *Attorney, Agent, or Firm* — MARSHALL, GERSTEIN & BORUN LLP

(57) ABSTRACT

Provided herein are antibodies which bind to ceruloplasmin and are useful for various applications, including detecting ceruloplasmin and immunocapturing ceruloplasmin in biological samples. The antibodies are useful in methods of measuring non-ceruloplasmin-bound copper concentrations and labile-bound copper concentrations in biological samples.

20 Claims, 15 Drawing Sheets

Specification includes a Sequence Listing.

(56) References Cited

FOREIGN PATENT DOCUMENTS

| | | | |
|---|---|---|---|
| WO | 2004/016740 | A2 | 2/2004 |
| WO | 2005/016950 | A1 | 2/2005 |
| WO | 2006/053301 | A2 | 5/2006 |
| WO | 2008/144757 | A1 | 11/2008 |
| WO | 2017/082213 | A1 | 5/2017 |
| WO | 2019/085804 | A1 | 5/2019 |
| WO | 2019/110619 | A1 | 6/2019 |
| WO | 2020/095866 | A1 | 5/2020 |
| WO | 2021/005080 | A1 | 1/2021 |
| WO | 2021/050850 | A1 | 3/2021 |

OTHER PUBLICATIONS

Barbariga et al., Ceruloplasmin functional changes in Parkinson's disease-cerebrospinal fluid, Molecular Neurodegeneration, 10(59):1-12 (Nov. 2015).
Bernevic et al., Online immunocapture ICP-MS for the determination of the metalloprotein ceruloplasmin in human serum, BMC Research Notes, 11(213): 1-5 (Apr. 2018).
Bird et al., Single-Chain Antigen-Binding Proteins, Science, 242(4877):423-426 (Oct. 1988).
Borras et al., Generic Approach for the Generation of Stable Humanized Single-chain Fv Fragments from Rabbit Monoclonal Antibodies, Protein Structure and Folding, 285(12): 9054-9066 (Mar. 2010).
Brummell et al., Probing the combining site of an anti-carbohydrate antibody by saturation-mutagenesis: Role of the heavy-chain CDR3 residues, Biochemistry, 32(4): 1180-1187 (Feb. 1, 1993).
Burks et al., In vitro scanning saturation mutagenesis of an antibody binding pocket, PNAS, 94(2):412-417 (Jan. 21, 1997).
Cepko et al., Construction and applications of a highly transmissible murine retrovirus shuttle vector, Cell, 37 (3): 1053-1062 (Jul. 1984).
Cheung et al., Epitope-specific antibody response to the surface antigen of duck hepatitis B virus in infected ducks, Virology, 176(2):546-552 (Jun. 1990).
Cruz et al., Immunogenicity and epitope mapping of foreign sequences via genetically engineered filamentous phage, Journal of Biological Chemistry, 263(9):4318-4322 (Mar. 1988).
Dakappagari et al., Internalizing Antibodies to the C-Type Lectins, L-SIGN and DC-SIGN, Inhibit Viral Glycoprotein Binding and Deliver Antigen to Human Dendritic Cells for the Induction of T Cell Responses, J Immunol, 176(1):426-440 (Jan. 2006).
Deans et al., Expression of an immunoglobulin heavy chain gene transfected into lymphocytes, PNAS, 81(5): 1292-1296 (Mar. 1, 1984).
Eum et al., Production and Characterization of Monoclonal Antibodies against Human Ceruloplasmin, Journal of Biochemistry and Molecular Biology, 38(1):71-76 (Jan. 2005).
European Application No. 21867683.1, European Search Report and Written Opinion, mailed Apr. 22, 2025.
Harlow et al., Antibodies: A Laboratory Manual, Cold Spring Harbor Press, (1988).
Holliger et al., "Diabodies": small bivalent and bispecific antibody fragments, PNAS, 90(14):6444-6448 (Jul. 15, 1993).
Huston et al., Protein engineering of antibody binding sites: recovery of specific activity in an anti-digoxin single-chain Fv analogue produced in *Escherichia coli*, PNAS, 85(16): 5879-5883 (Aug. 15, 1988).
Innis et al., PCR Protocols: A Guide to Methods and Applications, Academic Press, (1990).
International Application No. PCT/US2021/049890, International Preliminary Report on Patentability, mailed Dec. 8, 2022.
International Application No. PCT/US2021/049890, International Search Report and Written Opinion, mailed Feb. 2, 2022.
Johnsson et al., Comparison of methods for immobilization to carboxymethyl dextran sensor surfaces by analysis of the specific activity of monoclonal antibodies, Journal of Molecular Recognition, 8(1-2): 125-131 (Apr. 1995).
Johnsson et al., Immobilization of proteins to a carboxymethyldextran-modified gold surface for biospecific interaction analysis in surface plasmon resonance sensors, Analytical Biochemistry, 198(2):268-277 (Nov. 1991).
Jones et al., Replacing the complementarity-determining regions in a human antibody with those from a mouse, Nature, 321(1):522-525 (May 1986).
Jönsson et al., Real-time biospecific interaction analysis using surface plasmon resonance and a sensor chip technology, Biotechniques, 11(5):620-627 (Nov. 1991).
Kabat et al., Sequences of proteins of immunological interest, Bethesda, MD : U.S. Dept. of Health and Human Services, 5(1): (1991).
Kaufman, Identification of the components necessary for adenovirus translational control and their utilization in cDNA expression vectors, PNAS, 82(3):689-693 (Feb. 1, 1985).
Kinstler et al., Mono-N-terminal poly(ethylene glycol)-protein conjugates, Advanced Drug Delivery Reviews, 54 (4):477-485 (Jun. 2002).
Kirkland et al., Analysis of the fine specificity and cross-reactivity of monoclonal anti-lipid A antibodies, J Immunol, 137(11):3614-3619 (Dec. 1986).
Kobayashi et al., Tryptophan H33 plays an important role in pyrimidine (6-4) pyrimidone photoproduct binding by a high-affinity antibody, Protein Engineering, 12(10):879-884 (Oct. 1999).
Köhler et al., Continuous cultures of fused cells secreting antibody of predefined specificity, Nature, 256(1):495-497 (Aug. 1975).
Kostelny et al., Formation of a bispecific antibody by the use of leucine zippers, J Immunol, 148(5):1547-1553 (Mar. 1992).
Lusky et al., Inhibition of SV40 replication in simian cells by specific pBR322 DNA sequences, Nature, 293(1):79-81 (Sep. 1981).
McCafferty et al., Phage antibodies: filamentous phage displaying antibody variable domains, Nature, 348(1):552-554 (1990).
Moldenhauer et al., Identity of HML-1 Antigen on Intestinal Intraepithelial T Cells and of B-ly7 Antigen on Hairy Cell Leukaemia, Scandinavian Journal of Immunology, 32(2):77-82 (Aug. 1990).
Morel et al., Monoclonal antibodies to bovine serum albumin: Affinity and specificity determinations, Molecular Immunology, 25(1):7-15 (Jan. 1988).
Mulligan et al., Selection for animal cells that express the Escherichia coli gene coding for xanthine-guanine phosphoribosyltransferase, PNAS, 78(4):2072-2076 (Apr. 15, 1981).
Needleman et al., A general method applicable to the search for similarities in the amino acid sequence of two proteins, Journal of Molecular Biology, 48(3): 444-453 (Mar. 1970).
Okayama et al., A cDNA Cloning Vector That Permits Expression of cDNA Inserts in Mammalian Cells, Molecular and Cellular Biology, 3(2):280-289 (Mar. 2023).
Parmley et al., Antibody-selectable filamentous fd phage vectors: affinity purification of target genes, Gene, 73(2):305-318 (Dec. 1988).
Poljak, Production and structure of diabodies, Structure, 2(12): 1121-1123 (Dec. 1994).
Rader et al., A phage display approach for rapid antibody humanization: Designed combinatorial V gene libraries, PNAS, 95(15):8910-8915 (Jul. 21, 1998).
Rader et al., The Rabbit Antibody Repertoire as a Novel Source for the Generation of Therapeutic Human Antibodies, Protein Structure and Folding, 275(18):13668-13676 (May 2000).
Riechmann et al., Reshaping human antibodies for therapy, Nature, 332(1): 323-327 (Mar. 1988).
Roberts et al., Chemistry for peptide and protein PEGylation, Advanced Drug Delivery Reviews, 54(4):459-476 (Jun. 2002).
Rogers et al., Localization of Iodine-125-mIP-Des-Met14Bombesin (7-13)NH2 in Ovarian Carcinoma Induced to Express the Gastrin Releasing Peptide Receptor by Adenoviral Vector-Mediated Gene Transfer, Thejournal Ofnuclearmedicin, 38(8): 1-9 (Aug. 1997).
Sarver et al., Transformation and replication in mouse cells of a bovine papillomavirus—pML2 plasmid vector that can be rescued in bacteria, PNAS, 79(23):7147-7151 (Dec. 1, 1982).
Songsivilai et al., Bispecific antibody: a tool for diagnosis and treatment of disease, Clinical & Experimental Immunology, 79(3):315-321 (Mar. 1990).

(56) References Cited

OTHER PUBLICATIONS

Staelens et al., Humanization by variable domain resurfacing and grafting on a human IgG4, using a new approach for determination of non-human like surface accessible framework residues based on homology modelling of variable domains, Molecular Immunology, 43(8): 1243-1257 (Mar. 2006).
Steinberger et al., Generation and Characterization of a Recombinant Human CCR5-specific Antibody, Protein Structure and Folding, 275(46):36073-36078 (Nov. 2000).
Taylor et al., A transgenic mouse that expresses a diversity of human sequence heavy and light chain immunoglobulins, Nucleic Acids Research, 20(23):6287-6295 (Dec. 1992).
Tomizuka et al., Double trans-chromosomic mice: Maintenance of two individual human chromosome fragments containing Ig heavy and ? loci and expression of fully human antibodies, PNAS, 97(2):722-727 (Jan. 18, 2000).
Verhoeyen et al., Reshaping Human Antibodies: Grafting an Antilysozyme Activity, Science, 239(4847):1534-1536 (Mar. 1988).
Waldmeier et al., Transpo-mAb display: Transposition-mediated B cell display and functional screening of full-length IgG antibody libraries, Mabs, 8(1):726-740 (2016).
Ward et al., Binding activities of a repertoire of single immunoglobulin variable domains secreted from *Escherichia coli*, Nature, 341(1):544-546 (Oct. 1989).
Weber et al., From rabbit antibody repertoires to rabbit monoclonal antibodies, Exp Mol Med, 49(3):1-12 (Mar. 2017).
Wigler et al., Transformation of mammalian cells with genes from procaryotes and eucaryotes, Cell, 16(4):777-785 (Apr. 1979).
Woimant et al., New tools for Wilson's disease diagnosis: exchangeable copper fraction, Ann Transl Med, 7(2):1-9 (Apr. 2019).
Wright et al., Antibody variable region glycosylation: position effects on antigen binding and carbohydrate structure, The EMBO Journal, 10(10):2717-2723 (1991).
Xiong et al., Rapid laboratory diagnosis of Wilson's disease: One-step simultaneous detection of exchangeable copper and ceruloplasmin in serum based on nanotechnology, Sensors and Actuators B: Chemical, 281(1):713-719 (Feb. 2019).
Yu et al., A Humanized Anti-VEGF Rabbit Monoclonal Antibody Inhibits Angiogenesis and Blocks Tumor Growth in Xenograft Models, Plos One, 5(2):1-12 (Feb. 2010).
Yu et al., Development of humanized rabbit monoclonal antibodies against vascular endothelial growth factor receptor 2 with potential antitumor effects, Biochemical and Biophysical Research Communications, 436(3):543-550 (Jul. 2013).

* cited by examiner

SEQUENCE LISTING

<160> NUMBER OF SEQ ID NOS: 232

<210> SEQ ID NO 1
<211> LENGTH: 1065
<212> TYPE: PRT
<213> ORGANISM: Homo sapiens

<400> SEQUENCE: 1

```
Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr
            20                  25                  30

Trp Asp Tyr Ala Ser Asp His Gly Glu Lys Lys Leu Ile Ser Val Asp
        35                  40                  45

Thr Glu His Ser Asn Ile Tyr Leu Gln Asn Gly Pro Asp Arg Ile Gly
    50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110

Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140

Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
            180                 185                 190

Leu Ile Gly Pro Leu Ile Ile Cys Lys Lys Asp Ser Leu Asp Lys Glu
        195                 200                 205

Lys Glu Lys His Ile Asp Arg Glu Phe Val Val Met Phe Ser Val Val
```

-continued

```
    210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
            260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
    290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
            340                 345                 350

Gln Val Gln Glu Cys Asn Lys Ser Ser Ser Lys Asp Asn Ile Arg Gly
        355                 360                 365

Lys His Val Arg His Tyr Tyr Ile Ala Ala Glu Glu Ile Ile Trp Asn
    370                 375                 380

Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
                405                 410                 415

Gly Gly Ser Tyr Lys Lys Leu Val Tyr Arg Glu Tyr Thr Asp Ala Ser
            420                 425                 430

Phe Thr Asn Arg Lys Glu Arg Gly Pro Glu Glu Glu His Leu Gly Ile
        435                 440                 445

Leu Gly Pro Val Ile Trp Ala Glu Val Gly Asp Thr Ile Arg Val Thr
    450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
            500                 505                 510

Glu Thr Phe Thr Tyr Glu Trp Thr Val Pro Lys Glu Val Gly Pro Thr
        515                 520                 525

Asn Ala Asp Pro Val Cys Leu Ala Lys Met Tyr Tyr Ser Ala Val Glu
    530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
                565                 570                 575

Glu Phe Tyr Leu Phe Pro Thr Val Phe Asp Glu Asn Glu Ser Leu Leu
            580                 585                 590

Leu Glu Asp Asn Ile Arg Met Phe Thr Thr Ala Pro Asp Gln Val Asp
        595                 600                 605

Lys Glu Asp Glu Asp Phe Gln Glu Ser Asn Lys Met His Ser Met Asn
    610                 615                 620

Gly Phe Met Tyr Gly Asn Gln Pro Gly Leu Thr Met Cys Lys Gly Asp
625                 630                 635                 640
```

-continued

```
Ser Val Val Trp Tyr Leu Phe Ser Ala Gly Asn Glu Ala Asp Val His
                645                 650                 655

Gly Ile Tyr Phe Ser Gly Asn Thr Tyr Leu Trp Arg Gly Glu Arg Arg
            660                 665                 670

Asp Thr Ala Asn Leu Phe Pro Gln Thr Ser Leu Thr Leu His Met Trp
        675                 680                 685

Pro Asp Thr Glu Gly Thr Phe Asn Val Glu Cys Leu Thr Thr Asp His
    690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Glu Arg Thr Tyr Tyr Ile
                725                 730                 735

Ala Ala Val Glu Val Glu Trp Asp Tyr Ser Pro Gln Arg Glu Trp Glu
            740                 745                 750

Lys Glu Leu His His Leu Gln Glu Gln Asn Val Ser Asn Ala Phe Leu
        755                 760                 765

Asp Lys Gly Glu Phe Tyr Ile Gly Ser Lys Tyr Lys Lys Val Val Tyr
    770                 775                 780

Arg Gln Tyr Thr Asp Ser Thr Phe Arg Val Pro Val Glu Arg Lys Ala
785                 790                 795                 800

Glu Glu Glu His Leu Gly Ile Leu Gly Pro Gln Leu His Ala Asp Val
                805                 810                 815

Gly Asp Lys Val Lys Ile Ile Phe Lys Asn Met Ala Thr Arg Pro Tyr
            820                 825                 830

Ser Ile His Ala His Gly Val Gln Thr Glu Ser Ser Thr Val Thr Pro
        835                 840                 845

Thr Leu Pro Gly Glu Thr Leu Thr Tyr Val Trp Lys Ile Pro Glu Arg
    850                 855                 860

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
                885                 890                 895

Leu Ile Val Cys Arg Arg Pro Tyr Leu Lys Val Phe Asn Pro Arg Arg
            900                 905                 910

Lys Leu Glu Phe Ala Leu Leu Phe Leu Val Phe Asp Glu Asn Glu Ser
        915                 920                 925

Trp Tyr Leu Asp Asp Asn Ile Lys Thr Tyr Ser Asp His Pro Glu Lys
    930                 935                 940

Val Asn Lys Asp Asp Glu Glu Phe Ile Glu Ser Asn Lys Met His Ala
945                 950                 955                 960

Ile Asn Gly Arg Met Phe Gly Asn Leu Gln Gly Leu Thr Met His Val
                965                 970                 975

Gly Asp Glu Val Asn Trp Tyr Leu Met Gly Met Gly Asn Glu Ile Asp
            980                 985                 990

Leu His Thr Val His Phe His Gly  His Ser Phe Gln Tyr  Lys His Arg
        995                 1000                 1005

Gly Val  Tyr Ser Ser Asp Val  Phe Asp Ile Phe Pro  Gly Thr Tyr
    1010                 1015                 1020

Gln Thr  Leu Glu Met Phe Pro  Arg Thr Pro Gly Ile  Trp Leu Leu
    1025                 1030                 1035

His Cys  His Val Thr Asp His  Ile His Ala Gly Met  Glu Thr Thr
    1040                 1045                 1050
```

-continued

```
Tyr Thr  Val Leu Gln Asn Glu  Asp Thr Lys Ser Gly
    1055                 1060                 1065


<210> SEQ ID NO 2
<211> LENGTH: 1046
<212> TYPE: PRT
<213> ORGANISM: Homo sapiens

<400> SEQUENCE: 2

Lys Glu Lys His Tyr Tyr Ile Gly Ile Ile Glu Thr Thr Trp Asp Tyr
1               5                   10                  15

Ala Ser Asp His Gly Glu Lys Lys Leu Ile Ser Val Asp Thr Glu His
            20                  25                  30

Ser Asn Ile Tyr Leu Gln Asn Gly Pro Asp Arg Ile Gly Arg Leu Tyr
        35                  40                  45

Lys Lys Ala Leu Tyr Leu Gln Tyr Thr Asp Glu Thr Phe Arg Thr Thr
    50                  55                  60

Ile Glu Lys Pro Val Trp Leu Gly Phe Leu Gly Pro Ile Ile Lys Ala
65                  70                  75                  80

Glu Thr Gly Asp Lys Val Tyr Val His Leu Lys Asn Leu Ala Ser Arg
                85                  90                  95

Pro Tyr Thr Phe His Ser His Gly Ile Thr Tyr Tyr Lys Glu His Glu
            100                 105                 110

Gly Ala Ile Tyr Pro Asp Asn Thr Thr Asp Phe Gln Arg Ala Asp Asp
        115                 120                 125

Lys Val Tyr Pro Gly Glu Gln Tyr Thr Tyr Met Leu Leu Ala Thr Glu
    130                 135                 140

Glu Gln Ser Pro Gly Glu Gly Asp Gly Asn Cys Val Thr Arg Ile Tyr
145                 150                 155                 160

His Ser His Ile Asp Ala Pro Lys Asp Ile Ala Ser Gly Leu Ile Gly
                165                 170                 175

Pro Leu Ile Ile Cys Lys Lys Asp Ser Leu Asp Lys Glu Lys Glu Lys
            180                 185                 190

His Ile Asp Arg Glu Phe Val Val Met Phe Ser Val Val Asp Glu Asn
        195                 200                 205

Phe Ser Trp Tyr Leu Glu Asp Asn Ile Lys Thr Tyr Cys Ser Glu Pro
    210                 215                 220

Glu Lys Val Asp Lys Asp Asn Glu Asp Phe Gln Glu Ser Asn Arg Met
225                 230                 235                 240

Tyr Ser Val Asn Gly Tyr Thr Phe Gly Ser Leu Pro Gly Leu Ser Met
                245                 250                 255

Cys Ala Glu Asp Arg Val Lys Trp Tyr Leu Phe Gly Met Gly Asn Glu
            260                 265                 270

Val Asp Val His Ala Ala Phe Phe His Gly Gln Ala Leu Thr Asn Lys
        275                 280                 285

Asn Tyr Arg Ile Asp Thr Ile Asn Leu Phe Pro Ala Thr Leu Phe Asp
    290                 295                 300

Ala Tyr Met Val Ala Gln Asn Pro Gly Glu Trp Met Leu Ser Cys Gln
305                 310                 315                 320

Asn Leu Asn His Leu Lys Ala Gly Leu Gln Ala Phe Phe Gln Val Gln
                325                 330                 335

Glu Cys Asn Lys Ser Ser Ser Lys Asp Asn Ile Arg Gly Lys His Val
            340                 345                 350

Arg His Tyr Tyr Ile Ala Ala Glu Glu Ile Ile Trp Asn Tyr Ala Pro
        355                 360                 365
```

```
Ser Gly Ile Asp Ile Phe Thr Lys Glu Asn Leu Thr Ala Pro Gly Ser
    370                 375                 380

Asp Ser Ala Val Phe Phe Glu Gln Gly Thr Thr Arg Ile Gly Gly Ser
385                 390                 395                 400

Tyr Lys Lys Leu Val Tyr Arg Glu Tyr Thr Asp Ala Ser Phe Thr Asn
                405                 410                 415

Arg Lys Glu Arg Gly Pro Glu Glu Glu His Leu Gly Ile Leu Gly Pro
            420                 425                 430

Val Ile Trp Ala Glu Val Gly Asp Thr Ile Arg Val Thr Phe His Asn
        435                 440                 445

Lys Gly Ala Tyr Pro Leu Ser Ile Glu Pro Ile Gly Val Arg Phe Asn
    450                 455                 460

Lys Asn Asn Glu Gly Thr Tyr Tyr Ser Pro Asn Tyr Asn Pro Gln Ser
465                 470                 475                 480

Arg Ser Val Pro Pro Ser Ala Ser His Val Ala Pro Thr Glu Thr Phe
                485                 490                 495

Thr Tyr Glu Trp Thr Val Pro Lys Glu Val Gly Pro Thr Asn Ala Asp
            500                 505                 510

Pro Val Cys Leu Ala Lys Met Tyr Tyr Ser Ala Val Glu Pro Thr Lys
        515                 520                 525

Asp Ile Phe Thr Gly Leu Ile Gly Pro Met Lys Ile Cys Lys Lys Gly
    530                 535                 540

Ser Leu His Ala Asn Gly Arg Gln Lys Asp Val Asp Lys Glu Phe Tyr
545                 550                 555                 560

Leu Phe Pro Thr Val Phe Asp Glu Asn Glu Ser Leu Leu Leu Glu Asp
                565                 570                 575

Asn Ile Arg Met Phe Thr Thr Ala Pro Asp Gln Val Asp Lys Glu Asp
            580                 585                 590

Glu Asp Phe Gln Glu Ser Asn Lys Met His Ser Met Asn Gly Phe Met
        595                 600                 605

Tyr Gly Asn Gln Pro Gly Leu Thr Met Cys Lys Gly Asp Ser Val Val
    610                 615                 620

Trp Tyr Leu Phe Ser Ala Gly Asn Glu Ala Asp Val His Gly Ile Tyr
625                 630                 635                 640

Phe Ser Gly Asn Thr Tyr Leu Trp Arg Gly Glu Arg Arg Asp Thr Ala
                645                 650                 655

Asn Leu Phe Pro Gln Thr Ser Leu Thr Leu His Met Trp Pro Asp Thr
            660                 665                 670

Glu Gly Thr Phe Asn Val Glu Cys Leu Thr Thr Asp His Tyr Thr Gly
        675                 680                 685

Gly Met Lys Gln Lys Tyr Thr Val Asn Gln Cys Arg Arg Gln Ser Glu
    690                 695                 700

Asp Ser Thr Phe Tyr Leu Gly Glu Arg Thr Tyr Tyr Ile Ala Ala Val
705                 710                 715                 720

Glu Val Glu Trp Asp Tyr Ser Pro Gln Arg Glu Trp Glu Lys Glu Leu
                725                 730                 735

His His Leu Gln Glu Gln Asn Val Ser Asn Ala Phe Leu Asp Lys Gly
            740                 745                 750

Glu Phe Tyr Ile Gly Ser Lys Tyr Lys Lys Val Val Tyr Arg Gln Tyr
        755                 760                 765

Thr Asp Ser Thr Phe Arg Val Pro Val Glu Arg Lys Ala Glu Glu Glu
    770                 775                 780
```

His Leu Gly Ile Leu Gly Pro Gln Leu His Ala Asp Val Gly Asp Lys
785 790 795 800

Val Lys Ile Ile Phe Lys Asn Met Ala Thr Arg Pro Tyr Ser Ile His
805 810 815

Ala His Gly Val Gln Thr Glu Ser Ser Thr Val Thr Pro Thr Leu Pro
820 825 830

Gly Glu Thr Leu Thr Tyr Val Trp Lys Ile Pro Glu Arg Ser Gly Ala
835 840 845

Gly Thr Glu Asp Ser Ala Cys Ile Pro Trp Ala Tyr Tyr Ser Thr Val
850 855 860

Asp Gln Val Lys Asp Leu Tyr Ser Gly Leu Ile Gly Pro Leu Ile Val
865 870 875 880

Cys Arg Arg Pro Tyr Leu Lys Val Phe Asn Pro Arg Arg Lys Leu Glu
885 890 895

Phe Ala Leu Leu Phe Leu Val Phe Asp Glu Asn Glu Ser Trp Tyr Leu
900 905 910

Asp Asp Asn Ile Lys Thr Tyr Ser Asp His Pro Glu Lys Val Asn Lys
915 920 925

Asp Asp Glu Glu Phe Ile Glu Ser Asn Lys Met His Ala Ile Asn Gly
930 935 940

Arg Met Phe Gly Asn Leu Gln Gly Leu Thr Met His Val Gly Asp Glu
945 950 955 960

Val Asn Trp Tyr Leu Met Gly Met Gly Asn Glu Ile Asp Leu His Thr
965 970 975

Val His Phe His Gly His Ser Phe Gln Tyr Lys His Arg Gly Val Tyr
980 985 990

Ser Ser Asp Val Phe Asp Ile Phe Pro Gly Thr Tyr Gln Thr Leu Glu
995 1000 1005

Met Phe Pro Arg Thr Pro Gly Ile Trp Leu Leu His Cys His Val
1010 1015 1020

Thr Asp His Ile His Ala Gly Met Glu Thr Thr Tyr Thr Val Leu
1025 1030 1035

Gln Asn Glu Asp Thr Lys Ser Gly
1040 1045

<210> SEQ ID NO 3
<211> LENGTH: 323
<212> TYPE: PRT
<213> ORGANISM: Oryctolagus cuniculus

<400> SEQUENCE: 3

Gly Gln Pro Lys Ala Pro Ser Val Phe Pro Leu Ala Pro Cys Cys Gly
1 5 10 15

Asp Thr Pro Ser Ser Thr Val Thr Leu Gly Cys Leu Val Lys Gly Tyr
20 25 30

Leu Pro Glu Pro Val Thr Val Thr Trp Asn Ser Gly Thr Leu Thr Asn
35 40 45

Gly Val Arg Thr Phe Pro Ser Val Arg Gln Ser Ser Gly Leu Tyr Ser
50 55 60

Leu Ser Ser Val Val Ser Val Thr Ser Ser Ser Gln Pro Val Thr Cys
65 70 75 80

Asn Val Ala His Pro Ala Thr Asn Thr Lys Val Asp Lys Thr Val Ala
85 90 95

Pro Ser Thr Cys Ser Lys Pro Thr Cys Pro Pro Pro Glu Leu Leu Gly
100 105 110

Gly Pro Ser Val Phe Ile Phe Pro Pro Lys Pro Lys Asp Thr Leu Met
115 120 125

Ile Ser Arg Thr Pro Glu Val Thr Cys Val Val Val Asp Val Ser Gln
130 135 140

Asp Asp Pro Glu Val Gln Phe Thr Trp Tyr Ile Asn Asn Glu Gln Val
145 150 155 160

Arg Thr Ala Arg Pro Pro Leu Arg Glu Gln Gln Phe Asn Ser Thr Ile
165 170 175

Arg Val Val Ser Thr Leu Pro Ile Thr His Gln Asp Trp Leu Arg Gly
180 185 190

Lys Glu Phe Lys Cys Lys Val His Asn Lys Ala Leu Pro Ala Pro Ile
195 200 205

Glu Lys Thr Ile Ser Lys Ala Arg Gly Gln Pro Leu Glu Pro Lys Val
210 215 220

Tyr Thr Met Gly Pro Pro Arg Glu Glu Leu Ser Ser Arg Ser Val Ser
225 230 235 240

Leu Thr Cys Met Ile Asn Gly Phe Tyr Pro Ser Asp Ile Ser Val Glu
245 250 255

Trp Glu Lys Asn Gly Lys Ala Glu Asp Asn Tyr Lys Thr Thr Pro Ala
260 265 270

Val Leu Asp Ser Asp Gly Ser Tyr Phe Leu Tyr Ser Lys Leu Ser Val
275 280 285

Pro Thr Ser Glu Trp Gln Arg Gly Asp Val Phe Thr Cys Ser Val Met
290 295 300

His Glu Ala Leu His Asn His Tyr Thr Gln Lys Ser Ile Ser Arg Ser
305 310 315 320

Pro Gly Lys

<210> SEQ ID NO 4
<211> LENGTH: 103
<212> TYPE: PRT
<213> ORGANISM: Oryctolagus cuniculus

<400> SEQUENCE: 4

Asp Pro Val Ala Pro Thr Val Leu Ile Phe Pro Pro Ala Ala Asp Gln
1 5 10 15

Val Ala Thr Gly Thr Val Thr Ile Val Cys Val Ala Asn Lys Tyr Phe
20 25 30

Pro Asp Val Thr Val Thr Trp Glu Val Asp Gly Thr Thr Gln Thr Thr
35 40 45

Gly Ile Glu Asn Ser Lys Thr Pro Gln Asn Ser Ala Asp Cys Thr Tyr
50 55 60

Asn Leu Ser Ser Thr Leu Thr Leu Thr Ser Thr Gln Tyr Asn Ser His
65 70 75 80

Lys Glu Tyr Thr Cys Lys Val Thr Gln Gly Thr Thr Ser Val Val Gln
85 90 95

Ser Phe Asn Arg Gly Asp Cys
100

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Ser Tyr Gly Met Gly
1               5

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ile Ser Ser Ser Gly Thr Tyr Tyr Ala Asn Trp Ala Lys Gly
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Phe Ala Gly Gly Ala Tyr Asp Ile
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ala Ser Gln Ser Val Val Ser Asn Asn Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Ala Ser Thr Leu Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gly Val Tyr Asn Asn Val Asp Thr
1               5

<210> SEQ ID NO 11
<211> LENGTH: 7

<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Phe Ser Leu Ser Ser Tyr
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ser Ser Ser Gly
1

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Tyr Phe Ala Gly Gly Ala Tyr Asp Ile
1               5

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Gln Ala Ser Gln Ser Val Val Ser Asn Asn Tyr Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Phe Ala Ser Thr Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Leu Gly Val Tyr Asn Asn Val Asp Thr 1 5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Gly Phe Ser Leu Ser Ser Tyr Gly
1 5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Ile Ser Ser Ser Gly Thr
1 5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Ala Arg Tyr Phe Ala Gly Gly Ala Tyr Asp Ile
1 5 10

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gln Ser Val Val Ser Asn Asn Tyr
1 5

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Phe Ala Ser
1

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Leu Gly Val Tyr Asn Asn Val Asp Thr
1 5

<210> SEQ ID NO 23
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Gly Met Gly Trp Val Arg Gln Ala Pro Gly Lys Gly Leu Glu
50 55 60

Tyr Ile Gly Ile Ile Ser Ser Ser Gly Thr Tyr Tyr Ala Asn Trp Ala
65 70 75 80

Lys Gly Arg Phe Thr Ile Ser Arg Thr Ser Thr Thr Val Asp Leu Lys
85 90 95

Val Ala Ser Pro Thr Thr Glu Asp Thr Ala Thr Tyr Phe Cys Ala Arg
100 105 110

Tyr Phe Ala Gly Gly Ala Tyr Asp Ile Trp Gly Pro Gly Thr Leu Val
115 120 125

Thr Val Ser Leu
130

<210> SEQ ID NO 24
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Asp Met Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Ser
20 25 30

Val Ser Ala Ala Val Gly Gly Thr Val Thr Ile Asn Cys Gln Ala Ser
35 40 45

Gln Ser Val Val Ser Asn Asn Tyr Leu Ala Trp Phe Gln Gln Lys Pro
50 55 60

Gly Gln Pro Pro Lys Leu Leu Ile Tyr Phe Ala Ser Thr Leu Ala Ser
65 70 75 80

Gly Val Pro Ser Arg Phe Lys Gly Ser Gly Ser Gly Thr Gln Phe Thr
85 90 95

Leu Thr Ile Ser Asp Leu Glu Cys Asp Asp Ala Ala Thr Tyr Tyr Cys
100 105 110

Leu Gly Val Tyr Asn Asn Val Asp Thr Phe Gly Gly Gly Thr Glu Val
115 120 125

Val Val Lys Gly
    130

<210> SEQ ID NO 25
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Gly
            20                  25                  30

Met Gly Trp Val Arg Gln Ala Pro Gly Lys Gly Leu Glu Tyr Ile Gly
        35                  40                  45

Ile Ile Ser Ser Ser Gly Thr Tyr Tyr Ala Asn Trp Ala Lys Gly Arg
    50                  55                  60

Phe Thr Ile Ser Arg Thr Ser Thr Thr Val Asp Leu Lys Val Ala Ser
65                  70                  75                  80

Pro Thr Thr Glu Asp Thr Ala Thr Tyr Phe Cys Ala Arg Tyr Phe Ala
                85                  90                  95

Gly Gly Ala Tyr Asp Ile Trp Gly Pro Gly Thr Leu Val Thr Val Ser
            100                 105                 110

Leu

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Val Val Ser Asn
            20                  25                  30

Asn Tyr Leu Ala Trp Phe Gln Gln Lys Pro Gly Gln Pro Pro Lys Leu
        35                  40                  45

Leu Ile Tyr Phe Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Leu Gly Val Tyr Asn Asn
                85                  90                  95

Val Asp Thr Phe Gly Gly Gly Thr Glu Val Val Val Lys Gly
            100                 105                 110

<210> SEQ ID NO 27
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Gly Met Gly Trp Val Arg Gln Ala Pro Gly Lys Gly Leu Glu
    50                  55                  60

Tyr Ile Gly Ile Ile Ser Ser Ser Gly Thr Tyr Tyr Ala Asn Trp Ala
65                  70                  75                  80

Lys Gly Arg Phe Thr Ile Ser Arg Thr Ser Thr Thr Val Asp Leu Lys
                85                  90                  95

Val Ala Ser Pro Thr Thr Glu Asp Thr Ala Thr Tyr Phe Cys Ala Arg
            100                 105                 110

Tyr Phe Ala Gly Gly Ala Tyr Asp Ile Trp Gly Pro Gly Thr Leu Val
        115                 120                 125

Thr Val Ser Leu Gly Gln Pro Lys Ala Pro Ser Val Phe Pro Leu Ala
    130                 135                 140

Pro Cys Cys Gly Asp Thr Pro Ser Ser Thr Val Thr Leu Gly Cys Leu
145                 150                 155                 160

Val Lys Gly Tyr Leu Pro Glu Pro Val Thr Val Thr Trp Asn Ser Gly
                165                 170                 175

Thr Leu Thr Asn Gly Val Arg Thr Phe Pro Ser Val Arg Gln Ser Ser
            180                 185                 190

Gly Leu Tyr Ser Leu Ser Ser Val Val Ser Val Thr Ser Ser Ser Gln
        195                 200                 205

Pro Val Thr Cys Asn Val Ala His Pro Ala Thr Asn Thr Lys Val Asp
    210                 215                 220

Lys Thr Val Ala Pro Ser Thr Cys Ser Lys Pro Thr Cys Pro Pro Pro
225                 230                 235                 240

Glu Leu Leu Gly Gly Pro Ser Val Phe Ile Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Asp Asp Pro Glu Val Gln Phe Thr Trp Tyr Ile Asn
        275                 280                 285

Asn Glu Gln Val Arg Thr Ala Arg Pro Pro Leu Arg Glu Gln Gln Phe
    290                 295                 300

Asn Ser Thr Ile Arg Val Val Ser Thr Leu Pro Ile Thr His Gln Asp
305                 310                 315                 320

Trp Leu Arg Gly Lys Glu Phe Lys Cys Lys Val His Asn Lys Ala Leu
                325                 330                 335

Pro Ala Pro Ile Glu Lys Thr Ile Ser Lys Ala Arg Gly Gln Pro Leu
            340                 345                 350

Glu Pro Lys Val Tyr Thr Met Gly Pro Pro Arg Glu Glu Leu Ser Ser
        355                 360                 365

Arg Ser Val Ser Leu Thr Cys Met Ile Asn Gly Phe Tyr Pro Ser Asp
    370                 375                 380

Ile Ser Val Glu Trp Glu Lys Asn Gly Lys Ala Glu Asp Asn Tyr Lys
385                 390                 395                 400

Thr Thr Pro Ala Val Leu Asp Ser Asp Gly Ser Tyr Phe Leu Tyr Ser
                405                 410                 415

```
Lys Leu Ser Val Pro Thr Ser Glu Trp Gln Arg Gly Asp Val Phe Thr
            420                 425                 430

Cys Ser Val Met His Glu Ala Leu His Asn His Tyr Thr Gln Lys Ser
        435                 440                 445

Ile Ser Arg Ser Pro Gly Lys
    450                 455
```

<210> SEQ ID NO 28
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Met Asp Met Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ala Ser
        35                  40                  45

Gln Ser Val Val Ser Asn Asn Tyr Leu Ala Trp Phe Gln Gln Lys Pro
    50                  55                  60

Gly Gln Pro Pro Lys Leu Leu Ile Tyr Phe Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Leu Gly Val Tyr Asn Asn Val Asp Thr Phe Gly Gly Gly Thr Glu Val
        115                 120                 125

Val Val Lys Gly Asp Pro Val Ala Pro Thr Val Leu Leu Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235
```

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

```
Arg Tyr Tyr Met Ser
1               5
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Met Ile Tyr Pro Ser Ser Gly Ser Thr Trp Tyr Ala Ser Trp Val Lys
1 5 10 15

Gly

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Asp Arg Tyr Pro Gly Tyr Asn Gly Asp Ser Phe Asn Leu
1 5 10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln Ala Ser Gln Ser Val Tyr Asn Asn Asn Tyr Leu Ala
1 5 10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Ala Ser Lys Leu Ala Ile
1 5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Leu Gly Ser Tyr Gly Cys Asn Ser Val Asp Cys Asn Val
1 5 10

<210> SEQ ID NO 35
<211> LENGTH: 7
<212> TYPE: PRT
<213> ORGANISM: Artificial Sequence
<220> FEATURE:

<223> OTHER INFORMATION: Description of Artificial Sequence: Synthetic peptide

<400> SEQUENCE: 35

Gly Phe Ser Leu Ser Arg Tyr
1 5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Tyr Pro Ser Ser Gly Ser
1 5

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Asp Arg Tyr Pro Gly Tyr Asn Gly Asp Ser Phe Asn Leu
1 5 10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gln Ala Ser Gln Ser Val Tyr Asn Asn Asn Tyr Leu Ala
1 5 10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gln Ala Ser Lys Leu Ala Ile
1 5

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Leu Gly Ser Tyr Gly Cys Asn Ser Val Asp Cys Asn Val
1 5 10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Phe Ser Leu Ser Arg Tyr Tyr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Tyr Pro Ser Ser Gly Ser Thr
1               5

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Arg Asp Arg Tyr Pro Gly Tyr Asn Gly Asp Ser Phe Asn Leu
1               5                   10                  15

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ser Val Tyr Asn Asn Asn Tyr
1               5

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ala Ser
1

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Leu Gly Ser Tyr Gly Cys Asn Ser Val Asp Cys Asn Val
1               5                   10


<210> SEQ ID NO 47
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Arg Tyr Tyr Met Ser Trp Val Arg Gln Ala Pro Gly Lys Gly Leu Glu
    50                  55                  60

Trp Ile Gly Met Ile Tyr Pro Ser Ser Gly Ser Thr Trp Tyr Ala Ser
65                  70                  75                  80

Trp Val Lys Gly Arg Phe Thr Ile Ser Ala Thr Ala Thr Ser Val Asp
                85                  90                  95

Leu Lys Ile Thr Ser Pro Thr Thr Glu Asp Thr Ala Thr Tyr Phe Cys
            100                 105                 110

Val Arg Asp Arg Tyr Pro Gly Tyr Asn Gly Asp Ser Phe Asn Leu Trp
        115                 120                 125

Gly Gln Gly Thr Leu Val Thr Val Ser Ser
    130                 135


<210> SEQ ID NO 48
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Ser Thr Val Thr Ile Asn Cys Gln Ala Ser
        35                  40                  45

Gln Ser Val Tyr Asn Asn Asn Tyr Leu Ala Trp Phe Gln Gln Lys Pro
    50                  55                  60

Gly Gln Pro Pro Lys Arg Leu Ile Tyr Gln Ala Ser Lys Leu Ala Ile
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Gly Cys Asn Ser Val Asp Cys Asn Val Phe Gly Gly
        115                 120                 125

Gly Thr Glu Val Val Val Lys Gly
    130                 135
```

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Arg Tyr Tyr
            20                  25                  30

Met Ser Trp Val Arg Gln Ala Pro Gly Lys Gly Leu Glu Trp Ile Gly
        35                  40                  45

Met Ile Tyr Pro Ser Ser Gly Ser Thr Trp Tyr Ala Ser Trp Val Lys
    50                  55                  60

Gly Arg Phe Thr Ile Ser Ala Thr Ala Thr Ser Val Asp Leu Lys Ile
65                  70                  75                  80

Thr Ser Pro Thr Thr Glu Asp Thr Ala Thr Tyr Phe Cys Val Arg Asp
                85                  90                  95

Arg Tyr Pro Gly Tyr Asn Gly Asp Ser Phe Asn Leu Trp Gly Gln Gly
            100                 105                 110

Thr Leu Val Thr Val Ser Ser
        115
```

<210> SEQ ID NO 50
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

```
Ala Gln Val Leu Thr Gln Thr Ala Ser Pro Val Ser Ala Ala Val Gly
1               5                   10                  15

Ser Thr Val Thr Ile Asn Cys Gln Ala Ser Gln Ser Val Tyr Asn Asn
            20                  25                  30

Asn Tyr Leu Ala Trp Phe Gln Gln Lys Pro Gly Gln Pro Pro Lys Arg
        35                  40                  45

Leu Ile Tyr Gln Ala Ser Lys Leu Ala Ile Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ser Tyr Gly Cys
                85                  90                  95

Asn Ser Val Asp Cys Asn Val Phe Gly Gly Gly Thr Glu Val Val Val
            100                 105                 110

Lys Gly
```

<210> SEQ ID NO 51
<211> LENGTH: 461
<212> TYPE: PRT
<213> ORGANISM: Artificial Sequence
<220> FEATURE:
<223> OTHER INFORMATION: Description of Artificial Sequence: Synthetic
polypeptide -continued

<400> SEQUENCE: 51

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Arg Tyr Tyr Met Ser Trp Val Arg Gln Ala Pro Gly Lys Gly Leu Glu
    50                  55                  60

Trp Ile Gly Met Ile Tyr Pro Ser Ser Gly Ser Thr Trp Tyr Ala Ser
65                  70                  75                  80

Trp Val Lys Gly Arg Phe Thr Ile Ser Ala Thr Ala Thr Ser Val Asp
                85                  90                  95

Leu Lys Ile Thr Ser Pro Thr Thr Glu Asp Thr Ala Thr Tyr Phe Cys
            100                 105                 110

Val Arg Asp Arg Tyr Pro Gly Tyr Asn Gly Asp Ser Phe Asn Leu Trp
        115                 120                 125

Gly Gln Gly Thr Leu Val Thr Val Ser Ser Gly Gln Pro Lys Ala Pro
    130                 135                 140

Ser Val Phe Pro Leu Ala Pro Cys Cys Gly Asp Thr Pro Ser Ser Thr
145                 150                 155                 160

Val Thr Leu Gly Cys Leu Val Lys Gly Tyr Leu Pro Glu Pro Val Thr
                165                 170                 175

Val Thr Trp Asn Ser Gly Thr Leu Thr Asn Gly Val Arg Thr Phe Pro
            180                 185                 190

Ser Val Arg Gln Ser Ser Gly Leu Tyr Ser Leu Ser Ser Val Val Ser
        195                 200                 205

Val Thr Ser Ser Ser Gln Pro Val Thr Cys Asn Val Ala His Pro Ala
    210                 215                 220

Thr Asn Thr Lys Val Asp Lys Thr Val Ala Pro Ser Thr Cys Ser Lys
225                 230                 235                 240

Pro Thr Cys Pro Pro Pro Glu Leu Leu Gly Gly Pro Ser Val Phe Ile
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Asp Asp Pro Glu Val Gln
        275                 280                 285

Phe Thr Trp Tyr Ile Asn Asn Glu Gln Val Arg Thr Ala Arg Pro Pro
    290                 295                 300

Leu Arg Glu Gln Gln Phe Asn Ser Thr Ile Arg Val Val Ser Thr Leu
305                 310                 315                 320

Pro Ile Thr His Gln Asp Trp Leu Arg Gly Lys Glu Phe Lys Cys Lys
                325                 330                 335

Val His Asn Lys Ala Leu Pro Ala Pro Ile Glu Lys Thr Ile Ser Lys
            340                 345                 350

Ala Arg Gly Gln Pro Leu Glu Pro Lys Val Tyr Thr Met Gly Pro Pro
        355                 360                 365

Arg Glu Glu Leu Ser Ser Arg Ser Val Ser Leu Thr Cys Met Ile Asn
    370                 375                 380

Gly Phe Tyr Pro Ser Asp Ile Ser Val Glu Trp Glu Lys Asn Gly Lys
385                 390                 395                 400

Ala Glu Asp Asn Tyr Lys Thr Thr Pro Ala Val Leu Asp Ser Asp Gly
                405                 410                 415
```

-continued

```
Ser Tyr Phe Leu Tyr Ser Lys Leu Ser Val Pro Thr Ser Glu Trp Gln
            420                 425                 430

Arg Gly Asp Val Phe Thr Cys Ser Val Met His Glu Ala Leu His Asn
        435                 440                 445

His Tyr Thr Gln Lys Ser Ile Ser Arg Ser Pro Gly Lys
    450                 455                 460


<210> SEQ ID NO 52
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Ser Thr Val Thr Ile Asn Cys Gln Ala Ser
        35                  40                  45

Gln Ser Val Tyr Asn Asn Asn Tyr Leu Ala Trp Phe Gln Gln Lys Pro
    50                  55                  60

Gly Gln Pro Pro Lys Arg Leu Ile Tyr Gln Ala Ser Lys Leu Ala Ile
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Gly Cys Asn Ser Val Asp Cys Asn Val Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235


<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Asn Ala Met Ser
1               5
```

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Ile Ser Ser Arg Gly Ser Thr Tyr Tyr Ala Asn Trp Ala Lys Gly
1               5                   10                  15

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ser Leu Ala Gly Tyr Glu Pro Tyr Tyr Phe Lys Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ala Ser Glu Ser Ile Ser Ser Tyr Leu Ala
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ala Ser Asp Leu Ala Ser
1               5

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ser Tyr Tyr Gly Leu Ser Arg Asn Gly Tyr Gly Asn Val
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Phe Ser Leu Ser Ser Asn
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Ser Arg Gly Ser
1               5

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Ser Leu Ala Gly Tyr Glu Pro Tyr Tyr Phe Lys Leu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ala Ser Glu Ser Ile Ser Ser Tyr Leu Ala
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Ala Ser Asp Leu Ala Ser
1               5

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ser Tyr Tyr Gly Leu Ser Arg Asn Gly Tyr Gly Asn Val
1               5                   10

<210> SEQ ID NO 65
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Gly Phe Ser Leu Ser Ser Asn Ala
1 5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Ile Ser Ser Arg Gly Ser Thr
1 5

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Ala Arg Ser Ser Leu Ala Gly Tyr Glu Pro Tyr Tyr Phe Lys Leu
1 5 10 15

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Glu Ser Ile Ser Ser Tyr
1 5

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Gly Ala Ser
1

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Gln Ser Tyr Tyr Gly Leu Ser Arg Asn Gly Tyr Gly Asn Val 1 5 10

<210> SEQ ID NO 71
<211> LENGTH: 137
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Leu Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Arg Gly Ser Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ser Ser Leu Ala Gly Tyr Glu Pro Tyr Tyr Phe Lys Leu Trp Gly
        115                 120                 125

Gln Gly Thr Leu Val Thr Val Ser Ser
    130                 135
```

<210> SEQ ID NO 72
<211> LENGTH: 136
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 72

```
Met Asp Met Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Ala Ser
            20                  25                  30

Pro Val Ser Ala Ala Val Gly Gly Thr Val Thr Ile Lys Cys Gln Ala
        35                  40                  45

Ser Glu Ser Ile Ser Ser Tyr Leu Ala Trp Tyr Gln Gln Lys Pro Gly
    50                  55                  60

Gln Pro Pro Lys Leu Leu Ile Tyr Gly Ala Ser Asp Leu Ala Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Ser Tyr Tyr Gly Leu Ser Arg Asn Gly Tyr Gly Asn Val Phe Gly Gly
        115                 120                 125

Gly Thr Glu Val Val Val Lys Gly
    130                 135
```

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Gln Ser Leu Glu Glu Ser Gly Gly Arg Leu Val Thr Pro Gly Thr Leu
1               5                   10                  15

Leu Thr Leu Thr Cys Thr Val Ser Gly Phe Ser Leu Ser Ser Asn Ala
            20                  25                  30

Met Ser Trp Val Arg Gln Ala Pro Gly Glu Gly Leu Glu Trp Ile Gly
        35                  40                  45

Thr Ile Ser Ser Arg Gly Ser Thr Tyr Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ser Ser
                85                  90                  95

Leu Ala Gly Tyr Glu Pro Tyr Tyr Phe Lys Leu Trp Gly Gln Gly Thr
            100                 105                 110

Leu Val Thr Val Ser Ser
        115
```

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Asp Val Val Met Thr Gln Thr Ala Ser Pro Val Ser Ala Ala Val Gly
1               5                   10                  15

Gly Thr Val Thr Ile Lys Cys Gln Ala Ser Glu Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Gly Ala Ser Asp Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Gly Leu Ser Arg
                85                  90                  95

Asn Gly Tyr Gly Asn Val Phe Gly Gly Gly Thr Glu Val Val Val Lys
            100                 105                 110

Gly
```

<210> SEQ ID NO 75
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

-continued

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Leu Leu Thr Leu Thr Cys Thr Val Ser Gly Phe Ser Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Ser Arg Gly Ser Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ser Ser Leu Ala Gly Tyr Glu Pro Tyr Tyr Phe Lys Leu Trp Gly
        115                 120                 125

Gln Gly Thr Leu Val Thr Val Ser Ser Gly Gln Pro Lys Ala Pro Ser
    130                 135                 140

Val Phe Pro Leu Ala Pro Cys Cys Gly Asp Thr Pro Ser Ser Thr Val
145                 150                 155                 160

Thr Leu Gly Cys Leu Val Lys Gly Tyr Leu Pro Glu Pro Val Thr Val
                165                 170                 175

Thr Trp Asn Ser Gly Thr Leu Thr Asn Gly Val Arg Thr Phe Pro Ser
            180                 185                 190

Val Arg Gln Ser Ser Gly Leu Tyr Ser Leu Ser Ser Val Val Ser Val
        195                 200                 205

Thr Ser Ser Ser Gln Pro Val Thr Cys Asn Val Ala His Pro Ala Thr
    210                 215                 220

Asn Thr Lys Val Asp Lys Thr Val Ala Pro Ser Thr Cys Ser Lys Pro
225                 230                 235                 240

Thr Cys Pro Pro Pro Glu Leu Leu Gly Gly Pro Ser Val Phe Ile Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Asp Asp Pro Glu Val Gln Phe
        275                 280                 285

Thr Trp Tyr Ile Asn Asn Glu Gln Val Arg Thr Ala Arg Pro Pro Leu
    290                 295                 300

Arg Glu Gln Gln Phe Asn Ser Thr Ile Arg Val Val Ser Thr Leu Pro
305                 310                 315                 320

Ile Thr His Gln Asp Trp Leu Arg Gly Lys Glu Phe Lys Cys Lys Val
                325                 330                 335

His Asn Lys Ala Leu Pro Ala Pro Ile Glu Lys Thr Ile Ser Lys Ala
            340                 345                 350

Arg Gly Gln Pro Leu Glu Pro Lys Val Tyr Thr Met Gly Pro Pro Arg
        355                 360                 365

Glu Glu Leu Ser Ser Arg Ser Val Ser Leu Thr Cys Met Ile Asn Gly
    370                 375                 380

Phe Tyr Pro Ser Asp Ile Ser Val Glu Trp Glu Lys Asn Gly Lys Ala
385                 390                 395                 400

Glu Asp Asn Tyr Lys Thr Thr Pro Ala Val Leu Asp Ser Asp Gly Ser
                405                 410                 415

Tyr Phe Leu Tyr Ser Lys Leu Ser Val Pro Thr Ser Glu Trp Gln Arg
```

```
            420                 425                 430

Gly Asp Val Phe Thr Cys Ser Val Met His Glu Ala Leu His Asn His
        435                 440                 445

Tyr Thr Gln Lys Ser Ile Ser Arg Ser Pro Gly Lys
    450                 455                 460


<210> SEQ ID NO 76
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Asp Met Arg Ala Pro Thr Gln Leu Leu Gly Leu Leu Leu Leu Trp
1               5                   10                  15

Leu Pro Gly Ala Arg Cys Ala Asp Val Val Met Thr Gln Thr Ala Ser
            20                  25                  30

Pro Val Ser Ala Ala Val Gly Gly Thr Val Thr Ile Lys Cys Gln Ala
        35                  40                  45

Ser Glu Ser Ile Ser Ser Tyr Leu Ala Trp Tyr Gln Gln Lys Pro Gly
    50                  55                  60

Gln Pro Pro Lys Leu Leu Ile Tyr Gly Ala Ser Asp Leu Ala Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Ser Tyr Tyr Gly Leu Ser Arg Asn Gly Tyr Gly Asn Val Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235


<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Tyr Tyr Tyr Met Cys
1               5
```

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Cys Ile Tyr Val Ile Asp Asp Thr Ile Tyr Cys Ala Asn Trp Ala Lys
1 5 10 15

Gly

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Asp Gly Ser Ser Gly Ile Arg Asp Tyr Phe Asp Leu
1 5 10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Gln Ala Ser Glu Ser Val Ser Thr Trp Leu Ala
1 5 10

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Lys Ala Ser Asp Leu Ala Ser
1 5

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gln Gln Gly Tyr Thr Tyr Asn Asn Val Glu Asn Val
1 5 10

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gly Ile Asp Phe Ser Ser Tyr Tyr
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Tyr Val Ile Asp Asp Thr
1               5

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Asp Gly Ser Ser Gly Ile Arg Asp Tyr Phe Asp Leu
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gln Ala Ser Glu Ser Val Ser Thr Trp Leu Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Lys Ala Ser Asp Leu Ala Ser
1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gln Gln Gly Tyr Thr Tyr Asn Asn Val Glu Asn Val
1               5                   10

<210> SEQ ID NO 89
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Ile Asp Phe Ser Ser Tyr Tyr Tyr
1               5


<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Tyr Val Ile Asp Asp Thr Ile
1               5


<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Asp Gly Ser Ser Gly Ile Arg Asp Tyr Phe Asp Leu
1               5                   10


<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Ser Val Ser Thr Trp
1               5


<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Ala Ser
1


<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Gly Tyr Thr Tyr Asn Asn Val Glu Asn Val
```

-continued

```
1               5                   10


<210> SEQ ID NO 95
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Gly Leu Val Lys
            20                  25                  30

Pro Gly Gly Thr Leu Thr Leu Thr Cys Lys Ala Ser Gly Ile Asp Phe
        35                  40                  45

Ser Ser Tyr Tyr Tyr Met Cys Trp Val Arg Gln Ala Pro Gly Lys Gly
    50                  55                  60

Leu Glu Trp Ile Ala Cys Ile Tyr Val Ile Asp Asp Thr Ile Tyr Cys
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Asp Gly Ser Ser Gly Ile Arg Asp Tyr Phe Asp
        115                 120                 125

Leu Trp Gly Pro Gly Thr Leu Val Thr Val Ser Ser
    130                 135                 140


<210> SEQ ID NO 96
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Glu Ser Val Ser Thr Trp Leu Ala Trp Tyr Gln Gln Lys Pro Gly Gln
    50                  55                  60

Pro Pro Lys Leu Leu Ile Tyr Lys Ala Ser Asp Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Thr Tyr Asn Asn Val Glu Asn Val Phe Gly Gly Gly Thr Glu
        115                 120                 125

Val Val Val Lys Gly
    130
```

<210> SEQ ID NO 97
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Gln Gln Gln Leu Glu Glu Ser Gly Gly Gly Leu Val Lys Pro Gly Gly
1 5 10 15

Thr Leu Thr Leu Thr Cys Lys Ala Ser Gly Ile Asp Phe Ser Ser Tyr
20 25 30

Tyr Tyr Met Cys Val Arg Gln Ala Pro Gly Lys Gly Leu Glu Trp Ile
35 40 45

Ala Cys Ile Tyr Val Ile Asp Asp Thr Ile Tyr Cys Ala Asn Trp Ala
50 55 60

Lys Gly Arg Phe Thr Ile Ser Lys Thr Ser Ser Thr Thr Val Thr Leu
65 70 75 80

Gln Met Thr Ser Leu Thr Ala Ala Asp Thr Ala Thr Tyr Phe Cys Ala
85 90 95

Arg Asp Gly Ser Ser Gly Ile Arg Asp Tyr Phe Asp Leu Trp Gly Pro
100 105 110

Gly Thr Leu Val Thr Val Ser Ser
115 120

<210> SEQ ID NO 98
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Ala Tyr Asp Met Thr Gln Thr Pro Ala Ser Val Glu Val Ala Val Gly
1 5 10 15

Gly Thr Val Thr Ile Lys Cys Gln Ala Ser Glu Ser Val Ser Thr Trp
20 25 30

Leu Ala Trp Tyr Gln Gln Lys Pro Gly Gln Pro Pro Lys Leu Leu Ile
35 40 45

Tyr Lys Ala Ser Asp Leu Ala Ser Gly Val Pro Ser Arg Phe Lys Gly
50 55 60

Ser Gly Ser Gly Thr Glu Phe Thr Leu Thr Ile Ser Gly Val Glu Cys
65 70 75 80

Ala Asp Ala Ala Thr Tyr Tyr Cys Gln Gln Gly Tyr Thr Tyr Asn Asn
85 90 95

Val Glu Asn Val Phe Gly Gly Gly Thr Glu Val Val Val Lys Gly
100 105 110

<210> SEQ ID NO 99
<211> LENGTH: 463
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Met Glu Thr Gly Leu Arg Trp Leu Leu Leu Val Ala Val Leu Lys Gly
1 5 10 15

-continued

```
Val Gln Cys Gln Gln Gln Leu Glu Glu Ser Gly Gly Gly Leu Val Lys
            20                  25                  30

Pro Gly Gly Thr Leu Thr Leu Thr Cys Lys Ala Ser Gly Ile Asp Phe
        35                  40                  45

Ser Ser Tyr Tyr Tyr Met Cys Trp Val Arg Gln Ala Pro Gly Lys Gly
    50                  55                  60

Leu Glu Trp Ile Ala Cys Ile Tyr Val Ile Asp Asp Thr Ile Tyr Cys
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Asp Gly Ser Ser Gly Ile Arg Asp Tyr Phe Asp
        115                 120                 125

Leu Trp Gly Pro Gly Thr Leu Val Thr Val Ser Ser Gly Gln Pro Lys
    130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Ser Gln Pro Val Thr Cys Asn Val Ala His
    210                 215                 220

Pro Ala Thr Asn Thr Lys Val Asp Lys Thr Val Ala Pro Ser Thr Cys
225                 230                 235                 240

Ser Lys Pro Thr Cys Pro Pro Pro Glu Leu Leu Gly Gly Pro Ser Val
                245                 250                 255

Phe Ile Phe Pro Pro Lys Pro Lys Asp Thr Leu Met Ile Ser Arg Thr
            260                 265                 270

Pro Glu Val Thr Cys Val Val Val Asp Val Ser Gln Asp Asp Pro Glu
        275                 280                 285

Val Gln Phe Thr Trp Tyr Ile Asn Asn Glu Gln Val Arg Thr Ala Arg
    290                 295                 300

Pro Pro Leu Arg Glu Gln Gln Phe Asn Ser Thr Ile Arg Val Val Ser
305                 310                 315                 320

Thr Leu Pro Ile Thr His Gln Asp Trp Leu Arg Gly Lys Glu Phe Lys
                325                 330                 335

Cys Lys Val His Asn Lys Ala Leu Pro Ala Pro Ile Glu Lys Thr Ile
            340                 345                 350

Ser Lys Ala Arg Gly Gln Pro Leu Glu Pro Lys Val Tyr Thr Met Gly
        355                 360                 365

Pro Pro Arg Glu Glu Leu Ser Ser Arg Ser Val Ser Leu Thr Cys Met
    370                 375                 380

Ile Asn Gly Phe Tyr Pro Ser Asp Ile Ser Val Glu Trp Glu Lys Asn
385                 390                 395                 400

Gly Lys Ala Glu Asp Asn Tyr Lys Thr Thr Pro Ala Val Leu Asp Ser
                405                 410                 415

Asp Gly Ser Tyr Phe Leu Tyr Ser Lys Leu Ser Val Pro Thr Ser Glu
            420                 425                 430
```

```
Trp Gln Arg Gly Asp Val Phe Thr Cys Ser Val Met His Glu Ala Leu
        435                 440                 445

His Asn His Tyr Thr Gln Lys Ser Ile Ser Arg Ser Pro Gly Lys
    450                 455                 460


<210> SEQ ID NO 100
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Glu Ser Val Ser Thr Trp Leu Ala Trp Tyr Gln Gln Lys Pro Gly Gln
    50                  55                  60

Pro Pro Lys Leu Leu Ile Tyr Lys Ala Ser Asp Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Thr Tyr Asn Asn Val Glu Asn Val Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235


<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Asn Ala Met Ser
1               5


<210> SEQ ID NO 102
<211> LENGTH: 16
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Thr Ile Ser Thr Ala Gly Phe Thr Tyr Tyr Ala Ser Trp Ala Lys Gly
1 5 10 15

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Leu Leu Tyr Gly Pro Asn Ile
1 5

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Gln Ala Ser Pro Ser Ile Ser Asn Glu Leu Ser
1 5 10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Leu Ala Ser Thr Leu Ala Ser
1 5

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Gln Gly Ile Val Tyr Gly Pro Asp Tyr Val Val Gly
1 5 10

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Gly Ile Asp Leu Ser Ser Asn 1 5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Ser Thr Ala Gly Phe
1 5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Leu Leu Tyr Gly Pro Asn Ile
1 5

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gln Ala Ser Pro Ser Ile Ser Asn Glu Leu Ser
1 5 10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Leu Ala Ser Thr Leu Ala Ser
1 5

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Gln Gly Ile Val Tyr Gly Pro Asp Tyr Val Val Gly
1 5 10

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gly Ile Asp Leu Ser Ser Asn Ala
1 5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Ile Ser Thr Ala Gly Phe Thr
1 5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Ala Arg Leu Leu Tyr Gly Pro Asn Ile
1 5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Pro Ser Ile Ser Asn Glu
1 5

<210> SEQ ID NO 117
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Leu Ala Ser
1

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Gln Gly Ile Val Tyr Gly Pro Asp Tyr Val Val Gly
1 5 10

<210> SEQ ID NO 119

<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Gly Leu Val Thr Pro
            20                  25                  30

Gly Gly Thr Leu Thr Leu Thr Cys Thr Val Ser Gly Ile Asp Leu Ser
        35                  40                  45

Ser Asn Ala Met Ser Trp Val Arg Gln Ala Pro Gly Glu Gly Leu Glu
    50                  55                  60

Trp Ile Gly Thr Ile Ser Thr Ala Gly Phe Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Leu Leu Tyr Gly Pro Asn Ile Trp Gly Pro Gly Thr Leu Val Thr
        115                 120                 125

Val Ser Leu
    130
```

<210> SEQ ID NO 120
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Met Asp Met Arg Ala Pro Thr Gln Leu Leu Gly Leu Leu Leu Leu Trp
1               5                   10                  15

Leu Pro Gly Val Ile Cys Asp Pro Val Met Thr Gln Thr Pro Ala Ser
            20                  25                  30

Val Ser Glu Pro Val Gly Gly Thr Val Thr Ile Lys Cys Gln Ala Ser
        35                  40                  45

Pro Ser Ile Ser Asn Glu Leu Ser Trp Tyr Gln Gln Lys Pro Gly Gln
    50                  55                  60

Pro Pro Gln Leu Leu Ile Tyr Leu Ala Ser Thr Leu Ala Ser Gly Val
65                  70                  75                  80

Pro Ser Arg Phe Lys Gly Ser Arg Ser Gly Thr Glu Phe Thr Leu Thr
                85                  90                  95

Ile Ser Asp Leu Glu Cys Ala Asp Ala Ala Thr Tyr Tyr Cys Gln Gly
            100                 105                 110

Ile Val Tyr Gly Pro Asp Tyr Val Val Gly Phe Gly Gly Gly Thr Glu
        115                 120                 125

Val Val Val Lys Gly
    130
```

<210> SEQ ID NO 121
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Gln Ser Val Glu Glu Ser Gly Gly Gly Leu Val Thr Pro Gly Gly Thr
1 5 10 15

Leu Thr Leu Thr Cys Thr Val Ser Gly Ile Asp Leu Ser Ser Asn Ala
20 25 30

Met Ser Trp Val Arg Gln Ala Pro Gly Glu Gly Leu Glu Trp Ile Gly
35 40 45

Thr Ile Ser Thr Ala Gly Phe Thr Tyr Tyr Ala Ser Trp Ala Lys Gly
50 55 60

Arg Phe Thr Ile Ser Lys Thr Ser Thr Thr Val Asp Leu Lys Met Thr
65 70 75 80

Ser Leu Thr Ala Ala Asp Thr Ala Thr Tyr Phe Cys Ala Arg Leu Leu
85 90 95

Tyr Gly Pro Asn Ile Trp Gly Pro Gly Thr Leu Val Thr Val Ser Leu
100 105 110

<210> SEQ ID NO 122
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Asp Pro Val Met Thr Gln Thr Pro Ala Ser Val Ser Glu Pro Val Gly
1 5 10 15

Gly Thr Val Thr Ile Lys Cys Gln Ala Ser Pro Ser Ile Ser Asn Glu
20 25 30

Leu Ser Trp Tyr Gln Gln Lys Pro Gly Gln Pro Pro Gln Leu Leu Ile
35 40 45

Tyr Leu Ala Ser Thr Leu Ala Ser Gly Val Pro Ser Arg Phe Lys Gly
50 55 60

Ser Arg Ser Gly Thr Glu Phe Thr Leu Thr Ile Ser Asp Leu Glu Cys
65 70 75 80

Ala Asp Ala Ala Thr Tyr Tyr Cys Gln Gly Ile Val Tyr Gly Pro Asp
85 90 95

Tyr Val Val Gly Phe Gly Gly Gly Thr Glu Val Val Val Lys Gly
100 105 110

<210> SEQ ID NO 123
<211> LENGTH: 454
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 123

Met Glu Thr Gly Leu Arg Trp Leu Leu Leu Val Ala Val Leu Lys Gly
1 5 10 15

Val Gln Cys Gln Ser Val Glu Glu Ser Gly Gly Gly Leu Val Thr Pro
20 25 30

Gly Gly Thr Leu Thr Leu Thr Cys Thr Val Ser Gly Ile Asp Leu Ser
35 40 45

-continued

```
Ser Asn Ala Met Ser Trp Val Arg Gln Ala Pro Gly Glu Gly Leu Glu
    50                  55                  60

Trp Ile Gly Thr Ile Ser Thr Ala Gly Phe Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Leu Leu Tyr Gly Pro Asn Ile Trp Gly Pro Gly Thr Leu Val Thr
        115                 120                 125

Val Ser Leu Gly Gln Pro Lys Ala Pro Ser Val Phe Pro Leu Ala Pro
    130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Thr His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
        435                 440                 445

Ser Arg Ser Pro Gly Lys
    450
```

<210> SEQ ID NO 124
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

```
Met Asp Met Arg Ala Pro Thr Gln Leu Leu Gly Leu Leu Leu Leu Trp
1               5                   10                  15

Leu Pro Gly Val Ile Cys Asp Pro Val Met Thr Gln Thr Pro Ala Ser
            20                  25                  30

Val Ser Glu Pro Val Gly Gly Thr Val Thr Ile Lys Cys Gln Ala Ser
        35                  40                  45

Pro Ser Ile Ser Asn Glu Leu Ser Trp Tyr Gln Gln Lys Pro Gly Gln
    50                  55                  60

Pro Pro Gln Leu Leu Ile Tyr Leu Ala Ser Thr Leu Ala Ser Gly Val
65                  70                  75                  80

Pro Ser Arg Phe Lys Gly Ser Arg Ser Gly Thr Glu Phe Thr Leu Thr
                85                  90                  95

Ile Ser Asp Leu Glu Cys Ala Asp Ala Ala Thr Tyr Tyr Cys Gln Gly
            100                 105                 110

Ile Val Tyr Gly Pro Asp Tyr Val Val Gly Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

```
Arg Phe Tyr Tyr Met Cys
1               5
```

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Cys Ile Tyr Ala Gly Arg Thr Gly Asn Thr Tyr Tyr Ala Ser Trp Ala
1 5 10 15

Lys Gly

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Ala Ser Gly Asp Phe Leu Ala Tyr Thr Tyr Ala Met Asp Leu
1 5 10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Gln Ala Ser Gln Ser Val Asp Asn Asn Asn Tyr Leu Ala
1 5 10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Glu Ala Ser Lys Leu Ala Ser
1 5

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Ala Gly Gly Tyr Ser Ser Ser Ala Asp Ala Asn Ala
1 5 10

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Gly Phe Asp Leu Ser Arg Phe Tyr
1 5

<210> SEQ ID NO 132
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Tyr Ala Gly Arg Thr Gly Asn
1 5

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Ala Ser Gly Asp Phe Leu Ala Tyr Thr Tyr Ala Met Asp Leu
1 5 10

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Gln Ala Ser Gln Ser Val Asp Asn Asn Asn Tyr Leu Ala
1 5 10

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Glu Ala Ser Lys Leu Ala Ser
1 5

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Ala Gly Gly Tyr Ser Ser Ser Ala Asp Ala Asn Ala
1 5 10

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Gly Phe Asp Leu Ser Arg Phe Tyr Tyr 1 5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Ile Tyr Ala Gly Arg Thr Gly Asn Thr
1 5

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Ala Arg Ala Ser Gly Asp Phe Leu Ala Tyr Thr Tyr Ala Met Asp Leu
1 5 10 15

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Gln Ser Val Asp Asn Asn Asn Tyr
1 5

<210> SEQ ID NO 141
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Glu Ala Ser
1

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Ala Gly Gly Tyr Ser Ser Ser Ala Asp Ala Asn Ala
1 5 10

<210> SEQ ID NO 143
<211> LENGTH: 142
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Lys Ala Ser Gly Phe Asp Leu Ser
35 40 45

Arg Phe Tyr Tyr Met Cys Trp Val Arg Gln Ala Pro Gly Lys Gly Leu
50 55 60

Glu Trp Ile Ala Cys Ile Tyr Ala Gly Arg Thr Gly Asn Thr Tyr Tyr
65 70 75 80

Ala Ser Trp Ala Lys Gly Arg Phe Thr Ile Ser Lys Thr Ser Ser Thr
85 90 95

Thr Val Thr Leu Gln Met Thr Ser Leu Thr Ala Ala Asp Thr Ala Thr
100 105 110

Tyr Phe Cys Ala Arg Ala Ser Gly Asp Phe Leu Ala Tyr Thr Tyr Ala
115 120 125

Met Asp Leu Trp Gly Pro Gly Thr Leu Val Thr Val Ser Ser
130 135 140

<210> SEQ ID NO 144
<211> LENGTH: 135
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 144

Met Asp Met Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ala Ser
20 25 30

Val Ser Ala Ala Val Gly Gly Thr Val Thr Ile Ser Cys Gln Ala Ser
35 40 45

Gln Ser Val Asp Asn Asn Asn Tyr Leu Ala Trp Tyr Gln Gln Lys Pro
50 55 60

Gly Gln Pro Pro Lys Leu Leu Ile Tyr Glu Ala Ser Lys Leu Ala Ser
65 70 75 80

Gly Val Pro Ser Arg Phe Ser Gly Ser Gly Ser Gly Thr Gln Phe Thr
85 90 95

Leu Thr Ile Ser Asp Val Gln Cys Asp Asp Ala Thr Thr Tyr Tyr Cys
100 105 110

Ala Gly Gly Tyr Ser Ser Ser Ala Asp Ala Asn Ala Phe Gly Gly Gly
115 120 125

Thr Glu Val Val Val Lys Gly
130 135

<210> SEQ ID NO 145
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 145

```
Gln Ser Leu Glu Glu Ser Gly Gly Asp Leu Val Lys Pro Gly Ala Ser
1               5                   10                  15

Leu Thr Leu Thr Cys Lys Ala Ser Gly Phe Asp Leu Ser Arg Phe Tyr
            20                  25                  30

Tyr Met Cys Trp Val Arg Gln Ala Pro Gly Lys Gly Leu Glu Trp Ile
        35                  40                  45

Ala Cys Ile Tyr Ala Gly Arg Thr Gly Asn Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ala Ser Gly Asp Phe Leu Ala Tyr Thr Tyr Ala Met Asp Leu
            100                 105                 110

Trp Gly Pro Gly Thr Leu Val Thr Val Ser Ser
        115                 120


<210> SEQ ID NO 146
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Ala Val Leu Thr Gln Thr Pro Ala Ser Val Ser Ala Ala Val Gly
1               5                   10                  15

Gly Thr Val Thr Ile Ser Cys Gln Ala Ser Gln Ser Val Asp Asn Asn
            20                  25                  30

Asn Tyr Leu Ala Trp Tyr Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Thr Thr Tyr Tyr Cys Ala Gly Gly Tyr Ser Ser
                85                  90                  95

Ser Ala Asp Ala Asn Ala Phe Gly Gly Gly Thr Glu Val Val Val Lys
            100                 105                 110

Gly


<210> SEQ ID NO 147
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Phe Asp Leu Ser
        35                  40                  45
```

-continued

```
Arg Phe Tyr Tyr Met Cys Trp Val Arg Gln Ala Pro Gly Lys Gly Leu
    50                  55                  60

Glu Trp Ile Ala Cys Ile Tyr Ala Gly Arg Thr Gly Asn Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Ala Ser Gly Asp Phe Leu Ala Tyr Thr Tyr Ala
        115                 120                 125

Met Asp Leu Trp Gly Pro Gly Thr Leu Val Thr Val Ser Ser Gly Gln
    130                 135                 140

Pro Lys Ala Pro Ser Val Phe Pro Leu Ala Pro Cys Cys Gly Asp Thr
145                 150                 155                 160

Pro Ser Ser Thr Val Thr Leu Gly Cys Leu Val Lys Gly Tyr Leu Pro
                165                 170                 175

Glu Pro Val Thr Val Thr Trp Asn Ser Gly Thr Leu Thr Asn Gly Val
            180                 185                 190

Arg Thr Phe Pro Ser Val Arg Gln Ser Ser Gly Leu Tyr Ser Leu Ser
        195                 200                 205

Ser Val Val Ser Val Thr Ser Ser Ser Gln Pro Val Thr Cys Asn Val
    210                 215                 220

Ala His Pro Ala Thr Asn Thr Lys Val Asp Lys Thr Val Ala Pro Ser
225                 230                 235                 240

Thr Cys Ser Lys Pro Thr Cys Pro Pro Pro Glu Leu Leu Gly Gly Pro
                245                 250                 255

Ser Val Phe Ile Phe Pro Pro Lys Pro Lys Asp Thr Leu Met Ile Ser
            260                 265                 270

Arg Thr Pro Glu Val Thr Cys Val Val Val Asp Val Ser Gln Asp Asp
        275                 280                 285

Pro Glu Val Gln Phe Thr Trp Tyr Ile Asn Asn Glu Gln Val Arg Thr
    290                 295                 300

Ala Arg Pro Pro Leu Arg Glu Gln Gln Phe Asn Ser Thr Ile Arg Val
305                 310                 315                 320

Val Ser Thr Leu Pro Ile Thr His Gln Asp Trp Leu Arg Gly Lys Glu
                325                 330                 335

Phe Lys Cys Lys Val His Asn Lys Ala Leu Pro Ala Pro Ile Glu Lys
            340                 345                 350

Thr Ile Ser Lys Ala Arg Gly Gln Pro Leu Glu Pro Lys Val Tyr Thr
        355                 360                 365

Met Gly Pro Pro Arg Glu Glu Leu Ser Ser Arg Ser Val Ser Leu Thr
    370                 375                 380

Cys Met Ile Asn Gly Phe Tyr Pro Ser Asp Ile Ser Val Glu Trp Glu
385                 390                 395                 400

Lys Asn Gly Lys Ala Glu Asp Asn Tyr Lys Thr Thr Pro Ala Val Leu
                405                 410                 415

Asp Ser Asp Gly Ser Tyr Phe Leu Tyr Ser Lys Leu Ser Val Pro Thr
            420                 425                 430

Ser Glu Trp Gln Arg Gly Asp Val Phe Thr Cys Ser Val Met His Glu
        435                 440                 445

Ala Leu His Asn His Tyr Thr Gln Lys Ser Ile Ser Arg Ser Pro Gly
    450                 455                 460

Lys
```

465

<210> SEQ ID NO 148
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 148

Met Asp Met Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ala Ser
20 25 30

Val Ser Ala Ala Val Gly Gly Thr Val Thr Ile Ser Cys Gln Ala Ser
35 40 45

Gln Ser Val Asp Asn Asn Asn Tyr Leu Ala Trp Tyr Gln Gln Lys Pro
50 55 60

Gly Gln Pro Pro Lys Leu Leu Ile Tyr Glu Ala Ser Lys Leu Ala Ser
65 70 75 80

Gly Val Pro Ser Arg Phe Ser Gly Ser Gly Ser Gly Thr Gln Phe Thr
85 90 95

Leu Thr Ile Ser Asp Val Gln Cys Asp Asp Ala Thr Thr Tyr Tyr Cys
100 105 110

Ala Gly Gly Tyr Ser Ser Ser Ala Asp Ala Asn Ala Phe Gly Gly Gly
115 120 125

Thr Glu Val Val Val Lys Gly Asp Pro Val Ala Pro Thr Val Leu Ile
130 135 140

Phe Pro Pro Ala Ala Asp Gln Val Ala Thr Gly Thr Val Thr Ile Val
145 150 155 160

Cys Val Ala Asn Lys Tyr Phe Pro Asp Val Thr Val Thr Trp Glu Val
165 170 175

Asp Gly Thr Thr Gln Thr Thr Gly Ile Glu Asn Ser Lys Thr Pro Gln
180 185 190

Asn Ser Ala Asp Cys Thr Tyr Asn Leu Ser Ser Thr Leu Thr Leu Thr
195 200 205

Ser Thr Gln Tyr Asn Ser His Lys Glu Tyr Thr Cys Lys Val Thr Gln
210 215 220

Gly Thr Thr Ser Val Val Gln Ser Phe Asn Arg Gly Asp Cys
225 230 235

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Ser Tyr Trp Met Cys
1 5

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Cys Ile Tyr Gly Gly Asp Gly Thr Ser Tyr Phe Ala Gly Trp Ala Lys
1 5 10 15

Gly

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Ala Asp Tyr Tyr Val Tyr Val Asp Gly Gly Tyr Gly His Ala Tyr Asp
1 5 10 15

Leu

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Gln Ala Ser Asp Asp Ile Tyr Ser Tyr Leu Ala
1 5 10

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Asp Ala Ser Ser Leu Pro Ser
1 5

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Gln Asn Tyr Tyr Gly Ser Ser Ser Ser Val His Ala
1 5 10

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Gly Phe Asp Phe Ser Ser Tyr 1 5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Tyr Gly Gly Asp Gly Thr
1 5

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Ala Asp Tyr Tyr Val Tyr Val Asp Gly Gly Tyr Gly His Ala Tyr Asp
1 5 10 15

Leu

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Gln Ala Ser Asp Asp Ile Tyr Ser Tyr Leu Ala
1 5 10

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Asp Ala Ser Ser Leu Pro Ser
1 5

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Gln Asn Tyr Tyr Gly Ser Ser Ser Ser Val His Ala
1 5 10

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Gly Phe Asp Phe Ser Ser Tyr Trp
1 5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Ile Tyr Gly Gly Asp Gly Thr Ser
1 5

<210> SEQ ID NO 163
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 163

Ala Arg Ala Asp Tyr Tyr Val Tyr Val Asp Gly Gly Tyr Gly His Ala
1 5 10 15

Tyr Asp Leu

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 164

Asp Asp Ile Tyr Ser Tyr
1 5

<210> SEQ ID NO 165
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Asp Ala Ser
1

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Gln Asn Tyr Tyr Gly Ser Ser Ser Ser Val His Ala

-continued

```
1               5                   10


<210> SEQ ID NO 167
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Asp Phe
        35                  40                  45

Ser Ser Tyr Trp Met Cys Trp Val Arg Gln Ala Pro Gly Lys Arg Pro
    50                  55                  60

Glu Trp Ile Ala Cys Ile Tyr Gly Gly Asp Gly Thr Ser Tyr Phe Ala
65                  70                  75                  80

Gly Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Ala Asp Tyr Tyr Val Tyr Val Asp Gly Gly Tyr Gly
        115                 120                 125

His Ala Tyr Asp Leu Trp Gly Pro Gly Thr Leu Val Thr Val Ser Ser
    130                 135                 140


<210> SEQ ID NO 168
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Asp Met Arg Ala Pro Thr Gln Leu Leu Gly Leu Leu Leu Leu Trp
1               5                   10                  15

Leu Pro Gly Ala Arg Cys Val Asp Ile Val Met Thr Gln Thr Pro Ala
            20                  25                  30

Ser Val Glu Ala Ala Val Gly Gly Ser Val Thr Ile Lys Cys Gln Ala
        35                  40                  45

Ser Asp Asp Ile Tyr Ser Tyr Leu Ala Trp Tyr Gln Gln Lys Pro Gly
    50                  55                  60

Gln Pro Pro Lys Leu Leu Ile Phe Asp Ala Ser Ser Leu Pro Ser Gly
65                  70                  75                  80

Val Pro Ser Arg Phe Lys Gly Ser Gly Ser Gly Thr Gln Phe Thr Leu
                85                  90                  95

Thr Ile Ser Gly Val Gln Cys Ala Asp Ala Ala Thr Tyr Tyr Cys Gln
            100                 105                 110

Asn Tyr Tyr Gly Ser Ser Ser Ser Val His Ala Phe Gly Gly Gly Thr
        115                 120                 125

Glu Val Val Val Lys Gly
    130
```

<210> SEQ ID NO 169
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 169

```
Gln Glu Gln Leu Val Glu Ser Gly Gly Gly Leu Val Gln Pro Glu Gly
1               5                   10                  15

Ser Leu Thr Leu Thr Cys Lys Ala Ser Gly Phe Asp Phe Ser Ser Tyr
            20                  25                  30

Trp Met Cys Trp Val Arg Gln Ala Pro Gly Lys Arg Pro Glu Trp Ile
        35                  40                  45

Ala Cys Ile Tyr Gly Gly Asp Gly Thr Ser Tyr Phe Ala Gly Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Ala Asp Tyr Tyr Val Tyr Val Asp Gly Gly Tyr Gly His Ala Tyr
            100                 105                 110

Asp Leu Trp Gly Pro Gly Thr Leu Val Thr Val Ser Ser
        115                 120                 125
```

<210> SEQ ID NO 170
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 170

```
Asp Ile Val Met Thr Gln Thr Pro Ala Ser Val Glu Ala Ala Val Gly
1               5                   10                  15

Gly Ser Val Thr Ile Lys Cys Gln Ala Ser Asp Asp Ile Tyr Ser Tyr
            20                  25                  30

Leu Ala Trp Tyr Gln Gln Lys Pro Gly Gln Pro Pro Lys Leu Leu Ile
        35                  40                  45

Phe Asp Ala Ser Ser Leu Pro Ser Gly Val Pro Ser Arg Phe Lys Gly
    50                  55                  60

Ser Gly Ser Gly Thr Gln Phe Thr Leu Thr Ile Ser Gly Val Gln Cys
65                  70                  75                  80

Ala Asp Ala Ala Thr Tyr Tyr Cys Gln Asn Tyr Tyr Gly Ser Ser Ser
                85                  90                  95

Ser Val His Ala Phe Gly Gly Gly Thr Glu Val Val Val Lys Gly
            100                 105                 110
```

<210> SEQ ID NO 171
<211> LENGTH: 467
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 171

```
Met Glu Thr Gly Leu Arg Trp Leu Leu Leu Val Ala Val Leu Lys Gly
1               5                   10                  15
```

```
Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Asp Phe
        35                  40                  45

Ser Ser Tyr Trp Met Cys Trp Val Arg Gln Ala Pro Gly Lys Arg Pro
    50                  55                  60

Glu Trp Ile Ala Cys Ile Tyr Gly Gly Asp Gly Thr Ser Tyr Phe Ala
65                  70                  75                  80

Gly Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Ala Asp Tyr Tyr Val Tyr Val Asp Gly Gly Tyr Gly
        115                 120                 125

His Ala Tyr Asp Leu Trp Gly Pro Gly Thr Leu Val Thr Val Ser Ser
    130                 135                 140

Gly Gln Pro Lys Ala Pro Ser Val Phe Pro Leu Ala Pro Cys Cys Gly
145                 150                 155                 160

Asp Thr Pro Ser Ser Thr Val Thr Leu Gly Cys Leu Val Lys Gly Tyr
                165                 170                 175

Leu Pro Glu Pro Val Thr Val Thr Trp Asn Ser Gly Thr Leu Thr Asn
            180                 185                 190

Gly Val Arg Thr Phe Pro Ser Val Arg Gln Ser Ser Gly Leu Tyr Ser
        195                 200                 205

Leu Ser Ser Val Val Ser Val Thr Ser Ser Ser Gln Pro Val Thr Cys
    210                 215                 220

Asn Val Ala His Pro Ala Thr Asn Thr Lys Val Asp Lys Thr Val Ala
225                 230                 235                 240

Pro Ser Thr Cys Ser Lys Pro Thr Cys Pro Pro Pro Glu Leu Leu Gly
                245                 250                 255

Gly Pro Ser Val Phe Ile Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Asp Asp Pro Glu Val Gln Phe Thr Trp Tyr Ile Asn Asn Glu Gln Val
    290                 295                 300

Arg Thr Ala Arg Pro Pro Leu Arg Glu Gln Gln Phe Asn Ser Thr Ile
305                 310                 315                 320

Arg Val Val Ser Thr Leu Pro Ile Thr His Gln Asp Trp Leu Arg Gly
                325                 330                 335

Lys Glu Phe Lys Cys Lys Val His Asn Lys Ala Leu Pro Ala Pro Ile
            340                 345                 350

Glu Lys Thr Ile Ser Lys Ala Arg Gly Gln Pro Leu Glu Pro Lys Val
        355                 360                 365

Tyr Thr Met Gly Pro Pro Arg Glu Glu Leu Ser Ser Arg Ser Val Ser
    370                 375                 380

Leu Thr Cys Met Ile Asn Gly Phe Tyr Pro Ser Asp Ile Ser Val Glu
385                 390                 395                 400

Trp Glu Lys Asn Gly Lys Ala Glu Asp Asn Tyr Lys Thr Thr Pro Ala
                405                 410                 415

Val Leu Asp Ser Asp Gly Ser Tyr Phe Leu Tyr Ser Lys Leu Ser Val
            420                 425                 430
```

Pro Thr Ser Glu Trp Gln Arg Gly Asp Val Phe Thr Cys Ser Val Met
435 440 445

His Glu Ala Leu His Asn His Tyr Thr Gln Lys Ser Ile Ser Arg Ser
450 455 460

Pro Gly Lys
465

<210> SEQ ID NO 172
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Met Asp Met Arg Ala Pro Thr Gln Leu Leu Gly Leu Leu Leu Leu Trp
1 5 10 15

Leu Pro Gly Ala Arg Cys Val Asp Ile Val Met Thr Gln Thr Pro Ala
20 25 30

Ser Val Glu Ala Ala Val Gly Gly Ser Val Thr Ile Lys Cys Gln Ala
35 40 45

Ser Asp Asp Ile Tyr Ser Tyr Leu Ala Trp Tyr Gln Gln Lys Pro Gly
50 55 60

Gln Pro Pro Lys Leu Leu Ile Phe Asp Ala Ser Ser Leu Pro Ser Gly
65 70 75 80

Val Pro Ser Arg Phe Lys Gly Ser Gly Ser Gly Thr Gln Phe Thr Leu
85 90 95

Thr Ile Ser Gly Val Gln Cys Ala Asp Ala Ala Thr Tyr Tyr Cys Gln
100 105 110

Asn Tyr Tyr Gly Ser Ser Ser Ser Val His Ala Phe Gly Gly Gly Thr
115 120 125

Glu Val Val Val Lys Gly Asp Pro Val Ala Pro Thr Val Leu Ile Phe
130 135 140

Pro Pro Ala Ala Asp Gln Val Ala Thr Gly Thr Val Thr Ile Val Cys
145 150 155 160

Val Ala Asn Lys Tyr Phe Pro Asp Val Thr Val Thr Trp Glu Val Asp
165 170 175

Gly Thr Thr Gln Thr Thr Gly Ile Glu Asn Ser Lys Thr Pro Gln Asn
180 185 190

Ser Ala Asp Cys Thr Tyr Asn Leu Ser Ser Thr Leu Thr Leu Thr Ser
195 200 205

Thr Gln Tyr Asn Ser His Lys Glu Tyr Thr Cys Lys Val Thr Gln Gly
210 215 220

Thr Thr Ser Val Val Gln Ser Phe Asn Arg Gly Asp Cys
225 230 235

<210> SEQ ID NO 173
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Thr Tyr Ala Met Gly
1 5

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Ile Ile Tyr Gly Gly Ser Gly Thr Phe Tyr Ala Ser Trp Ala Lys Gly
1               5                   10                  15

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Asp Gly Asp Asp Ser Tyr Phe Asp Tyr Phe Asn Leu
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Gln Ser Asn Glu Asn Ile Gly Ser Asn Leu Ala
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Gly Ala Ser Thr Leu Thr Ser
1               5

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Leu Gly Gly Tyr Leu Ser Thr Ser Asp Thr Thr
1               5                   10

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Gly Phe Ser Leu Ser Thr Tyr
1 5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Tyr Gly Gly Ser Gly
1 5

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Asp Gly Asp Asp Ser Tyr Phe Asp Tyr Phe Asn Leu
1 5 10

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 182

Gln Ser Asn Glu Asn Ile Gly Ser Asn Leu Ala
1 5 10

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 183

Gly Ala Ser Thr Leu Thr Ser
1 5

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 184

Leu Gly Gly Tyr Leu Ser Thr Ser Asp Thr Thr
1 5 10

<210> SEQ ID NO 185
<211> LENGTH: 8
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 185

Gly Phe Ser Leu Ser Thr Tyr Ala
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Tyr Gly Gly Ser Gly Thr
1               5

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Arg Asp Gly Asp Asp Ser Tyr Phe Asp Tyr Phe Asn Leu
1               5                   10

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Glu Asn Ile Gly Ser Asn
1               5

<210> SEQ ID NO 189
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Ala Ser
1

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Gly Gly Tyr Leu Ser Thr Ser Asp Thr Thr
1               5                   10

<210> SEQ ID NO 191
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Ala Met Gly Trp Val Arg Gln Ala Pro Gly Lys Gly Leu Glu
    50                  55                  60

Tyr Ile Gly Ile Ile Tyr Gly Gly Ser Gly Thr Phe Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Asp Gly Asp Asp Ser Tyr Phe Asp Tyr Phe Asn Leu Trp Gly Gln
        115                 120                 125

Gly Thr Leu Val Thr Val Ser Ser
    130                 135
```

<210> SEQ ID NO 192
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 192

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ala Ser
            20                  25                  30

Val Ser Ala Ala Val Gly Gly Thr Val Ser Ile Ser Cys Gln Ser Asn
        35                  40                  45

Glu Asn Ile Gly Ser Asn Leu Ala Trp Tyr Gln Gln Lys Pro Gly Gln
    50                  55                  60

Pro Pro Lys Leu Leu Ile Tyr Gly Ala Ser Thr Leu Thr Ser Gly Val
65                  70                  75                  80

Pro Ser Arg Phe Lys Gly Ser Gly Ser Gly Thr Ala Phe Thr Leu Thr
                85                  90                  95

Ile Ser Gly Val Gln Cys Asp Asp Ala Ala Thr Tyr Tyr Cys Leu Gly
            100                 105                 110

Gly Tyr Leu Ser Thr Ser Asp Thr Thr Phe Gly Gly Gly Thr Ala Val
        115                 120                 125

Val Val Lys Gly
    130
```

<210> SEQ ID NO 193

<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 193

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Thr Tyr Ala
20 25 30

Met Gly Trp Val Arg Gln Ala Pro Gly Lys Gly Leu Glu Tyr Ile Gly
35 40 45

Ile Ile Tyr Gly Gly Ser Gly Thr Phe Tyr Ala Ser Trp Ala Lys Gly
50 55 60

Arg Phe Thr Ile Ser Lys Thr Ser Thr Thr Val Asp Leu Lys Ile Thr
65 70 75 80

Ser Pro Thr Thr Glu Asp Thr Ala Thr Tyr Phe Cys Ala Arg Asp Gly
85 90 95

Asp Asp Ser Tyr Phe Asp Tyr Phe Asn Leu Trp Gly Gln Gly Thr Leu
100 105 110

Val Thr Val Ser Ser
115

<210> SEQ ID NO 194
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 194

Ala Ala Val Leu Thr Gln Thr Pro Ala Ser Val Ser Ala Ala Val Gly
1 5 10 15

Gly Thr Val Ser Ile Ser Cys Gln Ser Asn Glu Asn Ile Gly Ser Asn
20 25 30

Leu Ala Trp Tyr Gln Gln Lys Pro Gly Gln Pro Pro Lys Leu Leu Ile
35 40 45

Tyr Gly Ala Ser Thr Leu Thr Ser Gly Val Pro Ser Arg Phe Lys Gly
50 55 60

Ser Gly Ser Gly Thr Ala Phe Thr Leu Thr Ile Ser Gly Val Gln Cys
65 70 75 80

Asp Asp Ala Ala Thr Tyr Tyr Cys Leu Gly Gly Tyr Leu Ser Thr Ser
85 90 95

Asp Thr Thr Phe Gly Gly Gly Thr Ala Val Val Val Lys Gly
100 105 110

<210> SEQ ID NO 195
<211> LENGTH: 459
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 195

Met Glu Thr Gly Leu Arg Trp Leu Leu Leu Val Ala Val Leu Lys Gly
1 5 10 15

-continued

```
Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Ala Met Gly Trp Val Arg Gln Ala Pro Gly Lys Gly Leu Glu
    50                  55                  60

Tyr Ile Gly Ile Ile Tyr Gly Gly Ser Gly Thr Phe Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Asp Gly Asp Asp Ser Tyr Phe Asp Tyr Phe Asn Leu Trp Gly Gln
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Thr His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
        355                 360                 365

Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Ser Lys Leu Ser Val Pro Thr Ser Glu Trp Gln Arg Gly
            420                 425                 430

Asp Val Phe Thr Cys Ser Val Met His Glu Ala Leu His Asn His Tyr
```

```
        435                 440                 445

Thr Gln Lys Ser Ile Ser Arg Ser Pro Gly Lys
    450                 455


<210> SEQ ID NO 196
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ala Ser
            20                  25                  30

Val Ser Ala Ala Val Gly Gly Thr Val Ser Ile Ser Cys Gln Ser Asn
        35                  40                  45

Glu Asn Ile Gly Ser Asn Leu Ala Trp Tyr Gln Gln Lys Pro Gly Gln
    50                  55                  60

Pro Pro Lys Leu Leu Ile Tyr Gly Ala Ser Thr Leu Thr Ser Gly Val
65                  70                  75                  80

Pro Ser Arg Phe Lys Gly Ser Gly Ser Gly Thr Ala Phe Thr Leu Thr
                85                  90                  95

Ile Ser Gly Val Gln Cys Asp Asp Ala Ala Thr Tyr Tyr Cys Leu Gly
            100                 105                 110

Gly Tyr Leu Ser Thr Ser Asp Thr Thr Phe Gly Gly Gly Thr Ala Val
        115                 120                 125

Val Val Lys Gly Asp Pro Val Ala Pro Thr Val Leu Ile Phe Pro Pro
    130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
        195                 200                 205

Tyr Asn Ser His Lys Glu Tyr Thr Cys Lys Val Thr Gln Gly Thr Thr
    210                 215                 220

Ser Val Val Gln Ser Phe Asn Arg Gly Asp Cys
225                 230                 235


<210> SEQ ID NO 197
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197

cagtcggtgg aggagtccgg gggtcgcctg gtcacgcctg ggacacccct gacactcacc      60

tgcacagtct ctggattctc cctcagtagc tatggaatgg gctgggtccg ccaggctcca     120

gggaaggggc tggaatacat cggaatcatt agtagtagtg gtacatacta cgcgaactgg     180

gcgaaaggcc gattcaccat ctccagaacc tcgaccacgg tggatctgaa agtcgccagt     240
```

ccgacaaccg aggacacggc cacctatttc tgtgccagat attttgctgg tggtgcctat 300
gacatctggg gcccaggcac cctggtcacc gtctcctta 339

<210> SEQ ID NO 198
<211> LENGTH: 330
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 198
gctcaagtgc tgacccagac tccatcctcc gtgtctgcag ctgtgggagg cacagtcacc 60
atcaattgcc aggccagtca gagtgttgtt agtaacaact acctagcctg gtttcagcag 120
aaaccagggc agcctcccaa gctcctgatc tattttgcat ccactctggc atctggggtc 180
ccatcgcggt tcaaaggcag tggatctggg acacagttca ctctcaccat cagcgacctg 240
gagtgtgacg atgctgccac ttactactgt ctaggcgttt ataataatgt tgatactttc 300
ggcggaggga ccgaggtggt ggtcaaaggt 330

<210> SEQ ID NO 199
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 199
cagtcggtgg aggagtccgg gggtcgcctg gtcacgcctg ggacacccct gacactcacc 60
tgcacagcct ctggattctc cctcagtagg tactatatga gctgggtccg ccaggctcca 120
gggaaggggc tggaatggat cggaatgatt tatcctagta gtggcagtac atggtacgcg 180
agctgggtga aaggccgatt caccatctcc gcaaccgcga cctcggtgga tttgaaaatc 240
accagtccga caaccgagga cacggccacc tatttctgtg tcagagatcg ttaccctggt 300
tataatggtg attcatttaa tttgtggggc cagggcaccc tggtcaccgt ctcctca 357

<210> SEQ ID NO 200
<211> LENGTH: 342
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 200
gcccaagtgc tgacccagac tgcatcgccc gtgtctgcag ctgtgggaag cacagtcacc 60
atcaattgcc aggccagtca gagtgtttat aataacaact acttagcctg gtttcagcag 120
aaaccagggc agcctcccaa gcgcctgatc taccaggcat ccaaactggc aattggggtc 180
ccatcgcggt tcagtggcag tggatctgga acacagttca ctctcaccat cagcgacgtg 240
cagtgtgacg atgctgccac ttactactgt ctaggcagtt atggttgtaa tagtgttgat 300
tgtaatgttt tcggcggagg gaccgaggtg gtggtcaaag gt 342

<210> SEQ ID NO 201
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 201
cagtcgctgg aggagtccgg gggtcgcctg gtcacgcctg ggacactcct gacactcacc 60
tgcaccgtct ctggattctc cctcagtagc aatgcaatga gctgggtccg ccaggctcca 120
ggggaggggc tggagtggat cggaaccatt agtagtcgtg gtagcacata ctacgcgaac 180
tgggcgaaag gccgattcac catctccaaa acctcgacca cggtggatct gaaaatcacc 240
agtccgacaa ccgaggacac ggccacctat ttctgtgcca gaagtagtct tgctggttat 300
gagccttact attttaagtt gtggggccag ggcaccctgg tcaccgtctc ctca 354

<210> SEQ ID NO 202
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 202
gacgtcgtga tgacccagac tgcatccccc gtgtctgcag ctgtgggagg cacagtcacc 60
atcaagtgcc aggccagtga gagcattagt agctacttag cctggtatca gcagaaacca 120
gggcagcctc ccaagctcct gatctatggt gcatccgatc tggcatctgg ggtcccatcg 180
cggttcaaag gcagtggatc tgggacagag ttcactctca ccatcagtga cctggagtgt 240
gccgatgctg ccacttacta ctgtcaaagt tattatggtc ttagccgtaa tggttatggg 300
aatgttttcg gcggagggac cgaggtggtg gtcaaaggt 339

<210> SEQ ID NO 203
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203
cagcagcagc tggaggagtc cgggggaggc ctggtcaagc ctggaggaac cctgacactc 60
acctgcaaag cctctggaat cgacttcagt agctactact acatgtgctg ggtccgccag 120
gctccaggga aggggctgga gtggatcgcg tgcatttatg ttattgatga tactatttac 180
tgcgcgaact gggcgaaagg ccgattcacc atctccaaaa cctcgtcgac cacggtgact 240
ctgcaaatga ccagtctgac agccgcggac acggccacgt atttctgtgc gagagatgga 300
agtagtggta ttcgtgatta cttcgacttg tggggcccag gcaccctggt caccgtctcc 360
tca 363

<210> SEQ ID NO 204
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 204
gcctatgata tgacccagac tccagcctct gtggaggtag ctgtgggagg cacagtcacc 60
atcaagtgcc aggccagtga gagcgttagc acttggttag cctggtatca gcagaaacca 120
gggcagcctc ccaagctcct gatctataag gcatccgatc tggcatctgg ggtcccatcg 180
cggttcaaag gcagtggatc tgggacagag ttcactctca ccatcagcgg cgtggagtgt 240
gccgatgctg ccacttacta ctgtcaacag gggtatactt ataataatgt tgaaaatgtt 300
ttcggcggag ggaccgaggt ggtggtcaaa ggt 333

<210> SEQ ID NO 205
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
cagtcggtgg aggagtccgg aggaggcctg gtaacgcctg gaggaaccct gacactcacc 60
tgcacagtct ctggaatcga cctcagtagc aatgcaatga gctgggtccg ccaggctcca 120
ggggagggac tggaatggat cggaaccatt agtactgctg gtttcacata ttacgcgagc 180
tgggcgaaag gccgattcac catctccaaa acctcgacca cggtggatct gaaaatgacc 240
agtctgacag ccgcggacac ggccacctat ttctgtgcca gacttcttta tggtcctaac 300
atctggggcc caggcaccct ggtcaccgtc tcctta 336

<210> SEQ ID NO 206
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206
gaccctgtga tgacccagac tccagcctcc gtgtctgaac ctgtgggagg cacagtcacc 60
atcaagtgcc aggccagtcc gagcattagc aatgaattat cctggtatca gcagaaacca 120
gggcagcctc cccagctcct gatctatctg gcatctactc tggcatctgg ggtcccatcg 180
cggttcaaag gcagtagatc tgggacagag ttcactctca ccatcagcga cctggagtgt 240
gccgatgctg ccacttacta ctgtcaaggc attgtttatg gtcctgatta tgttgttggt 300
ttcggcggag ggaccgaggt ggtggtcaaa ggt 333

<210> SEQ ID NO 207
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
cagtcgttgg aggagtccgg gggagacctg gtcaagcctg gggcatccct gacactcacc 60
tgcaaagcct ctggattcga cctcagtagg ttctactaca tgtgctgggt ccgccaggct 120
ccagggaagg ggctggagtg gatcgcatgc atttatgctg gtcgtactgg taacacttac 180
tacgcgagct gggcgaaagg ccgattcacc atctccaaaa cctcgtcgac cacggtgact 240
ctgcaaatga ccagtctgac agccgcggac acggccacct atttctgtgc gagagccagt 300
ggtgattttc ttgcttatac ttatgctatg gacttgtggg gcccaggcac cctggtcacc 360
gtctcctca 369

<210> SEQ ID NO 208
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208
gccgccgtgc tgacccagac tccagcctcc gtgtctgcag ctgtgggagg cacagtcacc 60
atcagttgcc aggccagtca gagtgttgat aataacaact acttagcctg gtatcagcag 120
aaaccagggc agcctcccaa gctcctgatc tacgaagcat ccaagctggc atctggggtc 180
ccatcgcggt tcagtggcag tggatctggg acacagttca ctctcaccat cagcgacgtg 240
cagtgtgacg atgctaccac ttactactgt gcaggcggtt atagtagtag tgctgatgcg 300
aatgctttcg gcggagggac cgaggtggtg gtcaaaggt 339

<210> SEQ ID NO 209
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209
caggagcagc tggtggagtc cgggggaggc ctggtccagc ctgagggatc cctgacactc 60
acctgcaaag cctctggatt cgacttcagt agctactgga tgtgctgggt ccgccaggct 120
ccagggaaga ggcctgagtg gatcgcatgc atttatggtg gtgatggtac ttcatacttt 180
gcgggctggg cgaaaggccg cttcaccatc tccaaaacct cgtcgaccac ggtgactctg 240
caaatgacca gcctcacagc cgcggacacg gccacctatt tctgtgcgcg agccgattac 300
tacgtttatg ttgatggtgg ttatggtcat gcttatgact tgtggggccc aggcaccctg 360
gtcaccgtct cctca 375

<210> SEQ ID NO 210
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210
gacattgtga tgacccagac tccagcctcc gtggaggcag ctgtgggagg ctcagtcacc 60
atcaagtgcc aggccagtga cgacatttat agttacttgg cctggtatca gcagaaacca 120
gggcagcctc ccaagctcct gatctttgat gcatcctctc tgccatctgg ggtcccatcg 180
cgcttcaaag gcagtggatc tgggacacag ttcactctca ccatcagcgg cgtgcagtgt 240
gccgatgctg ccacttatta ctgtcaaaac tattatggta gtagtagtag tgttcatgct 300
ttcggcggag ggaccgaggt ggtggtcaaa ggt 333

<210> SEQ ID NO 211
<211> LENGTH: 351
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 211
cagtcggtgg aggagtccgg gggtcgcctg gtcacgcctg ggacacccct gacactcacc     60
tgcacagtct ctggattctc cctcagtacc tatgcaatgg gctgggtccg ccaggctcca    120
gggaaggggc tggagtacat cggaatcatt tatggtggta gtggtacatt ctacgcgagc    180
tgggcgaaag gccgattcac catctccaaa acctcgacca cggtggatct gaaaatcacc    240
agtccgacaa ccgaggacac ggccacctat ttctgtgcca gagatggtga tgatagttat    300
ttcgactact ttaacttgtg gggccaaggc accctggtca ccgtctcctc a             351

<210> SEQ ID NO 212
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
gccgccgtgc tgacccagac tccagcctcc gtgtctgcag ctgtgggagg cacagtcagc     60
atcagttgcc agtccaatga gaacattggt agtaatttag cctggtatca gcagaaacca    120
gggcagcctc ccaagctcct gatttatggt gcatccactc tgacatctgg ggtcccatcg    180
cggttcaaag gcagtgggtc tgggacagcg ttcactctca ccatcagcgg cgtgcagtgt    240
gacgatgctg ccacttacta ctgtctaggc ggttatttga gtactagtga tacgactttc    300
ggcggaggga ccgcggtggt ggtcaaaggt                                     330

<210> SEQ ID NO 213
<211> LENGTH: 1311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
cagtcggtgg aggagtccgg gggtcgcctg gtcacgcctg ggacacccct gacactcacc     60
tgcacagtct ctggattctc cctcagtagc tatggaatgg gctgggtccg ccaggctcca    120
gggaaggggc tggaatacat cggaatcatt agtagtagtg gtacatacta cgcgaactgg    180
gcgaaaggcc gattcaccat ctccagaacc tcgaccacgg tggatctgaa agtcgccagt    240
ccgacaaccg aggacacggc cacctatttc tgtgccagat attttgctgg tggtgcctat    300
gacatctggg gcccaggcac cctggtcacc gtctccttag ggcaacctaa ggctccatca    360
gtgttcccac tggccccctg ctgcggggac acacccagct ccacggtgac cctgggctgc    420
ctggtcaaag gctacctccc ggagccagtg accgtgacct ggaactcggg caccctcacc    480
aatggggtac gcaccttccc gtccgtccgg cagtcctcag gcctctactc gctgagcagc    540
gtggtgagcg tgacctcaag cagccagccc gtcacctgca acgtggccca cccagccacc    600
aacaccaaag tggacaagac cgttgcaccc tcgacatgca gcaagcccac gtgcccaccc    660
cctgaactcc tgggggggacc gtctgtgttc atcttccccc caaaacccaa ggacaccctc    720
atgatctcac gcacccccga ggtcacatgc gtggtggtgg acgtgagcca ggatgacccc    780
gaggtgcagt tcacatggta cataaacaac gagcaggtgc gcaccgcccg gccgccgcta    840

```
cgggagcagc agttcaacag cacgatccgc gtggtcagca ccctccccat cacgcaccag    900

gactggctga ggggcaagga gttcaagtgc aaagtccaca acaaggcact cccggccccc    960

atcgagaaaa ccatctccaa agccagaggg cagcccctgg agccgaaggt ctacaccatg   1020

ggccctcccc gggaggaact gagcagcagg tcggtcagcc tgacctgcat gatcaacggc   1080

ttctaccctt ccgacatctc ggtggagtgg gagaagaacg ggaaggcaga ggacaactac   1140

aagaccacgc cggccgtgct ggacagcgac ggctcctact tcctctacag caagctctca   1200

gtgcccacga gtgagtggca gcggggcgac gtgttcacct gctccgtgat gcacgaggcc   1260

ttgcacaacc actacacgca gaagtccatc tcccgctctc cgggtaaatg a            1311


<210> SEQ ID NO 214
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214

gctcaagtgc tgacccagac tccatcctcc gtgtctgcag ctgtgggagg cacagtcacc     60

atcaattgcc aggccagtca gagtgttgtt agtaacaact acctagcctg gtttcagcag    120

aaaccagggc agcctcccaa gctcctgatc tattttgcat ccactctggc atctggggtc    180

ccatcgcggt tcaaaggcag tggatctggg acacagttca ctctcaccat cagcgacctg    240

gagtgtgacg atgctgccac ttactactgt ctaggcgttt ataataatgt tgatactttc    300

ggcggaggga ccgaggtggt ggtcaaaggt gatccagttg cacctactgt cctcctcttc    360

ccaccagctg ctgatcaggt ggcaactgga acagtcacca tcgtgtgtgt ggcgaataaa    420

tactttcccg atgtcaccgt cacctgggag gtggatggca ccacccaaac aactggcatc    480

gagaacagta aaacaccgca gaattctgca gattgtacct acaacctcag cagcactctg    540

acactgacca gcacacagta caacagccac aaagagtaca cctgcaaggt gacccagggc    600

acgacctcag tcgtccagag cttcaacagg ggtgactgct ag                       642


<210> SEQ ID NO 215
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215

cagtcggtgg aggagtccgg gggtcgcctg gtcacgcctg ggacacccct gacactcacc     60

tgcacagcct ctggattctc cctcagtagg tactatatga gctgggtccg ccaggctcca    120

gggaaggggc tggaatggat cggaatgatt tatcctagta gtggcagtac atggtacgcg    180

agctgggtga aaggccgatt caccatctcc gcaaccgcga cctcggtgga tttgaaaatc    240

accagtccga caaccgagga cacggccacc tatttctgtg tcagagatcg ttaccctggt    300

tataatggtg attcatttaa tttgtggggc cagggcaccc tggtcaccgt ctcctcaggg    360

caacctaagg ctccatcagt gttcccactg gccccctgct gcggggacac acccagctcc    420

acggtgaccc tgggctgcct ggtcaaaggc tacctcccgg agccagtgac cgtgacctgg    480

aactcgggca ccctcaccaa tggggtacgc accttcccgt ccgtccggca gtcctcaggc    540

ctctactcgc tgagcagcgt ggtgagcgtg acctcaagca gccagcccgt cacctgcaac    600
```

```
gtggcccacc cagccaccaa caccaaagtg gacaagaccg ttgcaccctc gacatgcagc    660

aagcccacgt gcccaccccc tgaactcctg gggggaccgt ctgtgttcat cttcccccca    720

aaacccaagg acaccctcat gatctcacgc acccccgagg tcacatgcgt ggtggtggac    780

gtgagccagg atgaccccga ggtgcagttc acatggtaca taaacaacga gcaggtgcgc    840

accgcccggc cgccgctacg ggagcagcag ttcaacagca cgatccgcgt ggtcagcacc    900

ctccccatca cgcaccagga ctggctgagg ggcaaggagt tcaagtgcaa agtccacaac    960

aaggcactcc cggcccccat cgagaaaacc atctccaaag ccagagggca gcccctggag   1020

ccgaaggtct acaccatggg ccctccccgg gaggaactga gcagcaggtc ggtcagcctg   1080

acctgcatga tcaacggctt ctacccttcc gacatctcgg tggagtggga gaagaacggg   1140

aaggcagagg acaactacaa gaccacgccg gccgtgctgg acagcgacgg ctcctacttc   1200

ctctacagca agctctcagt gcccacgagt gagtggcagc ggggcgacgt gttcacctgc   1260

tccgtgatgc acgaggcctt gcacaaccac tacacgcaga agtccatctc ccgctctccg   1320

ggtaaatga                                                           1329
```

<210> SEQ ID NO 216
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 216

```
gcccaagtgc tgacccagac tgcatcgccc gtgtctgcag ctgtgggaag cacagtcacc     60

atcaattgcc aggccagtca gagtgtttat aataacaact acttagcctg gtttcagcag    120

aaaccagggc agcctcccaa gcgcctgatc taccaggcat ccaaactggc aattggggtc    180

ccatcgcggt tcagtggcag tggatctgga acacagttca ctctcaccat cagcgacgtg    240

cagtgtgacg atgctgccac ttactactgt ctaggcagtt atggttgtaa tagtgttgat    300

tgtaatgttt tcggcggagg gaccgaggtg gtggtcaaag gtgatccagt tgcacctact    360

gtcctcatct tcccaccagc tgctgatcag gtggcaactg gaacagtcac catcgtgtgt    420

gtggcgaata aatactttcc cgatgtcacc gtcacctggg aggtggatgg caccacccaa    480

acaactggca tcgagaacag taaaacaccg cagaattctg cagattgtac ctacaacctc    540

agcagcactc tgacactgac cagcacacag tacaacagcc acaaagagta cacctgcaag    600

gtgacccagg gcacgacctc agtcgtccag agcttcaaca ggggtgactg ctag          654
```

<210> SEQ ID NO 217
<211> LENGTH: 1326
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 217

```
cagtcgctgg aggagtccgg gggtcgcctg gtcacgcctg ggacactcct gacactcacc     60

tgcaccgtct ctggattctc cctcagtagc aatgcaatga gctgggtccg ccaggctcca    120

ggggaggggc tggagtggat cggaaccatt agtagtcgtg gtagcacata ctacgcgaac    180

tgggcgaaag gccgattcac catctccaaa acctcgacca cggtggatct gaaaatcacc    240
```

-continued

```
agtccgacaa ccgaggacac ggccacctat ttctgtgcca gaagtagtct tgctggttat    300

gagccttact attttaagtt gtggggccag ggcaccctgg tcaccgtctc ctcagggcaa    360

cctaaggctc catcagtgtt cccactggcc ccctgctgcg gggacacacc cagctccacg    420

gtgaccctgg gctgcctggt caaaggctac ctcccggagc cagtgaccgt gacctggaac    480

tcgggcaccc tcaccaatgg ggtacgcacc ttcccgtccg tccggcagtc ctcaggcctc    540

tactcgctga gcagcgtggt gagcgtgacc tcaagcagcc agcccgtcac ctgcaacgtg    600

gcccacccag ccaccaacac caaagtggac aagaccgttg caccctcgac atgcagcaag    660

cccacgtgcc cacccccctga actcctgggg ggaccgtctg tgttcatctt ccccccaaaa    720

cccaaggaca ccctcatgat ctcacgcacc cccgaggtca catgcgtggt ggtggacgtg    780

agccaggatg accccgaggt gcagttcaca tggtacataa acaacgagca ggtgcgcacc    840

gcccggccgc cgctacggga gcagcagttc aacagcacga tccgcgtggt cagcaccctc    900

cccatcacgc accaggactg gctgaggggc aaggagttca agtgcaaagt ccacaacaag    960

gcactcccgg cccccatcga gaaaaccatc tccaaagcca gagggcagcc cctggagccg   1020

aaggtctaca ccatgggccc tccccgggag gaactgagca gcaggtcggt cagcctgacc   1080

tgcatgatca acggcttcta cccttccgac atctcggtgg agtgggagaa gaacgggaag   1140

gcagaggaca actacaagac cacgccggcc gtgctggaca gcgacggctc ctacttcctc   1200

tacagcaagc tctcagtgcc cacgagtgag tggcagcggg gcgacgtgtt cacctgctcc   1260

gtgatgcacg aggccttgca caaccactac acgcagaagt ccatctcccg ctctccgggt   1320

aaatga                                                               1326
```

<210> SEQ ID NO 218
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 218

```
gacgtcgtga tgacccagac tgcatccccc gtgtctgcag ctgtgggagg cacagtcacc     60

atcaagtgcc aggccagtga gagcattagt agctacttag cctggtatca gcagaaacca    120

gggcagcctc ccaagctcct gatctatggt gcatccgatc tggcatctgg ggtcccatcg    180

cggttcaaag gcagtggatc tgggacagag ttcactctca ccatcagtga cctggagtgt    240

gccgatgctg ccacttacta ctgtcaaagt tattatggtc ttagccgtaa tggttatggg    300

aatgttttcg gcggagggac cgaggtggtg gtcaaaggtg atccagttgc acctactgtc    360

ctcatcttcc caccagctgc tgatcaggtg gcaactggaa cagtcaccat cgtgtgtgtg    420

gcgaataaat actttcccga tgtcaccgtc acctgggagg tggatggcac cacccaaaca    480

actggcatcg agaacagtaa aacaccgcag aattctgcag attgtaccta caacctcagc    540

agcactctga cactgaccag cacacagtac aacagccaca aagagtacac ctgcaaggtg    600

acccagggca cgacctcagt cgtccagagc ttcaacaggg gtgactgcta g             651
```

<210> SEQ ID NO 219
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 219
cagcagcagc tggaggagtc cgggggaggc ctggtcaagc ctggaggaac cctgacactc 60
acctgcaaag cctctggaat cgacttcagt agctactact acatgtgctg ggtccgccag 120
gctccaggga aggggctgga gtggatcgcg tgcatttatg ttattgatga tactatttac 180
tgcgcgaact gggcgaaagg ccgattcacc atctccaaaa cctcgtcgac cacggtgact 240
ctgcaaatga ccagtctgac agccgcggac acggccacgt atttctgtgc gagagatgga 300
agtagtggta ttcgtgatta cttcgacttg tggggcccag gcaccctggt caccgtctcc 360
tcagggcaac ctaaggctcc atcagtgttc ccactggccc cctgctgcgg ggacacaccc 420
agctccacgg tgaccctggg ctgcctggtc aaaggctacc tcccggagcc agtgaccgtg 480
acctggaact cgggcaccct caccaatggg gtacgcacct tcccgtccgt ccggcagtcc 540
tcaggcctct actcgctgag cagcgtggtg agcgtgacct caagcagcca gcccgtcacc 600
tgcaacgtgg cccacccagc caccaacacc aaagtggaca agaccgttgc accctcgaca 660
tgcagcaagc ccacgtgccc accccctgaa ctcctggggg gaccgtctgt gttcatcttc 720
cccccaaaac ccaaggacac cctcatgatc tcacgcaccc ccgaggtcac atgcgtggtg 780
gtggacgtga gccaggatga ccccgaggtg cagttcacat ggtacataaa caacgagcag 840
gtgcgcaccg cccggccgcc gctacgggag cagcagttca acagcacgat ccgcgtggtc 900
agcaccctcc ccatcacgca ccaggactgg ctgaggggca aggagttcaa gtgcaaagtc 960
cacaacaagg cactcccggc ccccatcgag aaaaccatct ccaaagccag agggcagccc 1020
ctggagccga aggtctacac catgggccct ccccgggagg aactgagcag caggtcggtc 1080
agcctgacct gcatgatcaa cggcttctac ccttccgaca tctcggtgga gtgggagaag 1140
aacgggaagg cagaggacaa ctacaagacc acgccggccg tgctggacag cgacggctcc 1200
tacttcctct acagcaagct ctcagtgccc acgagtgagt ggcagcgggg cgacgtgttc 1260
acctgctccg tgatgcacga ggccttgcac aaccactaca cgcagaagtc catctcccgc 1320
tctccgggta aatga 1335

<210> SEQ ID NO 220
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 220
gcctatgata tgacccagac tccagcctct gtggaggtag ctgtgggagg cacagtcacc 60
atcaagtgcc aggccagtga gagcgttagc acttggttag cctggtatca gcagaaacca 120
gggcagcctc ccaagctcct gatctataag gcatccgatc tggcatctgg ggtcccatcg 180
cggttcaaag gcagtggatc tgggacagag ttcactctca ccatcagcgg cgtggagtgt 240
gccgatgctg ccacttacta ctgtcaacag ggtatactt ataataatgt tgaaaatgtt 300
ttcggcggag ggaccgaggt ggtggtcaaa ggtgatccag ttgcacctac tgtcctcatc 360
ttcccaccag ctgctgatca ggtggcaact ggaacagtca ccatcgtgtg tgtggcgaat 420
aaatactttc ccgatgtcac cgtcacctgg gaggtggatg gcaccaccca aacaactggc 480
atcgagaaca gtaaaacacc gcagaattct gcagattgta cctacaacct cagcagcact 540
ctgacactga ccagcacaca gtacaacagc cacaaagagt acacctgcaa ggtgacccag 600
ggcacgacct cagtcgtcca gagcttcaac aggggtgact gctag 645

<210> SEQ ID NO 221
<211> LENGTH: 1308
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 221
cagtcggtgg aggagtccgg aggaggcctg gtaacgcctg gaggaaccct gacactcacc 60
tgcacagtct ctggaatcga cctcagtagc aatgcaatga gctgggtccg ccaggctcca 120
ggggagggac tggaatggat cggaaccatt agtactgctg gtttcacata ttacgcgagc 180
tgggcgaaag gccgattcac catctccaaa acctcgacca cggtggatct gaaaatgacc 240
agtctgacag ccgcggacac ggccacctat ttctgtgcca gacttcttta tggtcctaac 300
atctggggcc caggcaccct ggtcaccgtc tccttagggc aacctaaggc tccatcagtg 360
ttcccactgg ccccctgctg cggggacaca cccagctcca cggtgaccct gggctgcctg 420
gtcaaaggct acctcccgga gccagtgacc gtgacctgga actcgggcac cctcaccaat 480
ggggtacgca ccttcccgtc cgtccggcag tcctcaggcc tctactcgct gagcagcgtg 540
gtgagcgtga cctcaagcag ccagcccgtc acctgcaacg tggcccaccc agccaccaac 600
accaaagtgg acaagaccgt tgcaccctcg acatgcagca agcccacgtg cccaccccct 660
gaactcctgg ggggaccgtc tgtgttcatc ttccccccaa aacccaagga caccctcatg 720
atctcacgca cccccgaggt cacatgcgtg gtggtggacg tgagccagga tgaccccgag 780
gtgcagttca catggtacat aaacaacgag caggtgcgca ccgcccggcc gccgctacgg 840
gagcagcagt tcaacagcac gatccgcgtg gtcagcaccc tccccatcac gcaccaggac 900
tggctgaggg gcaaggagtt caagtgcaaa gtccacaaca aggcactccc ggcccccatc 960
gagaaaacca tctccaaagc cagagggcag cccctggagc cgaaggtcta caccatgggc 1020
cctccccggg aggaactgag cagcaggtcg gtcagcctga cctgcatgat caacggcttc 1080
tacccttccg acatctcggt ggagtgggag aagaacggga aggcagagga caactacaag 1140
accacgccgg ccgtgctgga cagcgacggc tcctacttcc tctacagcaa gctctcagtg 1200
cccacgagtg agtggcagcg gggcgacgtg ttcacctgct ccgtgatgca cgaggccttg 1260
cacaaccact acacgcagaa gtccatctcc cgctctccgg gtaaatga 1308

<210> SEQ ID NO 222
<211> LENGTH: 645
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 222
gaccctgtga tgacccagac tccagcctcc gtgtctgaac ctgtgggagg cacagtcacc 60
atcaagtgcc aggccagtcc gagcattagc aatgaattat cctggtatca gcagaaacca 120
gggcagcctc cccagctcct gatctatctg gcatctactc tggcatctgg ggtcccatcg 180
cggttcaaag gcagtagatc tgggacagag ttcactctca ccatcagcga cctggagtgt 240
gccgatgctg ccacttacta ctgtcaaggc attgtttatg gtcctgatta tgttgttggt 300

-continued

```
ttcggcggag ggaccgaggt ggtggtcaaa ggtgatccag ttgcacctac tgtcctcatc    360

ttcccaccag ctgctgatca ggtggcaact ggaacagtca ccatcgtgtg tgtggcgaat    420

aaatactttc ccgatgtcac cgtcacctgg gaggtggatg gcaccaccca aacaactggc    480

atcgagaaca gtaaaacacc gcagaattct gcagattgta cctacaacct cagcagcact    540

ctgacactga ccagcacaca gtacaacagc cacaaagagt acacctgcaa ggtgacccag    600

ggcacgacct cagtcgtcca gagcttcaac aggggtgact gctag                    645
```

<210> SEQ ID NO 223
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 223

```
cagtcgttgg aggagtccgg gggagacctg gtcaagcctg ggcatccct gacactcacc      60

tgcaaagcct ctggattcga cctcagtagg ttctactaca tgtgctgggt ccgccaggct    120

ccagggaagg ggctggagtg gatcgcatgc atttatgctg gtcgtactgg taacacttac    180

tacgcgagct gggcgaaagg ccgattcacc atctccaaaa cctcgtcgac cacggtgact    240

ctgcaaatga ccagtctgac agccgcggac acggccacct atttctgtgc gagagccagt    300

ggtgattttc ttgcttatac ttatgctatg gacttgtggg gcccaggcac cctggtcacc    360

gtctcctcag ggcaacctaa ggctccatca gtgttcccac tggcccccctg ctgcggggac    420

acacccagct ccacggtgac cctgggctgc ctggtcaaag gctacctccc ggagccagtg    480

accgtgacct ggaactcggg caccctcacc aatggggtac gcaccttccc gtccgtccgg    540

cagtcctcag gcctctactc gctgagcagc gtggtgagcg tgacctcaag cagccagccc    600

gtcacctgca acgtggccca cccagccacc aacaccaaag tggacaagac cgttgcaccc    660

tcgacatgca gcaagcccac gtgcccaccc cctgaactcc tgggggggacc gtctgtgttc    720

atcttccccc caaaacccaa ggacaccctc atgatctcac gcacccccga ggtcacatgc    780

gtggtggtgg acgtgagcca ggatgacccc gaggtgcagt tcacatggta cataaacaac    840

gagcaggtgc gcaccgcccg gccgccgcta cgggagcagc agttcaacag cacgatccgc    900

gtggtcagca ccctccccat cacgcaccag gactggctga ggggcaagga gttcaagtgc    960

aaagtccaca acaaggcact cccggccccc atcgagaaaa ccatctccaa agccagaggg   1020

cagcccctgg agccgaaggt ctacaccatg ggccctcccc gggaggaact gagcagcagg   1080

tcggtcagcc tgacctgcat gatcaacggc ttctaccctt ccgacatctc ggtggagtgg   1140

gagaagaacg ggaaggcaga ggacaactac aagaccacgc cggccgtgct ggacagcgac   1200

ggctcctact tcctctacag caagctctca gtgcccacga gtgagtggca gcggggcgac   1260

gtgttcacct gctccgtgat gcacgaggcc ttgcacaacc actacacgca gaagtccatc   1320

tcccgctctc cgggtaaatg a                                              1341
```

<210> SEQ ID NO 224
<211> LENGTH: 651
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 224

```
gccgccgtgc tgacccagac tccagcctcc gtgtctgcag ctgtgggagg cacagtcacc     60

atcagttgcc aggccagtca gagtgttgat aataacaact acttagcctg gtatcagcag    120

aaaccagggc agcctcccaa gctcctgatc tacgaagcat ccaagctggc atctggggtc    180

ccatcgcggt tcagtggcag tggatctggg acacagttca ctctcaccat cagcgacgtg    240

cagtgtgacg atgctaccac ttactactgt gcaggcggtt atagtagtag tgctgatgcg    300

aatgctttcg gcggagggac cgaggtggtg gtcaaaggtg atccagttgc acctactgtc    360

ctcatcttcc caccagctgc tgatcaggtg gcaactggaa cagtcaccat cgtgtgtgtg    420

gcgaataaat actttcccga tgtcaccgtc acctgggagg tggatggcac cacccaaaca    480

actggcatcg agaacagtaa aacaccgcag aattctgcag attgtaccta caacctcagc    540

agcactctga cactgaccag cacacagtac aacagccaca aagagtacac ctgcaaggtg    600

acccagggca cgacctcagt cgtccagagc ttcaacaggg gtgactgcta g             651
```

<210> SEQ ID NO 225
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 225

```
caggagcagc tggtggagtc cgggggaggc ctggtccagc ctgagggatc cctgacactc     60

acctgcaaag cctctggatt cgacttcagt agctactgga tgtgctgggt ccgccaggct    120

ccagggaaga ggcctgagtg gatcgcatgc atttatggtg gtgatggtac ttcatacttt    180

gcgggctggg cgaaaggccg cttcaccatc tccaaaacct cgtcgaccac ggtgactctg    240

caaatgacca gcctcacagc cgcggacacg gccacctatt tctgtgcgcg agccgattac    300

tacgtttatg ttgatggtgg ttatggtcat gcttatgact tgtggggccc aggcaccctg    360

gtcaccgtct cctcagggca acctaaggct ccatcagtgt tcccactggc cccctgctgc    420

ggggacacac ccagctccac ggtgaccctg ggctgcctgg tcaaaggcta cctcccggag    480

ccagtgaccg tgacctggaa ctcgggcacc ctcaccaatg ggtacgcac cttcccgtcc     540

gtccggcagt cctcaggcct ctactcgctg agcagcgtgg tgagcgtgac ctcaagcagc    600

cagcccgtca cctgcaacgt ggcccaccca gccaccaaca ccaaagtgga caagaccgtt    660

gcaccctcga catgcagcaa gcccacgtgc ccaccccctg aactcctggg gggaccgtct    720

gtgttcatct tcccccaaa acccaaggac accctcatga tctcacgcac ccccgaggtc     780

acatgcgtgg tggtggacgt gagccaggat gaccccgagg tgcagttcac atggtacata    840

aacaacgagc aggtgcgcac cgcccggccg ccgctacggg agcagcagtt caacagcacg    900

atccgcgtgg tcagcaccct ccccatcacg caccaggact ggctgagggg caaggagttc    960

aagtgcaaag tccacaacaa ggcactcccg gccccatcg agaaaaccat ctccaaagcc    1020

agagggcagc ccctggagcc gaaggtctac accatgggcc ctccccggga ggaactgagc   1080

agcaggtcgg tcagcctgac ctgcatgatc aacggcttct acccttccga catctcggtg   1140

gagtgggaga agaacgggaa ggcagaggac aactacaaga ccacgccggc cgtgctggac   1200

agcgacggct cctacttcct ctacagcaag ctctcagtgc ccacgagtga gtggcagcgg   1260

ggcgacgtgt tcacctgctc cgtgatgcac gaggccttgc acaaccacta cacgcagaag   1320

tccatctccc gctctccggg taaatga                                       1347
```

<210> SEQ ID NO 226
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 226
gacattgtga tgacccagac tccagcctcc gtggaggcag ctgtgggagg ctcagtcacc 60
atcaagtgcc aggccagtga cgacatttat agttacttgg cctggtatca gcagaaacca 120
gggcagcctc ccaagctcct gatctttgat gcatcctctc tgccatctgg ggtcccatcg 180
cgcttcaaag gcagtggatc tgggacacag ttcactctca ccatcagcgg cgtgcagtgt 240
gccgatgctg ccacttatta ctgtcaaaac tattatggta gtagtagtag tgttcatgct 300
ttcggcggag ggaccgaggt ggtggtcaaa ggtgatccag ttgcacctac tgtcctcatc 360
ttcccaccag ctgctgatca ggtggcaact ggaacagtca ccatcgtgtg tgtggcgaat 420
aaatactttc ccgatgtcac cgtcacctgg gaggtggatg gcaccaccca aacaactggc 480
atcgagaaca gtaaaacacc gcagaattct gcagattgta cctacaacct cagcagcact 540
ctgacactga ccagcacaca gtacaacagc cacaaagagt acacctgcaa ggtgacccag 600
ggcacgacct cagtcgtcca gagcttcaac aggggtgact gctag 645

<210> SEQ ID NO 227
<211> LENGTH: 1323
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 227
cagtcggtgg aggagtccgg gggtcgcctg gtcacgcctg ggacacccct gacactcacc 60
tgcacagtct ctggattctc cctcagtacc tatgcaatgg gctgggtccg ccaggctcca 120
gggaaggggc tggagtacat cggaatcatt tatggtggta gtggtacatt ctacgcgagc 180
tgggcgaaag gccgattcac catctccaaa acctcgacca cggtggatct gaaaatcacc 240
agtccgacaa ccgaggacac ggccacctat ttctgtgcca gagatggtga tgatagttat 300
ttcgactact ttaacttgtg gggccaaggc accctggtca ccgtctcctc agggcaacct 360
aaggctccat cagtgttccc actggccccc tgctgcgggg acacacccag ctccacggtg 420
accctgggct gcctggtcaa aggctacctc ccggagccag tgaccgtgac ctggaactcg 480
ggcaccctca ccaatggggt acgcaccttc ccgtccgtcc ggcagtcctc aggcctctac 540
tcgctgagca gcgtggtgag cgtgacctca agcagccagc ccgtcacctg caacgtggcc 600
cacccagcca ccaacaccaa agtggacaag accgttgcac cctcgacatg cagcaagccc 660
acgtgcccac cccctgaact cctgggggga ccgtctgtgt tcatcttccc cccaaaaccc 720
aaggacaccc tcatgatctc acgcaccccc gaggtcacat gcgtggtggt ggacgtgagc 780
caggatgacc ccgaggtgca gttcacatgg tacataaaca acgagcaggt gcgcaccgcc 840
cggccgccgc tacgggagca gcagttcaac agcacgatcc gcgtggtcag caccctcccc 900
atcacgcacc aggactggct gaggggcaag gagttcaagt gcaaagtcca caacaaggca 960
ctcccggccc ccatcgagaa aaccatctcc aaagccagag ggcagcccct ggagccgaag 1020
gtctacacca tgggccctcc ccgggaggaa ctgagcagca ggtcggtcag cctgacctgc 1080
atgatcaacg gcttctaccc ttccgacatc tcggtggagt gggagaagaa cgggaaggca 1140
gaggacaact acaagaccac gccggccgtg ctggacagcg acggctccta cttcctctac 1200
agcaagctct cagtgcccac gagtgagtgg cagcggggcg acgtgttcac ctgctccgtg 1260
atgcacgagg ccttgcacaa ccactacacg cagaagtcca tctcccgctc tccgggtaaa 1320
tga 1323

<210> SEQ ID NO 228
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 228
gccgccgtgc tgacccagac tccagcctcc gtgtctgcag ctgtgggagg cacagtcagc 60
atcagttgcc agtccaatga gaacattggt agtaatttag cctggtatca gcagaaacca 120
gggcagcctc ccaagctcct gatttatggt gcatccactc tgacatctgg ggtcccatcg 180
cggttcaaag gcagtgggtc tgggacagcg ttcactctca ccatcagcgg cgtgcagtgt 240
gacgatgctg ccacttacta ctgtctaggc ggttatttga gtactagtga tacgactttc 300
ggcggaggga ccgcggtggt ggtcaaaggt gatccagttg cacctactgt cctcatcttc 360
ccaccagctg ctgatcaggt ggcaactgga acagtcacca tcgtgtgtgt ggcgaataaa 420
tactttcccg atgtcaccgt cacctgggag gtggatggca ccacccaaac aactggcatc 480
gagaacagta aaacaccgca gaattctgca gattgtacct acaacctcag cagcactctg 540
acactgacca gcacacagta caacagccac aaagagtaca cctgcaaggt gacccagggc 600
acgacctcag tcgtccagag cttcaacagg ggtgactgct ag 642

<210> SEQ ID NO 229
<211> LENGTH: 972
<212> TYPE: DNA
<213> ORGANISM: Oryctolagus cuniculus

<400> SEQUENCE: 229
gggcaaccta aggctccatc agtgttccca ctggcccccct gctgcgggga cacacccagc 60
tccacggtga ccctgggctg cctggtcaaa ggctacctcc cggagccagt gaccgtgacc 120
tggaactcgg gcaccctcac caatggggta cgcaccttcc cgtccgtccg gcagtcctca 180
ggcctctact cgctgagcag cgtggtgagc gtgacctcaa gcagccagcc cgtcacctgc 240
aacgtggccc acccagccac caacaccaaa gtggacaaga ccgttgcacc ctcgacatgc 300
agcaagccca cgtgcccacc ccctgaactc ctgggggggac cgtctgtgtt catcttcccc 360
ccaaaaccca aggacaccct catgatctca cgcacccccg aggtcacatg cgtggtggtg 420
gacgtgagcc aggatgaccc cgaggtgcag ttcacatggt acataaacaa cgagcaggtg 480
cgcaccgccc ggccgccgct acgggagcag cagttcaaca gcacgatccg cgtggtcagc 540
accctcccca tcacgcacca ggactggctg aggggcaagg agttcaagtg caaagtccac 600
aacaaggcac tcccggcccc catcgagaaa accatctcca aagccagagg gcagcccctg 660
gagccgaagg tctacaccat gggccctccc cgggaggaac tgagcagcag gtcggtcagc 720
ctgacctgca tgatcaacgg cttctaccct tccgacatct cggtggagtg ggagaagaac 780

-continued

```
gggaaggcag aggacaacta caagaccacg ccggccgtgc tggacagcga cggctcctac    840

ttcctctaca gcaagctctc agtgcccacg agtgagtggc agcggggcga cgtgttcacc    900

tgctccgtga tgcacgaggc cttgcacaac cactacacgc agaagtccat ctcccgctct    960

ccgggtaaat ga                                                        972


<210> SEQ ID NO 230
<211> LENGTH: 312
<212> TYPE: DNA
<213> ORGANISM: Oryctolagus cuniculus

<400> SEQUENCE: 230

gatccagttg cacctactgt cctcatcttc ccaccagctg ctgatcaggt ggcaactgga     60

acagtcacca tcgtgtgtgt ggcgaataaa tactttcccg atgtcaccgt cacctgggag    120

gtggatggca ccacccaaac aactggcatc gagaacagta aaacaccgca gaattctgca    180

gattgtacct acaacctcag cagcactctg acactgacca gcacacagta caacagccac    240

aaagagtaca cctgcaaggt gacccagggc acgacctcag tcgtccagag cttcaacagg    300

ggtgactgct ag                                                        312


<210> SEQ ID NO 231
<211> LENGTH: 13
<212> TYPE: PRT
<213> ORGANISM: Homo sapiens

<400> SEQUENCE: 231

Gly Ala Tyr Pro Leu Ser Ile Glu Pro Ile Gly Val Arg
1               5                   10


<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: (13C5,15N)Val

<400> SEQUENCE: 232

Gly Ala Tyr Pro Leu Ser Ile Glu Pro Ile Gly Val Arg
1               5                   10
```

ANTI-CERULOPLASMIN ANTIBODIES AND USES THEREOF

RELATED APPLICATIONS

This application is the U.S. National Phase Application of PCT/US2021/049890, filed on Sep. 10, 2021, and claims priority to U.S. provisional patent application Ser. No. 63/077,155, filed Sep. 11, 2020, the content of which is hereby incorporated by reference.

SEQUENCE LISTING

The instant application contains a Sequence Listing which has been submitted electronically in ASCII format and is hereby incorporated by reference in its entirety. Said ASCII copy, created on Sep. 3, 2021, is named 0621WO_SL.txt and is 180,926 bytes in size.

BACKGROUND

Copper is an essential element, but detrimental to the body when present in excess amounts. A majority of copper (>90%) is transported in the body by ceruloplasmin ("CP"), a copper containing plasma ferroxidase which plays an essential role in mammalian iron homeostasis. Disruption of copper homeostasis is associated with a number of diseases and disorders (copper-metabolism-associated diseases and disorders), including Wilson disease, which is caused by genetic mutations in the Cu-loading enzyme ATP7B in humans. The defect in this enzyme leads to the accumulation of copper in tissues which exceeds the capacity of ceruloplasmin, giving rise to free non-ceruloplasmin bound copper circulating in the blood and accumulating in tissues and organs. Circulating non-ceruloplasmin bound copper ("NCC") may loosely bind with plasma proteins to form complexes ("labile-bound copper" or "LBC"). The fraction of circulating total copper which is not bound to ceruloplasmin comprises "free copper," which may contribute to, and be indicative of, copper toxicities observed in Wilson disease.

Measurement of free copper levels can be used for diagnosing, managing, and treating patients with copper metabolism-associated disorders, such as Wilson disease. However, many currently available methods estimate, but do not directly measure, free copper concentrations. For example, in many currently available free copper measurement methods, only total blood copper and ceruloplasmin levels are measured directly, and these levels are then inputted into a formula to estimate free copper levels. This estimation method has drawbacks because it assumes that free copper and ceruloplasmin levels are directly correlated, and that ceruloplasmin is always bound by six copper atoms. In reality, the number of copper atoms associated with ceruloplasmin is highly heterogeneous.

As a result, the estimation method for determining NCC concentration is often problematic, such as in clinical settings. For instance, the estimation method can yield physiologically impossible negative NCC concentrations, which have been reported in up to 20-50% of Wilson disease patients evaluated with the method.

Accordingly, there remains an unmet need for efficient, accurate, and direct methods for measuring concentrations of free copper in biological samples from patients with copper metabolism-associated diseases and disorders.

SUMMARY

Provided herein are anti-ceruloplasmin antibodies (e.g., monoclonal anti-ceruloplasmin antibodies), and mixtures thereof (e.g., antibody compositions, antibody mixtures, or antibody cocktails), which are highly efficient in immunocapturing ceruloplasmin (e.g., human ceruloplasmin) from biological samples, such as human plasma and serum samples. These antibodies and antibody mixtures are useful, e.g., for immunodepleting ceruloplasmin from the biological samples, thus enabling direct measurement of free copper (i.e., NCC or LBC) more accurately than conventional estimation methods. This, in turn, may allow for more accurate diagnosis, selection, and treatment of patients with copper metabolism-associated diseases or disorders (e.g., Wilson disease).

Accordingly, in one aspect, provided herein are antibodies which bind to human ceruloplasmin (SEQ ID NO: 1) and comprises heavy chain variable region CDR1, CDR2, and CDR3 sequences and light chain variable region CDR1, CDR2, and CDR3 sequences of the heavy and light chain variable region pairs selected from the group consisting of (a) SEQ ID NOs: 25 and 26, respectively,
(b) SEQ ID NOs: 49 and 50, respectively,
(c) SEQ ID NOs: 73 and 74, respectively,
(d) SEQ ID NOs: 97 and 98, respectively,
(e) SEQ ID NOs: 121 and 122, respectively,
(f) SEQ ID NOs: 145 and 146, respectively,
(g) SEQ ID NOs: 169 and 170, respectively, and
(h) SEQ ID NOs: 193 and 194, respectively.

In another aspect, provided herein are antibodies which bind to human ceruloplasmin (SEQ ID NO: 1), comprising:

(a) heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively;

(b) heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively;

(c) heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively, (d) heavy chain variable region CDR1, CDR2, and CDR3 sequences comprising the amino acid sequences set forth in SEQ ID NOs: 77, 78, and 79, respectively, and light chain variable region CDR1, CDR2, and CDR3 sequences comprising the amino acid sequences set forth in SEQ ID NOs: 80, 81, and 82, respectively;

(e) heavy chain variable region CDR1, CDR2, and CDR3 sequences comprising the amino acid sequences set forth in SEQ ID NOs: 101, 102, and 103, respectively, and light chain variable region CDR1, CDR2, and CDR3 sequences comprising the amino acid sequences set forth in SEQ ID NOs: 104, 105, and 106, respectively;

(f) heavy chain variable region CDR1, CDR2, and CDR3 sequences comprising the amino acid sequences set forth in SEQ ID NOs: 125, 126, and 127, respectively, and light chain variable region CDR1, CDR2, and CDR3 sequences comprising the amino acid sequences set forth in SEQ ID NOs: 128, 129, and 130, respectively;

(g) heavy chain variable region CDR1, CDR2, and CDR3 sequences comprising the amino acid sequences set forth in SEQ ID NOs: 149, 150, and 151, respectively, and light chain variable region CDR1, CDR2, and CDR3 sequences comprising the amino acid sequences set forth in SEQ ID NOs: 152, 153, and 154, respectively; or (h) heavy chain variable region CDR1, CDR2, and CDR3 sequences comprising the amino acid sequences set forth in SEQ ID NOs: 173, 174, and 175, respectively, and light chain variable region CDR1, CDR2, and CDR3 sequences comprising the amino acid sequences set forth in SEQ ID NOs: 176, 177, and 178, respectively.

In another aspect, provided herein are antibodies which bind to human ceruloplasmin (SEQ ID NO: 1) and comprise heavy and light chain variable regions, wherein the heavy chain variable region comprises an amino acid sequence which is at least 90% identical to the amino acid sequence selected from the group consisting of SEQ ID NOs: 25, 49, 73, 97, 121, 145, 169, and 193 and/or the light chain variable region comprises an amino acid sequence which is at least 90% identical to the amino acid sequence selected from the group consisting of SEQ ID NOs: 26, 50, 74, 98, 122, 146, 170, and 194.

In another aspect, provided herein are antibodies which bind to human ceruloplasmin (SEQ ID NO: 1) and comprise heavy and light chain variable regions comprising amino acid sequences which are at least 85% identical, such as at least 90%, 95%, 96%, 97%, 98%, 99%, or 99.5% identical, to the amino acid sequences selected from the group consisting of:

(a) SEQ ID NOs: 25 and 26, respectively,
(b) SEQ ID NOs: 49 and 50, respectively,
(c) SEQ ID NOs: 73 and 74, respectively,
(d) SEQ ID NOs: 97 and 98, respectively,
(e) SEQ ID NOs: 121 and 122, respectively,
(f) SEQ ID NOs: 145 and 146, respectively,
(g) SEQ ID NOs: 169 and 170, respectively, and
(h) SEQ ID NOs: 193 and 194, respectively.

In another aspect, provided herein are antibodies which bind to human ceruloplasmin (SEQ ID NO: 1) and comprise heavy and light chain variable regions comprising the amino acid sequences selected from the group consisting of:

(a) SEQ ID NOs: 25 and 26, respectively,
(b) SEQ ID NOs: 49 and 50, respectively,
(c) SEQ ID NOs: 73 and 74, respectively,
(d) SEQ ID NOs: 97 and 98, respectively,
(e) SEQ ID NOs: 121 and 122, respectively,
(f) SEQ ID NOs: 145 and 146, respectively,
(g) SEQ ID NOs: 169 and 170, respectively, and
(h) SEQ ID NOs: 193 and 194, respectively.

In another aspect, provided herein are antibodies which bind to human ceruloplasmin (SEQ ID NO: 1) and comprise heavy and light chains comprising amino acid sequences which are at least 80% identical, such as at least 85%, 90%, 95%, 96%, 97%, 98%, 99%, or 99.5% identical, to the amino acid sequences selected from the group consisting of:

(a) SEQ ID NOs: 27 and 28, respectively,
(b) SEQ ID NOs: 51 and 52, respectively,
(c) SEQ ID NOs: 75 and 76, respectively,
(d) SEQ ID NOs: 99 and 100, respectively,
(e) SEQ ID NOs: 123 and 124, respectively,
(f) SEQ ID NOs: 147 and 148, respectively,
(g) SEQ ID NOs: 171 and 172, respectively, and
(h) SEQ ID NOs: 195 and 196, respectively.

In another aspect, provided herein are antibodies which bind to human ceruloplasmin (SEQ ID NO: 1) and comprise heavy and light chains comprising the amino acid sequences selected from the group consisting of:

(a) SEQ ID NOs: 27 and 28, respectively,
(b) SEQ ID NOs: 51 and 52, respectively,
(c) SEQ ID NOs: 75 and 76, respectively
(d) SEQ ID NOs: 99 and 100, respectively,
(e) SEQ ID NOs: 123 and 124, respectively,
(f) SEQ ID NOs: 147 and 148, respectively,
(g) SEQ ID NOs: 171 and 172, respectively, and
(h) SEQ ID NOs: 195 and 196, respectively.

In another aspect, provided herein are antibodies which bind to human ceruloplasmin (SEQ ID NO: 1) and compete for binding to ceruloplasmin with an anti-ceruloplasmin antibody described herein.

In another aspect, provided herein are antibodies which bind to human ceruloplasmin (SEQ ID NO: 1) and bind to the same epitope on human ceruloplasmin as an anti-ceruloplasmin antibody described herein.

In some embodiments, the antibody is a monoclonal antibody. In some embodiments, the antibody is an IgG1, IgG2, IgG3, or IgG4 antibody, or a variant thereof. In some embodiments, the antibody is a rabbit antibody (e.g., a rabbit IgG antibody). In some embodiments, the antibody binds to ceruloplasmin in a biological sample (e.g., human plasma or serum sample). In some embodiments, the biological sample is human plasma with lithium heparin. In some embodiments, the antibody binds to purified human ceruloplasmin.

In another aspect, provided herein are immunoconjugates comprising the anti-ceruloplasmin antibody described herein, linked to an agent, such as a detectable label.

In another aspect, provided herein are nucleic acids, or sets of nucleic acids, which encode the heavy and/or light chains, or variable regions thereof, of the anti-ceruloplasmin antibodies described herein. In some embodiments, the nucleic acids comprise a nucleotide sequence selected from the group consisting of SEQ ID NOs: 197-228. Also provided are expression vectors, or set of expression vectors, comprising the nucleic acids, as well as cells comprising the nucleic acids, or set of nucleic acids, or expression vector, or set of expression vectors described herein.

In another aspect, provided herein are antibody mixtures comprising two or three antibodies which bind to human ceruloplasmin (SEQ ID NO: 1), wherein the two or three antibodies are selected from the group consisting of:

(a) an isolated antibody comprising heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively;

(b) an isolated antibody heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively; and (c) an isolated antibody heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively.

In some embodiments, the two or three antibodies comprise heavy and light chain variable regions comprising the amino acid sequences selected from the group consisting of: (a) SEQ ID NOs: 25 and 26, respectively, (b) SEQ ID NOs: 49 and 50, respectively, and (c) SEQ ID NOs: 73 and 74, respectively. In other embodiments, the two or three antibodies comprise heavy and light chains comprising the amino acid sequences selected from the group consisting of: (a) SEQ ID NOs: 27 and 28, respectively, (b) SEQ ID NOs: 51 and 52, respectively, and (c) SEQ ID NOs: 75 and 76, respectively. In some embodiments, the antibody mixture comprises two antibodies selected from subparts (a)-(c), for example, in an (a):(b), (a):(c), (b):(a), (b):(c), (c):(a), or (c):(b) ratio of 2:1. In some embodiments, the antibody mixture comprises the antibodies of subparts (a), (b), and (c), for example, in a (a):(b):(c), (a):(c):(b), (b):(a):(c), (b):(c):(a), (c):(a):(b), or (c):(b):(a) ratio of 2:1:1.

In some embodiments, the antibody or antibodies in the antibody mixture are immobilized onto a solid support, such as immunocapture beads, agarose resin, chromatography plate, streptavidin plate, or titer plate. In some embodiments, the antibody or antibodies in the antibody mixture are configured to immobilize onto a solid support after complexing with ceruloplasmin. Exemplary immunocapture beads include streptavidin-coated beads, tosylactivated beads, Protein G beads, Protein A beads, and Protein A/G beads. In some embodiments, the immunocapture beads are magnetic immunocapture beads. In some embodiments, the antibody or antibodies in the antibody mixture are irreversibly linked to the immunocapture beads.

In another aspect, provided herein are kits for measuring copper concentration in a biological sample comprising the anti-ceruloplasmin antibodies or antibody mixtures described herein and instructions for use. In some embodiments, the kit further comprises a chelator.

In another aspect, provided herein are methods of measuring non-ceruloplasmin bound copper concentration in a biological sample, the method comprising:

(a) contacting the biological sample with an immunocapture reagent comprising an anti-ceruloplasmin antibody or antibody mixture described herein to form immunocaptured ceruloplasmin,
(b) removing the immunocaptured ceruloplasmin to obtain a non-ceruloplasmin sample, and
(c) measuring copper concentration in the non-ceruloplasmin sample.

In some embodiments of the methods disclosed herein, the copper concentration in the non-ceruloplasmin sample is measured using inductively coupled plasma mass spectrometry (ICP-MS).

In another aspect, provided herein are methods of measuring labile-bound copper concentration in a biological sample, the method comprising:

(a) contacting the biological sample with an immunocapture reagent comprising an anti-ceruloplasmin antibody or antibody mixture described herein to form immunocaptured ceruloplasmin,
(b) removing the immunocaptured ceruloplasmin to obtain a non-ceruloplasmin sample,
(c) contacting the non-ceruloplasmin sample with a chelator (e.g., penicillamine, trientine hydrochloride, trientine tetrahydrochloride, and EDTA) which binds to labile-bound copper,
(d) removing non-labile-bound copper to obtain a labile-bound copper sample, and
(e) measuring copper concentration in the labile-bound copper sample.

In some embodiments of the methods described herein, the copper concentration in the labile-bound copper sample is measured using inductively coupled plasma mass spectrometry (ICP-MS). In some embodiments, the method further comprises introducing an internal standard to the labile-bound copper sample prior to the measuring of the copper concentration. In some embodiments, the internal standard comprises at least one of copper and rhodium. In some embodiments, the chelator is selected from the group consisting of penicillamine, trientine hydrochloride, trientine tetrahydrochloride, and EDTA. In some embodiments, the chelator comprises EDTA. In some embodiments, the removing of the non-labile-bound copper further comprises obtaining a non-labile-bound copper sample. In some embodiments, the method comprises measuring copper concentration in the non-labile-bound copper sample. In some embodiments, the non-labile bound copper sample comprises molybdenum. In some embodiments, the method further comprises measuring molybdenum concentration in the non-labile bound copper sample.

In some embodiments of the methods described herein, the removing of the immunocaptured ceruloplasmin further comprises obtaining an immunocaptured ceruloplasmin sample. In some embodiments, the method further comprises measuring ceruloplasmin concentration in the immunocaptured ceruloplasmin sample. In some embodiments, the ceruloplasmin concentration is measured using mass spectrometry. In some embodiments, the mass spectrometry has an analyte detection limit of at least about 5 μg/mL. In some embodiments, the mass spectrometry comprises liquid chromatography mass spectrometry (LC-MS). In some embodiments, the ceruloplasmin concentration in the biological sample is less than about 200 μg/mL.

In some embodiments of the methods disclosed herein, the method further comprises measuring copper concentration in the immunocaptured ceruloplasmin sample. In some embodiments, the copper concentration in the immunocaptured ceruloplasmin sample is measured using inductively coupled plasma mass spectrometry In another aspect, provided herein is a method of identifying a patient having a copper metabolism associated disease or disorder, the method comprising:

measuring the concentration of non-ceruloplasmin-bound copper or labile-bound copper in a biological sample from the patient according to a method of measurement described herein; and using the concentration of non-ceruloplasmin-bound copper or labile-bound copper in the biological sample to identify the patient having the disease or disorder.

In another aspect, provided herein is a method of treating a patient who has been diagnosed as having a copper metabolism associated disease or disorder using a method of measurement described herein, the method comprising administering to the patient an effective amount of a therapeutic agent to treat the disease or disorder. In some embodiments, the therapeutic agent is selected from the group consisting of: bis-choline tetrathiomolybdate, zinc, trientine hydrochloride, trientine tetrahydrochloride, and penicillamine.

In some embodiments of the methods described herein, the biological sample is human plasma or human serum. In some embodiments, the biological sample is from a patient who has or is suspected of having a copper metabolism-associated disease or disorder, for example, Wilson disease, copper toxicity, copper deficiency, Menkes disease, and aceruloplasminemia.

DETAILED DESCRIPTION

I. Overview

Figure 1:
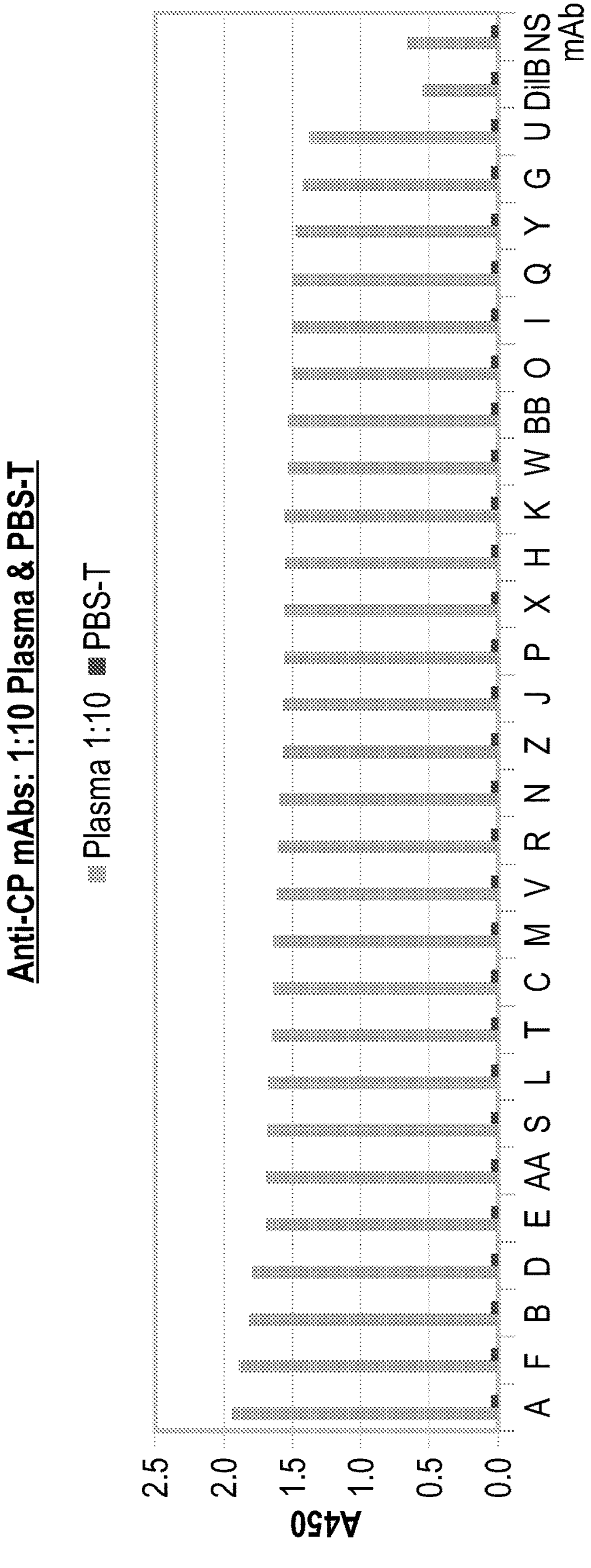
FIG. 1 is a graph showing the ability of 28 anti-CP monoclonal antibodies (mAbs) to bind to endogenous human ceruloplasmin (CP) in lithium-heparin plasma diluted 1:10 with PBS-T in an ELISA. Absorbance was read at A450 nm. "DilB" means "dilution buffer" and corresponds to no mAb captured, and "NS mAb" means "non-specific monoclonal antibody."

Provided herein are antibodies which bind to ceruloplasmin (e.g., human ceruloplasmin), as well as antibody mixtures comprising the same, that are useful for various applications, such as methods for measuring free copper concentration in a biological sample (e.g., a human plasma or serum sample) and standard molecular biology methods such as ELISA, immunoblotting, and co-immunoprecipitation. Also provided are methods for diagnosing and treating copper metabolism-associated disorders based on determining free copper concentrations using the methods of measurement described herein.

II. Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The term "about" as used herein when referring to a measurable value such as an amount, a temporal duration and the like, is encompasses variations of up to 10% from the specified value. Unless otherwise indicated, all numbers expressing quantities of ingredients, properties such as molecular weight, reaction conditions, etc., used herein are to be understood as being modified by the term "about".

As used herein, "administering" refers to the physical introduction of a composition comprising a therapeutic agent to a subject, using any of the various methods and delivery systems known to those skilled in the art. Exemplary routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intra-arterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually, or topically. Administering can also be performed, for example, once, a plurality of times, and/or over one or more extended periods.

The term "antibody" as used herein refers to polypeptides comprising at least one antibody derived antigen binding site (e.g., VH/VL region or Fv, or CDR), and includes whole antibodies and any antigen binding fragments (i.e., "antigen-binding portions") or single chains thereof. Antibodies include known forms of antibodies. For example, the antibody can be a human antibody, a humanized antibody, a bispecific antibody, or a chimeric antibody. A whole "antibody" refers to a glycoprotein comprising at least two heavy (H) chains and two light (L) chains inter-connected by disulfide bonds, in which each heavy chain is comprised of a heavy chain variable region (abbreviated herein as $V_H$) and a heavy chain constant region; and each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The antibody also can be of any of the following isotypes: IgG1, IgG2, IgG3, IgG4, IgM, IgA1, IgA2, IgAsec, IgD, and IgE, or equivalent isotype in other species (e.g., rabbit). The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

As used herein, an "antibody mixture" or "antibody combination" refers to a mixture (e.g., composition) that contains a plurality of distinct antibody (e.g., monoclonal antibody) populations. For example, an antibody mixture can be a mixture of two or more distinct antibodies (e.g., monoclonal antibodies) present in a single composition in a suitable buffer. In some embodiments, the antibody mixture is immobilized to a solid support (e.g., beads, microplate) and used to, e.g., immunocapture or immunodeplete a protein (e.g., ceruloplasmin) from a sample (e.g., a biological sample such as plasma or serum). In some embodiments, the antibody mixture is prepared (and optionally stored) in a suitable buffer.

As used herein, an "antigen" is an entity (e.g., a proteinaceous entity or peptide) to which an antibody binds.

The term "antigen-binding portion" of an antibody, as used herein, refers to one or more fragments of an antibody that retain the ability to specifically bind to an antigen (e.g., ceruloplamsin), e.g., a Fab, Fab'2, scFv, SMIP, Affibody®, nanobody, or a domain antibody. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). In one embodiment of the invention, the formulation contains an antigen-binding portions described in U.S. Pat. Nos. 6,090,382 and 6,258,562, each incorporated by reference herein.

As used herein, the term "binds to the same epitope" with reference to two or more antibodies means that the antibodies bind to the same segment of amino acid residues, as determined by a given method. Techniques for determining whether an antibody binds to the same epitope as another antibody include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

As used herein, "bis-choline tetrathiomolybdate" (also known as BC-TTM, tiomolibdate choline, tiomolibdic acid, WTX101, and ALXN1840) refers to an investigational, oral, first-in-class copper-protein-binding molecule being developed for the treatment of Wilson disease. BC-TTM has the following structure:

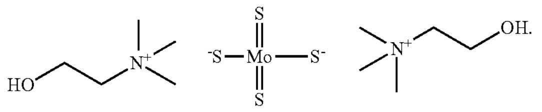

BC-TTM is believed to improve control of copper due to rapid and irreversible formation of Cu-tetrathiomolybdate-albumin tripartite complexes ("TPC") leading to rapid de-coppering.

The term "bispecific" or "bifunctional antibody" as used herein means an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "ceruloplasmin" or "CP" as used herein refers to a ferroxidase enzyme which functions as a major copper-carrying protein in the blood. Human CP has the amino acid sequence set forth below (GenBank Accession No. NP_000087; human CP precursor, with leader sequence in bold underline; SEQ ID NO: 1). Mature human CP without the leader

```
                                          (SEQ ID NO: 1)
MKILILGIFLFLCSTPAWAKEKHYYIGIIETTWDYASDHGEKKLISVDT

EHSNIYLQNGPDRIGRLYKKALYLQYTDETFRTTIEKPVWLGFLGPIIK

AETGDKVYVHLKNLASRPYTFHSHGITYYKEHEGAIYPDNTTDFQRADD

KVYPGEQYTYMLLATEEQSPGEGDGNCVTRIYHSHIDAPKDIASGLIGP

LIICKKDSLDKEKEKHIDREFVVMFSVVDENFSWYLEDNIKTYCSEPEK

VDKDNEDFQESNRMYSVNGYTFGSLPGLSMCAEDRVKWYLFGMGNEVDV

HAAFFHGQALTNKNYRIDTINLFPATLFDAYMVAQNPGEWMLSCQNLNH

LKAGLQAFFQVQECNKSSSKDNIRGKHVRHYYIAAEEIIWNYAPSGIDI

FTKENLTAPGSDSAVFFEQGTTRIGGSYKKLVYREYTDASFTNRKERGP

EEEHLGILGPVIWAEVGDTIRVTFHNKGAYPLSIEPIGVRFNKNNEGTY

YSPNYNPQSRSVPPSASHVAPTETFTYEWTVPKEVGPTNADPVCLAKMY

YSAVEPTKDIFTGLIGPMKICKKGSLHANGRQKDVDKEFYLFPTVFDEN

ESLLLEDNIRMFTTAPDQVDKEDEDFQESNKMHSMNGFMYGNQPGLTMC

KGDSVVWYLFSAGNEADVHGIYFSGNTYLWRGERRDTANLFPQTSLTLH

MWPDTEGTFNVECLTTDHYTGGMKQKYTVNQCRRQSEDSTFYLGERTYY

IAAVEVEWDYSPQREWEKELHHLQEQNVSNAFLDKGEFYIGSKYKKVVY

RQYTDSTFRVPVERKAEEEHLGILGPQLHADVGDKVKIIFKNMATRPYS

IHAHGVQTESSTVTPTLPGETLTYVWKIPERSGAGTEDSACIPWAYYST

VDQVKDLYSGLIGPLIVCRRPYLKVFNPRRKLEFALLFLVFDENESWYL

DDNIKTYSDHPEKVNKDDEEFIESNKMHAINGRMFGNLQGLTMHVGDEV

NWYLMGMGNEIDLHTVHFHGHSFQYKHRGVYSSDVFDIFPGTYQTLEMF

PRTPGIWLLHCHVTDHIHAGMETTYTVLQNEDTKSG
```

A "chimeric antibody" as used herein refers to an antibody in which the variable regions are derived from one species and the constant regions are derived from another species, such as an antibody in which the variable regions are derived from a rabbit antibody and the constant regions are derived from a human antibody.

Antibodies that "compete with another antibody for binding to a target," as used herein, refer to antibodies that inhibit (partially or completely) the binding of the other antibody to the target. In certain embodiments, an antibody competes with, and inhibits binding of another antibody to a target by at least 10%, 15%, 20%, 25%, 30%, 35%, 40%, 45%, 50%, 55%, 60%, 65%, 70%, 75%, 80%, 85%, 90%, 95%, or 100%. Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance). Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Competition assays can also be conducted as described in Example 3.

As used herein, "conservative sequence modifications" of the sequences set forth herein means nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

As used herein, the term "DNA" includes coding single stranded DNAs, double stranded DNAs consisting of said coding DNAs and of complementary DNAs thereto, or the complementary (single stranded) DNAs themselves.

As used herein, the term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The terms "effective amount" or "therapeutically effective amount" are used interchangeably, and refer to an amount of formulation or antibody effective to alleviate or ameliorate symptoms of disease or to prolong the survival of the subject being treated. Determination of a therapeutically effective amount is within the capability of those skilled in the art, especially in light of the detailed disclosure provided herein. Therapeutically effective dosages may be determined by using in vitro and in vivo methods.

As used herein, the terms "epitope" or "antigenic determinant" refer to a site on an antigen to which an immunoglobulin or antibody specifically binds. Epitopes can be formed both from contiguous amino acids (usually a linear epitope) or noncontiguous amino acids juxtaposed by tertiary folding of a protein (usually a conformational epitope).

As used herein, an "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

As used herein, the term "free copper" refers to the fraction of total copper which is not bound to ceruloplasmin. Free copper thus comprises non-ceruloplasmin-bound copper present in the blood of a subject (such as NCC or LBC).

As used herein, a "humanized" antibody refers to an antibody in which some, most or all of the amino acids outside the CDR domains of a non-human antibody are replaced with corresponding amino acids derived from human immunoglobulins.

As used herein, the term "immunocapture" refers to a method for isolating a protein (e.g., ceruloplasmin) or protein complex from a sample (e.g., a biological sample) using the specific binding of that protein/complex to an antibody (e.g., an anti-ceruloplasmin mAb described herein). An immunocapture antibody may, but need not, be immobilized to a surface, such as a bead, a microtiter plate, or nitrocellulose. In other embodiments, the immunocapture of a protein or protein complex may occur in solution (wherein the antibody is not immobilized).

As used herein, the term "immunodepletion" refers to removing a protein (e.g., ceruloplasmin) from a sample (e.g., by removing the immunocaptured protein). In some embodiments, immunodepletion yields a sample which is essentially free of the immunodepeleted protein (e.g., less than 10%, e.g., less than 9%, less than 8%, less than 7%, less than 6%, less than 5%, less than 4%, less than 3%, less than 2%, or less than 1% of the original amount of the protein of interest remaining).

As used herein, an "isolated" antibody or antigen binding fragment is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 95% by weight of antibody, and in some embodiments, to greater than 99% by weight.

As used herein, "isotype" refers to the antibody class (e.g., IgG1, IgG2, IgG3, IgG4, IgM, IgA1, IgA2, IgD, and IgE antibody, or equivalents in other species) that is encoded by the heavy chain constant region genes.

The terms "$k_{assoc}$" or "$k_a$", as used herein, are intended to refer to the association rate of a particular antibody-antigen interaction, whereas the terms "$k_{dis}$" or "$k_a$," as used herein, are intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. For example, a method for determining the $K_D$ of an antibody is by using surface plasmon resonance, such as using a biosensor system such as a Biacore system or flow cytometry and Scatchard analysis.

The terms "LBC" or "labile-bound copper" as used herein refer to the fraction of total copper which is bound to albumin, transcuprein, and other less abundant plasma proteins. LBC thus comprises the fraction of total copper which is not bound to either ceruloplasmin or in tetrathiomolybdate-Cu-albumin tripartite complexes ("TPC"). In certain embodiments, the LBC fraction is directly measured using an LBC assay. For example, in certain embodiments, the LBC assay is as disclosed in PCT Patent Application Publication No. WO2021/05080, filed on Sep. 11, 2020, and U.S. Provisional Patent Application Nos. 62/899,498, filed Sep. 12, 2019, 62/944,498 filed Dec. 6, 2019, and 62/958,432, filed Jan. 8, 2020, herein incorporated by reference in their entirety. In a biological sample in which no TPC is present, the NCC and the LBC fractions are the same.

The term "monoclonal antibody" or "mAb" as used herein, includes an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. The monoclonal antibodies to be used in accordance with the formulations disclosed herein may be made by the hybridoma method first described by Kohler, et al., (1975) *Nature* 256: 495 or other methods known in the art. A "polyclonal antibody" is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

As used herein, a "native sequence Fc region" or "native sequence Fc" comprises an amino acid sequence that is identical to the amino acid sequence of an Fc region found in nature.

As used herein, the term "non-ceruloplasmin-bound copper" or "NCC" refers to the fraction of total copper that is not bound to ceruloplasmin (i.e., circulating non-ceruloplasmin-bound copper). Under many currently available methods, NCC is estimated using direct measurements of total copper and CP in the blood (such as, e.g., serum or plasma) and the following formula:

$$NCC[\mu M] = \frac{\text{Total plasma Cu } [\mu g/L] - \left(3.15 * \text{ceruloplasmin } \left[\frac{mg}{L}\right]\right)}{63.5\ [\mu g/\mu mol]}.$$

The calculation is premised on an assumption that six copper atoms are always bound to a single CP molecule, and that NCC and ceruloplasmin concentrations are directly correlated. In reality, CP may show considerable heterogeneity in the number of copper atoms associated per CP molecule. In fact, 6-8 copper atoms can actually bind to CP, and in Wilson disease usually fewer than six copper atoms are associated per CP molecule. In certain embodiments disclosed herein, the NCC fraction is directly measured using a NCC assay. For example, in certain embodiments, the NCC assay is as disclosed as the "NCC assay" in PCT Patent Application Publication No. WO2021/05080, filed on Sep. 11, 2020, and U.S. Provisional Patent Application Nos. 62/899,498, filed Sep. 12, 2019, 62/944,498 filed Dec. 6, 2019, and 62/958,432, filed Jan. 8, 2020, herein incorporated by reference in their entirety.

In subjects treated with BC-TTM, NCC comprises the fraction of total copper that is either (1) bound to albumin, transcuprein, and other less abundant plasma proteins (collectively referred to as LBC) or (2) bound in tetrathiomolybdate-Cu-albumin tripartite complexes ("TPC"). Thus, in a biological sample from a subject who has been treated with BC-TTM, NCC=LBC+TPC.

The term "nucleic acid molecule," as used herein, is intended to include DNA molecules and RNA molecules. A nucleic acid molecule may be single-stranded or double-stranded, and may be cDNA. Nucleic acids, e.g., cDNA, may be mutated, in accordance with standard techniques, to provide gene sequences. For coding sequences, these mutations may affect the corresponding amino acid sequence as desired. In particular, DNA sequences substantially homologous to or derived from native V, D, J, constant, switches and other such sequences described herein are contemplated (where "derived" indicates that a sequence is identical or modified from another sequence). The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. *Current Protocols in Molecular Biology, Greene Publishing and* Wiley Interscience, New York (1987).

As used herein, the term "patient" includes human and other mammalian subjects that receive either prophylactic or therapeutic treatment.

The "percent identity" as used herein between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "sample" refers to tissue, body fluid, or a cell (or a fraction of any of the foregoing) taken from a patient or a subject. In some embodiments, the body fluid is plasma or serum.

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., recombinant human ceruloplasmin, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, unless otherwise indicated, an antibody that "specifically binds to human ceruloplasmin" refers to an antibody that binds to soluble or cell bound human ceruloplasmin with a $K_D$ of $10^{-7}$ M or less, such as approximately less than $10^{-8}$ M, $10^{-9}$ M or $10^{-10}$ M or even lower.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

For nucleic acids, the term "substantial homology" as used herein indicates that two nucleic acids, or designated sequences thereof, when optimally aligned and compared, are identical, with appropriate nucleotide insertions or deletions, in at least about 80% of the nucleotides, usually at least about 90% to 95%, and for example at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and for example at least about 98% to 99.5% of the amino acids.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J Mol. Recognit.* 8:125-131; and Johnsson, B., et al. (1991) *Anal. Biochem.* 198:268-277.

The terms "treat," "treating," and "treatment," as used herein, refer to therapeutic measures described herein. The methods of "treatment" employ administration to a subject the combination disclosed herein in order to cure, delay, reduce the severity of, or ameliorate, one or more symptoms of the disease or disorder or recurring disease or disorder, or in order to prolong the survival of a subject beyond that expected in the absence of such treatment.

As used herein, "total copper" refers to the sum of all copper species in the blood (for example, in serum or plasma) of a subject. Total copper includes both ceruloplasmin (CP)-bound copper and all species of non-ceruloplasmin bound copper (such as NCC, LBC, and TPC). In general, total copper may be directly measured with high sensitivity and specificity by mass-spectroscopy, such as inductively coupled plasma-mass spectrometry (ICP-MS).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, other forms of expression vectors, such as viral vectors (e.g., replication defective retroviruses, adenoviruses and adeno-associated viruses), which serve equivalent functions are also contemplated.

As used herein, "Wilson disease" is an inherited disorder associated with mutations in the copper transporting ATPase ATP7B, resulting in impaired, non-functional or impaired ATP7B protein activity.

Various aspects described herein are described in further detail in the following subsections.

III. Anti-Ceruloplasmin Antibodies and Antibody Mixtures

Provided herein are anti-ceruloplasmin antibodies (e.g., isolated monoclonal anti-ceruloplasmin antibodies) that are characterized by particular structural and/or functional features. In part, the disclosure pertains to anti-ceruloplasmin antibodies having defined CDR, variable region, and heavy and light chain sequences.

Accordingly, in one aspect, provided herein are isolated monoclonal antibodies which bind to ceruloplasmin (e.g., human ceruloplasmin which has the amino acid sequence of SEQ ID NO: 1 or 2) and comprise heavy chain variable region CDR1, CDR2, and CDR3 sequences and light chain variable region CDR1, CDR2, and CDR3 sequences of the heavy and light chain variable region pairs selected from the group consisting of:

(a) SEQ ID NOs: 25 and 26, respectively,
(b) SEQ ID NOs: 49 and 50, respectively,
(c) SEQ ID NOs: 73 and 74, respectively,
(d) SEQ ID NOs: 97 and 98, respectively,
(e) SEQ ID NOs: 121 and 122, respectively,
(f) SEQ ID NOs: 145 and 146, respectively,
(g) SEQ ID NOs: 169 and 170, respectively, and
(h) SEQ ID NOs: 193 and 194, respectively.

In some embodiments, the CDR sequences are defined based on Kabat numbering. In other embodiments, the CDR sequences are defined based on Chothia numbering system. In other embodiments, the CDR sequences are defined based on the IMGT numbering system.

In another aspect, provided herein are isolated monoclonal antibodies which bind to ceruloplasmin (e.g., human ceruloplasmin which has the amino acid sequence of SEQ ID NO: 1 or 2) and comprise:

(a) heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively;
(b) heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively;
(c) heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively;
(d) heavy chain variable region CDR1, CDR2, and CDR3 sequences comprising the amino acid sequences set forth in SEQ ID NOs: 77, 78, and 79, respectively, and light chain variable region CDR1, CDR2, and CDR3 sequences comprising the amino acid sequences set forth in SEQ ID NOs: 80, 81, and 82, respectively;
(e) heavy chain variable region CDR1, CDR2, and CDR3 sequences comprising the amino acid sequences set forth in SEQ ID NOs: 101, 102, and 103, respectively, and light chain variable region CDR1, CDR2, and CDR3 sequences comprising the amino acid sequences set forth in SEQ ID NOs: 104, 105, and 106, respectively;
(f) heavy chain variable region CDR1, CDR2, and CDR3 sequences comprising the amino acid sequences set forth in SEQ ID NOs: 125, 126, and 127, respectively, and light chain variable region CDR1, CDR2, and CDR3 sequences comprising the amino acid sequences set forth in SEQ ID NOs: 128, 129, and 130, respectively;

(g) heavy chain variable region CDR1, CDR2, and CDR3 sequences comprising the amino acid sequences set forth in SEQ ID NOs: 149, 150, and 151, respectively, and light chain variable region CDR1, CDR2, and CDR3 sequences comprising the amino acid sequences set forth in SEQ ID NOs: 152, 153, and 154, respectively; or (h) heavy chain variable region CDR1, CDR2, and CDR3 sequences comprising the amino acid sequences set forth in SEQ ID NOs: 173, 174, and 175, respectively, and light chain variable region CDR1, CDR2, and CDR3 sequences comprising the amino acid sequences set forth in SEQ ID NOs: 176, 177, and 178, respectively.

In another aspect, provided herein are isolated monoclonal antibodies which bind to ceruloplasmin (e.g., human ceruloplasmin which has the amino acid sequence of SEQ ID NO: 1 or 2) and comprise:

(a) heavy chain variable region CDR1, CDR2, and CDR3 sequences comprising the amino acid sequences set forth in SEQ ID NOs: 11, 12, and 13, respectively, and light chain variable region CDR1, CDR2, and CDR3 sequences comprising the amino acid sequences set forth in SEQ ID NOs: 14, 15, and 16, respectively;

(b) heavy chain variable region CDR1, CDR2, and CDR3 sequences comprising the amino acid sequences set forth in SEQ ID NOs: 35, 36, and 37, respectively, and light chain variable region CDR1, CDR2, and CDR3 sequences comprising the amino acid sequences set forth in SEQ ID NOs: 38, 39, and 40, respectively;

(c) heavy chain variable region CDR1, CDR2, and CDR3 sequences comprising the amino acid sequences set forth in SEQ ID NOs: 59, 60, and 61, respectively, and light chain variable region CDR1, CDR2, and CDR3 sequences comprising the amino acid sequences set forth in SEQ ID NOs: 62, 63, and 64, respectively;

(d) heavy chain variable region CDR1, CDR2, and CDR3 sequences comprising the amino acid sequences set forth in SEQ ID NOs: 83, 84, and 85, respectively, and light chain variable region CDR1, CDR2, and CDR3 sequences comprising the amino acid sequences set forth in SEQ ID NOs: 86, 87, and 88, respectively;

(e) heavy chain variable region CDR1, CDR2, and CDR3 sequences comprising the amino acid sequences set forth in SEQ ID NOs: 107, 108, and 109, respectively, and light chain variable region CDR1, CDR2, and CDR3 sequences comprising the amino acid sequences set forth in SEQ ID NOs: 110, 111, and 112, respectively;

(f) heavy chain variable region CDR1, CDR2, and CDR3 sequences comprising the amino acid sequences set forth in SEQ ID NOs: 131, 132, and 133, respectively, and light chain variable region CDR1, CDR2, and CDR3 sequences comprising the amino acid sequences set forth in SEQ ID NOs: 134, 135, and 136, respectively;

(g) heavy chain variable region CDR1, CDR2, and CDR3 sequences comprising the amino acid sequences set forth in SEQ ID NOs: 155, 156, and 157, respectively, and light chain variable region CDR1, CDR2, and CDR3 sequences comprising the amino acid sequences set forth in SEQ ID NOs: 158, 159, and 160, respectively; or (h) heavy chain variable region CDR1, CDR2, and CDR3 sequences comprising the amino acid sequences set forth in SEQ ID NOs: 179, 180, and 181, respectively, and light chain variable region CDR1, CDR2, and CDR3 sequences comprising the amino acid sequences set forth in SEQ ID NOs: 182, 183, and 184, respectively.

In another aspect, provided herein are isolated monoclonal antibodies which bind to ceruloplasmin (e.g., human ceruloplasmin which has the amino acid sequence of SEQ ID NO: 1 or 2) and comprise:

(a) heavy chain variable region CDR1, CDR2, and CDR3 sequences comprising the amino acid sequences set forth in SEQ ID NOs: 17, 18, and 19, respectively, and light chain variable region CDR1, CDR2, and CDR3 sequences comprising the amino acid sequences set forth in SEQ ID NOs: 20, 21, and 22, respectively;

(b) heavy chain variable region CDR1, CDR2, and CDR3 sequences comprising the amino acid sequences set forth in SEQ ID NOs: 41, 42, and 43, respectively, and light chain variable region CDR1, CDR2, and CDR3 sequences comprising the amino acid sequences set forth in SEQ ID NOs: 44, 45, and 46, respectively;

(c) heavy chain variable region CDR1, CDR2, and CDR3 sequences comprising the amino acid sequences set forth in SEQ ID NOs: 65, 66, and 67, respectively, and light chain variable region CDR1, CDR2, and CDR3 sequences comprising the amino acid sequences set forth in SEQ ID NOs: 68, 69, and 70, respectively;

(d) heavy chain variable region CDR1, CDR2, and CDR3 sequences comprising the amino acid sequences set forth in SEQ ID NOs: 89, 90, and 91, respectively, and light chain variable region CDR1, CDR2, and CDR3 sequences comprising the amino acid sequences set forth in SEQ ID NOs: 92, 93, and 94, respectively;

(e) heavy chain variable region CDR1, CDR2, and CDR3 sequences comprising the amino acid sequences set forth in SEQ ID NOs: 113, 114, and 115, respectively, and light chain variable region CDR1, CDR2, and CDR3 sequences comprising the amino acid sequences set forth in SEQ ID NOs: 116, 117, and 118, respectively;

(f) heavy chain variable region CDR1, CDR2, and CDR3 sequences comprising the amino acid sequences set forth in SEQ ID NOs: 137, 138, and 139, respectively, and light chain variable region CDR1, CDR2, and CDR3 sequences comprising the amino acid sequences set forth in SEQ ID NOs: 140, 141, and 142, respectively;

(g) heavy chain variable region CDR1, CDR2, and CDR3 sequences comprising the amino acid sequences set forth in SEQ ID NOs: 161, 162, and 163, respectively, and light chain variable region CDR1, CDR2, and CDR3 sequences comprising the amino acid sequences set forth in SEQ ID NOs: 164, 165, and 166, respectively; or (h) heavy chain variable region CDR1, CDR2, and CDR3 sequences comprising the amino acid sequences set forth in SEQ ID NOs: 185, 186, and 187, respectively, and light chain variable region CDR1, CDR2, and CDR3 sequences comprising the amino acid sequences set forth in SEQ ID NOs: 188, 189, and 190, respectively.

In another aspect, provided herein are isolated monoclonal antibodies which bind to ceruloplasmin (e.g., human ceruloplasmin which has the amino acid sequence of SEQ ID NO: 1 or 2) and comprise heavy and light chain variable regions, wherein the heavy chain variable region comprises an amino acid sequence which is at least 75%, for example, 80%, 85%, 90%, 95%, 96%, 97%, 98%, 99%, or 100% identical to the amino acid sequence selected from the group consisting of SEQ ID NOs: 25, 49, 73, 97, 121, 145, 169, and 193.

In another aspect, provided herein are isolated monoclonal antibodies which bind to ceruloplasmin (e.g., human ceruloplasmin which has the amino acid sequence of SEQ ID NO: 1 or 2) and comprise heavy and light chain variable regions, wherein the light chain variable region comprises an amino acid sequence which is at least 75%, for example, 80%, 85%, 90%, 95%, 96%, 97%, 98%, 99%, or 100% identical to the amino acid sequence selected from the group consisting of SEQ ID NOs: 26, 50, 74, 98, 122, 146, 170, and 194. In yet another aspect, provided herein are isolated monoclonal antibodies which bind to ceruloplasmin (e.g., human ceruloplasmin which has the amino acid sequence of SEQ ID NO: 1 or 2) and comprise heavy and light chain variable regions, wherein the heavy chain variable region comprises an amino acid sequence which is at least 75%, for example, 80%, 85%, 90%, 95%, 96%, 97%, 98%, 99%, or 100% identical to the amino acid sequence selected from the group consisting of SEQ ID NOs: 25, 49, 73, 97, 121, 145, 169, and 193, and/or the light chain variable region comprises an amino acid sequence which is at least 75%, for example, 80%, 85%, 90%, 95%, 96%, 97%, 98%, 99%, or 100% identical to the amino acid sequence selected from the group consisting of SEQ ID NOs: 26, 50, 74, 98, 122, 146, 170, and 194.

In another aspect, provided herein are isolated monoclonal antibodies which bind to ceruloplasmin (e.g., human ceruloplasmin which has the amino acid sequence of SEQ ID NO: 1 or 2) and comprise heavy and light chain variable regions comprising amino acid sequences which are at least 75%, for example, 80%, 85%, 90%, 95%, 96%, 97%, 98%, 99%, or 100% identical to the amino acid sequences selected from the group consisting of:

(a) SEQ ID NOs: 25 and 26, respectively,
(b) SEQ ID NOs: 49 and 50, respectively,
(c) SEQ ID NOs: 73 and 74, respectively,
(d) SEQ ID NOs: 97 and 98, respectively,
(e) SEQ ID NOs: 121 and 122, respectively,
(f) SEQ ID NOs: 145 and 146, respectively,
(g) SEQ ID NOs: 169 and 170, respectively, and
(h) SEQ ID NOs: 193 and 194, respectively.

In another aspect, provided herein are isolated monoclonal antibodies which bind to ceruloplasmin (e.g., human ceruloplasmin which has the amino acid sequence of SEQ ID NO: 1 or 2) and comprise heavy and light chain variable regions comprising the amino acid sequences selected from the group consisting of:

(a) SEQ ID NOs: 25 and 26, respectively,
(b) SEQ ID NOs: 49 and 50, respectively,
(c) SEQ ID NOs: 73 and 74, respectively,
(d) SEQ ID NOs: 97 and 98, respectively,
(e) SEQ ID NOs: 121 and 122, respectively,
(f) SEQ ID NOs: 145 and 146, respectively,
(g) SEQ ID NOs: 169 and 170, respectively, and
(h) SEQ ID NOs: 193 and 194, respectively.

In another aspect, provided herein are isolated monoclonal antibodies which bind to ceruloplasmin (e.g., human ceruloplasmin which has the amino acid sequence of SEQ ID NO: 1 or 2) and comprise heavy and light chains comprising amino acid sequences which are at least 75%, for example, 80%, 85%, 90%, 95%, 96%, 97%, 98%, 99%, or 100% identical to the amino acid sequences selected from the group consisting of:

(a) SEQ ID NOs: 27 and 28, respectively,
(b) SEQ ID NOs: 51 and 52, respectively,
(c) SEQ ID NOs: 75 and 76, respectively,
(d) SEQ ID NOs: 99 and 100, respectively,
(e) SEQ ID NOs: 123 and 124, respectively,
(f) SEQ ID NOs: 147 and 148, respectively,
(g) SEQ ID NOs: 171 and 172, respectively, and
(h) SEQ ID NOs: 195 and 196, respectively.

In another aspect, provided herein are isolated monoclonal antibodies which bind to ceruloplasmin (e.g., human ceruloplasmin which has the amino acid sequence of SEQ ID NO: 1 or 2) and comprise heavy and light chains comprising the amino acid sequences selected from the group consisting of:

(a) SEQ ID NOs: 27 and 28, respectively,
(b) SEQ ID NOs: 51 and 52, respectively,
(c) SEQ ID NOs: 75 and 76, respectively,
(d) SEQ ID NOs: 99 and 100, respectively,
(e) SEQ ID NOs: 123 and 124, respectively,
(f) SEQ ID NOs: 147 and 148, respectively,
(g) SEQ ID NOs: 171 and 172, respectively, and
(h) SEQ ID NOs: 195 and 196, respectively.

In another aspect, provided herein are anti-ceruloplasmin antibodies which bind to the same epitope on human ceruloplasmin as the anti-ceruloplasmin antibodies described herein (reference antibodies), i.e., bind to the same epitope on human ceruloplasmin as a reference antibody comprising:

(a) heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively (or an antibody having the CDR sequences of mAb E defined by the Chothia or IMGT numbering system);
(b) heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively (or an antibody having the CDR sequences of mAb C defined by the Chothia or IMGT numbering system);
(c) heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively (or an antibody having the CDR sequences of mAb G defined by the Chothia or IMGT numbering system);
(d) heavy chain variable region CDR1, CDR2, and CDR3 sequences comprising the amino acid sequences set forth in SEQ ID NOs: 77, 78, and 79, respectively, and light chain variable region CDR1, CDR2, and CDR3 sequences comprising the amino acid sequences set forth in SEQ ID NOs: 80, 81, and 82, respectively (or an antibody having the CDR sequences of mAb B defined by the Chothia or IMGT numbering system);
(e) heavy chain variable region CDR1, CDR2, and CDR3 sequences comprising the amino acid sequences set forth in SEQ ID NOs: 101, 102, and 103, respectively, and light chain variable region CDR1, CDR2, and CDR3 sequences comprising the amino acid sequences set forth in SEQ ID NOs: 104, 105, and 106, respectively (or an antibody having the CDR sequences of mAb F defined by the Chothia or IMGT numbering system);

(f) heavy chain variable region CDR1, CDR2, and CDR3 sequences comprising the amino acid sequences set forth in SEQ ID NOs: 125, 126, and 127, respectively, and light chain variable region CDR1, CDR2, and CDR3 sequences comprising the amino acid sequences set forth in SEQ ID NOs: 128, 129, and 130, respectively (or an antibody having the CDR sequences of mAb A defined by the Chothia or IMGT numbering system);

(g) heavy chain variable region CDR1, CDR2, and CDR3 sequences comprising the amino acid sequences set forth in SEQ ID NOs: 149, 150, and 151, respectively, and light chain variable region CDR1, CDR2, and CDR3 sequences comprising the amino acid sequences set forth in SEQ ID NOs: 152, 153, and 154, respectively (or an antibody having the CDR sequences of mAb D defined by the Chothia or IMGT numbering system);

(h) heavy chain variable region CDR1, CDR2, and CDR3 sequences comprising the amino acid sequences set forth in SEQ ID NOs: 173, 174, and 175, respectively, and light chain variable region CDR1, CDR2, and CDR3 sequences comprising the amino acid sequences set forth in SEQ ID NOs: 176, 177, and 178, respectively (or an antibody having the CDR sequences of mAb H defined by the Chothia or IMGT numbering system);

(i) a heavy chain variable region comprising the amino acid sequence set forth in SEQ ID NO: 25, and a light chain variable region comprising the amino acid sequence set forth in SEQ ID NO: 26;

(j) a heavy chain variable region comprising the amino acid sequence set forth in SEQ ID NO: 49, and a light chain variable region comprising the amino acid sequence set forth in SEQ ID NO: 50;

(k) a heavy chain variable region comprising the amino acid sequence set forth in SEQ ID NO: 73, and a light chain variable region comprising the amino acid sequence set forth in SEQ ID NO: 74;

(l) a heavy chain variable region comprising the amino acid sequence set forth in SEQ ID NO: 97, and a light chain variable region comprising the amino acid sequence set forth in SEQ ID NO: 98;

(m) a heavy chain variable region comprising the amino acid sequence set forth in SEQ ID NO: 121, and a light chain variable region comprising the amino acid sequence set forth in SEQ ID NO: 122;

(n) a heavy chain variable region comprising the amino acid sequence set forth in SEQ ID NO: 145, and a light chain variable region comprising the amino acid sequence set forth in SEQ ID NO: 146;

(o) a heavy chain variable region comprising the amino acid sequence set forth in SEQ ID NO: 169, and a light chain variable region comprising the amino acid sequence set forth in SEQ ID NO: 170;

(p) a heavy chain variable region comprising the amino acid sequence set forth in SEQ ID NO: 193, and a light chain variable region comprising the amino acid sequence set forth in SEQ ID NO: 194;

(q) a heavy chain comprising the amino acid sequence set forth in SEQ ID NO: 27, and a light chain comprising the amino acid sequence set forth in SEQ ID NO: 28;

(r) a heavy chain comprising the amino acid sequence set forth in SEQ ID NO: 51, and a light chain comprising the amino acid sequence set forth in SEQ ID NO: 52;

(s) a heavy chain comprising the amino acid sequence set forth in SEQ ID NO: 75, and a light chain comprising the amino acid sequence set forth in SEQ ID NO: 76;

(t) a heavy chain comprising the amino acid sequence set forth in SEQ ID NO: 99, and a light chain comprising the amino acid sequence set forth in SEQ ID NO: 100;

(u) a heavy chain comprising the amino acid sequence set forth in SEQ ID NO: 123, and a light chain comprising the amino acid sequence set forth in SEQ ID NO: 124;

(v) a heavy chain comprising the amino acid sequence set forth in SEQ ID NO: 147, and a light chain comprising the amino acid sequence set forth in SEQ ID NO: 148;

(w) a heavy chain comprising the amino acid sequence set forth in SEQ ID NO: 171, and a light chain comprising the amino acid sequence set forth in SEQ ID NO: 172; or (x) a heavy chain comprising the amino acid sequence set forth in SEQ ID NO: 195, and a light chain comprising the amino acid sequence set forth in SEQ ID NO: 196.

In another aspect, provided herein are anti-ceruloplasmin antibodies which compete for binding to human ceruloplasmin with the anti-ceruloplasmin antibodies described herein (reference antibodies), e.g., compete for binding to human ceruloplasmin with a reference antibody comprising:

(a) heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively (or an antibody having the CDR sequences of mAb E defined by the Chothia or IMGT numbering system);

(b) heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively (or an antibody having the CDR sequences of mAb C defined by the Chothia or IMGT numbering system);

(c) heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively (or an antibody having the CDR sequences of mAb G defined by the Chothia or IMGT numbering system);

(d) heavy chain variable region CDR1, CDR2, and CDR3 sequences comprising the amino acid sequences set forth in SEQ ID NOs: 77, 78, and 79, respectively, and light chain variable region CDR1, CDR2, and CDR3 sequences comprising the amino acid sequences set forth in SEQ ID NOs: 80, 81, and 82, respectively (or an antibody having the CDR sequences of mAb B defined by the Chothia or IMGT numbering system);

(e) heavy chain variable region CDR1, CDR2, and CDR3 sequences comprising the amino acid sequences set forth in SEQ ID NOs: 101, 102, and 103, respectively, and light chain variable region CDR1, CDR2, and CDR3 sequences comprising the amino acid sequences set forth in SEQ ID NOs: 104, 105, and 106, respectively (or an antibody having the CDR sequences of mAb F defined by the Chothia or IMGT numbering system);

(f) heavy chain variable region CDR1, CDR2, and CDR3 sequences comprising the amino acid sequences set forth in SEQ ID NOs: 125, 126, and 127, respectively, and light chain variable region CDR1, CDR2, and CDR3 sequences comprising the amino acid sequences set forth in SEQ ID NOs: 128, 129, and 130, respectively (or an antibody having the CDR sequences of mAb A defined by the Chothia or IMGT numbering system);

(g) heavy chain variable region CDR1, CDR2, and CDR3 sequences comprising the amino acid sequences set forth in SEQ ID NOs: 149, 150, and 151, respectively, and light chain variable region CDR1, CDR2, and CDR3 sequences comprising the amino acid sequences set forth in SEQ ID NOs: 152, 153, and 154, respectively (or an antibody having the CDR sequences of mAb D defined by the Chothia or IMGT numbering system);

(h) heavy chain variable region CDR1, CDR2, and CDR3 sequences comprising the amino acid sequences set forth in SEQ ID NOs: 173, 174, and 175, respectively, and light chain variable region CDR1, CDR2, and CDR3 sequences comprising the amino acid sequences set forth in SEQ ID NOs: 176, 177, and 178, respectively (or an antibody having the CDR sequences of mAb H defined by the Chothia or IMGT numbering system);

(i) a heavy chain variable region comprising the amino acid sequence set forth in SEQ ID NO: 25, and a light chain variable region comprising the amino acid sequence set forth in SEQ ID NO: 26;

(j) a heavy chain variable region comprising the amino acid sequence set forth in SEQ ID NO: 49, and a light chain variable region comprising the amino acid sequence set forth in SEQ ID NO: 50;

(k) a heavy chain variable region comprising the amino acid sequence set forth in SEQ ID NO: 73, and a light chain variable region comprising the amino acid sequence set forth in SEQ ID NO: 74;

(l) a heavy chain variable region comprising the amino acid sequence set forth in SEQ ID NO: 97, and a light chain variable region comprising the amino acid sequence set forth in SEQ ID NO: 98;

(m) a heavy chain variable region comprising the amino acid sequence set forth in SEQ ID NO: 121, and a light chain variable region comprising the amino acid sequence set forth in SEQ ID NO: 122;

(n) a heavy chain variable region comprising the amino acid sequence set forth in SEQ ID NO: 145, and a light chain variable region comprising the amino acid sequence set forth in SEQ ID NO: 146;

(o) a heavy chain variable region comprising the amino acid sequence set forth in SEQ ID NO: 169, and a light chain variable region comprising the amino acid sequence set forth in SEQ ID NO: 170;

(p) a heavy chain variable region comprising the amino acid sequence set forth in SEQ ID NO: 193, and a light chain variable region comprising the amino acid sequence set forth in SEQ ID NO: 194;

(q) a heavy chain comprising the amino acid sequence set forth in SEQ ID NO: 27, and a light chain comprising the amino acid sequence set forth in SEQ ID NO: 28;

(r) a heavy chain comprising the amino acid sequence set forth in SEQ ID NO: 51, and a light chain comprising the amino acid sequence set forth in SEQ ID NO: 52;

(s) a heavy chain comprising the amino acid sequence set forth in SEQ ID NO: 75, and a light chain comprising the amino acid sequence set forth in SEQ ID NO: 76;

(t) a heavy chain comprising the amino acid sequence set forth in SEQ ID NO: 99, and a light chain comprising the amino acid sequence set forth in SEQ ID NO: 100;

(u) a heavy chain comprising the amino acid sequence set forth in SEQ ID NO: 123, and a light chain comprising the amino acid sequence set forth in SEQ ID NO: 124;

(v) a heavy chain comprising the amino acid sequence set forth in SEQ ID NO: 147, and a light chain comprising the amino acid sequence set forth in SEQ ID NO: 148;

(w) a heavy chain comprising the amino acid sequence set forth in SEQ ID NO: 171, and a light chain comprising the amino acid sequence set forth in SEQ ID NO: 172; or (x) a heavy chain comprising the amino acid sequence set forth in SEQ ID NO: 195, and a light chain comprising the amino acid sequence set forth in SEQ ID NO: 196.

In some embodiments, the anti-ceruloplasmin antibodies described herein compete for binding to human ceruloplasmin with a reference antibody or reference antibodies from among (a)-(x) listed above, e.g., as assessed using methods known in the art, e.g., as shown in Example 3. In some embodiments, an antibody competes with, and inhibits binding of another antibody to a target by at least 10%, for example, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, 100%, 10%-100%, 25%-100%, 50%-100%, 75%-100%, 10%-75%, 25%-75%, 50%-75%, 10%-50%, 25%-50%, or 10%-25%.

In some embodiments, the anti-ceruloplasmin antibodies described herein bind to human ceruloplasmin with a $K_D$ of about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-7}$ M to about $10^{-12}$ M, about $10^{-7}$ M to about $10^{-11}$ M, about $10^{-7}$ M to about $10^{-10}$ M, about $10^{-8}$ M to about $10^{-12}$ M, about $10^{-9}$ M to about $10^{-12}$ M, about $10^{-10}$ M to about $10^{-12}$ M, about $10^{-10}$ M to about $10^{-11}$ M, about $10^{-9}$ M to about $10^{-11}$ M, or about $10^{-10}$ M to about $10^{-11}$ M.

Also provided herein are antibody mixtures (e.g., antibody compositions or antibody cocktails) comprising two or three antibodies (in a single combined formulation or separate formulations) which bind to ceruloplasmin (e.g., human ceruloplasmin which has the amino acid sequence of SEQ ID NO: 1 or 2), wherein the two or three antibodies are selected from anti-ceruloplasmin antibodies (e.g., monoclonal anti-ceruloplasmin antibodies) comprising the heavy and light chain CDR sequences, heavy and light chain variable region sequences, or heavy and light chain sequences of mAbs E, C, G, B, F, A, D, and H. In some embodiments, the antibody mixture comprises two antibodies, which are present in a ratio ranging from 10:1 to 1:1. In other embodiments, the antibody mixture comprises three antibodies, which are present in a ratio ranging from 1-3:1-3:1-3, such as 2:1:1.

In a particular embodiment, the antibody mixture (e.g., antibody composition) comprises two or three antibodies which bind to ceruloplasmin (e.g., human ceruloplasmin which has the amino acid sequence of SEQ ID NO: 1 or 2), wherein the two or three antibodies are selected from the group consisting of:

(a) an isolated antibody comprising heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively (or an antibody having the CDR sequences of mAb E defined by the Chothia or IMGT numbering system);

(b) an isolated antibody heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively (or an antibody having the CDR sequences of mAb C defined by the Chothia or IMGT numbering system); or (c) an isolated antibody heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively (or an antibody having the CDR sequences of mAb G defined by the Chothia or IMGT numbering system).

In some embodiments, the two or three antibodies comprise heavy and light chain variable regions comprising the amino acid sequences selected from the group consisting of:

(a) SEQ ID NOs: 25 and 26, respectively,
(b) SEQ ID NOs: 49 and 50, respectively, and
(c) SEQ ID NOs: 73 and 74, respectively.

In some embodiments, the two or three antibodies comprise heavy and light chains comprising the amino acid sequences selected from the group consisting of:

(a) SEQ ID NOs: 27 and 28, respectively,
(b) SEQ ID NOs: 51 and 52, respectively, and
(c) SEQ ID NOs: 75 and 76, respectively.

In some embodiments, the antibody mixture comprises two antibodies selected from subparts (a)-(c) (corresponding to embodiments relating to anti-CP mAbs E, C, and G, respectively, mentioned above). For example, the two antibodies are selected from the group consisting of: subparts (a) and (b), (a) and (c), and (b) and (c). In some embodiments, the two antibodies are present in an (a):(b), (a):(c), (b):(a), (b):(c), (c):(a), or (c):(b) ratio of 1-10:1-10, e.g., 10:1, 9:1, 8:1, 7:1, 6:1, 5:1, 4:1, 3:1, 2:1, or 1:1. In a particular embodiment, the two antibodies are present in an (a):(b), (a):(c), (b):(a), (b):(c), (c):(a), or (c):(b) ratio of 2:1.

In some embodiments, the antibody mixture comprises antibodies of subparts (a)-(c) (corresponding to embodiments relating to anti-CP mAbs E, C, and G, respectively, as mentioned above). In some embodiments, the three antibodies are present in an (a):(b):(c), (a):(c):(b), (b):(a):(c), (b):(c):(a), (c):(a):(b), or (c):(b):(a) ratio of 1-10:1-10:1-10, e.g., 1-3:1-3:1-3, for example, 3:1:1, 2:1:1, 1:1:1, 3:3:2, 3:3:1, 3:2:2, 3:2:1, 2:3:1, 2:2:1, 2:3:1, 1:3:1, or 1:2:1. In a particular embodiment, the three antibodies are present in an (a):(b):(c), (a):(c):(b), (b):(a):(c), (b):(c):(a), (c):(a):(b), or (c):(b):(a) ratio of 2:1:1.

Standard assays to evaluate the binding ability of the antibodies toward human ceruloplasmin are known in the art, including for example, ELISAs, Western blots, and RIAs. Suitable assays are also described in detail in the Examples. The binding kinetics (e.g., binding affinity) of the antibodies also can be assessed by standard assays known in the art, such as by surface plasmon resonance (Biacore analysis) and the Octet assay.

In some embodiments, the anti-ceruloplasmin antibodies or antibody mixtures described herein are used to capture (e.g., immunocapture) ceruloplasmin (e.g., human ceruloplasmin having the sequence set forth in SEQ ID NO: 1 or 2) in a biological sample, such as serum or plasma. In some embodiments, the anti-ceruloplasmin antibodies or antibody mixtures immunocapture at least about 70%, for example, about 75%, about 80%, about 85%, about 90%, about 95%, about 96%, about 97%, about 98%, about 99%, about 100%, about 70% to about 100%, about 75% to about 100%, about 80% to about 100%, about 85% to about 100%, about 90% to about 100%, about 95% to about 100%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, or about 90% to about 99% of ceruloplasmin the biological sample. In some embodiments, immunocapture of ceruloplasmin and subsequent removal of the immunocaptured ceruloplasmin in a biological sample yields a biological sample which is essentially free of ceruloplasmin. In some embodiments, immunocapture of ceruloplasmin and subsequent removal of the immunocaptured ceruloplasmin in a biological sample yields a biological sample which is essentially free of ceruloplasmin-bound copper.

In some embodiments, the anti-ceruloplasmin antibodies or antibody mixtures described herein are used to deplete (e.g., immunodeplete) ceruloplasmin (e.g., human ceruloplasmin, for example, human ceruloplasmin bound to copper) from a biological sample, such as serum or plasma. In some embodiments, the anti-ceruloplasmin antibodies or antibody mixtures deplete at least about 70%, for example, about 75%, about 80%, about 85%, about 90%, about 95%, about 96%, about 97%, about 98%, about 99%, about 100%, about 70% to about 100%, about 75% to about 100%, about 80% to about 100%, about 85% to about 100%, about 90% to about 100%, about 95% to about 100%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, or about 90% to about 99% of ceruloplasmin from the biological sample. In some embodiments, depletion of ceruloplasmin in a biological sample yields a biological sample which is essentially free of ceruloplasmin. In some embodiments, depletion of ceruloplasmin in a biological sample yields a biological sample which is essentially free of ceruloplasmin-bound copper.

In some embodiments, about 15% or less, for example, about 14% or less, about 13% or less, about 12% or less, about 11% or less, about 10% or less, about 9% or less, about 8% or less, about 7% or less, about 6% or less, about 5% or less, about 4% or less, about 3% or less, about 2% or less, about 1% or less, 0-15%, 0-14%, 0-13%, 0-12%, 0-10%, 0-9%, 0-8%, 0-7%, 0-6%, 0-5% 0-4%, 0-3%, 0-2%, or 0-1% of ceruloplasmin remains in a biological sample (e.g., serum or plasma) after immunocapture and subsequent removal of the immunocaptured ceruloplasmin, or after immunodepletion of ceruloplasmin using the anti-ceruloplasmin antibodies or antibody mixtures described herein.

In some embodiments, the anti-ceruloplasmin antibodies and antibody mixtures described herein are used to immunocapture or immunodeplete ceruloplasmin from a biological sample to allow for the direct measurement of free copper concentrations (i.e., non-ceruloplasmin bound copper or NCC) or labile-bound copper (LBC) concentrations.

In some embodiments, the anti-ceruloplasmin antibodies described herein are bound (covalently or non-covalently) to a solid support. Any suitable solid support known in the art can be used. For example, in some embodiments, the solid support is selected from the group consisting of immunocapture beads, agarose resin, chromatography plate, streptavidin plate, and titer plate (e.g., a microtiter plate). In some embodiments, the immunocapture beads are magnetic immunocapture beads. In some embodiments, the immunocapture beads are streptavidin-coated beads, Protein G beads, Protein A beads, or Protein A/G beads. In some embodiments, the immunocapture beads are tosylactivated beads (e.g., tosylactivated paramagnetic beads), for example, tosylactivated Dynabeads® (e.g., Dynabeads® M-280 and M-450 from Thermo Fisher Scientific). In some embodiments, the antibody or antibodies in the antibody mixture are irreversibly linked to the solid support. In some embodiments, the antibody or antibody mixture (i.e., antibodies in the antibody mixture) is irreversibly linked to immunocapture beads.

An antibody that exhibits one or more of the functional properties described above (e.g., biochemical, immunochemical, cellular, physiological or other biological activities, or the like) as determined according to methodologies known to the art and described herein, will be understood to relate to a statistically significant difference in the particular activity relative to that seen in the absence of the antibody (e.g., or when a control antibody of irrelevant specificity is present). For example, the anti-ceruloplasmin antibody-induced increases in a measured parameter (e.g., immunocapture or immunodepletion efficiency) effects a statistically significant increase by at least 10% of the measured parameter, such as by at least 20%, 30%, 40%, 50%, 60%, 70%, 80%, 90%, 95%, or 100% (i.e., 2 fold), 3 fold, 5 fold or 10 fold. Conversely, anti-ceruloplasmin antibody-induced decreases in a measured parameter (e.g., amount of ceruloplasmin remaining in a biological sample) effects a statistically significant decrease by at least 10%, 20%, 30%, 40%, 50%, 60%, 70%, 80%, 90%, 95%, 97%, 98%, 99%, or 100%.

In some embodiments, a VH domain of the anti-ceruloplasmin antibodies described herein is linked to a constant domain to form a heavy chain, e.g., a full-length heavy chain. In some embodiments, the VH domain is linked to the constant domain of a human immunoglobulin, e.g., IgG1, IgG2, IgG3, IgG4, IgM, IgA1, IgA2, IgAsec, IgD, and IgE, or variants thereof (e.g., variants comprising Fc regions with reduced or no effector function), or an equivalent from another species (e.g., rabbit). In some embodiments, the VH domain is linked to the constant domain of a rabbit immunoglobulin (e.g., the heavy chain constant domain of SEQ ID NO: 3). Similarly, a VL domain of the anti-ceruloplasmin antibodies described herein described herein is linked to a constant domain (e.g., a human constant domain or a rabbit constant domain of SEQ ID NO: 4) to form a light chain, e.g., a full-length light chain.

In certain embodiments, the variant or altered constant region has at least one amino acid substitution, insertion, and/or deletion, compared to a native sequence constant region or to the constant region of a parent polypeptide, e.g. from about 1 to about 100 amino acid substitutions, insertions, and/or deletions in a native sequence constant region or in the constant region of the parent polypeptide. In some embodiments, the variant or altered constant region herein will possess at least about 70% homology (similarity) or identity with a native sequence constant region and/or with a constant region of a parent polypeptide, and in some instances at least about 75% and in other instances at least about 80% homology or identity therewith, and in other embodiments at least about 85%, 90% or 95% homology or identity therewith. The variant or altered constant region may also contain one or more amino acid deletions or insertions. Additionally, the variant constant region may contain one or more amino acid substitutions, deletions, or insertions that results in altered post-translational modifications, including, for example, an altered glycosylation pattern. Recombinant DNA technology may be used to engineer one or more amino acid substitutions, deletions, or insertions in the antibodies, e.g., in the variable region and/or constant region. Standard DNA mutagenesis techniques as described in, e.g., Sambrook et al. (1989) "Molecular Cloning: A Laboratory Manual, 2$^{nd}$ Edition," Cold Spring Harbor Laboratory Press, Cold Spring Harbor, N.Y.; Harlow and Lane (1988); Borrebaek, *Antibody Engineering—A practical guide* (1992); Johne et al., *J Immunol Methods* 160:191-198 (1993), International Publication No. WO 06/53301; and U.S. Pat. No. 7,704,497.

The anti-ceruloplasmin antibodies disclosed herein include all known forms of antibodies and other protein scaffolds with antibody-like properties. For example, the antibody can be a humanized antibody, bispecific antibody, an immunoconjugate, a chimeric antibody (e.g., a chimeric antibody having rabbit variable region sequences and human constant region sequences), or a protein scaffold with antibody-like properties, such as fibronectin or ankyrin repeats. The antibody also can be a Fab, Fab'2, scFv, affibody, avimer, nanobody, or a domain antibody. Full-length antibodies can be prepared from $V_H$ and $V_L$ sequences using standard recombinant DNA techniques and nucleic acids encoding the desired constant region sequences can be operatively linked to the variable region sequences. Exemplary sequences of anti-ceruloplasmin antibodies are shown in Table 19.

The anti-ceruloplasmin antibodies, and mixtures of anti-ceruloplasmin antibodies (e.g., mAb cocktails), described herein are stable over a long period. In certain embodiments, the antibodies or mixture of antibodies have a shelf-life of at least 9 months, for example, at least 10 months, at least 11 months, at least 12 months, at least 18 months, at least 24 months, at least 36 months, 9-36 months, 9-24 months, 9-18 months, 12-36 months, 12-24 months, 12-18 months, 18-36 months, 18-24 months, or 24-36 months, e.g., in a liquid state or solid state, e.g., at a temperature of 2-8° C. Stability can be measured, for example, by CP binding activity of the antibody or mixture of antibodies, e.g., by ELISA as described in the Examples. In certain embodiments, the antibodies or mixture of antibodies described herein show less than a 20% loss (e.g., less than a 15% loss, less than a 10% loss, or less than a 5% loss) of CP binding activity relative to baseline (e.g., freshly prepared antibody or antibody mixture) for at least 3 months, at least 6 months, at least 9 months, at least 10 months, at least 11 months, at least 12 months, at least 18 months, at least 24 months, at least 36 months, 3-9 months, 3-12 months, 3-24 months, 3-36 months, 6-9 months, 6-12 months, 6-24 months, 6-36 months, 9-12 months, 9-24 months, 9-36 months, 12-24 months, 12-36 months, 18-24 months, 18-36 months, or 24-36 months, e.g., when stored at a temperature of 2-8° C., e.g., when using the method described in the Examples.

IV. Nucleic Acids

Also provided herein are nucleic acid molecules that encode the antibodies described herein. The nucleic acids may be present in whole cells, in a cell lysate, or in a partially purified or substantially pure form. Accordingly, also provided herein are host cells comprising these nucleic acid molecules, as well as expression vectors comprising these nucleic acid molecules. A nucleic acid described herein can be, for example, DNA or RNA and may or may not contain intronic sequences. In certain embodiments, the nucleic acid is a cDNA molecule.

Nucleic acids described herein can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, provided herein are nucleic acid molecules that encode the VH and/or VL sequences, or heavy and/or light chain sequences, of any of the anti-ceruloplasmin antibodies described herein. For example, in some embodiments, provided are nucleic acids comprising a nucleotide sequence selected from the group consisting of SEQ ID NOs: 197-228. In some embodiments, provided are nucleic acids encoding the heavy and/or light chain variable region, or heavy and/or light chain, or antigen-binding portion thereof, within the nucleotide sequence selected from the group consisting of SEQ ID NOs: 197-228. Host cells comprising the nucleic acids (e.g., nucleic acid molecules), or set of nucleic acids, described herein also are provided.

Once DNA fragments encoding variable region segments are obtained, these DNA fragments can be further manipulated by standard recombinant DNA techniques, for example, to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region (e.g., SEQ ID NO: 229 or 230) or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. In some embodiments, the heavy chain constant region is a rabbit heavy chain constant region.

The heavy chain constant region can be an IgG1, IgG2, IgG3, IgG4, IgA, IgE, IgM or IgD constant region, or equivalent from other species (e.g., rabbit). For a Fab fragment heavy chain gene, the VH-encoding DNA can be operatively linked to another DNA molecule encoding only the heavy chain CH1 constant region. The heavy chain constant region can also be a rabbit IgG constant region (e.g., SEQ ID NO: 229).

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991)) and DNA fragments encompassing these regions can be obtained by standard PCR amplification. The light chain constant region can be a kappa or lambda constant region. In some embodiments, the light chain constant region is a rabbit light chain constant region (e.g., SEQ ID NO: 230).

In some embodiments, nucleic acid molecules encoding the heavy and light chain variable regions, or heavy and light chains, are present in a single expression vector. In some embodiments, nucleic acid molecules encoding the heavy and light chain variable regions, or heavy and light chains, are present in multiple expression vectors (set of expression vectors) which can be introduced into a host cell together such that the heavy and light chain variable regions, or heavy and light chains, are co-expressed in the cell.

scFv genes can be created by operatively linking the VH- and VL-encoding DNA fragments to another fragment encoding a flexible linker known in the art such that the VH and VL sequences can be expressed as a contiguous single-chain protein, with the VL and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Also provided herein are nucleic acid molecules with conservative sequence modifications (i.e., substitutions that do not alter the resulting amino acid sequence upon translation of nucleic acid molecule), e.g., for codon optimization.

IV. Methods of Production

Suitable methods for producing an antibody (e.g., an anti-ceruloplasmin antibody) or antigen-binding fragments thereof, in accordance with the disclosure are known in the art (see, e.g., U.S. Pat. Nos. 7,427,665; 7,435,412; and 7,408,041, the disclosures of each of which are incorporated herein by reference in their entirety) and described herein. Recombinant techniques may be used to produce antibodies based on the sequence of the monoclonal antibodies.

Recombinant DNA technology can be used to modify one or more characteristics of the antibodies produced in non-human cells. Thus, chimeric antibodies can be constructed (e.g., an antibody comprising a rabbit variable region and a human constant region). Moreover, antibodies can be humanized by CDR grafting and, optionally, framework modification. See U.S. Pat. Nos. 5,225,539 and 7,393,648, the contents of each of which are incorporated herein by reference.

Recombinant DNA technology can be used to produce the antibodies according to established procedure, including procedures in bacterial or mammalian cell culture. In such embodiments, the selected cell culture system secretes the antibody product.

In some embodiments, the process for the production of an antibody disclosed herein includes culturing a host, e.g., *E. coli* or a mammalian cell (e.g., CHO cell), which has been transformed with a hybrid vector. The vector includes one or more expression cassettes containing a promoter operably linked to a first DNA sequence encoding a signal peptide linked in the proper reading frame to a second DNA sequence encoding the antibody protein (e.g., the heavy and/or light chain variable region, or the heavy and light chain, of an anti-ceruloplasmin antibody described herein). The antibody protein is then collected and isolated. Optionally, the expression cassette may include a promoter operably linked to a polycistronic (e.g., bicistronic) DNA sequence encoding antibody proteins each individually operably linked to a signal peptide in the proper reading frame.

Large quantities of the desired antibodies can also be obtained by multiplying mammalian cells in vivo. Multiplication of mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g., in an airlift reactor or in a continuous stirrer reactor), and immobilized or entrapped cell culture (e.g., in hollow fibers, microcapsules, on agarose microbeads or ceramic cartridges).

The foregoing, and other, techniques are discussed in, for example, Kohler and Milstein, (1975) *Nature* 256:495-497; U.S. Pat. No. 4,376,110; Harlow and Lane, *Antibodies: a Laboratory Manual*, (1988) Cold Spring Harbor, the disclosures of which are all incorporated herein by reference. Techniques for the preparation of recombinant antibody molecules are described in the above references and also in, e.g.: WO 97/08320; U.S. Pat. Nos. 5,427,908; 5,508,717; Smith (1985) *Science* 225:1315-1317; Parmley and Smith (1988) *Gene* 73:305-318; De La Cruz et al. (1988) *J. Biol. Chem.* 263:4318-4322; U.S. Pat. Nos. 5,403,484; 5,223,409; WO 88/06630; WO 92/15679; U.S. Pat. Nos. 5,780,279; 5,571,698; 6,040,136; Davis et al. (1999) *Cancer Metastasis Rev.* 18(4):421-5; and Taylor et al. (1992) *Nucleic Acids Research* 20: 6287-6295; Tomizuka et al. (2000) *Proc. Natl. Acad. Sci. USA* 97(2): 722-727, the contents of each of which are incorporated herein by reference in their entirety.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with one or more surface polypeptides derived from a ceruloplasmin-expressing cell line or synthetic ceruloplasmin fragment peptides, or with Protein-A or -G.

The antibodies and fragments thereof can be "chimeric." Chimeric antibodies and antigen-binding fragments thereof comprise portions from two or more different species (e.g., rabbit and human). Chimeric antibodies can be produced with rabbit variable regions of desired specificity spliced into human constant domain gene segments (for example, U.S. Pat. No. 4,816,567).

Also contemplated are "humanized" forms of the non-human (e.g., rabbit) antibodies (e.g., humanized form of the anti-ceruloplasmin antibodies disclosed herein). Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006)*Mol Immunol* 43:1243-1257. Methods for humanizing rabbit antibodies are known in the art (see, e.g., US2009/0104187, US2016/0347864, US2018/0127493, U.S. Pat. No. 9,593,161, WO04/016740, WO08/144757, WO05/016950, Weber et al., Experimental & Molecular Medicine 2017; 49:e305; Yu et al., PLoS ONE 2010; 5; e9072; Yu et al., Biochem Biophys Res Commun 2013; 436:543-50; Borras et al., J Biol Chem 2010; 285:9054-66; Rader et al., J Biol Chem 2000; 275:13668-76; Steinberger et al., J Biol Chem 2000; 275:36073-78; Waldmeier et al., MAbs 2016; 8:726-70; Rader et al., PNAS 1998; 95:8910-15.

In some embodiments, humanized forms of non-human (e.g., rabbit) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

In some embodiments, a recombinant DNA comprising an insert coding for a heavy chain variable domain and/or for a light chain variable domain of an anti-ceruloplasmin antibody, or for a heavy chain and/or for a light chain expressing cell line is produced.

Furthermore, a DNA encoding a heavy chain variable domain and/or a light chain variable domain of anti-ceruloplasmin antibodies, or a heavy chain and/or a light chain of anti-ceruloplasmin antibodies, can be enzymatically or chemically synthesized to contain the authentic DNA sequence coding for a heavy chain variable domain and/or for the light chain variable domain, or for a heavy chain and/or for a light chain, or a mutant thereof. A mutant of the authentic DNA is a DNA encoding a heavy chain variable domain and/or a light chain variable domain, or a heavy chain and/or a light chain, of the above-mentioned antibodies in which one or more amino acids are deleted, inserted, or exchanged with one or more other amino acids. In some embodiments, said modification(s) are outside the CDRs of the heavy chain variable domain and/or of the light chain variable domain of the antibody in humanization and expression optimization applications.

As used herein, the term "mutant DNA" also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain. The term "mutant" is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods known in the art.

Accordingly, the monoclonal antibodies can be naked antibodies that are not conjugated to other agents, for example, a detectable label. Alternatively, the monoclonal antibody can be conjugated to an agent such as, for example, at least one of a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), a detectable label (e.g., an NMR or X-ray contrasting agent, fluorescent molecule, etc.), or a moiety to facilitate binding to a solid support (e.g., his-tag, flag-tag, myc-tag, HA-tag, and the like).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing selectable marker drug resistance genes such as *E. coli* gpt (Mulligan and Berg (1981) *Proc Natl Acad Sci USA,* 78:2072) or Tn5 neo (Southern and Berg (1982)*Mol Appl Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), polyoma virus (Deans et al. (1984) *Proc Natl Acad Sci USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983)*Mol Cell Biol* 3:280; Cepko et al. (1984) *Cell* 37:1053; and Kaufman (1985) *Proc Natl Acad Sci USA* 82:689.

V. Immunoconjugates

The anti-ceruloplasmin antibodies described herein can be modified following their expression and purification. The modifications can be covalent or non-covalent modifications. Such modifications can be introduced into the antibodies by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies.

In some embodiments, the antibodies can be conjugated to a heterologous moiety. The heterologous moiety can be, e.g., a heterologous polypeptide or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies or fragments or to facilitate immunocapture and/or immunodepletion. Heterologous polypeptides also include polypeptides that are useful as diagnostic or detectable markers, for example, luciferase, green fluorescent protein (GFP), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescence protein (GFP), DyLight 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase. Heterologous polypeptides can be incorporated into the anti-ceruloplasmin antibodies as fusion proteins. Methods for generating nucleic acids encoding an antibody-heterologous polypeptide fusion protein are well known in the art of antibody engineering and described in, e.g., Dakappagari et al. (2006) *J Immunol* 176:426-440.

Two proteins (e.g., an anti-ceruloplasmin antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α (2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the anti-ceruloplasmin antibodies described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an anti-ceruloplasmin antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) *Handbook of Radiopharmaceuticals: Radiochemistry and Applications*, John Wiley and Sons (ISBN 0471495603).

In some embodiments, the anti-ceruloplasmin antibodies described herein can be modified, e.g., with a moiety that improves the stabilization. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody (or fragment) by at least 1.5 (e.g., at least 2, 5, 10, 15, 20, 25, 30, 40, or 50 or more) fold.

In some embodiments, the anti-ceruloplasmin antibodies described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

VI. Methods of Use

Provided herein are methods of using the anti-ceruloplasmin antibodies and antibody mixtures described herein. The antibody and antibody mixtures are particularly useful for immunocapturing ceruloplasmin (e.g., human ceruloplasmin) from, e.g., biological samples such as human serum or plasma. Immunocaptured ceruloplasmin can then be removed from the biological sample to yield a biological sample from which ceruloplasmin is essentially depleted (e.g., less than 10%, for example, less than 9%, less than 8%, less than 7%, less than 6%, less than 5%, less than 4%, less than 3%, less than 2%, less than 1% ceruloplasmin remaining), allowing for the direct measurement of free copper concentrations, such as NCC or LBC concentrations. The antibodies and antibody mixtures described herein are also useful for measuring LBC concentrations, as described in further detail below. The antibodies and antibody mixtures are also suitable for use in standard molecular biology methods, such as ELISA, immunoblotting, and co-immunoprecipitation.

Methods of Measuring Free Copper

Provided herein are methods for measuring copper concentration in biological samples. For example, the disclosed methods provide efficient and accurate direct measurement of free copper in a sample, and eliminate some of the issues associated with currently used methods, such as biologically impossible negative values of estimated NCC, which is based on incorrect assumptions from the characteristics of fully-functional, non-Wilson disease, CP values. The methods disclosed herein provide an accurate and reliable quantitation of free copper because they directly measure free copper (i.e., are not an estimate).

Thus, in one aspect, provided herein is a method of measuring free copper concentration in a biological sample. In this method, the sample is contacted with an immunocapture reagent which binds to ceruloplasmin (i.e., the anti-ceruloplasmin antibodies and antibody mixtures described herein) and the captured ceruloplasmin is removed, thus obtaining a non-ceruloplasmin sample. Free copper concentration is then measured in the non-ceruloplasmin sample.

In general, any sample containing ceruloplasmin is a biological sample (e.g., serum, plasma) and can be used in the methods described herein. One of the hallmarks of Wilson disease is a serum ceruloplasmin concentration of less than 200 μg/mL. Thus, in some embodiments, the biological samples used in the methods described herein are those in which the ceruloplasmin concentration is less than about 200 μg/mL. In some embodiments, the samples used in the methods described herein are those in which the ceruloplasmin concentration is in the range of about 200 μg/mL to about 400 μg/mL.

In certain embodiments, the sample is a human plasma or human serum sample. In some embodiments, the sample is human plasma. In some embodiments, the sample is human serum. In some embodiments, the sample is a mammalian plasma or mammalian serum sample.

In the methods described herein, the sample is contacted with an immuno-capture reagent which binds to ceruloplasmin (i.e., an anti-ceruloplasmin antibody or antibody mixture described herein). Removing the captured ceruloplasmin yields a non-ceruloplasmin sample.

In certain embodiments, the anti-ceruloplasmin antibodies or antibody mixture described herein are immobilized on a solid support and used as the immune-capture reagent. In some embodiments, the anti-ceruloplasmin antibodies or antibody mixture described herein are configured to immobilize onto a solid support after complexing with ceruloplasmin. Any suitable solid support known in the art can be used. For example, in certain embodiments, the solid support is at least one solid support selected from magnetic beads, agarose resin, chromatography plate, streptavidin plate, and titer plate. In at least one embodiment, the solid support is magnetic beads. In another embodiment, the solid support is selected from agarose resin, chromatography plate, streptavidin plate, and titer plate.

Figure 9A:
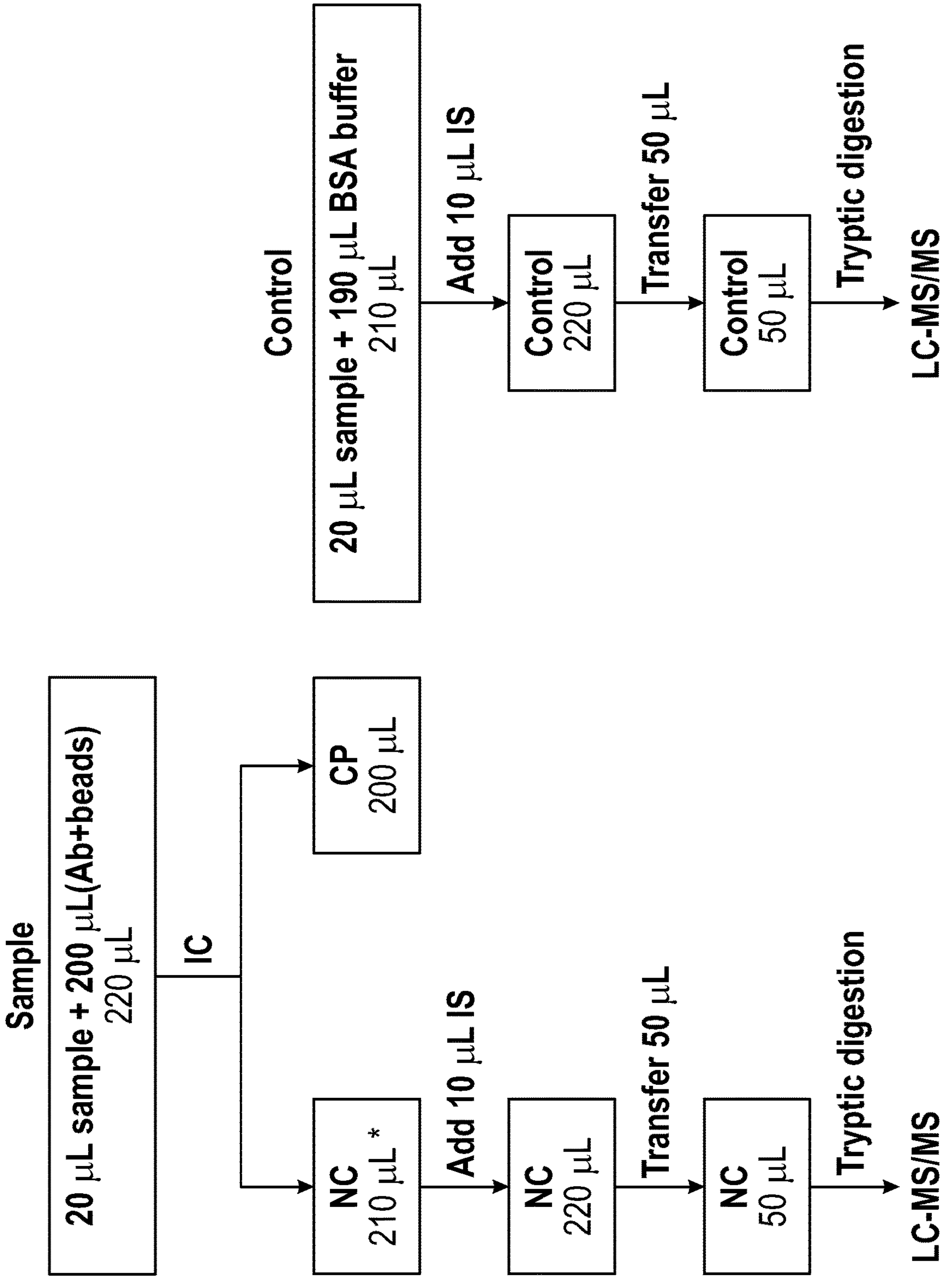
FIG. 9A is a schematic of a method used to assess immunocapture efficiency of the anti-CP mAbs. "IC" means immunocapture, "CP" means ceruloplasmin, "NC" means non-ceruloplasmin, "IS" means internal standard, and "LC-MS/MS" means liquid chromatography with tandem mass spectrometry.
Figure 9B:
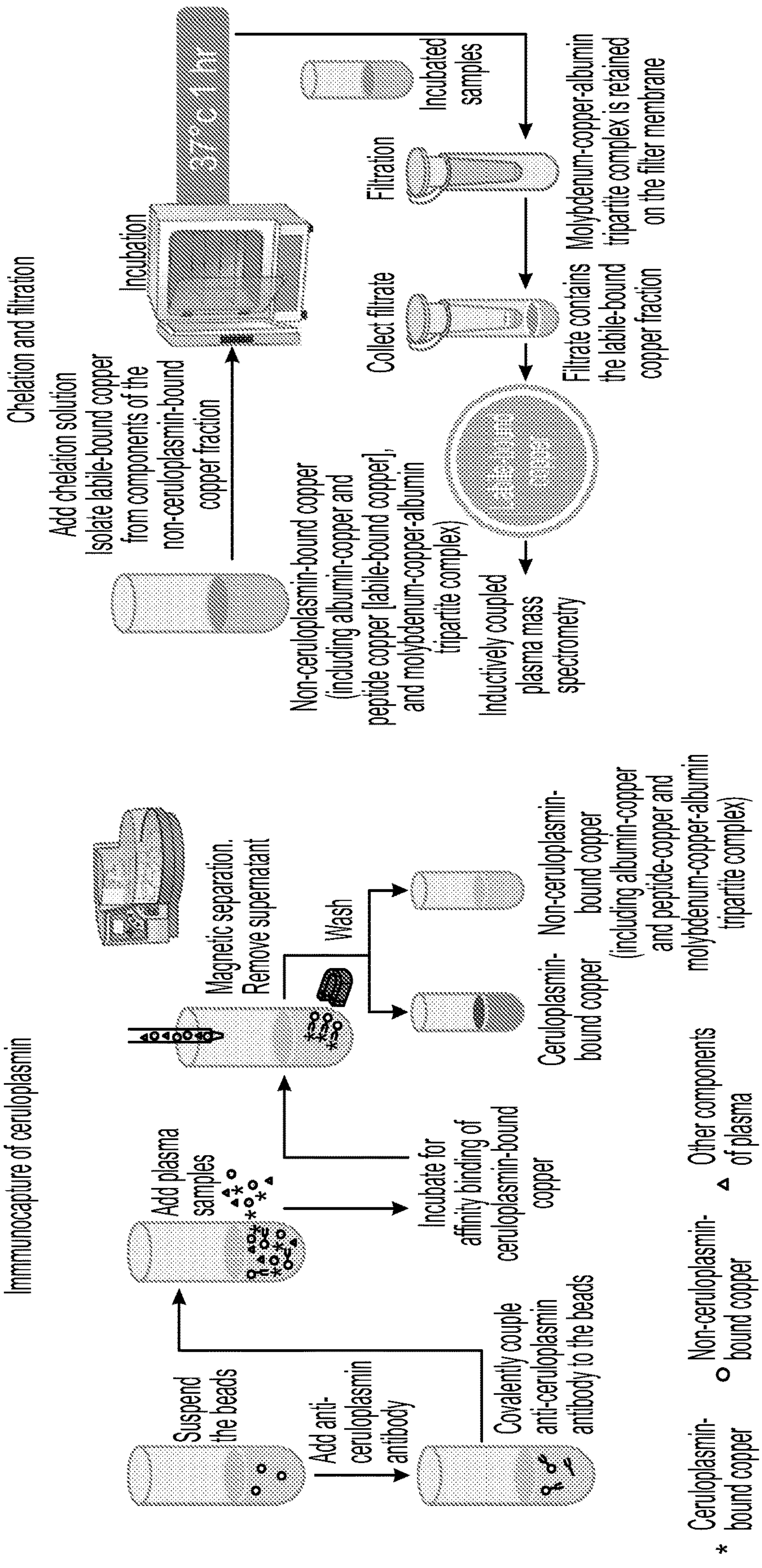
FIG. 9B is a graphic representation of a non-ceruloplasmin-bound copper assay (left panel) and a labile-bound copper assay (left panel and right panel, combined), in which the anti-CP mAbs and mAb mixtures disclosed herein may be used as the anti-CP antibody.
Figure 10A:
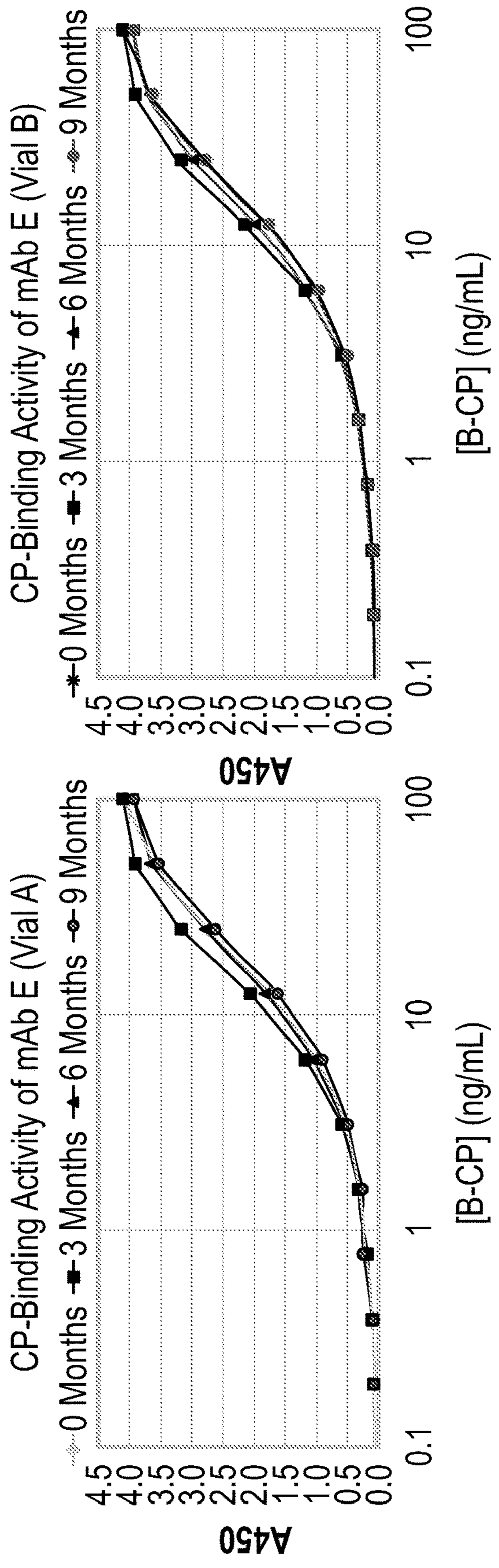
FIGS. 10A-10D are graphs showing the CP-binding activity of mAb E (FIG. 10A), mAb C (FIG. 10B), mAb G (FIG. 10C), and the mAb mix (1,2,3) (i.e., mAbs E:C:G at a 2:1:1 ratio) (FIG. 10D) over the course of 9 months. Absorbance was read at A450 nm.
Figure 10B:
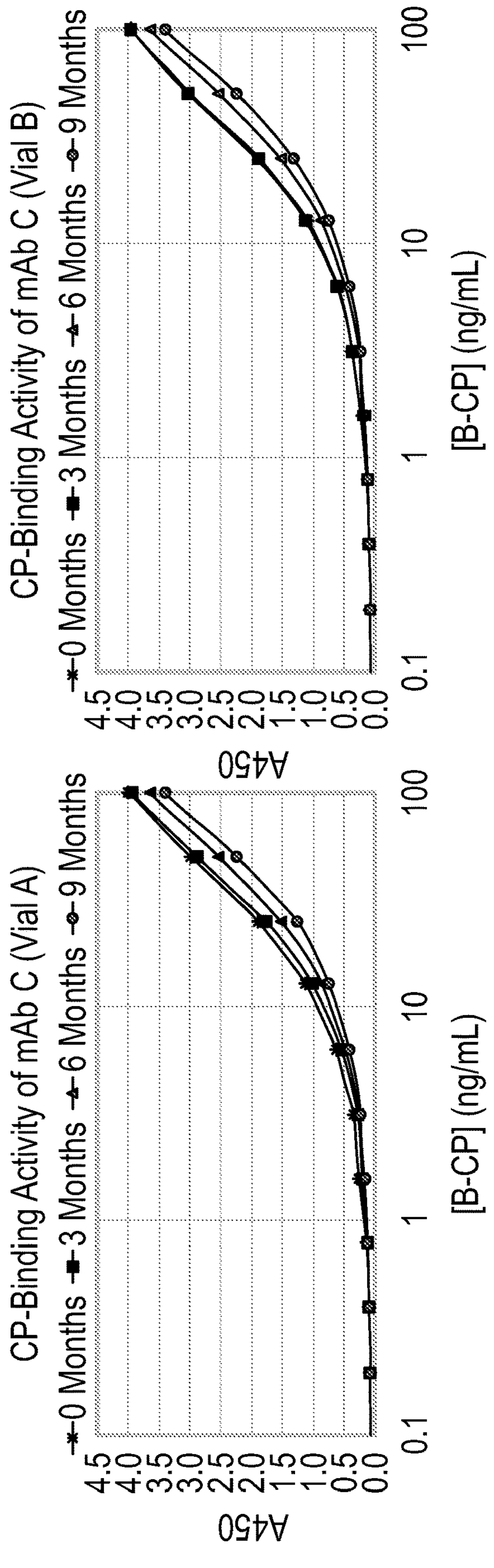
Figure 10C:
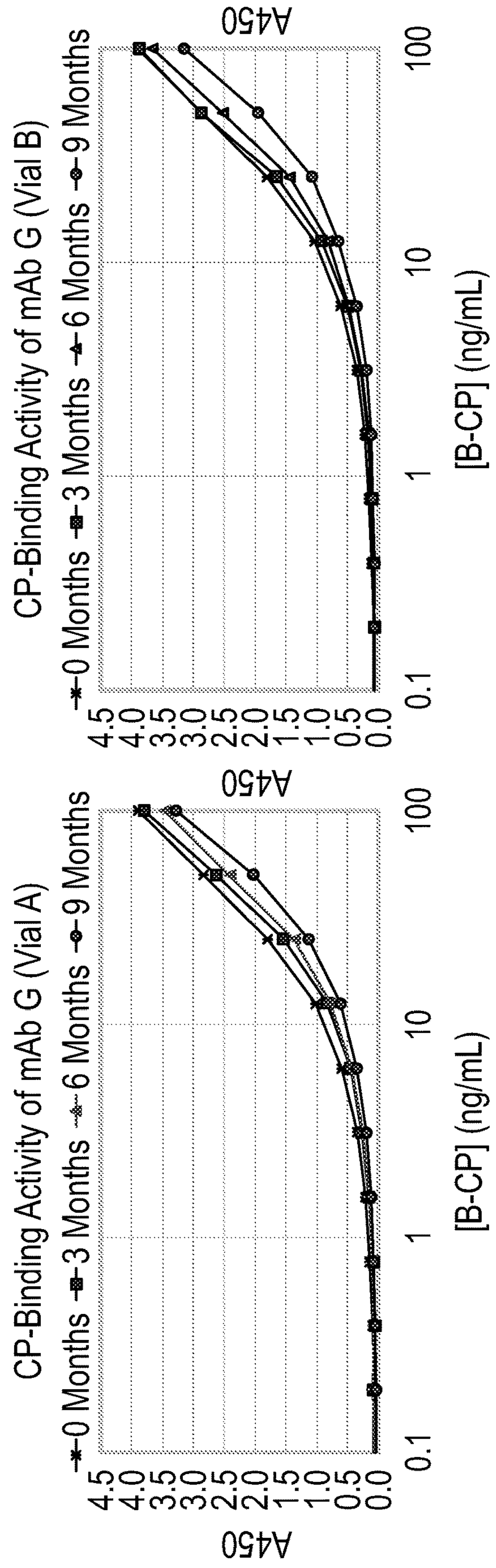
Figure 10D:
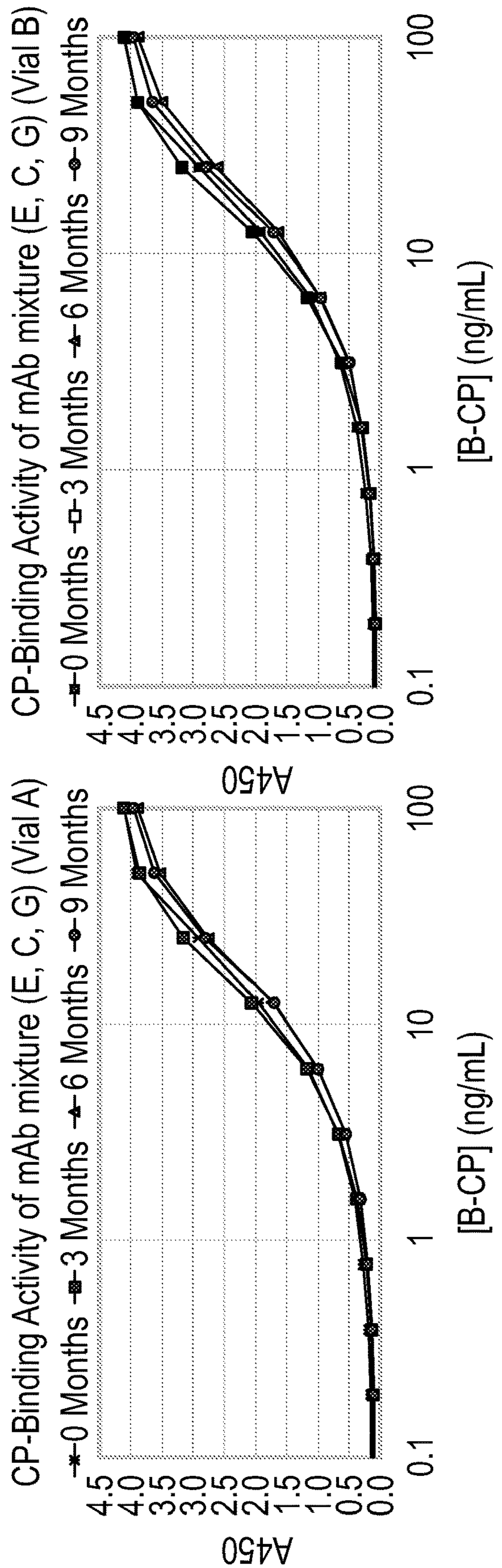

An exemplary embodiment of a method comprising coating beads with an anti-CP antibody or antibody mixture as disclosed herein, combining the resulting antibody-coated beads with a CP-containing sample, incubating the coated beads with the sample, and then removing the beads, resulting in a non-ceruloplasmin sample and a ceruloplasmin sample is graphically shown in FIG. 9B (left panel).

The anti-CP antibodies and antibody mixtures described herein show high efficiency of CP depletion, which can be determined by measuring ceruloplasmin in biological samples (e.g., plasma or serum samples) post-immunocapture. In some embodiments, the anti-ceruloplasmin antibodies or antibody mixtures deplete at least about 70%, for example, about 75%, about 80%, about 85%, about 90%, about 95%, about 96%, about 97%, about 98%, about 99%, about 100%, about 70% to about 100%, about 75% to about 100%, about 80% to about 100%, about 85% to about 100%, about 90% to about 100%, about 95% to about 100%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, or about 90% to about 99% of ceruloplasmin from the biological sample. In some embodiments, depletion of ceruloplasmin in a biological sample yields a biological sample which is essentially free of ceruloplasmin. In some embodiments, depletion of ceruloplasmin in a biological sample yields a biological sample which is essentially free of ceruloplasmin-bound copper.

In some embodiments, about 15% or less, for example, about 14% or less, about 13% or less, about 12% or less, about 11% or less, about 10% or less, about 9% or less, about 8% or less, about 7% or less, about 6% or less, about 5% or less, about 4% or less, about 3% or less, about 2% or less, about 1% or less, 0-15%, 0-14%, 0-13%, 0-12%, 0-10%, 0-9%, 0-8%, 0-7%, 0-6%, 0-5% 0-4%, 0-3%, 0-2%, or 0-1% of ceruloplasmin remains in a biological sample (e.g., serum or plasma) after immunocapture or depletion of ceruloplasmin using the anti-ceruloplasmin antibodies or antibody mixtures described herein.

In some embodiments, copper concentration in the non-ceruloplasmin sample is measured. In general, measuring the copper concentration is performed using inductively coupled plasma mass spectrometry (ICP-MS). Other analytical methods suitable for measuring copper concentration can be used including, but not limited to, inductively coupled plasma-optical emission spectroscopy (ICP-OES), and Zeeman graphite furnace atomic absorption spectroscopy (GFAAS).

In some embodiments, prior to measuring the copper concentration, an internal standard is introduced to the non-ceruloplasmin sample. In certain embodiments, the internal standard comprises at least one of copper, rhodium, and indium. In certain embodiments, the internal standard comprises at least one of copper and rhodium.

In the methods described herein, ceruloplasmin is removed by the anti-ceruloplasmin antibodies and antibody mixtures described herein to obtain a non-ceruloplasmin sample and an immunocaptured ceruloplasmin sample. In some embodiments, the immuno-captured ceruloplasmin sample can be further evaluated. For example, in certain embodiments, the methods described herein further comprise measuring the ceruloplasmin concentration of the immuno-captured ceruloplasmin sample. In general, the ceruloplasmin concentration is measured using mass spectrometry. Other analytical methods suitable for measuring protein concentration in a sample can also be used. In some embodiments, the mass spectrometry or other analytical methods have an analyte (i.e., ceruloplasmin) detection limit of at least about 5 μg/mL. Ceruloplasmin concentration can be performed using, e.g., liquid chromatography mass spectrometry (LC-MS). In other embodiments, the methods described herein further comprise measuring the copper concentration of the immunocaptured ceruloplasmin sample. The copper concentration can be measured as provided above with respect to measuring copper in the non-ceruloplasmin sample (e.g., using inductively coupled plasma mass spectrometry).

Direct measurement of copper concentration and ceruloplasmin concentration in the immuno-captured ceruloplasmin sample can provide a ratio of copper to ceruloplasmin, which can be used as another diagnostic parameter for copper metabolism-associated disorders, such as Wilson disease, and treatment. Accordingly, in one embodiment, the methods described herein further comprise determining the ratio of copper to ceruloplasmin based on the concentration of copper and the concentration of ceruloplasmin in the immuno-captured ceruloplasmin.

One of the therapeutic agents used to treat Wilson disease is bis-choline tetrathiomolybdate (BC-TTM), which removes excess copper by associating it with the tetrathiomolybdate anion. When tetrathiomolybdate binds to copper which is associated with proteins in tissue or blood, a tightly bound tripartite complex with the protein/copper (typically albumin/copper) is formed. Formation of this tetrathiomolybdate-copper-albumin tripartite complex ("TPC") is a hallmark of the BC-TTM mechanism of action, and differentiates BC-TTM from chelators, which do not form a protein complex with copper. As a result, molybdenum (Mo) has been used as a surrogate measurement to estimate BC-TTM exposure and adjust effective therapeutic doses.

The methods provided herein allow for direct quantification of NCC even in patients receiving BC-TTM. For example, the methods also allow for direct measurement of copper concentration in tetrathiomolybdate-copper-albumin tripartite complex (TPC, also known as MAC or Mo-Alb-Cu).

Thus, in some embodiments, the methods described herein further comprise contacting the non-ceruloplasmin sample with a molybdenum-capture reagent to obtain a molybdenum sample. The molybdenum-capture reagent may be a chelation competition reagent or a detergent. In some embodiments, the method further comprises measuring a molybdenum-bound copper concentration in the molybdenum sample. The copper concentration can be measured as provided above with respect to measuring copper in the non-ceruloplasmin sample. For example, the copper concentration of the molybdenum sample is measured using inductively coupled plasma mass spectrometry. The accurate non-ceruloplasmin-bound copper concentration may be obtained by subtracting the copper concentration of the molybdenum sample from the copper concentration in the non-ceruloplasmin sample. In some embodiments, the non-ceruloplasmin sample is subjected to ultrafiltration or contacted by an immuno-capture reagent to remove plasma ultrafiltration copper prior to contacting with the molybdenum-capture reagent.

In some embodiments, the methods provided herein further comprise contacting the non-ceruloplasmin sample with a chelator which binds to labile-bound copper present in the sample. In some embodiments, such chelator does not bind copper present in TPC. TPC can then be removed from the sample, leaving a sample comprising labile-bound copper ("labile-bound copper sample").

The chelator used in the methods described herein may be chosen from any chelator which binds to labile-bound copper, such as, as non-limiting examples, trientine hydrochloride, trientine tetrahydrochloride, penicillamine, and ethylenediaminetetraacetic acid (also known as EDTA). In some embodiments, the chelator comprises EDTA.

Following the addition of the chelator, the resulting sample optionally may be mixed and/or incubated. The TPC may be removed from the non-ceruloplasmin sample by any suitable technique known to those of ordinary skill in the art including, as a non-limiting example, filtration. In some embodiments, the sample is centrifuged following removal of the TPC.

As provided above, the methods described herein further comprise measuring the concentration of copper in the labile-bound copper sample. In general, measuring the copper concentration may be performed using inductively coupled plasma mass spectrometry (ICP-MS). Other analytical methods suitable for measuring copper concentration can be used including, but not limited to, inductively coupled plasma-optical emission spectroscopy (ICP-OES), and Zeeman graphite furnace atomic absorption spectroscopy (GFAAS).

An exemplary embodiment of a method further comprising contacting a non-ceruloplasmin sample with a chelator, incubating the resulting mixture, removing the TPC, and measuring the concentration of copper in the labile-bound copper sample is graphically shown in FIG. 9B (right panel).

In some embodiments, prior to measuring the copper concentration, an internal standard is introduced to the labile-bound copper sample. In some embodiments, the internal standard comprises at least one of copper, rhodium, and indium. In some embodiments, the internal standard comprises at least one of copper and rhodium.

Methods of Identifying or Diagnosing a Patient

Also provided herein are methods of identifying or diagnosing a patient having a copper metabolism-associated disease or disorder, the method comprising measuring the concentration of non-ceruloplasmin-bound copper in a sample from the patient according to the methods described herein, and identifying or diagnosing the patient having the disease or disorder using the concentration of non-ceruloplasmin-bound copper.

In another aspect, provided herein are methods of identifying or diagnosing a patient having a copper metabolism associated disease or disorder, the method including measuring the concentration of labile-bound copper in a sample from the patient according to the methods described herein, and identifying or diagnosing the patient having the disease or disorder using the concentration of labile-bound copper.

In some embodiments, the copper metabolism-associated disease or disorder is Wilson disease. In some embodiments, the copper metabolism-associated disease or disorder is copper toxicity (e.g., from high exposure to copper sulfate fungicides, ingesting drinking water high in copper, overuse of copper supplements, etc.). In some embodiments, the copper metabolism-associated disease or disorder is copper deficiency, Menkes disease, or aceruloplasminemia. In some embodiments, the copper metabolism-associated disease or disorder is one or more disease or disorder selected from the group consisting of academic underachievement, acne, attention-deficit/hyperactivity disorder, amyotrophic lateral sclerosis, atherosclerosis, autism, autoimmune disease, Alzheimer's disease, Candida overgrowth, chronic fatigue, cirrhosis, depression, elevated adrenaline activity, elevated cuproproteins, elevated norepinephrine activity, emotional meltdowns, fibromyalgia, frequent anger, geriatric-related impaired copper excretion, high anxiety, hair loss, hepatic disease, hyperactivity, hypothyroidism, intolerance to estrogen, intolerance to birth control pills, Kayser-Fleischer rings, learning disabilities, low dopamine activity, multiple sclerosis, neurological problems, oxidative stress, Parkinson's disease, poor concentration, poor focus, poor immune function, ringing in ears, allergies, sensitivity to food dyes, sensitivity to shellfish, skin metal intolerance, skin sensitivity, sleep problems, and white spots on fingernails.

Methods of Treatment

Provided herein are methods of treating and monitoring treatment of a patient having a copper metabolism-associated disease or disorder (e.g., a disease or disorder diagnosed using the antibodies, antibody mixtures, and methods described herein).

In some embodiments of the methods of treatment as described herein, the copper metabolism associated disease or disorder is Wilson disease. In some embodiments of the methods of treatment as described herein, the copper metabolism associated disease or disorder is copper toxicity (e.g., from high exposure to copper sulfate fungicides, ingesting drinking water high in copper, overuse of copper supplements, etc.). In some embodiments of the methods of treatment as described herein, the copper metabolism associated disease or disorder is copper deficiency, Menkes disease, or aceruloplasminemia. In some embodiments of the methods of treatment as described herein, the copper metabolism associated disease or disorder is at least one selected from academic underachievement, acne, attention-deficit/hyperactivity disorder, amyotrophic lateral sclerosis, atherosclerosis, autism, autoimmune disease, Alzheimer's disease, Candida overgrowth, chronic fatigue, cirrhosis, depression, elevated adrenaline activity, elevated cuproproteins, elevated norepinephrine activity, emotional meltdowns, fibromyalgia, frequent anger, geriatric-related impaired copper excretion, high anxiety, hair loss, hepatic disease, hyperactivity, hypothyroidism, intolerance to estrogen, intolerance to birth control pills, Kayser-Fleischer rings, learning disabilities, low dopamine activity, multiple sclerosis, neurological problems, oxidative stress, Parkinson's disease, poor concentration, poor focus, poor immune function, ringing in ears, allergies, sensitivity to food dyes, sensitivity to shellfish, skin metal intolerance, skin sensitivity, sleep problems, and white spots on fingernails.

In some embodiments, the methods include measuring the concentration of non-ceruloplasmin-bound copper or labile-bound copper in a sample from the patient according to the methods using the antibody or antibody mixtures described herein; diagnosing the patient with the copper metabolism associated disease or disorder using the concentration of non-ceruloplasmin-bound copper or labile-bound copper; and administering an effective amount of a therapeutic agent to the patient with the disease or disorder.

In some embodiments, the methods include administering an effective amount of a therapeutic agent to the patient having the copper metabolism associated disease or disorder, wherein the patient has been identified as having the disease or disorder using the concentration of non-ceruloplasmin-bound copper or labile-bound copper in a sample from the patient as measured by one or more of the methods using the antibody or antibody mixtures described herein.

In some embodiments, the method includes administering a first effective amount of a therapeutic agent to the patient; measuring the concentration of non-ceruloplasmin-bound copper or labile-bound copper in a sample from the patient according to the methods using the antibody or antibody mixtures described herein; adjusting the first effective amount of the therapeutic agent using the concentration of non-ceruloplasmin-bound copper or labile-bound copper to obtain a second effective amount; and administering the second effective amount of the therapeutic agent to the patient with the disease or disorder, wherein the second effective amount of the therapeutic agent is determined by a method comprising measuring the concentration of non-ceruloplasmin-bound copper or labile-bound copper in the sample from the patient according to the methods using the antibody or antibody mixtures described herein.

Treatment for Wilson disease targets removing copper accumulated in body tissues followed by preventing re-accumulation of copper. D-penicillamine and trientine are two chelators which may be used to treat symptomatic Wilson disease. D-penicillamine may be considered a first-line therapy; however, some patients require a switch to trientine after experiencing adverse events. Non-limiting examples of penicillamine include CUPRIMINE® (Valeant Pharmaceuticals, Inc.) and DEPEN® (Mylan Specialty LP). Trientine may also be used as a first-line therapy. Non-limiting examples of trientine include trientine hydrochloride (such as SYPRINE® (Valeant Pharmaceuticals, Inc.)) and trientine tetrahydrochloride (such as CUPRIOR® (gm-porphan SA)). The goal of treatment may include prevention of copper re-accumulation and maintenance therapy. Zinc salts (non-limiting examples include GALZIN® (zinc acetate) (Teva Pharmaceuticals) and WILZIN® (zine acetate dihydrate) (Recordati Rare Diseases)) may be used for maintenance treatment and may also be used as a first-line therapy in patients including, for example, asymptomatic patients, to reduce copper absorption. In the past, ammonium tetrathiomolybdate has been studied as a potential treatment option. Bis-choline tetrathiomolybdate (BC-TTM), a copper-protein-binding-agent, may also be used for the treatment of Wilson disease. BC-TTM is capable of rapidly forming copper protein complexes with high specificity, de-toxifying free copper in the liver and blood, and promoting biliary excretion of copper.

In some embodiments, the therapeutic agent is selected from the group consisting of bis-choline tetrathiomolybdate, zinc (or zinc salts), trientine hydrochloride, trientine tetrahydrochloride, and penicillamine. In other embodiments, the therapeutic agent comprises bis-choline tetrathiomolybdate. In some embodiments, the therapeutic agent is formulated in a pharmaceutical composition comprising a pharmaceutically acceptable carrier.

A therapeutically effective amount of BC-TTM has been previously established. For example, in certain embodiments, BC-TTM may be administered in the range of about 15 to 60 mg per day. In certain embodiments, BC-TTM is administered in an amount of about 15 mg daily. In certain embodiments, BC-TTM is administered in an amount of about 30 mg daily (e.g., about 15 mg taken twice daily or two 15 mg tablets taken once daily). In certain embodiments, BC-TTM is administered in an amount of about 45 mg daily (e.g., about 15 mg taken trice daily or three 15 mg tablets taken once daily). In certain embodiments, BC-TTM is administered in an amount of about 60 mg daily (e.g., about 15 mg taken four times daily or four 15 mg tablets taken once daily).

In certain other embodiments, BC-TTM may be administered in the range of about 15 to 60 mg every other day. In certain embodiments, BC-TTM is administered in an amount of about 60 mg every other day. In certain embodiments, BC-TTM is administered in an amount of about 15 mg every other day. In certain embodiments, BC-TTM is administered in an amount of about 30 mg every other day. In certain embodiments, BC-TTM is administered in an amount of about 45 mg every other day. In certain embodiments, BC-TTM is administered in an amount of about 60 mg every other day.

In some embodiments, the second effective amount is lower than the first effective amount. In other embodiments, the second effective amount is higher than the first effective amount.

In another aspect, provided herein are methods of identifying a subject as suited for treatment with bis-choline tetrathiomolybdate, the method including measuring the concentration of non-ceruloplasmin-bound copper in a sample from the subject according to the methods using the antibody or antibody mixtures described herein, identifying the subject as suited for treatment with bis-choline tetrathiomolybdate using the concentration of non-ceruloplasmin-bound copper, and optionally administering a therapeutically effective amount of bis-choline tetrathiomolybdate to the subject identified as suited for treatment with bis-choline tetrathiomolybdate.

In another aspect, provided herein are methods of identifying a subject as suited for treatment with bis-choline tetrathiomolybdate, the method including measuring the concentration of labile-bound copper in a sample from the subject according to the methods using the antibody or antibody mixtures described herein, identifying the subject as suited for treatment with bis-choline tetrathiomolybdate using the concentration of labile-bound copper, and optionally administering a therapeutically effective amount of bis-choline tetrathiomolybdate to the subject identified as suited for treatment with bis-choline tetrathiomolybdate.

Biomarker for Copper Metabolism

Free copper concentration in a biological sample may be indicative of the concentration of free copper that may be circulating in a patient's blood and accumulating in the patient's tissues and organs. NCC and/or LBC, as measured by the NCC assay and LBC assay methods using the antibody or antibody mixtures described herein, therefore may be biomarkers for a patient's copper metabolism. More particularly, NCC and/or LBC as measured by the NCC assay and NBC assay methods using the antibody or antibody mixtures described herein may be used to diagnose, identify, or monitor treatment of a patient having a copper metabolism-associated disorder or disease described herein.

The biomarker may be Compared to specific, validated reference ranges for free copper concentrations in healthy subjects or patients, which can serve as a threshold level. In some embodiments, the biomarker is compared to a threshold, e.g., specific, validated reference ranges for free copper concentrations in particular patient population sub-groups of interest, such as, for example, ethnicity, age, gender, co-morbidities, and other factors.

VII. Kits

Provided herein are kits for measuring copper concentrations, in particular, free copper concentration (e.g., NCC and/or LBC), in a biological sample (e.g., a human plasma or serum sample).

In some embodiments, the kits comprise an anti-ceruloplasmin antibody or antibody mixture described herein, optionally contained in a single vial or container, and include instructions for use, e.g., for immunocapture of ceruloplasmin from a sample (e.g., a biological sample). In some embodiments, the kits comprise an anti-ceruloplasmin antibody or antibody mixture described herein, a chelator described herein, and instructions for use.

The kits may also include a label indicating the intended use of the contents of the kit. The term label includes any writing, marketing materials or recorded material supplied on or with the kit, or which otherwise accompanies the kit. In some embodiments, the instructions for use include specific, validated reference ranges (thresholds) for free copper concentrations in particular population subgroups of interest, such as for example, ethnicity, age, gender, comorbidities, and other factors.

In some embodiments, the kits disclosed herein may be used to identify or diagnose a patient with a copper-metabolism-associated disorder or disease. In other embodiments, the kits disclosed herein may be used to monitor free copper in a patient over time.

In some embodiments, the kits described herein may form part of a kit comprising a therapeutic agent for use in treating a copper metabolism-associated disease or disorder, such as Wilson disease, and instructions for use.

The present invention is further illustrated by the following examples which should not be construed as further limiting. The contents of Sequence Listing, figures and all references, patents and published patent applications cited throughout this application are expressly incorporated herein by reference.

EXAMPLES

Commercially available reagents referred to in the Examples below were used according to manufacturer's instructions unless otherwise indicated. Unless otherwise noted, the present invention used known procedures for recombinant DNA technology, such as those described in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

Example 1: Generation of Anti-Ceruloplasmin (Anti-CP) Monoclonal Antibodies

A series of monoclonal antibodies (mAbs) against ceruloplasmin (CP) were generated by immunization of three different rabbits with purified human ceruloplasmin (Athens Research & Technology).

Peripheral blood mononuclear cells (PBMC) were isolated from the immunized rabbits by density gradient centrifugation using Ficoll Paque (GE Healthcare). Purified human ceruloplasmin was conjugated with DyLight 488 through available primary amines and incubated with the rabbit PBMC together with fluorescently labeled antibodies specific for rabbit IgG and IgM (Bethyl Laboratories).

Using a FACSJazz (Becton Dickinson), ceruloplasmin-binding, IgG positive cells were individually sorted into the wells of 96-well plates and provided with human IL-2 (ProSpec), human IL-21 (ProSpec), and soluble rabbit CD40L to stimulate proliferation and antibody secretion. After 12 days, 96-well culture supernatants were evaluated by ELISA for the presence of antibodies capable of binding ceruloplasmin. 250 of 1,336 wells were found to contain ceruloplasmin-specific antibody.

Cloning of individual antibody heavy and light chain pairs was attempted for 36 B-cell cultures exhibiting robust ceruloplasmin binding by ELISA (12 per rabbit to sample the antibody diversity of each). Briefly, IGHG VH and IGK1 VL were amplified by RT-PCR and then cloned into bacterial plasmid vectors to generate full length heavy and light chains. These vectors included a CMV promoter and a growth hormone polyadenylation signal sequence to facilitate expression in mammalian cells. Full length heavy and light chain expression vectors were cotransfected into suspension adapted HEK-293 cells in 6-well plates for transient production of antibody for subsequent screening.

Through a combination of VH and VL PCR product visualization by agarose gel electrophoresis, VH and VL sequence analysis, transient conditioned medium rabbit IgG quantitation, and transient conditioned medium ceruloplasmin binding activity assay, it was determined that 29 of the 36 cloning attempts resulted in the recovery of both VH and VL and the successful transient production of recombinant antibody capable of binding human ceruloplasmin, and that 28 of the antibodies were unique by sequence.

Example 2: Characterization of Anti-CP mAbs

A total of 28 functional anti-CP mAbs were obtained from the process described in Example 1 and tested for various properties.

Ceruloplasmin binding by the 28 recombinant anti-CP mAbs was tested as follows. Clear 96-well plates (Nunc, Maxisorp) were coated and incubated overnight at 4 degrees with 10 ug/mL goat anti-rabbit IgG-Fc (Bethyl Laboratories) in BupH carbonate-bicarbonate buffer (ThermoFisher). The coating solution was discarded, and the plates were blocked with 1% BSA in PBS at room temperature for 2 hours and then the blocking solution was discarded. The 28 anti-CP mAb transient conditioned media were diluted to 50 ng/mL in PBS-T containing 1% BSA and incubated on the blocked plates for 1 hour at room temperature. Negative control wells were incubated with PBS-T containing 1% BSA alone or with transient conditioned medium containing non-CP-specific rabbit mAb at 50 ng/mL.

Following 3 washes with TBS-T, captured mAbs were interrogated with one of the following for 1 hour at room temperature:

20 ng/mL purified human ceruloplasmin (Athens Research & Technology) diluted in PBS-T, 1:10 Li-Heparin normal human plasma diluted in PBS-T, 1:10,000 Li-Heparin normal human plasma diluted in PBS-T, or PBS-T alone.

Following 3 washes with TBS-T, bound ceruloplasmin was probed with biotinylated polyclonal goat anti-ceruloplasmin (Bethyl Laboratories) at 100 ng/mL diluted in PBS-T containing 1% BSA for 1 hour at room temperature.

Following 3 washes with TBS-T, the wells were incubated with HRP-conjugated streptavidin (ThermoFisher) at 40 ng/mL in Stabilzyme (Surmodics) for 30 minutes at room temperature.

Following 3 washes with TBS-T, anti-CP mAb bound ceruloplasmin was detected through the biotinylated goat anti-ceruloplasmin/streptavidin-HRP complex by addition of TMB substrate (Surmodics) at room temperature. The HRP-TMB reaction was stopped after 15 minutes by the addition of 0.18 M sulfuric acid and absorbance at 450 nm measured using a spectrophotometer.

Figure 2:
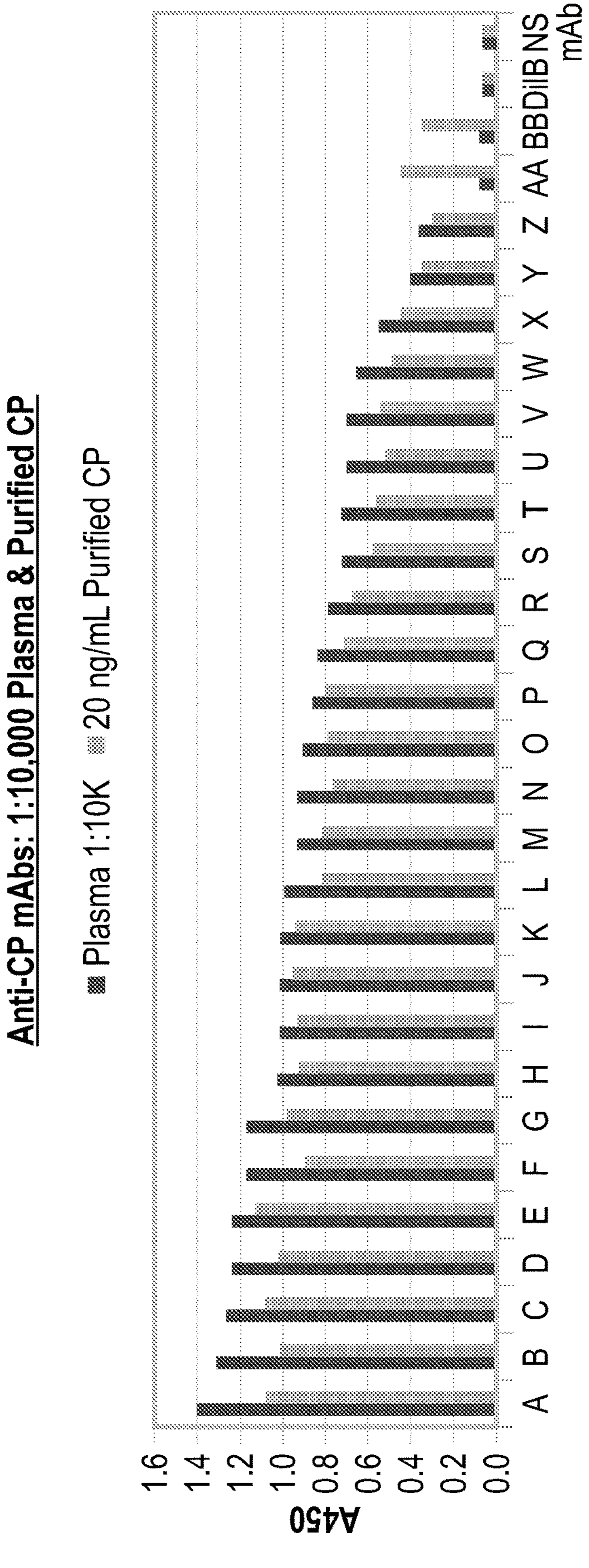
FIG. 2 is a graph showing the ability of 28 anti-CP mAbs to bind to endogenous human CP in lithium-heparin plasma diluted 1:10 with PBS-T, or 20 ng/mL purified CP in an ELISA. Absorbance was read at A450 nm. "DilB" means "dilution buffer" and corresponds to no mAb captured, and "NS mAb" means "non-specific monoclonal antibody."
Figure 3:
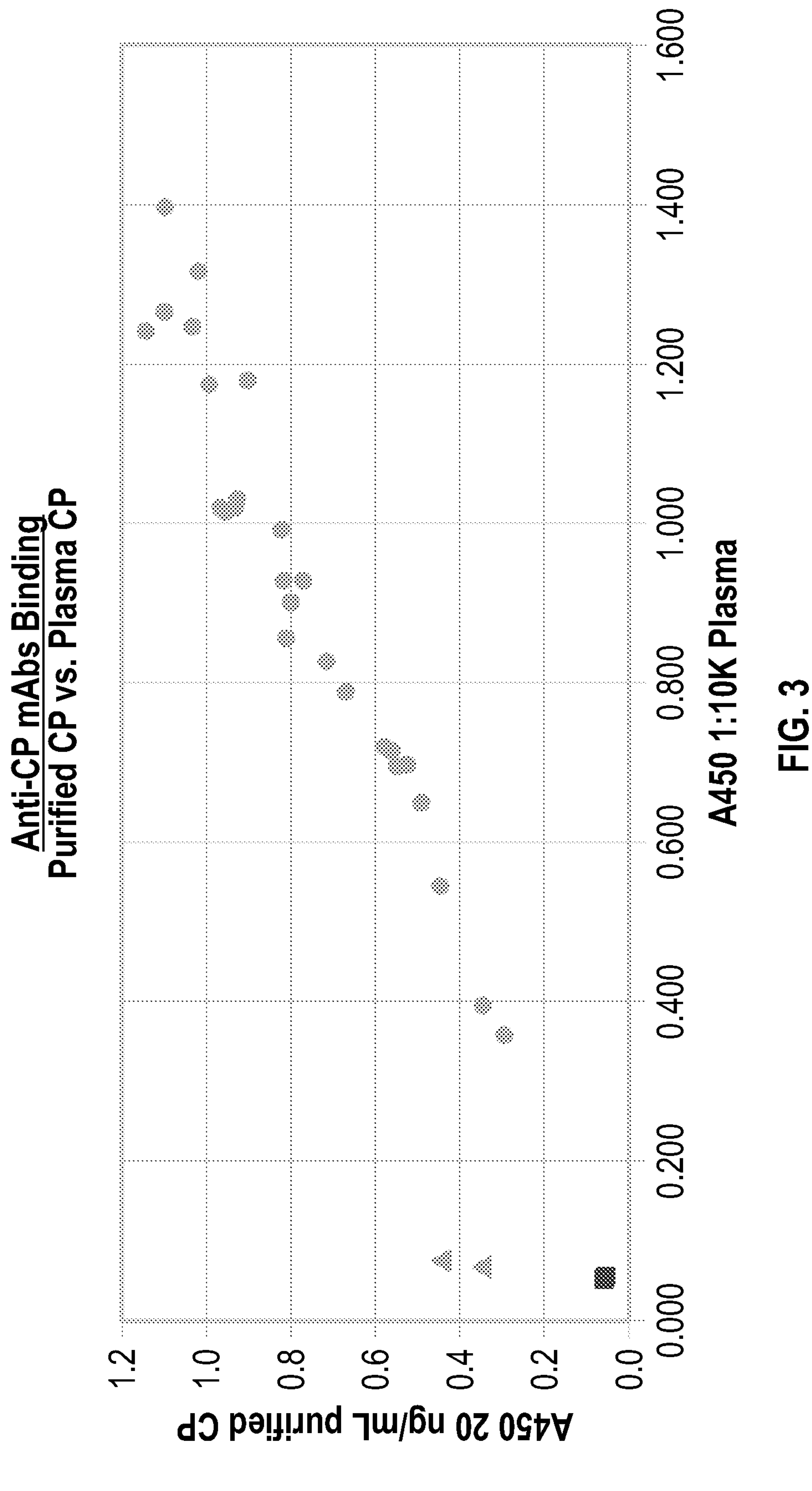
FIG. 3 is a graph showing correlations in CP binding strength of anti-CP antibodies between 1:10,000 plasma and purified CP samples.

As shown in FIG. 1, while background was high for 1:10 plasma (see dilution buffer ("DilB"), which corresponds to no mAb captured, and non-CP-specific antibody ("NS mAb")), all 28 mAbs bound to endogenous human CP. Given the uniformly high signal across antibodies, ranking was not possible from this data. Accordingly, the anti-CP mAbs were additionally tested using further diluted plasma (1:10,000), which allowed for the ranking of CP binding strength with good correlation between the results for each analyte (i.e., 1:10,000 plasma and purified CP), as shown in FIGS. 2 and 3. In FIG. 3, DilB and NS mAb are shown as squares. Two mAbs (AA and BB, shown as triangles in FIG. 3) showed poor correlation between binding to plasma CP and purified CP.

Next, the anti-CP mAbs were tested for their ability to immunodeplete CP from purified CP in NETN buffer. Briefly, 50 uL Protein G Dynabeads were incubated with 6 ug of unpurified mAb for 2.5 hours. mAb CM was removed and beads were incubated with 10 ug purified CP in NETN buffer overnight. CP solution was removed (post-immunoprecipitation ("IP") input) and beads were washed with NETN and bound protein eluted with gel loading buffer. 500 of eluate was run on an SDS-PAGE gel for subsequent Western blotting with the A80-124A polyclonal antibody and detection with a rabbit anti-goat-HRP secondary antibody. Pre-IP input (0.33 ug) was included on the gel along with Ips performed using A80-124A (positive control) and polyclonal non-immune rabbit IgG (negative control). 3.3% of post-IP input was analyzed in the same manner as the protein released from the beads.

Figure 4:
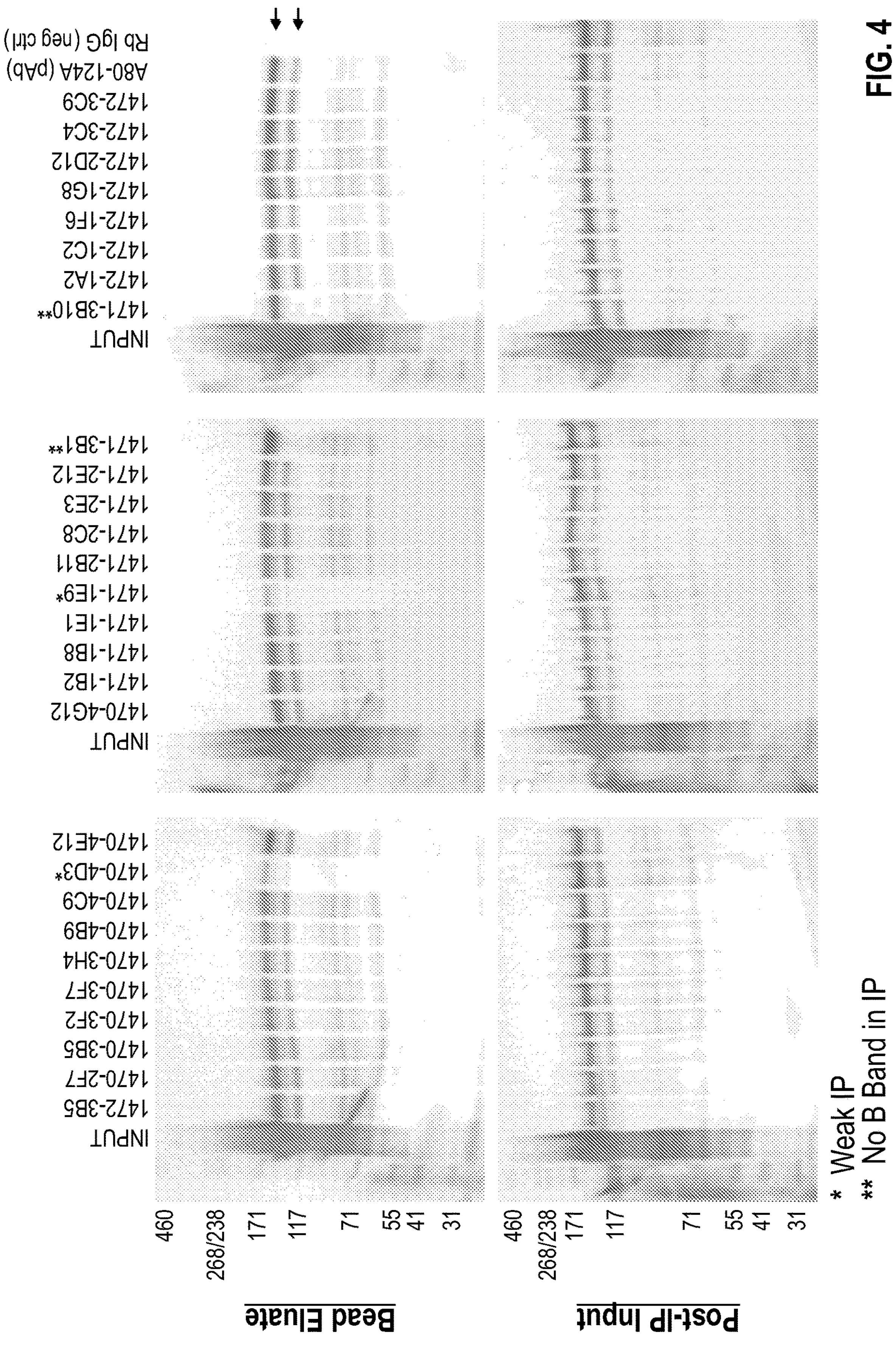
FIG. 4 is a series of Western blot images showing the ability of anti-CP antibodies to immunocapture CP from purified CP in NETN buffer. Rabbit IgG was used as a negative control. The positive control was a polyclonal anti-CP antibody (A80-124A). The top panel shows immunocapture results, and the bottom panel shows the amount of CP removed as a post-immunoprecipitation input.
Figure 5A:
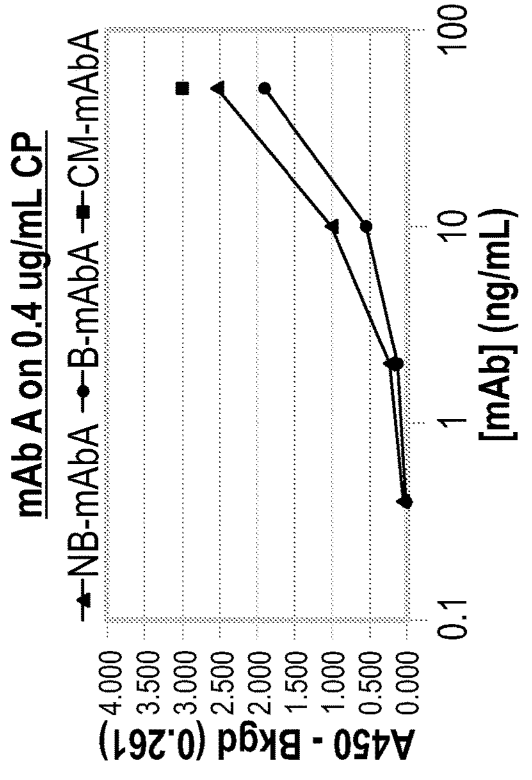
FIGS. 5A-5H are graphs showing the ability of 8 anti-CP mAbs (A, B, C, D, E, F, G, and H) to bind CP coated on plates at 0.4 ug/mL in an ELISA. Absorbance was read at A450 nm. "B-" indicates the respective mAb was biotinylated, "NB-" indicates the respective mAb was not biotinylated, and "CM-" indicates the respective mAb was in unpurified transient transfection conditioned medium.
Figure 5B:
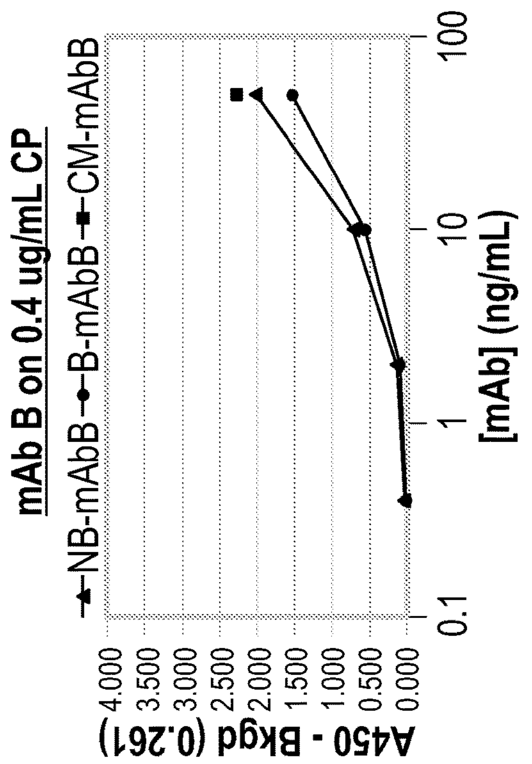
Figure 5C:
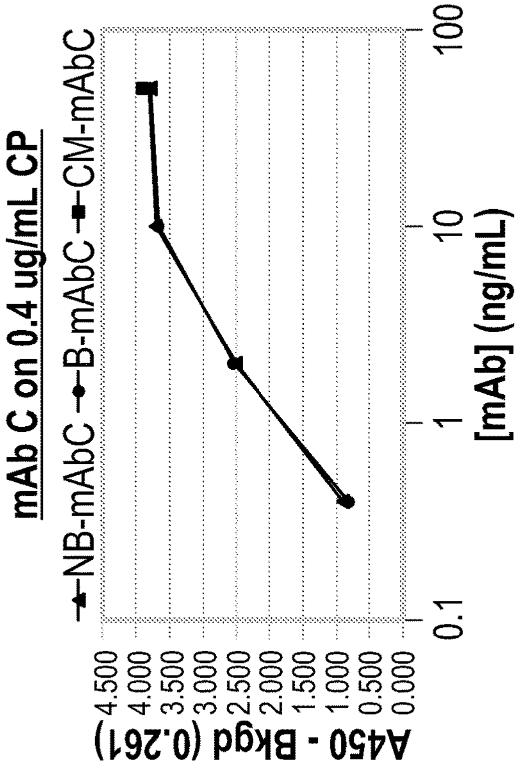
Figure 5D:
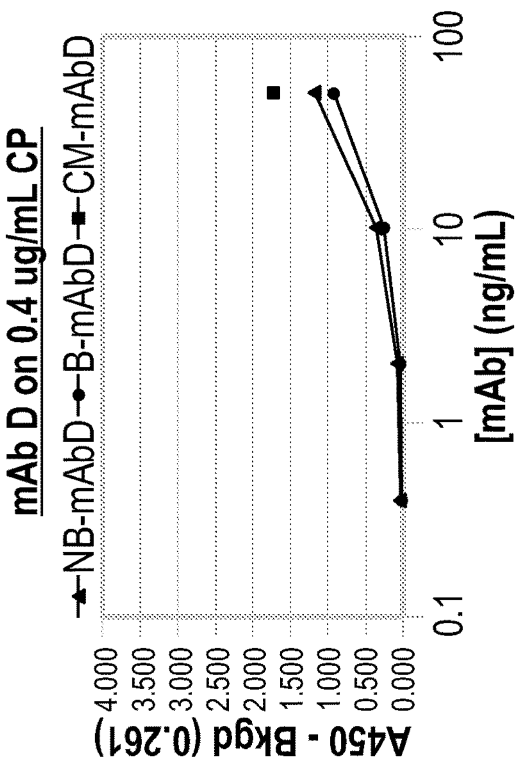
Figure 5E:
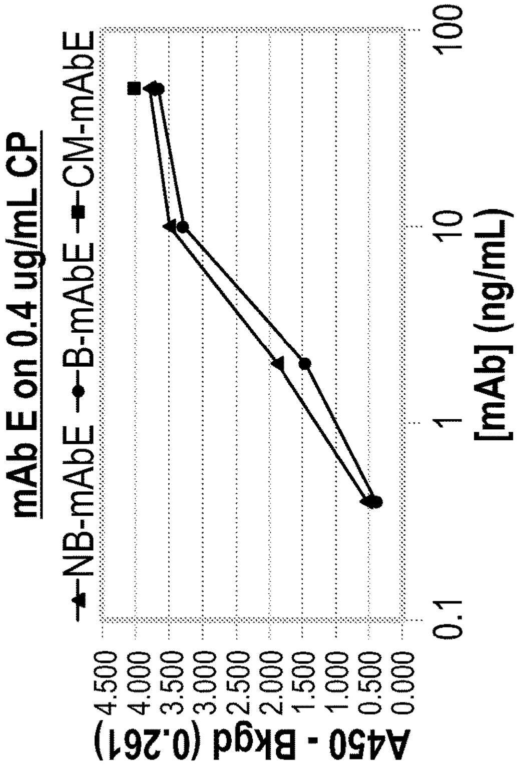
Figure 5F:
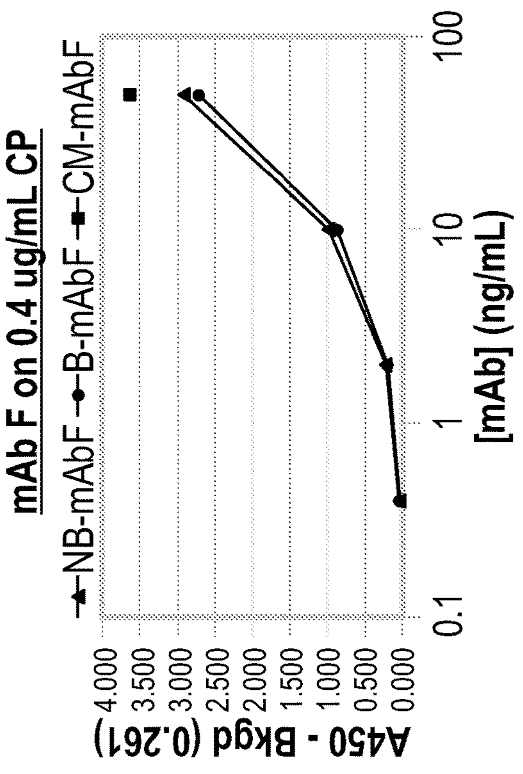
Figure 5G:
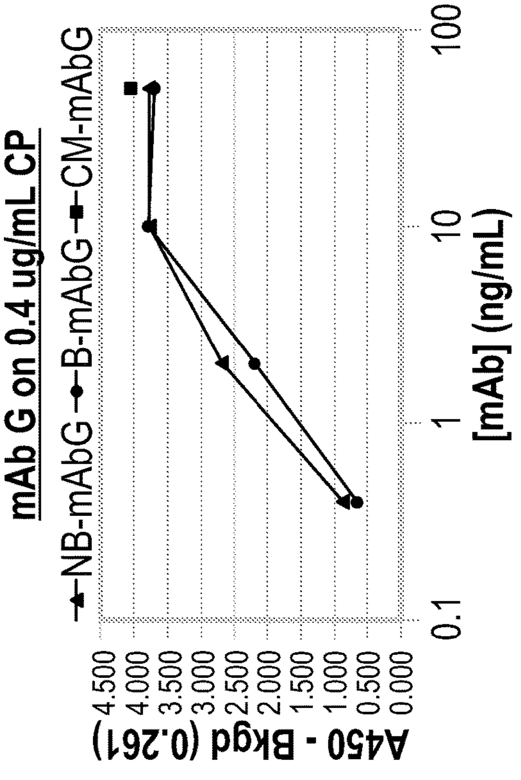
Figure 5H:
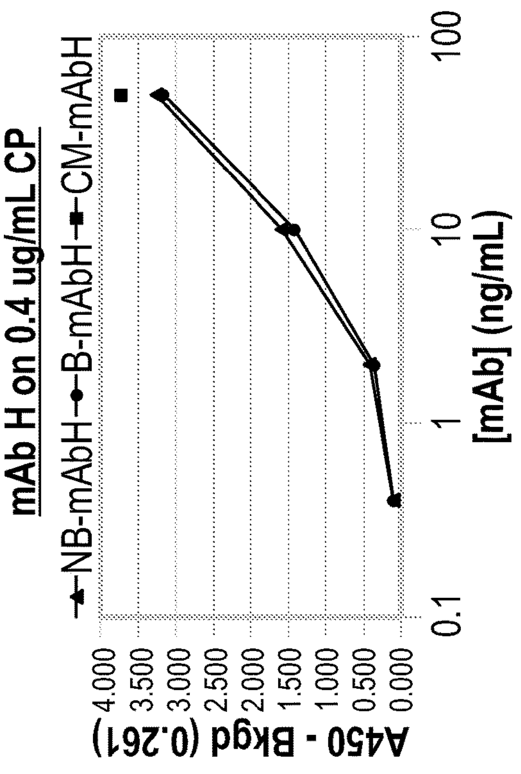

As shown in FIG. 4, all of the anti-CP mAbs and polyclonal antibodies were able to capture CP. A summary of the physical characteristics of the mAbs discussed above (ranked high to low with respect to CP binding strength based on 1:10K plasma) is provided in Table 1.

TABLE 1

Physical characteristics of anti-CP antibodies

| Anti CP mAb | [IgG] (ug/mL) | Clonotype | A450 Plasma 1:10K | A450 20 ng/ml CP | Comments |
|---|---|---|---|---|---|
| A | 27.3 | X1 | 1.399 | 1.094 | |
| B | 28.9 | R1 | 1.317 | 1.016 | |
| C | 48.1 | T1 | 1.267 | 1.093 | |
| D | 24.1 | Y1 | 1.247 | 1.027 | |
| E | 44.3 | B3 | 1.244 | 1.138 | |
| F | 50.2 | F1 | 1.181 | 0.899 | |
| G | 132.9 | S1 | 1.176 | 0.987 | |
| H | 39.7 | E1 | 1.031 | 0.924 | |
| I | 26.1 | E1?[4] | 1.021 | 0.929 | |
| J | 42.8 | B1 | 1.020 | 0.962 | |
| K | 12.7 | I1 | 1.016 | 0.952 | |
| l | 41.2 | W1 | 0.995 | 0.816 | |
| M | 124.1 | AB1 | 0.930 | 0.766 | |
| N | 48.6 | V1 | 0.930 | 0.815 | |
| O | 82.9 | C1 | 0.902 | 0.795 | |
| P | 80.8 | O1 | 0.857 | 0.808 | |
| O | 92.6 | C2 | 0.829 | 0.710 | |
| R | 88.1 | Z1 | 0.789 | 0.665 | |
| S | 69.7 | P1 | 0.721 | 0.578 | |
| T | 35.9 | D1 | 0.714 | 0.554 | |
| U | 36.8 | Q1 | 0.698 | 0.520 | Incomplete IP |
| V | 29.9 | H1 | 0.696 | 0.546 | Incomplete IP |
| W | 90.2 | J1 | 0.650 | 0.492 | |
| X | 42.7 | N1 | 0.546 | 0.443 | |
| Y | 18.5 | L1 | 0.396 | 0.342 | |
| Z | 64.5 | G1 | 0.359 | 0.295 | |
| AA | 47.3 | U1 | 0.076 | 0.446 | Weak for IP |
| BB | 48.3 | M1 | 0.068 | 0.347 | Weak for IP |

[1]IgG concentration refers to the unpurified transient transfection conditioned medium (CM)

[2]Clonotype describes the relatedness of the mAbs based primarily on CDR3 homology. The clonotype letter indicates a family while unique numbers indicate unique family members.

[3]A450 columns represent data from the ELISA experiments.

[4]Ambiguity due to sequence data quality.

Based on the ranking of binding strength shown in Table 1, the top 8 anti-CP mAbs were selected and their binding properties further characterized, as follows.

The 8 anti-CP mAbs were produced by transient transfection in suspension-adapted HEK-293 cells at 50 mL scale and purified using Protein A. Antibody yields are shown in Table 2.

TABLE 2

Anti-CP antibody yields

| Anti-CP mAb | Yield (mg) |
|---|---|
| A | 1.3 |
| B | 0.8 |
| C | 0.4 |
| D | 1.3 |
| E | 1.0 |
| F | 1.1 |
| G | 1.8 |
| H | 1.3 |

To assess the binding of these 8 anti-CP mAbs to CP, the antibodies were biotinylated with a Biotin:mAb molar ratio of 50:1. In anticipation of using the biotinylated mAbs in a competition binning ELISA on coated CP, the 8 anti-CP mAbs were evaluated for their ability to bind CP coated at 10, 2, and 0.4 ug/mL. The original CMs generated in accordance with Example 1 were tested at 50 ng/mL and both the biotinylated and non-biotinylated, purified anti-CP mAbs were tested at 50, 10, 2, and 0.4 ng/mL. FIGS. 5A-5H show the binding of anti-CP mAbs to CP coated at 0.4 ug/mL and detected using an anti-rabbit IgG secondary antibody, where "B-" indicates biotinylated, purified anti-CP mAb; "NB-" indicates non-biotinylated, purified anti-CP mAb; and "CM-" indicates unpurified transient transfection conditioned medium anti-CP mAb.

All 8 anti-CP mAbs bound to coated CP, and biotinylation had little or no effect on CP binding. Purified anti-CP mAbs bound coated CP similarly to the original unpurified CMs.

Figure 6:
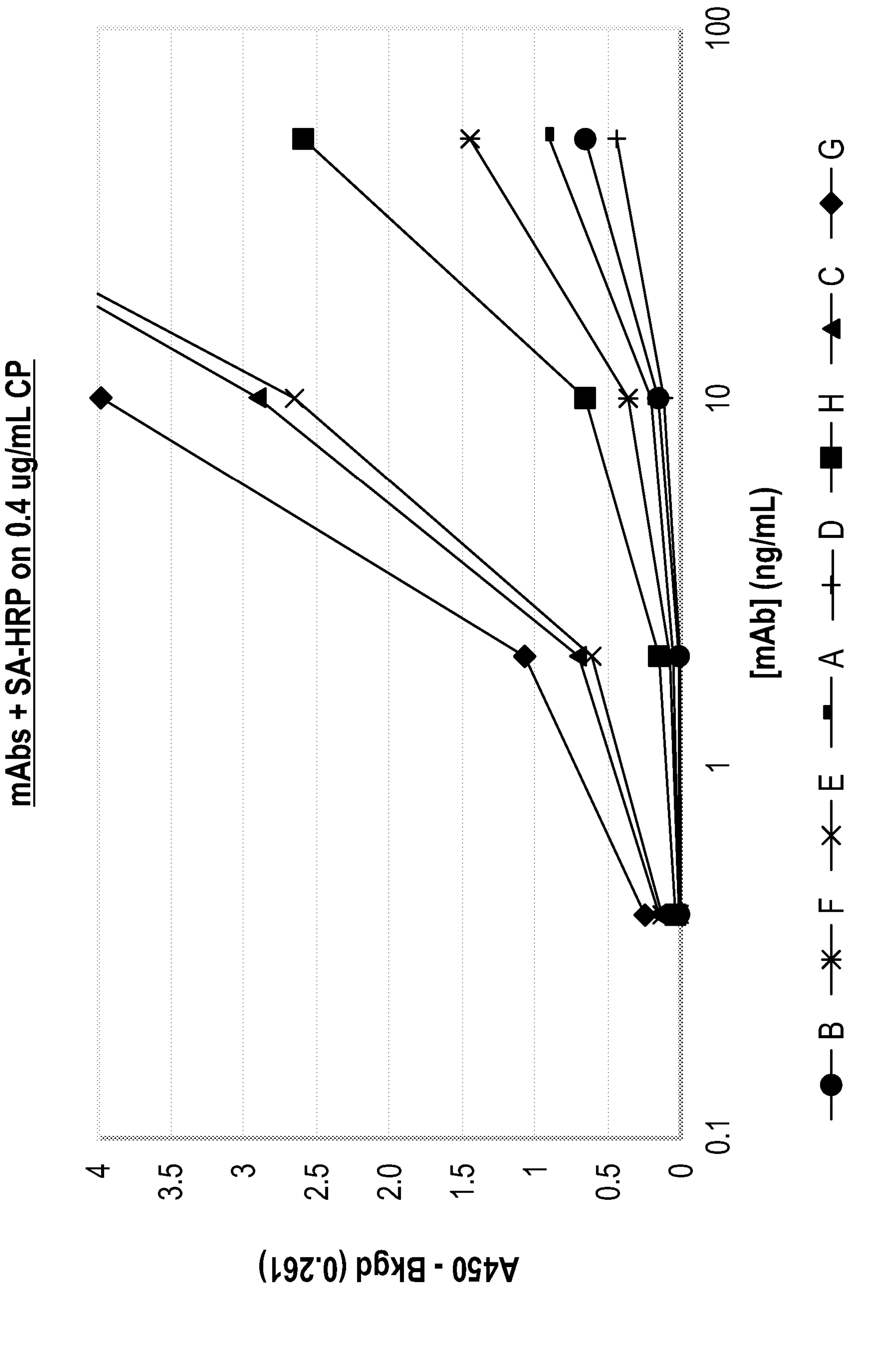
FIG. 6 is a graph showing the binding activity of the indicated biotinylated anti-CP mAbs at different concentrations to coated CP when detected with streptavidin-HRP (SA-HRP) in an ELISA. Absorbance was read at A450 nm.
Figure 7:
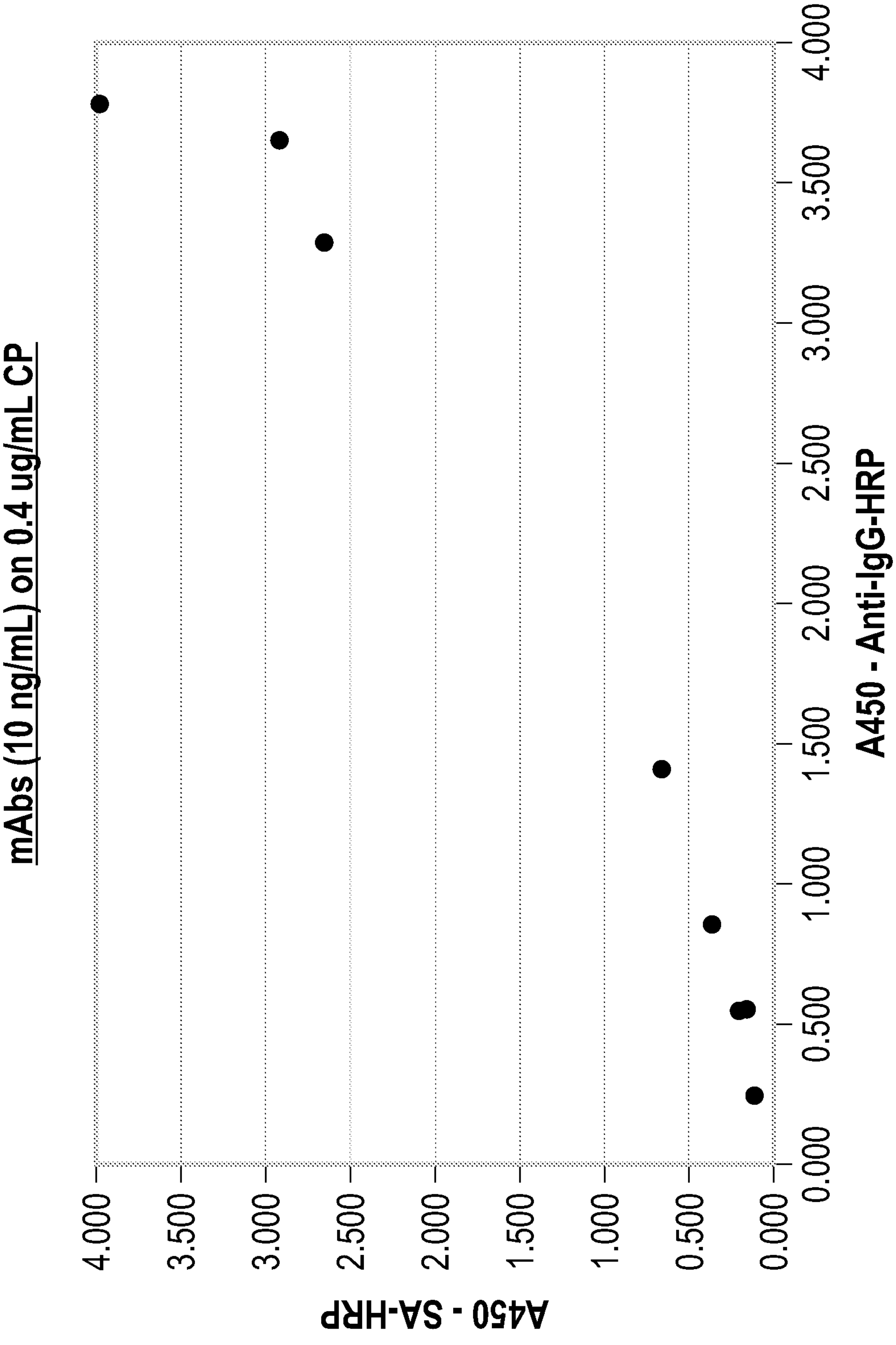
FIG. 7 is a graph showing correlations in binding of biotinylated anti-CP antibodies to 0.4 ug/mL CP when detected using anti-rabbit HRP or SA-HRP.
Figure 8:
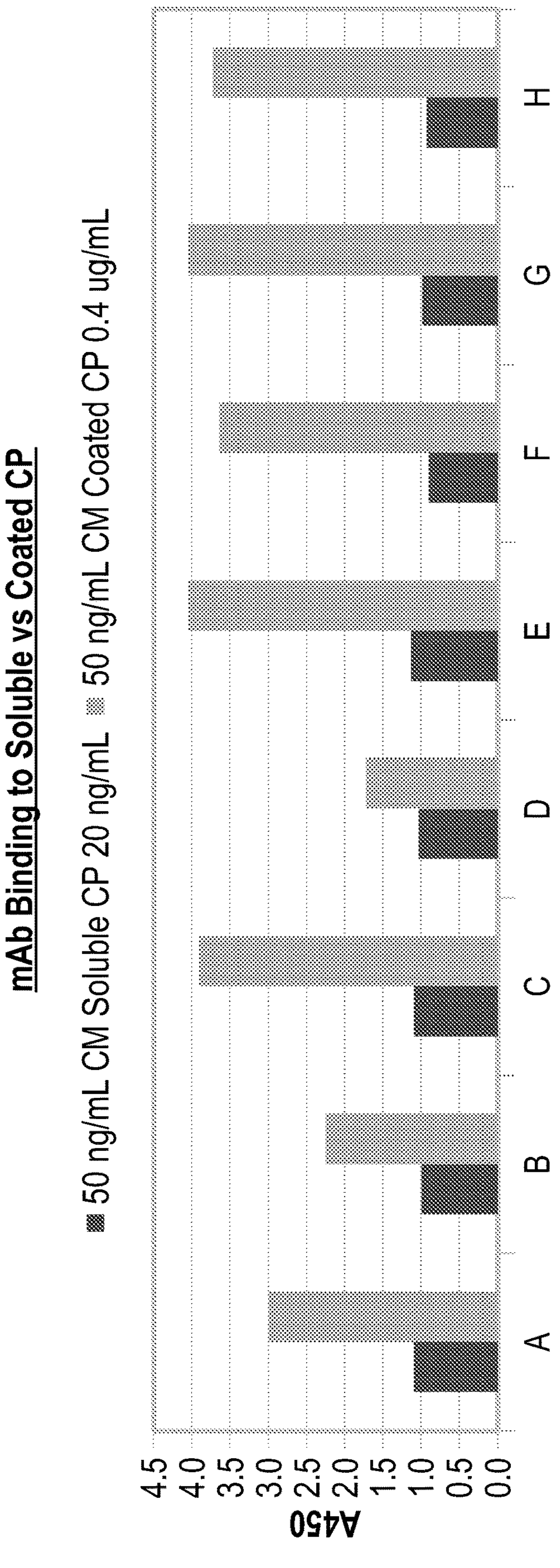
FIG. 8 is a graph comparing the binding of anti-CP mAbs to soluble and coated CP by ELISA. Absorbance was read at A450 nm. "CM" means unpurified transient transfection conditioned medium.

As shown in FIG. 6, the signal strength for binding of the biotinylated anti-CP mAbs to coated CP when detected with streptavidin-HRP (SA-HRP) was lower than when detected with anti-rabbit IgG-HRP. The strongest binders to coated CP were mAbs C, E, and G. The signal obtained for binding of biotinylated mAbs as detected by anti-rabbit HRP and SA-HRP under non-saturating conditions (0.4 ug/mL CP coating, 10 ng/ml mAb) were generally well correlated, suggesting that all mAbs were biotinylated to a similar extent (FIG. 7). Notably, a number of the mAbs appeared to bind coated CP relatively less well than they bound CP in solution (FIG. 8).

Example 3: Competition Binning of Purified Anti-CP mAbs

To assess whether any of the 8 anti-CP antibodies competed with each other for binding to CP, the following ELISA study was performed.

Briefly, CP was coated onto plates at 0.4 ug/mL overnight. Plates were then blocked with 1% BSA for 4 hours, incubated with 10 ug/mL unlabeled blocking antibody for 1 hour, and then, without washing, 50 ng/mL of biotinylated probe antibody for 1 hour. Plates were washed and subsequently incubated with SA-HRP for 30 minutes, followed by another wash. Plates were then incubated with TMB substrate for either 30 minutes or 15 minutes, as noted below, and the reaction was stopped by adding 0.18 M sulfuric acid and read at A450. The experiment was performed on two plates with plate 1 having a TMB incubation time of 30 minutes and plate 2 having a TMB incubation time of 15 minutes. Weaker binders to coated CP were tested on plate 1 and stronger binders on plate 2, with some duplication across plates. Probe Ab/blocking Ab interactions are shown in Table 3, and a summary of the binning results for all 8 anti-CP mAbs and for the 5 mAbs showing the most robust signal on coated CP (as shown in FIG. 6) is provided in Tables 4 and 5.

TABLE 3

Anti-CP antibody binning results

| | | Blocking Ab (20 ug/mL) | | | | | | | | | |
|---|---|---|---|---|---|---|---|---|---|---|---|
| | | B | F | E | A | D | H | C | G | CP-pAb | Diluent |
| Probe Ab (50 ng/mL) | B | 2 | 95 | 87 | 94 | 34 | 204 | 78 | 98 | 2 | 100 |
| | F | 100 | 1 | 6 | 90 | 100 | 95 | 100 | 93 | 5 | 100 |
| | E | 93 | 62 | 4 | 94 | 95 | 93 | 95 | 95 | 7 | 100 |
| | A | 183 | −2 | 127 | 4 | 113 | 115 | 138 | 35 | 17 | 100 |
| | D | 98 | 100 | 98 | 107 | 7 | 9 | 72 | 100 | 10 | 100 |
| | H | 110 | 94 | 79 | 93 | 33 | 2 | 67 | 95 | 2 | 100 |
| | C | 95 | 97 | 99 | 100 | 93 | 85 | 1 | 97 | 3 | 100 |
| | G | 93 | 84 | 102 | 91 | 103 | 106 | 108 | 0 | 6 | 100 |
| | B-CP-pAb | 100 | 100 | 100 | 100 | 100 | 100 | 100 | 100 | ? | 100 |
| | Diluent | 0 | 0 | 0 | 0 | 0 | 0 | 0 | 0 | 0 | 0 |

Numbers in Table 3 correspond to percentages.
>75%: probe antibody binding not inhibited by blocking antibody (no competition)
25% ≤ x ≤ 75%: probe antibody binding partially inhibited by blocking antibody (partial competition)
<25%: probe antibody binding substantially inhibited by blocking antibody (substantial competition)

TABLE 4

Anti-CP antibody binning summary

| | | Blocking Ab (20 ug/mL) | | | | | | | | | |
|---|---|---|---|---|---|---|---|---|---|---|---|
| | | B | F | E | A | D | H | C | G | CP-pAb | Diluent |
| Probe Ab (50 ng/mL) | B | SI | NI | NI | NI | PI | NI | NI | NI | SI | NI |
| | F | NI | SI | SI | NI | NI | NI | NI | NI | SI | NI |
| | E | NI | PI | SI | NI | NI | NI | NI | NI | SI | NI |
| | A | NI | SI | NI | SI | NI | NI | NI | PI | SI | NI |
| | D | NI | NI | NI | NI | SI | SI | PI | NI | SI | NI |
| | H | NI | NI | NI | NI | PI | SI | PI | NI | SI | NI |
| | C | NI | NI | NI | NI | NI | NI | SI | NI | SI | NI |
| | G | NI | NI | NI | NI | NI | NI | NI | SI | SI | NI |
| | B-CP-pAb | NI | NI | NI | NI | NI | NI | NI | NI | | NI |
| | Diluent | SI | SI | SI | SI | SI | SI | SI | SI | SI | SI |

NI: no inhibition;
PI: partial inhibition;
SI: significant inhibition
B-: biotinylated

TABLE 5

Anti-CP antibody binning summary for 5 antibodies

| | | Blocking Ab (20 ug/mL) | | | | |
|---|---|---|---|---|---|---|
| | | F | E | H | C | G |
| Probe Ab (50 ng/mL) | F | SI | SI | NI | NI | NI |
| | E | PI | SI | NI | NI | NI |
| | H | NI | NI | SI | PI | NI |
| | C | NI | NI | NI | SI | NI |
| | G | NI | NI | NI | NI | SI |

NI: no inhibition;
PI: partial inhibition;
SI: significant inhibition

The mAbs E, C, and G were selected for further immunocapture testing based on their superior binding to both coated and solution phase CP (including endogenous plasma CP?), retention of binding to CP when biotinylated, and absence of cross-competition for binding to coated CP.

Example 4: Immunocapture Efficiency of Anti-CP mAbs Measured by CP Assay

To test the ability of E, C, and G, used alone and in a mixture of two or three anti-CP mAbs, to immunocapture CP in human lithium heparin plasma samples, the following CP assay was performed in which different mAbs, mAb mixtures, and polyclonal antibody (pAb) were evaluated for their efficiency to immunocapture human CP from human lithium heparin plasma. A schematic of the experimental procedure is shown in FIG. 9A.

CP is an endogenous component in human plasma. Thus, it was not feasible to prepare calibration standards or QC samples in plasma. The trace copper BSA buffer was used as a surrogate matrix to prepare calibration standards.

Preparations

Blocking buffer was prepared by adding about 0.1 mL of Tween-20 to about 1000 mL of 1×PBS buffer and mixing well.

BSA buffer (0.5 mg/mL) was prepared by diluting 250 μL of 20 mg/mL trace copper BSA solution with 9.75 mL of blocking buffer and mixing well. The trace copper BSA solution was prepared by adding EDTA solution to BSA solution followed by filtration through a 30 kDa molecular weight cutoff (MWCO) filter yielding 20 mg/mL trace copper BSA solution in water.

Tris buffer was prepared by diluting 50 mL 1 M Tris-HCl buffer (pH 8.5) in 950 mL purified water and mixing well to obtain 50 mM tris buffer solution (pH 8.5).

Dithiothreitol (DDT) solution was prepared by dissolving 92.4 mg of DTT with 10 mL of 50 mM tris buffer (pH 8.5) and mixing well to obtain 60 mM DTT solution.

Iodoacetamide solution was prepared by dissolving 185 mg iodoacetamide with 5 mL of 50 mM tris buffer (pH 8.5) and mixing well to obtain 200 mM iodoacetamide solution.

Trypsin solution was prepared by adding 1 mL of 50 mM tris buffer (pH 8.5) to 100 μg trypsin to obtain a final concentration of 0.1 mg/mL and mixing well.

Control samples were prepared by adding about 190 μL of BSA buffer (0.5 mg/mL) to about 20 μL of the sample.

To prepare anti-CP antibody coated beads, ~50 mg of magnetic beads (Dynabeads® M-280 Tosylactivated) were incubated with 500 μL of coupling buffer A (0.1 M Borate Buffer, pH 9.5) and 500 μL of coupling buffer C (3M ammonium sulfate in coupling buffer A, pH 9.5), in addition with 60 μL of 10 mg/mL anti-CP antibody overnight (~18 hrs) at 37° C. with rotation. After incubating with the antibody, the coated beads were added with 1 mL of coupling buffer D (5 mg/mL BSA in 50 mM tris, pH 8.5) and incubated at 37° C. for 1 hr with rotation. Finally, the antibody coated beads were re-suspended in 1.25 mL of BSA buffer at a final bead concentration of 40 mg/mL.

Immunocapture of CP

About 200 μL of beads (~8 mg) coated with anti-CP antibody (~96 μg) were added to about 20 μL of either human plasma or to CP prepared in BSA buffer (800 μg CP/mL) (i.e., STD8, see Table 10) in each well of a 96-well LoBind plate (Eppendorf). The plate was sealed, centrifuged at about 500 RPM for approximately 1 minute, and incubated at room temperature for approximately 1.5 hours on a plate shaker at 1000 RPM. The plate was centrifuged at about 500 RPM for approximately 1 minute.

The coated beads were removed from the wells using a KingFisher Flex Purification System (the remaining solution comprising a NCC fraction) and washed twice with about 300 μL of blocking buffer and once with about 300 μL of water. The CP on the beads was eluted by about 200 μL of 30 mM HCl over approximately 10 minutes. This immunocapture procedure isolated the CP and generated a NCC fraction (~210 μL).

Control samples were not subjected to immunocapture prior to IS spike, tryptic digestion, and analysis.

IS Spike

About 10 μL of internal standard (IS) spike (2 μg/mL GAYPLSIEPIG[($^{13}C_5$,$^{15}N$)Val]R peptide (SEQ ID NO: 232) in water) were added to each well. The wells were centrifuged at about 500 RPM for approximately 1 minute and then vortexed for approximately 1 minute at low setting. About 50 μL was transferred from each well to a new well on a new 96-well LoBind plate (Eppendorf).

Tryptic Digestion

The following were added to each well: about 10 μL of 1M tris buffer (pH 8.5), about 50 μL of 50 mM tris buffer (pH 8.5), and 10 μL of 60 mM DTT solution. The plate was sealed, centrifuged at about 500 RPM for approximately 1 minute, and incubated at about 60° C. on a plate shaker at about 900 RPM for approximately 60 minutes. After incubation with DTT, the temperature of the plate was allowed to cool down to about room temperature.

About 10 μL of 200 mM iodoacetamide solution was added to each well, and the plate was incubated under dark for approximately 30 minutes. About 20 μL trypsin (0.1 mg/mL) were added to each well, and the plate was incubated at about 60° C. on a plate shaker at about 900 RPM for approximately 1.5 hours. About 15 μL of 10% formic acid in water were added to each well. The plate was vortexed for approximately 3 minutes and centrifuged at about 3500 RPM for approximately 5 minutes.

Analysis

About 5 μL sample from each well was injected into liquid chromatography tandem mass spectrometer (LC-MS/MS) (SCIEX/API 6500) installed with a Waters ACQUITY UPLC BEH C18 column (50×2.1 mm, 1.7 micron) operating under the following conditions*:

TABLE 6

| LC-MS/MS conditions | | |
|---|---|---|
| Mass Spectrometer | Sciex API 6500 | |
| Interface | ESI | |
| Ionization Mode | Positive | |
| Detection Mode | MRM | |
| Analyte | GAYP Peptide* | GAYP Peptide IS* |
| MS Transitions | 686.7→541.0 | 689.7→544.0 |
| Dwell time | 200 msc | 200 msc |
| Settings*: | Voltage | 5500 |
| General | Temp | 375 |
| | GS1 | 60 |
| | GS2 | 40 |
| | CUR | 30 |
| | CAD | 8 |
| Settings*: | GAYP Peptide | DP: 110 |
| Compound Dependent | | CE: 27 |
| | | CXP: 21 |
| | | EP: 10 |
| | GAYP Peptide IS | DP: 110 |
| | | CE: 27 |
| | | CXP: 21 |
| | | EP: 10 |
| Data Acquisition Time | 3.5 min | |

*Note:
The instrument conditions may be adjusted to optimize the response.

The relative CP concentration, which is the ratio of the peak area of a signature peptide, GAYPLSIEPIGVR (SEQ ID NO: 231), relative to that of an internal standard (IS), GAYPLSIEPIG[($^{13}C_5$,$^{15}N$)Val]R (SEQ ID NO: 232), were determined in both the NCC fractions (n=3) and controls (n=3) for each sample, according to the following equation:

Relative CP concentration=[peak area of signature peptide]/[peak area of IS])

The immunocapture (IC) efficiency of the anti-CP antibody was determined by assessing the mean relative CP concentration in the NCC fractions (n=3) compared to that of the control samples (n=3), according to the following equation:

Immunocapture efficiency (%)=1−([mean relative CP concentration in NC]/[mean relative CP concentration in control]).

Results

Table 7 summarizes the IC efficiency of anti-CP mAbs, mAb mixtures, and pAb. As shown in Table 7, mAbs and mAb mixtures showed relatively consistent immunocapture efficiency across different CP concentrations in human lithium heparin plasma samples (377.3 μg/mL) and 800 μg/mL purified (>95% purity) CP (Sigma Aldrich) in BSA buffer. However, the immunocapture efficiency of the polyclonal antibody significantly dropped an average of 12% from the lower CP concentration (377.3 μg/mL) in plasma to the higher CP concentration (800 μg/mL), suggesting that the mAbs, alone and particularly when in a mixture, are more efficient at capturing CP than the polyclonal antibody. Specifically, under non-saturating conditions (800 μg/mL CP), each anti-CP mAb used alone showed greater immunocapture efficiency than the polyclonal anti-CP antibody. In addition, each antibody mixture which included two anti-CP mAbs showed stronger immunocapture efficiency than the anti-CP mAbs used alone. Finally, the antibody mixture with all three anti-CP mAbs showed the strongest immunocapture efficiency.

TABLE 7

Immunocapture efficiency of anti-CP mAbs, mAb mixtures, and pAb

| | Test | | | | | | | | | | | | |
|---|---|---|---|---|---|---|---|---|---|---|---|---|---|
| | 1 | | | | | 2 | | | 3 | | | | |
| Ab | mAb mix (1, 2, 3) | mAb mix (1, 2) | mAb mix (1, 3) | mAb1 | pAb | mAb mix (1, 2, 3) | mAb1 | pAb | mAb1 | mAb2 | mAb3 | mAb4 | pAb |
| Plasma (377.3 μg/mL) | 99.56% | 99.51% | 99.37% | 96.05% | 99.46% | 99.67% | 96.42% | 99.83% | 96.63% | 95.04% | 90.33% | 95.32% | 99.69% |
| CP in BSA Buffer (800 μg/mL) | 99.97% | 99.88% | 99.88% | 97.84% | 88.13% | 99.98% | 97.67% | 90.11% | 96.50% | 94.29% | 90.65% | 95.44% | 85.40% |

1. mAb1 corresponds to mAb E, mAb2 corresponds to mAb C, mAb3 corresponds to mAb G, mAb4 corresponds to an unrelated anti-CP antibody, and pAb corresponds to commercially available goat anti-human ceruloplasmin polyclonal antibodies from Bethyl Laboratories, Inc. (Montgomery, TX).
2. mAb mix (1, 2, 3) (96 μg total mAb per sample) is mAb1 (48 μg):mAb2 (24 μg):mAb3 (24 μg) = 2:1:1.
3. mAb mix (1, 2) (96 μg total mAb per sample) is mAb1 (64 μg):mAb2 (32 μg) = 2:1.
4. mAb mix (1, 3) (96 μg total mAb per sample) is mAb1 (64 μg):mAb3 (32 μg) = 2:1.

Example 5: CP-Depletion Comparison of Anti-CP Monoclonal and Polyclonal Antibodies Using CP Assay This Example compares anti-CP mAb mix (1,2,3) (i.e., mAbs E, C, and G present in a 2:1:1 ratio) with that of a commercially available goat anti-human ceruloplasmin polyclonal antibody from Bethyl Laboratories, Inc. (Montgomery, TX) (pAb), as assessed by measuring the mean CP concentrations remaining in NCC fractions following immunocapture of CP from CP samples by either the mAb mix (1,2,3) or pAb. The CP assay described in Example was used to conduct the experiment.

Briefly, six replicates of CP samples at two concentrations (i.e., human lithium heparin plasma and STD8 (see Table 10)) were subjected to immunocapture of CP using beads coated with either the mAb mix (1,2,3) or the pAb (lot #1). The coated beads were prepared according to the procedure described in Example 4. Namely, 0.6 mg antibody (either mAb mix (1,2,3) or pAb lot #1) was added to magnetic beads (Dynabeads® M-280 Tosylactivated) and incubated overnight, such that the final volume of coated beads in each tube was 1.25 mL.

To extract the CP from the samples, 200 μL antibody-coated beads were added to each 20 μL CP sample. The total amount of antibody (either the mAb mix (1,2,3) or the pAb lot #1) added to each CP sample was the same (i.e., a total of 96 μg antibody per sample).

The CP samples were then subjected to the remaining steps of the CP immunocapture described in Example 4, thereby isolating the CP and generating a NCC fraction per CP sample. The NCC fractions were then subjected to the remaining steps of the CP assay described in Example 4: namely, IS spike, tryptic digestion, and measurement of CP concentration using LC-MS/MS.

As shown in Table 8, the mean CP concentration in the CP-depleted NCC fractions at each concentration level was much lower with the mAb mix (1,2,3) than with pAb lot #1.

TABLE 8

CP-depletion using mAb mix (1, 2, 3) vs. pAb (lot #1)

| | CP concentration in Plasma pAb lot#1 | CP concentration in Plasma mAb mix (1, 2, 3) | CP concentration in STD8 pAb lot#1 | CP concentration in STD8 mAb mix (1, 2, 3) |
|---|---|---|---|---|
| Measured | 7.14 | BQL < 5.25 | 158 | BQL < 5.25 |
| CP Conc. | 18.3 | BQL < 5.25 | 200 | BQL < 5.25 |
| (μg/mL) | 9.04 | BQL < 5.25 | 214 | BQL < 5.25 |
| | 8.15 | BQL < 5.25 | 161 | BQL < 5.25 |
| | 15.3 | BQL < 5.25 | 227 | BQL < 5.25 |
| | 6.36 | BQL < 5.25 | 177 | BQL < 5.25 |
| Mean | 10.7 | BQL | 190 | BQL |
| SD | 4.9 | NA | 28.6 | NA |
| % CV | 45.7 | NA | 15.0 | NA |
| n | 6 | 6 | 6 | 6 |

STD8: CP standard calibrator (800 μg CP/mL BSA buffer);
BQL: below the limit of quantification;
NA: not applicable;
SD: standard deviation;
CV: coefficient of variation A further immunocapture experiment was conducted on CP samples at two concentrations (i.e., low and high QCs) using beads coated with either the mAb mix (1,2,3) or a different lot of the pAb (lot #2). The coated beads were prepared according to the method described above and in Example 4. Namely, the coated beads were prepared by adding the same amount of respective antibody for the mAb mix (1,2,3) and pAb lot #2 (0.6 mg) to the beads, and ultimately the same total amount of respective antibody (96 μg antibody per sample) was added to each 20 μL CP sample for immunocapture.

The CP samples were subjected to the same CP immunocapture steps described above and in Example 4, thereby isolating the CP and generating a NCC fraction per CP sample. The NCC fractions were then subjected to the remaining steps of the CP assay described above and in Example 4: namely, IS spike, tryptic digestion, and measurement of CP concentration using LC-MS/MS.

As shown in Table 9, the mean CP concentration in the CP-depleted NCC fractions at each concentration level was much lower with the mAb mix (1,2,3) than with pAb lot #2.

TABLE 9

CP-depletion using mAb mix (1, 2, 3) vs. pAb Lot#2

| | CP concentration (15 ug/mL) Low QC pAb lot#2 | CP concentration (15 ug/mL) Low QC mAb mix (1, 2, 3) | CP concentration (600 ug/mL) High QC pAb lot#2 | CP concentration (600 ug/mL) High QC mAb mix (1, 2, 3) |
|---|---|---|---|---|
| Measured CP Conc. (μg/mL) | BQL < 5.25 | BQL < 5.25 | ALQ > 840 | 21.0 |
| | BQL < 5.25 | BQL < 5.25 | 527 | 19.3 |
| | BQL < 5.25 | BQL < 5.25 | 748 | 9.4 |
| | BQL < 5.25 | BQL < 5.25 | 512 | 8.7 |
| | BQL < 5.25 | BQL < 5.25 | 679 | 8.8 |
| | BQL < 5.25 | BQL < 5.25 | 503 | 27.4 |
| Mean | BQL | BQL | 594 | 16.0 |
| SD | NA | NA | 112.0 | 8.0 |
| % CV | NA | NA | 18.9 | 50.0 |
| n | 6 | 6 | 5 | 6 |

BQL: below the limit of quantification;
ALQ: above the limit of quantitation;
NA: not applicable;
SD: standard deviation;
CV: coefficient of variation

Example 6: Quantification of CP Concentrations in Biological Samples

To qualify the capability of the anti-CP mAb mixture (1,2,3) for immunocapture and quantification of CP in human lithium heparin plasma, an accuracy and precision run on the ceruloplasmin-immunocapture-elution-digestion LC-MS/MS method (having an assay range of 5-800 μg/mL) of the CP assay described in Example 4 was performed, with approximately 96 μg of the anti-CP mAb mixture (1,2,3) being used for immunocapture of CP in each 20 μL sample.

LLOQ (5 μg/mL), Low QC (15.0 μg/mL), and Mid QC (250 μg/mL) samples were prepared with CP calibration standards in trace BSA buffer, and High QC (600 μg/mL) samples were prepared by spiking CP on top of pooled human lithium heparin plasma with the endogenous CP concentration pre-determined.

Briefly, about 20 μL of a calibration standard or a QC sample was added with about 200 μL coated beads, and then subjected to the CP immunocapture step disclosed in Example 4. The HCl eluted fractions, containing the captured CP, were then digested and injected in LC-MS/MS for analysis following the steps described in Example 4.

The calibration standard results shown in Table 10 and QC samples data presented in Table 11 met the pre-defined acceptance criteria, demonstrating that the anti-CP mAb mixture (1,2,3) can be used for determination of CP concentrations in lithium heparin human plasma.

TABLE 10

Back-Calculated Concentrations of CP Calibration Standards

| CP Calibration Standard (μg CP/mL BSA buffer) | Measured CP Concentration (μg/mL) | % Bias |
|---|---|---|
| STD1 (5.00 μg/mL) | 5.30 | 6.0 |
| STD2 (10.0 μg/mL) | 9.28 | −7.2 |
| STD3 (20.0 μg/mL) | 18.2 | −9.0 |
| STD4 (100 μg/mL) | 91.7 | −8.3 |
| STD5 (200 μg/mL) | 203 | 1.5 |
| STD6 (500 μg/mL) | 586 | −2.3 |
| STD7 (700 μg/mL) | 681 | 97.3 |
| STD8 (800 μg/mL) | 820 | 103 |
| Slope | 0.021505 | |
| Intercept | −0.035312 | |
| R-Squared | 0.9899 | |

TABLE 11

Intra-run Accuracy and Precision for Ceruloplasmin

| | QC LLOQ (5.00 μg CP/mL BSA buffer) | QC Low (15.0 μg CP/mL BSA buffer) | QC Mid (150 μg CP/mL BSA buffer) | QC High (600 μg CP/mL BSA buffer) |
|---|---|---|---|---|
| Measured CP Conc. (μg/mL) | 4.77 | 15.8 | 171 | 605 |
| | 5.52 | 15.7 | 178 | 732* |
| | 5.28 | 14.8 | 160 | 698 |
| | 5.25 | 15.3 | 169 | 709 |
| | 5.40 | 15.7 | 199* | 891* |
| | 5.55 | 14.2 | 154 | 599 |
| Mean | 5.30 | 15.3 | 172 | 706 |
| SD | 0.284 | 0.635 | 15.8 | 106 |
| % CV | 5.4 | 4.2 | 9.2 | 15.1 |
| % Bias | 5.9 | 1.7 | 14.6 | 17.6 |

*Value was out of the acceptable tolerance range and included in the statistical calculations.

Example 7: Quantification of LBC in Human Lithium Heparin Plasma and Serum

Non-ceruloplasmin bound copper (NCC) and labile-bound copper (LBC) assays are useful for diagnosing, treating, and monitoring copper metabolism-associated diseases by measuring concentrations of NCC and LBC, respectively, in a biological sample (e.g., plasma or serum). These two assays are described in detail in PCT Patent Application Publication No. WO2021/05080, filed on Sep. 11, 2020, and U.S. Provisional Patent Application Nos. 62/899,498, filed Sep. 12, 2019, 62/944,498, filed Dec. 6, 2019, and 62/958,432, filed Jan. 8, 2020, the contents of which are incorporated by reference. An exemplary embodiment of a NCC assay is graphically shown in FIG. 9B (left panel). An exemplary embodiment of a LBC assay is graphically shown in FIG. 9B (left panel and right panel combined).

In brief, the assays entail an initial step of removing CP from the sample using an immunocapture reagent which binds to CP (e.g., a mAb or mAb mixture as disclosed herein, such as the mAbs generated and characterized in the preceding Examples). The captured CP is removed, leaving a non-CP sample. In the NCC assay, copper concentration is measured in the NCC sample. In the LBC assay, the NCC sample is further contacted with a chelator which binds to LBC, as described in the experiment below. The non-LBC fraction is removed, leaving an LBC sample, and copper concentration is measured in the LBC sample by inductively coupled plasma mass spectrometry (ICP-MS). In some embodiments, the CP concentration in the eluted CP sample is also measured by LC-MS/MS, as described in Example 6.

LBC Assay

Matched sets of human lithium heparin plasma and serum from 52 healthy individuals were obtained from BIOIVT.

The concentration of LBC in the plasma and serum samples was determined by ICP-MS (Agilent 8900) after performing the validated LBC bioanalytical assay method as described in Example 10 of U.S. Provisional Application No. 62/958,432, filed Jan. 8, 2020, herein incorporated by reference in its entirety, with the anti-CP mAb mixture (1,2,3) disclosed herein replacing the goat anti-human CP antibody.

Briefly, CP was first removed by immunocapture with the anti-CP mAb mixture (1,2,3) to obtain a NCC fraction, followed by chelation of the NCC solution with EDTA, and then filtration to collect the labile bound form of copper in the filtrate.

More specifically, about 20 μL of each biological sample were added with about 200 μL beads coated with anti-CP mAb mixture (1,2,3) (~96 μg total anti-CP mAb per sample) to a well and then subjected to the immunocapture step disclosed in Example 4, generating an NCC fraction per sample.

About 200 μL of the NCC fraction for each sample was transferred to a clean, metal-free tube, and then about 60 μL of chelation spiking solution (45.5 mM EDTA (Sigma BioUltra) and 456 μM L-Histidine (Sigma BioUltra)) were added to each sample. The samples were gently mixed well and then incubated at approximately 37° C. for about 1 hour. Optionally, the tubes could be centrifuged.

Each incubated sample was transferred to a 2% nitric acid washed 30K MWCO centrifugal filter (regenerated cellulose membrane) (Millipore, AmiconUltra) and centrifuged at approximately 14,000×g for about 35 minutes at about 25° C.

About 200 μL of filtrate were transferred to a new clean, metal-free plastic tube, and about 600 μL of 0.1% $HNO_3$ in $H_2O$ were added to the metal-free plastic tubes.

About 10 μL of rhodium internal standard spike (100 ng/mL) were added to each of the above metal free tubes. Each tube was then centrifuged at approximately 3500 rpm for about 1 minute and vortexed to mix well.

Quantification of LBC was performed by ICP-MS (Agilent 8900) using rhodium as the internal standard and operating under the conditions and parameters summarized in Tables 12 and 13. A concentric MicroMist nebulizer was used, and the spray chamber temperature was kept at about 2° C. The analysis was performed in He MSMS gas mode.

TABLE 12

| ICP-MS Autosampler and Operation Conditions* Autosampler SPS4 | |
|---|---|
| Needle rinse 10 s pump speed 0.3 rps | Purified water |
| Wash 1 45 s, pump speed 0.3 rps | 5% $HNO_3/H_2O$ (v/v) |
| Wash 2 45 s, pump speed 0.3 rps | 5% $HNO_3/H_2O$ (v/v) |

TABLE 12-continued

| ICP-MS Autosampler and Operation Conditions* Autosampler SPS4 | |
|---|---|
| Needle rinse 10 s pump speed 0.3 rps | Purified water |
| Wash 3 60 s, pump speed 0.3 rps | 0.1% $HNO_3/H_2O$ (v/v) |
| Sample introduction 30 s, pump speed 0.5 rpm | |
| Stabilize 35 s, pump speed 0.1 rps | |

*Conditions may be adjusted to optimize response and minimize carryover.

TABLE 13

| ICP-MS Conditions** | | |
|---|---|---|
| Mass Spectrometer | Agilent 8900 | |
| Nebulizer | Concentric MicroMist nebulizer | |
| Spray chamber temp | 4° C. | |
| Operation mode | MSMS He gas mode | |
| | Parameters | |
| Plasma | RF power (W) | 1550 |
| | Sampling depth (mm) | 10 |
| | Nebulizer gas (L/min) | 1.04 |
| | Nebulizer pump (rps) | 0.10 |
| | Make up gas (L/min) | 0 |
| Cell | He Flow (mL/min) | 5.1 |
| | OctP Bias (V) | −18 |
| | OctP RF (V) | 180 |
| | Energy Discrimination (V) | 0 |
| Lenses | Omega Bias (V) | −120 |
| | Omega Lens (V) | 0 |
| | Cell Entrance (V) | −40 |
| | Cell Exit (V) | −50 |
| | Deflect (V) | −9.0 |
| Integration Time/Mass | Cu 63 | 0.99 sec |
| | Rh 103 (IS) | 0.1 sec |

**Instrument conditions may be adjusted to optimize response.

The ICP-MS system plasma was turned on and "Yes" clicked to perform Auto Tune. Autotune and tune check were performed using a tuning solution (Agilent). The ICP-MS system was equilibrated with the default setting of warming up. The samples were then introduced for ICP-MS measurement.

The processed samples were analyzed together with two calibration curves and quality controls (QCs) prepared in surrogate matrices (0.1% nitric acid in water) by ICP-MS. The standard samples and QCs, not being subjected to immunocapture, were initially diluted in 0.1% nitric acid with a dilution factor of 13.5 to account for the sample dilution factor occurring during the immunocapture process. About 200 μL of each diluted standard or QC sample were further diluted in 600 μL of 0.10% nitric acid followed by spiking with 10 μL of rhodium internal standard spike. The standard curves and QCs in surrogate matrices in all the runs met the pre-defined acceptance criteria.

The LBC concentration results in human plasma and serum from the 52 healthy individuals are shown in Table 14.

TABLE 14

Determination of LBC Concentrations in Human Lithium Heparin Plasma and Serum from 52 Healthy Individuals

| Healthy Individual | Gender | Age | LBC Conc. [ng/mL] in Human Li-H Plasma | LBC Conc. [ng/mL] in Human Serum |
|---|---|---|---|---|
| 1 | Female | 61 | 53.6 | 68.9 |
| 2 | Female | 51 | 60.2 | 66.5 |
| 3 | Female | 42 | 67.3 | 85.0 |

TABLE 14-continued

| Determination of LBC Concentrations in Human Lithium Heparin Plasma and Serum from 52 Healthy Individuals | | | | |
|---|---|---|---|---|
| Healthy Individual | Gender | Age | LBC Conc. [ng/mL] in Human Li-H Plasma | LBC Conc. [ng/mL] in Human Serum |
| 4 | Female | 36 | 110 | 115 |
| 5 | Female | 32 | 54.9 | 64.1 |
| 6 | Female | 24 | 76.5 | 95.8 |
| 7 | Male | 54 | 73.4 | 75.5 |
| 8 | Male | 22 | 72.0 | 80.6 |
| 9 | Male | 56 | 56.7 | 68.1 |
| 10 | Male | 50 | 55.6 | 64.3 |
| 11 | Male | 65 | 78.6 | 81.3 |
| 12 | Male | 35 | 63.6 | 76.1 |
| 13 | Male | 60 | 78.8 | 47.2 |
| 14 | Male | 48 | 58.9 | 46.5 |
| 15 | Male | 37 | 44.3 | 38.4 |
| 16 | Male | 42 | 39.0 | 37.3 |
| 17 | Male | 66 | 43.0 | 51.4 |
| 18 | Male | 62 | 43.9 | 43.9 |
| 19 | Male | 41 | 50.1 | 47.5 |
| 20 | Male | 59 | 77.0 | 47.4 |
| 21 | Male | 72 | 49.0 | 46.9 |
| 22 | Male | 38 | 52.0 | 41.2 |
| 23 | Male | 56 | 60.7 | 83.4 |
| 24 | Male | 31 | 59.1 | 53.8 |
| 25 | Male | 58 | 41.8 | 39.4 |
| 26 | Male | 45 | 99.0 | 54.4 |
| 27 | Male | 52 | 54.6 | 46.8 |
| 28 | Male | 62 | 42.4 | 40.5 |
| 29 | Male | 18 | 40.7 | 43.0 |
| 30 | Male | 38 | 44.5 | 58.2 |
| 31 | Male | 75 | 51.5 | 66.8 |
| 32 | Male | 55 | 54.0 | 72.7 |
| 33 | Male | 63 | 58.0 | 112 |
| 34 | Male | 62 | 75.0 | 112 |
| 35 | Male | 56 | 46.4 | 84.7 |
| 36 | Male | 65 | 64.2 | 89.0 |
| 37 | Male | 44 | 61.2 | 91.4 |
| 38 | Male | 67 | 72.6 | 91.8 |
| 39 | Male | 43 | 55.5 | 73.3 |
| 40 | Male | 64 | 48.0 | 66.5 |
| 41 | Male | 61 | 51.2 | 86.2 |
| 42 | Male | 38 | 72.1 | 101.0 |
| 43 | Male | 58 | 43.7 | 76.7 |
| 44 | Male | 60 | 64.1 | 88.0 |
| 45 | Male | 55 | 79.3 | 79.0 |
| 46 | Male | 38 | 53.3 | 66.2 |
| 47 | Male | 58 | 63.4 | 73.8 |
| 48 | Male | 36 | 72.2 | 136.0 |
| 49 | Male | 49 | 58.8 | 82.7 |
| 50 | Male | 23 | 55.1 | 53.1 |
| 51 | Male | 34 | 38.9 | 51.8 |
| 52 | Male | 55 | 46.0 | 48.5 |

Example 8: Quantification of Copper in Diluent and LBC in Biological Samples

In this Example, the performance of the anti-CP mAb mix (1,2,3) (i.e., mixture of antibodies E, C, and G in a 2:1:1 ratio) in a LBC assay, as assessed by intra-run accuracy and precision of measurements, was evaluated.

The following four QC concentration samples of copper were prepared in diluent (i.e., 0.1% nitric acid in water): 5 ng/mL (QC LLOQ), 15 ng/mL (QC Low), 250 ng/mL (QC Mid), and 750 ng/mL (QC High).

In addition, the following four QC concentration samples of copper were prepared in screened human plasma: 5 ng/mL+mean measured background concentration (QC Matrix LLOQ), 15 ng/mL+mean measured background concentration (QC Matrix Low), 250 ng/mL (QC Matrix Mid), and 750 mg/mL (QC Matrix High).

Briefly, 60 µL of the mAb mix (1,2,3) were used to coat Dynabeads® magnetic beads, and these beads were used for immunocapture of CP in human plasma samples (i.e., QC matrix samples) according to the immunocapture step disclosed in Example 7. Calibration samples and the resulting CP-depleted matrix samples were then subjected to the remaining steps of the LBC assay as described in Example 7.

As shown in Table 15 (Cu in diluent) and Table 16 (LBC in human plasma), intra-run accuracy of the copper measurements met the pre-defined acceptance criteria in diluent (i.e., accuracy within ±15% (within ±20% for LLOQ) and the pre-defined acceptance criteria in human plasma (accuracy within ±20% (within ±25% for LLOQ). These results suggest that the mAb mix (1,2,3) does not interfere with the accuracy and precision of copper measurements.

TABLE 15

| Intra-run accuracy and precision for Cu in diluent | | | | | |
|---|---|---|---|---|---|
| | QC LLOQ 5 ng/ml | QC Low 15 ng/ml | QC Mid 250 ng/mL | QC High 750 ng/mL | QC AQL 7500 ng/mL |
| | 5.90 | 16.0 | 246 | 739 | 7390 |
| | 5.48 | 15.9 | 250 | 734 | 7560 |
| | 13.7* | 15.4 | 243 | 735 | 7490 |
| | 5.41 | 16.1 | 249 | 746 | 7660 |
| | 5.58 | 15.6 | 250 | 757 | 7720 |
| | 5.51 | 15.4 | 250 | 755 | 7530 |
| Mean | 6.93 | 15.7 | 248 | 744 | 7560 |
| SD | 3.32 | 0.308 | 2.90 | 9.99 | 119.00 |
| % CV | 3.2 | 2.0 | 1.2 | 1.3 | 1.6 |
| % Bias | 11.5 | 4.7 | −0.8 | −0.8 | 0.8 |
| n | 6 | 6 | 6 | 6 | 6 |

*Value was out of acceptable tolerable range and excluded in statistical calculations

TABLE 16

| Intra-run accuracy and precision for LBC in human plasma | | | | |
|---|---|---|---|---|
| | QC Matrix LLOQ 13.2 ng/ml | QC Matrix Low 31.9 ng/ml | QC Matrix Mid 250 ng/ml | QC Matrix High 750 ng/ml |
| | 11.7 | 39.6* | 218 | 743 |
| | 12.1 | 30.0 | 240 | 719 |
| | 16.7* | 33.9 | 234 | 715 |
| | 13.2 | 29.6 | 246 | 731 |
| | 11.6 | 29.2 | 238 | 734 |
| | 10.7 | 38.1 | 229 | 717 |
| Intra-run Mean | 12.7 | 33.0 | 234 | 727 |
| Intra-run SD | 2.14 | 4.60 | 9.77 | 11.2 |
| Intra-run % CV | 16.9 | 13.9 | 4.2 | 1.5 |
| Intra-run % Bias | −3.8 | 3.4 | −6.4 | −3.1 |
| n | 6 | 6 | 6 | 6 |

*Value was out of acceptable tolerable range and excluded in statistical calculations

Example 9: Stability of mAb Mix (1,2,3)

In this Example, the stability (shelf-life) of the mAb mix (1,2,3), as well as each of the three antibodies individually in the mAb mix (1,2,3) (i.e., antibodies E, C, and G), was determined.

Briefly, mAbs E, C, and G, as well as the mAb mix (1,2,3) (i.e., 2:1:1 ratio of antibodies E:C:G), all at 10 mg/mL in BBS with 0.09% sodium azide, were aliquoted into two vials (A & B) each in sufficient volume to perform quarterly qualitative CP-binding ELISAs and analytical size exclusion chromatography (aSEC). The vials were stored at 4° C. Qualitative CP-binding ELISAs were performed as described in Example 2.

FIGS. 10A-10D show a comparison of the CP-binding activity of the antibodies and mAb mix (1,2,3) at all time points tested (i.e., 0 months, 3 months, 6 months, and 9 months). At 9 months, there was a trend toward decreasing activity with time for antibodies C and G, but no significant change in CP-binding activity for the mAb mix (1,2,3) or its most concentrated component, mAb E.

For aSEC determination of mAb integrity and homogeneity, 10 uL of a 10 mg/mL mAb stock was run over a BioRad Enrich SEC650 column, with a column volume of 24 mL, at 0.7 mL/min. Chromatograms for paired A and B vials were virtually identical. Table 17 summarizes the intact monomeric mAb peak area data as a percentage of total peak area, and shows that none of the individual mAbs or mAb mix (1,2,3) samples underwent significant changes in integrity or size homogeneity over the course of 9 months. Moreover, as shown in Table 18, which summarizes the main peak area (which is proportional to mAb concentration), none of the individual mAb or mAb mix (1,2,3) samples underwent significant changes in apparent monomeric mAb concentration over the course of 9 months.

TABLE 17

SEC analysis - monomeric peak area/all peak area

| | Main Peak Area/All Peaks Area (%) | | | |
|---|---|---|---|---|
| Sample | 0 months | 3 months | 6 months | 9 months |
| mAb E | 97.8 | 97.6 | 97.9 | 98.1 |
| mAb C | 92.0 | 90.9 | 91.3 | 91.4 |
| mAb G | 97.7 | 97.1 | 97.9 | 97.7 |
| mAb mix (1, 2, 3) | 96.4 | 95.9 | 95.9 | 95.9 |

TABLE 18

SEC analysis - main peak area

| | Main Peak Area (mAU × s) | | | |
|---|---|---|---|---|
| Sample | 0 months | 3 months | 6 months | 9 months |
| mAb E | 10,631.5 | 10,432.5 | 10,724.0 | 10,689.1 |
| mAb C | 9,719.3 | 9,208.2 | 9,591.7 | 9,475.9 |
| mAb G | 10,667.5 | 10,774.5 | 10,724.0 | 11,045.4 |
| mAb mix (1, 2, 3) | 10,410.0 | 10,299.0 | 10,682.8 | 10,530.0 |

In summary, the ELISA and aSEC data for the mAb mix (1,2,3) do not indicate any significant loss of either CP-binding activity, structural integrity/homogeneity, or concentration over the course of 9 months. At the individual antibody level, there was a minor time-dependent reduction in CP-binding activity for two of the three individual mAbs, but without a change in integrity, homogeneity, or concentration.

Example 10: Diagnosis of Copper Metabolism-Associated Diseases

This Example describes diagnosing patients with copper metabolism-associated diseases by measuring non-ceruloplasmin-bound copper or labile-bound copper levels in patient biological samples (e.g., serum or plasma) and comparing them to reference ranges for healthy subjects.

Reference (threshold) levels for non-ceruloplasmin-bound copper or labile-bound copper can be determined in non-affected healthy individuals. Briefly, healthy individuals have their blood drawn and tested according to the methods using the antibody or antibody mixtures described herein, e.g., the NCC and/or LBC assays described in Example 7. The resulting Cu levels are evaluated and subdivided according to ethnicity, age, gender, co-morbidities, and other factors. Reference levels can be determined with standard deviations for each sub-population. A minimum of 120 individuals are evaluated per sub-group.

Patients presenting with symptoms believed to be copper metabolism-related will have blood samples taken and analyzed according to the methods using the antibody or antibody mixtures described herein, e.g., the NCC and/or LBC assay described in Example 7. The resulting NCC or LBC values, as compared to the above relevant healthy reference ranges, are used to identify those patients with copper metabolism-related disorders, such as Wilson disease. Patients identified as having a copper metabolism-related disorder can be treated with therapeutic agents relevant for treating the particular disorder or disease. For example, patients diagnosed with Wilson disease can be treated with at least one therapeutic agent selected from at least one of BC-TTM, trientine hydrochloride, trientine tetrahydrochloride, zinc (or salts thereof), and/or penicillamine.

TABLE 19

Summary of Sequences.

| SEQ ID | Description | Sequence |
|---|---|---|
| 1 | Human ceruloplasmin, precursor (leader sequence underlined) | MKILILGIFLFLCSTPAWAKEKHYYIGIIETTWDYASDHGEKK LISVDTEHSNIYLQNGPDRIGRLYKKALYLQYTDETFRTTIEK PVWLGFLGPIIKAETGDKVYVHLKNLASRPYTFHSHGITYYKE HEGAIYPDNTTDFQRADDKVYPGEQYTYMLLATEEQSPGEGDG NCVTRIYHSHIDAPKDIASGLIGPLIICKKDSLDKEKEKHIDR EFVVMFSVVDENFSWYLEDNIKTYCSEPEKVDKDNEDFQESNR MYSVNGYTFGSLPGLSMCAEDRVKWYLFGMGNEVDVHAAFFHG QALTNKNYRIDTINLFPATLFDAYMVAQNPGEWMLSCQNLNHL KAGLQAFFQVQECNKSSSKDNIRGKHVRHYYIAAEEIIWNYAP SGIDIFTKENLTAPGSDSAVFFEQGTTRIGGSYKKLVYREYTD ASFTNRKERGPEEEHLGILGPVIWAEVGDTIRVTFHNKGAYPL SIEPIGVRFNKNNEGTYYSPNYNPQSRSVPPSASHVAPTETFT YEWTVPKEVGPTNADPVCLAKMYYSAVEPTKDIFTGLIGPMKI CKKGSLHANGRQKDVDKEFYLFPTVFDENESLLLEDNIRMFTT APDQVDKEDEDFQESNKMHSMNGFMYGNQPGLTMCKGDSVVWY LFSAGNEADVHGIYFSGNTYLWRGERRDTANLFPQTSLTLHMW |

TABLE 19-continued

| Summary of Sequences. | | |
|---|---|---|
| SEQ ID | Description | Sequence |
| | | PDTEGTFNVECLTTDHYTGGMKQKYTVNQCRRQSEDSTFYLGE RTYYIAAVEVEWDYSPQREWEKELHHLQEQNVSNAFLDKGEFY IGSKYKKVVYRQYTDSTFRVPVERKAEEEHLGILGPQLHADVG DKVKIIFKNMATRPYSIHAHGVQTESSTVTPTLPGETLTYVWK IPERSGAGTEDSACIPWAYYSTVDQVKDLYSGLIGPLIVCRRP YLKVENPRRKLEFALLFLVFDENESWYLDDNIKTYSDHPEKVN KDDEEFIESNKMHAINGRMFGNLQGLTMHVGDEVNWYLMGMGN EIDLHTVHFHGHSFQYKHRGVYSSDVFDIFPGTYQTLEMFPRT PGIWLLHCHVTDHIHAGMETTYTVLQNEDTKSG |
| 2 | Human ceruloplasmin, mature | KEKHYYIGIIETTWDYASDHGEKKLISVDTEHSNIYLQNGPDR IGRLYKKALYLQYTDETFRTTIEKPVWLGFLGPIIKAETGDKV YVHLKNLASRPYTFHSHGITYYKEHEGAIYPDNTTDFQRADDK VYPGEQYTYMLLATEEQSPGEGDGNCVTRIYHSHIDAPKDIAS GLIGPLIICKKDSLDKEKEKHIDREFVVMFSVVDENFSWYLED NIKTYCSEPEKVDKDNEDFQESNRMYSVNGYTFGSLPGLSMCA EDRVKWYLFGMGNEVDVHAAFFHGQALTNKNYRIDTINLFPAT LFDAYMVAQNPGEWMLSCQNLNHLKAGLQAFFQVQECNKSSSK DNIRGKHVRHYYIAAEEIIWNYAPSGIDIFTKENLTAPGSDSA VFFEQGTTRIGGSYKKLVYREYTDASFTNRKERGPEEEHLGIL GPVIWAEVGDTIRVTFHNKGAYPLSIEPIGVRFNKNNEGTYYS PNYNPQSRSVPPSASHVAPTETFTYEWTVPKEVGPTNADPVCL AKMYYSAVEPTKDIFTGLIGPMKICKKGSLHANGRQKDVDKEF YLFPTVFDENESLLLEDNIRMFTTAPDQVDKEDEDFQESNKMH SMNGFMYGNQPGLTMCKGDSVVWYLFSAGNEADVHGIYFSGNT YLWRGERRDTANLFPQTSLTLHMWPDTEGTFNVECLTTDHYTG GMKQKYTVNQCRRQSEDSTFYLGERTYYIAAVEVEWDYSPQRE WEKELHHLQEQNVSNAFLDKGEFYIGSKYKKVVYRQYTDSTFR VPVERKAEEEHLGILGPQLHADVGDKVKIIFKNMATRPYSIHA HGVQTESSTVTPTLPGETLTYVWKIPERSGAGTEDSACIPWAY YSTVDQVKDLYSGLIGPLIVCRRPYLKVFNPRRKLEFALLFLV FDENESWYLDDNIKTYSDHPEKVNKDDEEFIESNKMHAINGRM FGNLQGLTMHVGDEVNWYLMGMGNEIDLHTVHFHGHSFQYKHR GVYSSDVFDIFPGTYQTLEMFPRTPGIWLLHCHVTDHIHAGME TTYTVLQNEDTKSG |
| 3 | Rabbit heavy chain constant region | GQPKAPSVFPLAPCCGDTPSSTVTLGCLVKGYLPEPVTVTWNS GTLTNGVRTFPSVRQSSGLYSLSSVVSVTSSSQPVTCNVAHPA TNTKVDKTVAPSTCSKPTCPPPELLGGPSVFIFPPKPKDTLMI SRTPEVTCVVVDVSQDDPEVQFTWYINNEQVRTARPPLREQQF NSTIRVVSTLPITHQDWLRGKEFKCKVHNKALPAPIEKTISKA RGQPLEPKVYTMGPPREELSSRSVSLTCMINGFYPSDISVEWE KNGKAEDNYKTTPAVLDSDGSYFLYSKLSVPTSEWQRGDVFTC SVMHEALHNHYTQKSISRSPGK |
| 4 | Rabbit light chain constant region | DPVAPTVLIFPPAADQVATGTVTIVCVANKYFPDVTVTWEVDG TTQTTGIENSKTPQNSADCTYNLSSTLTLTSTQYNSHKEYTCK VTQGTTSVVQSFNRGDC |
| 5 | mAb E VHCDR1 (Kabat) | SYGMG |
| 6 | mAb E VHCDR2 (Kabat) | IISSSGTYYANWAKG |
| 7 | mAb E VHCDR3 (Kabat) | YFAGGAYDI |
| 8 | mAb E VLCDR1 (Kabat) | QASQSVVSNNYLA |
| 9 | mAb E VLCDR2 (Kabat) | FASTLAS |
| 10 | mAb E VLCDR3 (Kabat) | LGVYNNVDT |
| 11 | mAb E VHCDR1 (Chothia) | GFSLSSY |
| 12 | mAb E VHCDR2 (Chothia) | SSSG |
| 13 | mAb E VHCDR3 (Chothia) | YFAGGAYDI |
| 14 | mAb E VLCDR1 (Chothia) | QASQSVVSNNYLA |
| 15 | mAb E VLCDR2 (Chothia) | FASTLAS |
| 16 | mAb E VLCDR3 (Chothia) | LGVYNNVDT |
| 17 | mAb E VHCDR1 (IMGT) | GFSLSSYG |
| 18 | mAb E VHCDR2 (IMGT) | ISSSGT |

TABLE 19-continued

| Summary of Sequences. | | |
|---|---|---|
| SEQ ID | Description | Sequence |
| 19 | mAb E VHCDR3 (IMGT) | ARYFAGGAYDI |
| 20 | mAb E VLCDR1 (IMGT) | QSVVSNNY |
| 21 | mAb E VLCDR2 (IMGT) | FAS |
| 22 | mAb E VLCDR3 (IMGT) | LGVYNNVDT |
| 23 | mAb E VH | METGLRWLLLVAVLKGVQCQSVEESGGRLVTPGTPLTLTCTVS GFSLSSYGMGWVRQAPGKGLEYIGIISSSGTYYANWAKGRFTI SRTSTTVDLKVASPTTEDTATYFCARYFAGGAYDIWGPGTLVT VSL |
| 24 | mAb E VL | MDMRAPTQLLGLLLLWLPGATFAQVLTQTPSSVSAAVGGTVTI NCQASQSVVSNNYLAWFQQKPGQPPKLLIYFASTLASGVPSRF KGSGSGTQFTLTISDLECDDAATYYCLGVYNNVDTFGGGTEVV VKG |
| 25 | mAb E VH (w/o signal sequence) | QSVEESGGRLVTPGTPLTLTCTVSGFSLSSYGMGWVRQAPGKG LEYIGIISSSGTYYANWAKGRFTISRTSTTVDLKVASPTTEDT ATYFCARYFAGGAYDIWGPGTLVTVSL |
| 26 | mAb E VL (w/o signal sequence) | AQVLTQTPSSVSAAVGGTVTINCQASQSVVSNNYLAWFQQKPG QPPKLLIYFASTLASGVPSRFKGSGSGTQFTLTISDLECDDAA TYYCLGVYNNVDTFGGGTEVVVKG |
| 27 | mAb E HC | METGLRWLLLVAVLKGVQCQSVEESGGRLVTPGTPLTLTCTVS GFSLSSYGMGWVRQAPGKGLEYIGIISSSGTYYANWAKGRFTI SRTSTTVDLKVASPTTEDTATYFCARYFAGGAYDIWGPGTLVT VSLGQPKAPSVFPLAPCCGDTPSSTVTLGCLVKGYLPEPVTVT WNSGTLTNGVRTFPSVRQSSGLYSLSSVVSVTSSSQPVTCNVA HPATNTKVDKTVAPSTCSKPTCPPPELLGGPSVFIFPPKPKDT LMISRTPEVTCVVVDVSQDDPEVQFTWYINNEQVRTARPPLRE QQFNSTIRVVSTLPITHQDWLRGKEFKCKVHNKALPAPIEKTI SKARGQPLEPKVYTMGPPREELSSRSVSLTCMINGFYPSDISV EWEKNGKAEDNYKTTPAVLDSDGSYFLYSKLSVPTSEWQRGDV FTCSVMHEALHNHYTQKSISRSPGK |
| 28 | mAb ELC | MDMRAPTQLLGLLLLWLPGATFAQVLTQTPSSVSAAVGGTVTI NCQASQSVVSNNYLAWFQQKPGQPPKLLIYFASTLASGVPSRF KGSGSGTQFTLTISDLECDDAATYYCLGVYNNVDTFGGGTEVV VKGDPVAPTVLLFPPAADQVATGTVTIVCVANKYFPDVTVTWE VDGTTQTTGIENSKTPQNSADCTYNLSSTLTLTSTQYNSHKEY TCKVTQGTTSVVQSFNRGDC |
| 29 | mAb C VHCDR1 (Kabat) | RYYMS |
| 30 | mAb C VHCDR2 (Kabat) | MIYPSSGSTWYASWVKG |
| 31 | mAb C VHCDR3 (Kabat) | DRYPGYNGDSFNL |
| 32 | mAb C VLCDR1 (Kabat) | QASQSVYNNNYLA |
| 33 | mAb C VLCDR2 (Kabat) | QASKLAI |
| 34 | mAb C VLCDR3 (Kabat) | LGSYGCNSVDCNV |
| 35 | mAb C VHCDR1 (Chothia) | GFSLSRY |
| 36 | mAb C VHCDR2 (Chothia) | YPSSGS |
| 37 | mAb C VHCDR3 (Chothia) | DRYPGYNGDSFNL |
| 38 | mAb C VLCDR1 (Chothia) | QASQSVYNNNYLA |
| 39 | mAb C VLCDR2 (Chothia) | QASKLAI |
| 40 | mAb C VLCDR3 (Chothia) | LGSYGCNSVDCNV |
| 41 | mAb C VHCDR1 (IMGT) | GFSLSRYY |
| 42 | mAb C VHCDR2 (IMGT) | IYPSSGST |
| 43 | mAb C VHCDR3 (IMGT) | VRDRYPGYNGDSFNL |

TABLE 19-continued

Summary of Sequences.

| SEQ ID | Description | Sequence |
|---|---|---|
| 44 | mAb C VLCDR1 (IMGT) | QSVYNNNY |
| 45 | mAb C VLCDR2 (IMGT) | QAS |
| 46 | mAb C VLCDR3 (IMGT) | LGSYGCNSVDCNV |
| 47 | mAb C VH | METGLRWLLLVAVLKGVQCQSVEESGGRLVTPGTPLTLTCTAS GFSLSRYYMSWVRQAPGKGLEWIGMIYPSSGSTWYASWVKGRF TISATATSVDLKITSPTTEDTATYFCVRDRYPGYNGDSFNLWG QGTLVTVSS |
| 48 | mAb C VL | MDTRAPTQLLGLLLLWLPGATFAQVLTQTASPVSAAVGSTVTI NCQASQSVYNNNYLAWFQQKPGQPPKRLIYQASKLAIGVPSRF SGSGSGTQFTLTISDVQCDDAATYYCLGSYGCNSVDCNVFGGG TEVVVKG |
| 49 | mAb C VH (w/o signal sequence) | QSVEESGGRLVTPGTPLTLTCTASGFSLSRYYMSWVRQAPGKG LEWIGMIYPSSGSTWYASWVKGRFTISATATSVDLKITSPTTE DTATYFCVRDRYPGYNGDSFNLWGQGTLVTVSS |
| 50 | mAb C VL (w/o signal sequence) | AQVLTQTASPVSAAVGSTVTINCQASQSVYNNNYLAWFQQKPG QPPKRLIYQASKLAIGVPSRFSGSGSGTQFTLTISDVQCDDAA TYYCLGSYGCNSVDCNVFGGGTEVVVKG |
| 51 | mAb C HC | METGLRWLLLVAVLKGVQCQSVEESGGRLVTPGTPLTLTCTAS GFSLSRYYMSWVRQAPGKGLEWIGMIYPSSGSTWYASWVKGRF TISATATSVDLKITSPTTEDTATYFCVRDRYPGYNGDSFNLWG QGTLVTVSSGQPKAPSVFPLAPCCGDTPSSTVTLGCLVKGYLP EPVTVTWNSGTLTNGVRTFPSVRQSSGLYSLSSVVSVTSSSQP VTCNVAHPATNTKVDKTVAPSTCSKPTCPPPELLGGPSVFIFP PKPKDTLMISRTPEVTCVVVDVSQDDPEVQFTWYINNEQVRTA RPPLREQQFNSTIRVVSTLPITHQDWLRGKEFKCKVHNKALPA PIEKTISKARGQPLEPKVYTMGPPREELSSRSVSLTCMINGFY PSDISVEWEKNGKAEDNYKTTPAVLDSDGSYFLYSKLSVPTSE WQRGDVFTCSVMHEALHNHYTQKSISRSPGK |
| 52 | mAb C LC | MDTRAPTQLLGLLLLWLPGATFAQVLTQTASPVSAAVGSTVTI NCQASQSVYNNNYLAWFQQKPGQPPKRLIYQASKLAIGVPSRF SGSGSGTQFTLTISDVQCDDAATYYCLGSYGCNSVDCNVFGGG TEVVVKGDPVAPTVLIFPPAADQVATGTVTIVCVANKYFPDVT VTWEVDGTTQTTGIENSKTPQNSADCTYNLSSTLTLTSTQYNS HKEYTCKVTQGTTSVVQSFNRGDC |
| 53 | mAb G VHCDR1 (Kabat) | SNAMS |
| 54 | mAb G VHCDR2 (Kabat) | TISSRGSTYYANWAKG |
| 55 | mAb G VHCDR3 (Kabat) | SSLAGYEPYYFKL |
| 56 | mAb G VLCDR1 (Kabat) | QASESISSYLA |
| 57 | mAb G VLCDR2 (Kabat) | GASDLAS |
| 58 | mAb G VLCDR3 (Kabat) | QSYYGLSRNGYGNV |
| 59 | mAb G VHCDR1 (Chothia) | GFSLSSN |
| 60 | mAb G VHCDR2 (Chothia) | SSRGS |
| 61 | mAb G VHCDR3 (Chothia) | SSLAGYEPYYFKL |
| 62 | mAb G VLCDR1 (Chothia) | QASESISSYLA |
| 63 | mAb G VLCDR2 (Chothia) | GASDLAS |
| 64 | mAb G VLCDR3 (Chothia) | QSYYGLSRNGYGNV |
| 65 | mAb G VHCDR1 (IMGT) | GFSLSSNA |
| 66 | mAb G VHCDR2 (IMGT) | ISSRGST |
| 67 | mAb G VHCDR3 (IMGT) | ARSSLAGYEPYYFKL |
| 68 | mAb G VLCDR1 (IMGT) | ESISSY |
| 69 | mAb G VLCDR2 (IMGT) | GAS |

TABLE 19-continued

Summary of Sequences.

| SEQ ID | Description | Sequence |
|---|---|---|
| 70 | mAb G VLCDR3 (IMGT) | QSYYGLSRNGYGNV |
| 71 | mAb G VH | METGLRWLLLVAVLKGVQCQSLEESGGRLVTPGTLLTLTCTVS GFSLSSNAMSWVRQAPGEGLEWIGTISSRGSTYYANWAKGRFT ISKTSTTVDLKITSPTTEDTATYFCARSSLAGYEPYYFKLWGQ GTLVTVSS |
| 72 | mAb G VL | MDMRAPTQLLGLLLLWLPGARCADVVMTQTASPVSAAVGGTVT IKCQASESISSYLAWYQQKPGQPPKLLIYGASDLASGVPSRFK GSGSGTEFTLTISDLECADAATYYCQSYYGLSRNGYGNVFGGG TEVVVKG |
| 73 | mAb G VH (w/o signal sequence) | QSLEESGGRLVTPGTLLTLTCTVSGFSLSSNAMSWVRQAPGEG LEWIGTISSRGSTYYANWAKGRFTISKTSTTVDLKITSPTTED TATYFCARSSLAGYEPYYFKLWGQGTLVTVSS |
| 74 | mAb G VL (w/o signal sequence) | DVVMTQTASPVSAAVGGTVTIKCQASESISSYLAWYQ QKPGQPPKLLIYGASDLASGVPSRFKGSGSGTEFTLTISDLEC ADAATYYCQSYYGLSRNGYGNVFGGGTEVVVKG |
| 75 | mAb GHC | METGLRWLLLVAVLKGVQCQSLEESGGRLVTPGTLLTLTCTVS GFSLSSNAMSWVRQAPGEGLEWIGTISSRGSTYYANWAKGRFT ISKTSTTVDLKITSPTTEDTATYFCARSSLAGYEPYYFKLWGQ GTLVTVSSGQPKAPSVFPLAPCCGDTPSSTVTLGCLVKGYLPE PVTVTWNSGTLTNGVRTFPSVRQSSGLYSLSSVVSVTSSSQPV TCNVAHPATNTKVDKTVAPSTCSKPTCPPPELLGGPSVFIFPP KPKDTLMISRTPEVTCVVVDVSQDDPEVQFTWYINNEQVRTA RPPLREQQFNSTIRVVSTLPITHQDWLRGKEFKCKVHNKALPA PIEKTISKARGQPLEPKVYTMGPPREELSSRSVSLTCMINGFY PSDISVEWEKNGKAEDNYKTTPAVLDSDGSYFLYSKLSVPTSE WQRGDVFTCSVMHEALHNHYTQKSISRSPGK |
| 76 | mAb GLC | MDMRAPTQLLGLLLLWLPGARCADVVMTQTASPVSAAVGGTVT IKCQASESISSYLAWYQQKPGQPPKLLIYGASDLASGVPSRFK GSGSGTEFTLTISDLECADAATYYCQSYYGLSRNGYGNVFGGG TEVVVKGDPVAPTVLIFPPAADQVATGTVTIVCVANKYFPDVT VTWEVDGTTQTTGIENSKTPQNSADCTYNLSSTLTLTSTQYNS HKEYTCKVTQGTTSVVQSFNRGDC |
| 77 | mAb B VHCDR1 (Kabat) | SYYYMC |
| 78 | mAb B VHCDR2 (Kabat) | CIYVIDDTIYCANWAKG |
| 79 | mAb B VHCDR3 (Kabat) | DGSSGIRDYFDL |
| 80 | mAb B VLCDR1 (Kabat) | QASESVSTWLA |
| 81 | mAb B VLCDR2 (Kabat) | KASDLAS |
| 82 | mAb B VLCDR3 (Kabat) | QQGYTYNNVENV |
| 83 | mAb B VHCDR1 (Chothia) | GIDFSSYY |
| 84 | mAb B VHCDR2 (Chothia) | YVIDDT |
| 85 | mAb B VHCDR3 (Chothia) | DGSSGIRDYFDL |
| 86 | mAb B VLCDR1 (Chothia) | QASESVSTWLA |
| 87 | mAb B VLCDR2 (Chothia) | KASDLAS |
| 88 | mAb B VLCDR3 (Chothia) | QQGYTYNNVENV |
| 89 | mAb B VHCDR1 (IMGT) | GIDFSSYYY |
| 90 | mAb B VHCDR2 (IMGT) | IYVIDDTI |
| 91 | mAb B VHCDR3 (IMGT) | ARDGSSGIRDYFDL |
| 92 | mAb B VLCDR1 (IMGT) | ESVSTW |
| 93 | mAb B VLCDR2 (IMGT) | KAS |
| 94 | mAb B VLCDR3 (IMGT) | QQGYTYNNVENV |

TABLE 19-continued

| Summary of Sequences. | | |
|---|---|---|
| SEQ ID | Description | Sequence |
| 95 | mAb B VH | METGLRWLLLVAVLKGVQCQQQLEESGGGLVKPGGTLTLTCKASGIDFSSYYYMCWVRQAPGKGLEWIACIYVIDDTIYCANWAKGRFTISKTSSTTVTLQMTSLTAADTATYFCARDGSSGIRDYFDLWGPGTLVTVSS |
| 96 | mAb B VL | MDTRAPTQLLGLLLLWLPGARCAYDMTQTPASVEVAVGGTVTIKCQASESVSTWLAWYQQKPGQPPKLLIYKASDLASGVPSRFKGSGSGTEFTLTISGVECADAATYYCQQGYTYNNVENVFGGGTEVVVKG |
| 97 | mAb B VH (w/o signal sequence) | QQQLEESGGGLVKPGGTLTLTCKASGIDFSSYYYMCVRQAPGKGLEWIACIYVIDDTIYCANWAKGRFTISKTSSTTVTLQMTSLTAADTATYFCARDGSSGIRDYFDLWGPGTLVTVSS |
| 98 | mAb B VL (w/o signal sequence) | AYDMTQTPASVEVAVGGTVTIKCQASESVSTWLAWYQQKPGQPPKLLIYKASDLASGVPSRFKGSGSGTEFTLTISGVECADAATYYCQQGYTYNNVENVFGGGTEVVVKG |
| 99 | mAb B HC | METGLRWLLLVAVLKGVQCQQQLEESGGGLVKPGGTLTLTCKASGIDFSSYYYMCWVRQAPGKGLEWIACIYVIDDTIYCANWAKGRFTISKTSSTTVTLQMTSLTAADTATYFCARDGSSGIRDYFDLWGPGTLVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPTCPPPELLGGPSVFIFPPKPKDTLMISRTPEVTCVVVDVSQDDPEVQFTWYINNEQVRTARPPLREQQFNSTIRVVSTLPITHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYSKLSVPTSEWQRGDVFTCSVMHEALHNHYTQKSISRSPGK |
| 100 | mAb B LC | MDTRAPTQLLGLLLLWLPGARCAYDMTQTPASVEVAVGGTVTIKCQASESVSTWLAWYQQKPGQPPKLLIYKASDLASGVPSRFKGSGSGTEFTLTISGVECADAATYYCQQGYTYNNVENVFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC |
| 101 | mAb F VHCDR1 (Kabat) | SNAMS |
| 102 | mAb F VHCDR2 (Kabat) | TISTAGFTYYASWAKG |
| 103 | mAb F VHCDR3 (Kabat) | LLYGPNI |
| 104 | mAb F VLCDR1 (Kabat) | QASPSISNELS |
| 105 | mAb F VLCDR2 (Kabat) | LASTLAS |
| 106 | mAb F VLCDR3 (Kabat) | QGIVYGPDYVVG |
| 107 | mAb F VHCDR1 (Chothia) | GIDLSSN |
| 108 | mAb F VHCDR2 (Chothia) | STAGE |
| 109 | mAb F VHCDR3 (Chothia) | LLYGPNI |
| 110 | mAb F VLCDR1 (Chothia) | QASPSISNELS |
| 111 | mAb F VLCDR2 (Chothia) | LASTLAS |
| 112 | mAb F VLCDR3 (Chothia) | QGIVYGPDYVVG |
| 113 | mAb F VHCDR1 (IMGT) | GIDLSSNA |
| 114 | mAb F VHCDR2 (IMGT) | ISTAGFT |
| 115 | mAb F VHCDR3 (IMGT) | ARLLYGPNI |
| 116 | mAb F VLCDR1 (IMGT) | PSISNE |
| 117 | mAb F VLCDR2 (IMGT) | LAS |
| 118 | mAb F VLCDR3 (IMGT) | QGIVYGPDYVVG |

TABLE 19-continued

| Summary of Sequences. | | |
|---|---|---|
| SEQ ID | Description | Sequence |
| 119 | mAb F VH | METGLRWLLLVAVLKGVQCQSVEESGGGLVTPGGTLTLTCTVSGIDLSSNAMSWVRQAPGEGLEWIGTISTAGFTYYASWAKGRFTISKTSTTVDLKMTSLTAADTATYFCARLLYGPNIWGPGTLVTVSL |
| 120 | mAb F VL | MDMRAPTQLLGLLLLWLPGVICDPVMTQTPASVSEPVGGTVTIKCQASPSISNELSWYQQKPGQPPQLLIYLASTLASGVPSRFKGSRSGTEFTLTISDLECADAATYYCQGIVYGPDYVVGFGGGTEVVVKG |
| 121 | mAb F VH (w/o signal sequence) | QSVEESGGGLVTPGGTLTLTCTVSGIDLSSNAMSWVRQAPGEGLEWIGTISTAGFTYYASWAKGRFTISKTSTTVDLKMTSLTAADTATYFCARLLYGPNIWGPGTLVTVSL |
| 122 | mAb F VL (w/o signal sequence) | DPVMTQTPASVSEPVGGTVTIKCQASPSISNELSWYQQKPGQPPQLLIYLASTLASGVPSRFKGSRSGTEFTLTISDLECADAATYYCQGIVYGPDYVVGFGGGTEVVVKG |
| 123 | mAb F HC | METGLRWLLLVAVLKGVQCQSVEESGGGLVTPGGTLTLTCTVSGIDLSSNAMSWVRQAPGEGLEWIGTISTAGFTYYASWAKGRFTISKTSTTVDLKMTSLTAADTATYFCARLLYGPNIWGPGTLVTVSLGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPTCPPPELLGGPSVFIFPPKPKDTLMISRTPEVTCVVVDVSQDDPEVQFTWYINNEQVRTARPPLREQQFNSTIRVVSTLPITHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYSKLSVPTSEWQRGDVFTCSVMHEALHNHYTQKSISRSPGK |
| 124 | mAb F LC | MDMRAPTQLLGLLLLWLPGVICDPVMTQTPASVSEPVGGTVTIKCQASPSISNELSWYQQKPGQPPQLLIYLASTLASGVPSRFKGSRSGTEFTLTISDLECADAATYYCQGIVYGPDYVVGFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC |
| 125 | mAb A VHCDR1 (Kabat) | RFYYMC |
| 126 | mAb A VHCDR2 (Kabat) | CIYAGRTGNTYYASWAKG |
| 127 | mAb A VHCDR3 (Kabat) | ASGDFLAYTYAMDL |
| 128 | mAb A VLCDR1 (Kabat) | QASQSVDNNNYLA |
| 129 | mAb A VLCDR2 (Kabat) | EASKLAS |
| 130 | mAb A VLCDR3 (Kabat) | AGGYSSSADANA |
| 131 | mAb A VHCDR1 (Chothia) | GFDLSRFY |
| 132 | mAb A VHCDR2 (Chothia) | YAGRTGN |
| 133 | mAb A VHCDR3 (Chothia) | ASGDFLAYTYAMDL |
| 134 | mAb A VLCDR1 (Chothia) | QASQSVDNNNYLA |
| 135 | mAb A VLCDR2 (Chothia) | EASKLAS |
| 136 | mAb A VLCDR3 (Chothia) | AGGYSSSADANA |
| 137 | mAb A VHCDR1 (IMGT) | GFDLSRFYY |
| 138 | mAb A VHCDR2 (IMGT) | IYAGRTGNT |
| 139 | mAb A VHCDR3 (IMGT) | ARASGDFLAYTYAMDL |
| 140 | mAb A VLCDR1 (IMGT) | QSVDNNNY |
| 141 | mAb A VLCDR2 (IMGT) | EAS |
| 142 | mAb A VLCDR3 (IMGT) | AGGYSSSADANA |

TABLE 19-continued

| Summary of Sequences. | | |
|---|---|---|
| SEQ ID | Description | Sequence |
| 143 | mAb A VH | METGLRWLLLVAVLKGVQCQSLEESGGDLVKPGASLTLTCKAS GFDLSRFYYMCWVRQAPGKGLEWIACIYAGRTGNTYYASWAKG RFTISKTSSTTVTLQMTSLTAADTATYFCARASGDFLAYTYAM DLWGPGTLVTVSS |
| 144 | mAb A VL | MDMRAPTQLLGLLLLWLPGATFAAVLTQTPASVSAAVGGTVTI SCQASQSVDNNNYLAWYQQKPGQPPKLLIYEASKLASGVPSRF SGSGSGTQFTLTISDVQCDDATTYYCAGGYSSSADANAFGGGT EVVVKG |
| 145 | mAb A VH (w/o signal sequence) | QSLEESGGDLVKPGASLTLTCKASGFDLSRFYYMCWVRQAPGK GLEWIACIYAGRTGNTYYASWAKGRFTISKTSSTTVTLQMTSL TAADTATYFCARASGDFLAYTYAMDLWGPGTLVTVSS |
| 146 | mAb A VL (w/o signal sequence) | AAVLTQTPASVSAAVGGTVTISCQASQSVDNNNYLAWYQQKPG QPPKLLIYEASKLASGVPSRFSGSGSGTQFTLTISDVQCDDAT TYYCAGGYSSSADANAFGGGTEVVVKG |
| 147 | mAb A HC | METGLRWLLLVAVLKGVQCQSLEESGGDLVKPGASLTLTCKAS GFDLSRFYYMCWVRQAPGKGLEWIACIYAGRTGNTYYASWAKG RFTISKTSSTTVTLQMTSLTAADTATYFCARASGDFLAYTYAM DLWGPGTLVTVSSGQPKAPSVFPLAPCCGDTPSSTVTLGCLVK GYLPEPVTVTWNSGTLTNGVRTFPSVRQSSGLYSLSSVVSVTS SSQPVTCNVAHPATNTKVDKTVAPSTCSKPTCPPPELLGGPSV FIFPPKPKDTLMISRTPEVTCVVVDVSQDDPEVQFTWYINNEQ VRTARPPLREQQFNSTIRVVSTLPITHQDWLRGKEFKCKVHNK ALPAPIEKTISKARGQPLEPKVYTMGPPREELSSRSVSLTCMI NGFYPSDISVEWEKNGKAEDNYKTTPAVLDSDGSYFLYSKLSV PTSEWQRGDVFTCSVMHEALHNHYTQKSISRSPGK |
| 148 | mAb A LC | MDMRAPTQLLGLLLLWLPGATFAAVLTQTPASVSAAVGGTVTI SCQASQSVDNNNYLAWYQQKPGQPPKLLIYEASKLASGVPSRF SGSGSGTQFTLTISDVQCDDATTYYCAGGYSSSADANAFGGGT EVVVKGDPVAPTVLIFPPAADQVATGTVTIVCVANKYFPDVTV TWEVDGTTQTTGIENSKTPQNSADCTYNLSSTLTLTSTQYNSH KEYTCKVTQGTTSVVQSFNRGDC |
| 149 | mAb D VHCDR1 (Kabat) | SYWMC |
| 150 | mAb D VHCDR2 (Kabat) | CIYGGDGTSYFAGWAKG |
| 151 | mAb D VHCDR3 (Kabat) | ADYYVYVDGGYGHAYDL |
| 152 | mAb D VLCDR1 (Kabat) | QASDDIYSYLA |
| 153 | mAb D VLCDR2 (Kabat) | DASSLPS |
| 154 | mAb D VLCDR3 (Kabat) | QNYYGSSSSVHA |
| 155 | mAb D VHCDR1 (Chothia) | GFDFSSY |
| 156 | mAb D VHCDR2 (Chothia) | YGGDGT |
| 157 | mAb D VHCDR3 (Chothia) | ADYYVYVDGGYGHAYDL |
| 158 | mAb D VLCDR1 (Chothia) | QASDDIYSYLA |
| 159 | mAb D VLCDR2 (Chothia) | DASSLPS |
| 160 | mAb D VLCDR3 (Chothia) | QNYYGSSSSVHA |
| 161 | mAb D VHCDR1 (IMGT) | GFDFSSYW |
| 162 | mAb D VHCDR2 (IMGT) | IYGGDGTS |
| 163 | mAb D VHCDR3 (IMGT) | ARADYYVYVDGGYGHAYDL |
| 164 | mAb D VLCDR1 (IMGT) | DDIYSY |
| 165 | mAb D VLCDR2 (IMGT) | DAS |
| 166 | mAb D VLCDR3 (IMGT) | QNYYGSSSSVHA |

TABLE 19-continued

| Summary of Sequences. | | |
|---|---|---|
| SEQ ID | Description | Sequence |
| 167 | mAb D VH | METGLRWLLLVAVLKGVQCQEQLVESGGGLVQPEGSLTLTCKA SGFDFSSYWMCWVRQAPGKRPEWIACIYGGDGTSYFAGWAKGR FTISKTSSTTVTLQMTSLTAADTATYFCARADYYVYVDGGYGH AYDLWGPGTLVTVSS |
| 168 | mAb D VL | MDMRAPTQLLGLLLLWLPGARCVDIVMTQTPASVEAAVGGSVT IKCQASDDIYSYLAWYQQKPGQPPKLLIFDASSLPSGVPSRFK GSGSGTQFTLTISGVQCADAATYYCQNYYGSSSSVHAFGGGTE VVVKG |
| 169 | mAb D VH (w/o signal sequence) | QEQLVESGGGLVQPEGSLTLTCKASGFDFSSYWMCWVRQAPGK RPEWIACIYGGDGTSYFAGWAKGRFTISKTSSTTVTLQMTSLT AADTATYFCARADYYVYVDGGYGHAYDLWGPGTLVTVSS |
| 170 | mAb D VL (w/o signal sequence) | DIVMTQTPASVEAAVGGSVTIKCQASDDIYSYLAWYQ QKPGQPPKLLIFDASSLPSGVPSRFKGSGSGTQFTLTISGVQC ADAATYYCQNYYGSSSSVHAFGGGTEVVVKG |
| 171 | mAb D HC | METGLRWLLLVAVLKGVQCQEQLVESGGGLVQPEGSLTLTCKA SGFDFSSYWMCWVRQAPGKRPEWIACIYGGDGTSYFAGWAKGR FTISKTSSTTVTLQMTSLTAADTATYFCARADYYVYVDGGYGH AYDLWGPGTLVTVSSGQPKAPSVFPLAPCCGDTPSSTVTLGCL VKGYLPEPVTVTWNSGTLTNGVRTFPSVRQSSGLYSLSSVVSV TSSSQPVTCNVAHPATNTKVDKTVAPSTCSKPTCPPPELLGGP SVFIFPPKPKDTLMISRTPEVTCVVVDVSQDDPEVQFTWYINN EQVRTARPPLREQQFNSTIRVVSTLPITHQDWLRGKEFKCKVH NKALPAPIEKTISKARGQPLEPKVYTMGPPREELSSRSVSLTC MINGFYPSDISVEWEKNGKAEDNYKTTPAVLDSDGSYFLYSKL SVPTSEWQRGDVFTCSVMHEALHNHYTQKSISRSPGK |
| 172 | mAb D LC | MDMRAPTQLLGLLLLWLPGARCVDIVMTQTPASVEAAVGGSVT IKCQASDDIYSYLAWYQQKPGQPPKLLIFDASSLPSGVPSRFK GSGSGTQFTLTISGVQCADAATYYCQNYYGSSSSVHAFGGGTE VVVKGDPVAPTVLIFPPAADQVATGTVTIVCVANKYFPDVTVT WEVDGTTQTTGIENSKTPQNSADCTYNLSSTLTLTSTQYNSHK EYTCKVTQGTTSVVQSFNRGDC |
| 173 | mAb H VHCDR1 (Kabat) | TYAMG |
| 174 | mAb H VHCDR2 (Kabat) | IIYGGSGTFYASWAKG |
| 175 | mAb H VHCDR3 (Kabat) | DGDDSYFDYFNL |
| 176 | mAb H VLCDR1 (Kabat) | QSNENIGSNLA |
| 177 | mAb H VLCDR2 (Kabat) | GASTLTS |
| 178 | mAb H VLCDR3 (Kabat) | LGGYLSTSDTT |
| 179 | mAb H VHCDR1 (Chothia) | GFSLSTY |
| 180 | mAb H VHCDR2 (Chothia) | YGGSG |
| 181 | mAb H VHCDR3 (Chothia) | DGDDSYFDYFNL |
| 182 | mAb H VLCDR1 (Chothia) | QSNENIGSNLA |
| 183 | mAb H VLCDR2 (Chothia) | GASTLTS |
| 184 | mAb H VLCDR3 (Chothia) | LGGYLSTSDTT |
| 185 | mAb H VHCDR1 (IMGT) | GFSLSTYA |
| 186 | mAb H VHCDR2 (IMGT) | IYGGSGT |
| 187 | mAb H VHCDR3 (IMGT) | ARDGDDSYFDYFNL |
| 188 | mAb H VLCDR1 (IMGT) | ENIGSN |
| 189 | mAb H VLCDR2 (IMGT) | GAS |
| 190 | mAb H VLCDR3 (IMGT) | LGGYLSTSDTT |

TABLE 19-continued

Summary of Sequences.

| SEQ ID | Description | Sequence |
|---|---|---|
| 191 | mAb H VH | METGLRWLLLVAVLKGVQCQSVEESGGRLVTPGTPLTLTCTVS GFSLSTYAMGWVRQAPGKGLEYIGIIYGGSGTFYASWAKGRFT ISKTSTTVDLKITSPTTEDTATYFCARDGDDSYFDYFNLWGQG TLVTVSS |
| 192 | mAb H VL | MDTRAPTQLLGLLLLWLPGATFAAVLTQTPASVSAAVGGTVSI SCQSNENIGSNLAWYQQKPGQPPKLLIYGASTLTSGVPSRFKG SGSGTAFTLTISGVQCDDAATYYCLGGYLSTSDTTFGGGTAVV VKG |
| 193 | mAb H VH (w/o signal sequence) | QSVEESGGRLVTPGTPLTLTCTVSGFSLSTYAMGWVRQAPGKG LEYIGIIYGGSGTFYASWAKGRFTISKTSTTVDLKITSPTTED TATYFCARDGDDSYFDYFNLWGQGTLVTVSS |
| 194 | mAb H VL (w/o signal sequence) | AAVLTQTPASVSAAVGGTVSISCQSNENIGSNLAWYQQKPGQP PKLLIYGASTLTSGVPSRFKGSGSGTAFTLTISGVQCDDAATY YCLGGYLSTSDTTFGGGTAVVVKG |
| 195 | mAb H HC | METGLRWLLLVAVLKGVQCQSVEESGGRLVTPGTPLTLTCTVS GFSLSTYAMGWVRQAPGKGLEYIGIIYGGSGTFYASWAKGRFT ISKTSTTVDLKITSPTTEDTATYFCARDGDDSYFDYFNLWGQG TLVTVSSGQPKAPSVFPLAPCCGDTPSSTVTLGCLVKGYLPEP VTVTWNSGTLTNGVRTFPSVRQSSGLYSLSSVVSVTSSSQPVT CNVAHPATNTKVDKTVAPSTCSKPTCPPPELLGGPSVFIFPPK PKDTLMISRTPEVTCVVVDVSQDDPEVQFTWYINNEQVRTARP PLREQQFNSTIRVVSTLPITHQDWLRGKEFKCKVHNKALPAPI EKTISKARGQPLEPKVYTMGPPREELSSRSVSLTCMINGFYPS DISVEWEKNGKAEDNYKTTPAVLDSDGSYFLYSKLSVPTSEWQ RGDVFTCSVMHEALHNHYTQKSISRSPGK |
| 196 | mAb H LC | MDTRAPTQLLGLLLLWLPGATFAAVLTQTPASVSAAVGGTVSI SCQSNENIGSNLAWYQQKPGQPPKLLIYGASTLTSGVPSRFKG SGSGTAFTLTISGVQCDDAATYYCLGGYLSTSDTTFGGGTAVV VKGDPVAPTVLIFPPAADQVATGTVTIVCVANKYFPDVTVTWE VDGTTQTTGIENSKTPQNSADCTYNLSSTLTLTSTQYNSHKEY TCKVTQGTTSVVQSFNRGDC |
| 197 | mAb E VH (nucleotide) | CAGTCGGTGGAGGAGTCCGGGGGTCGCCTGGTCACGCCTGGGA CACCCCTGACACTCACCTGCACAGTCTCTGGATTCTCCCTCAG TAGCTATGGAATGGGCTGGGTCCGCCAGGCTCCAGGGAAGGGG CTGGAATACATCGGAATCATTAGTAGTAGTGGTACATACTACG CGAACTGGGCGAAAGGCCGATTCACCATCTCCAGAACCTCGAC CACGGTGGATCTGAAAGTCGCCAGTCCGACAACCGAGGACACG GCCACCTATTTCTGTGCCAGATATTTTGCTGGTGGTGCCTATG ACATCTGGGGCCCAGGCACCCTGGTCACCGTCTCCTTA |
| 198 | mAb E VL (nucleotide) | GCTCAAGTGCTGACCCAGACTCCATCCTCCGTGTCTGCAGCTG TGGGAGGCACAGTCACCATCAATTGCCAGGCCAGTCAGAGTGT TGTTAGTAACAACTACCTAGCCTGGTTTCAGCAGAAACCAGGG CAGCCTCCCAAGCTCCTGATCTATTTTGCATCCACTCTGGCAT CTGGGGTCCCATCGCGGTTCAAAGGCAGTGGATCTGGGACACA GTTCACTCTCACCATCAGCGACCTGGAGTGTGACGATGCTGCC ACTTACTACTGTCTAGGCGTTTATAATAATGTTGATACTTTCG GCGGAGGGACCGAGGTGGTGGTCAAAGGT |
| 199 | mAb C VH (nucleotide) | CAGTCGGTGGAGGAGTCCGGGGGTCGCCTGGTCACGCCTGGGA CACCCCTGACACTCACCTGCACAGCCTCTGGATTCTCCCTCAG TAGGTACTATATGAGCTGGGTCCGCCAGGCTCCAGGGAAGGGG CTGGAATGGATCGGAATGATTTATCCTAGTAGTGGCAGTACAT GGTACGCGAGCTGGGTGAAAGGCCGATTCACCATCTCCGCAAC CGCGACCTCGGTGGATTTGAAAATCACCAGTCCGACAACCGAG GACACGGCCACCTATTTCTGTGTCAGAGATCGTTACCCTGGTT ATAATGGTGATTCATTTAATTTGTGGGGCCAGGGCACCCTGGT CACCGTCTCCTCA |
| 200 | mAb C VL (nucleotide) | GCCCAAGTGCTGACCCAGACTGCATCGCCCGTGTCTGCAGCTG TGGGAAGCACAGTCACCATCAATTGCCAGGCCAGTCAGAGTGT TTATAATAACAACTACTTAGCCTGGTTTCAGCAGAAACCAGGG CAGCCTCCCAAGCGCCTGATCTACCAGGCATCCAAACTGGCAA TTGGGGTCCCATCGCGGTTCAGTGGCAGTGGATCTGGAACACA GTTCACTCTCACCATCAGCGACGTGCAGTGTGACGATGCTGCC ACTTACTACTGTCTAGGCAGTTATGGTTGTAATAGTGTTGATT GTAATGTTTTCGGCGGAGGGACCGAGGTGGTGGTCAAAGGT |

TABLE 19-continued

| Summary of Sequences. | | |
|---|---|---|
| SEQ ID | Description | Sequence |
| 201 | mAb G VH (nucleotide) | CAGTCGCTGGAGGAGTCCGGGGGTCGCCTGGTCACGCCTGGGA<br>CACTCCTGACACTCACCTGCACCGTCTCTGGATTCTCCCTCAG<br>TAGCAATGCAATGAGCTGGGTCCGCCAGGCTCCAGGGGAGGGG<br>CTGGAGTGGATCGGAACCATTAGTAGTCGTGGTAGCACATACT<br>ACGCGAACTGGGCGAAAGGCCGATTCACCATCTCCAAAACCTC<br>GACCACGGTGGATCTGAAAATCACCAGTCCGACAACCGAGGAC<br>ACGGCCACCTATTTCTGTGCCAGAAGTAGTCTTGCTGGTTATG<br>AGCCTTACTATTTTAAGTTGTGGGGCCAGGGCACCCTGGTCAC<br>CGTCTCCTCA |
| 202 | mAb G VL (nucleotide) | GACGTCGTGATGACCCAGACTGCATCCCCCGTGTCTGCAGCTG<br>TGGGAGGCACAGTCACCATCAAGTGCCAGGCCAGTGAGAGCAT<br>TAGTAGCTACTTAGCCTGGTATCAGCAGAAACCAGGGCAGCCT<br>CCCAAGCTCCTGATCTATGGTGCATCCGATCTGGCATCTGGGG<br>TCCCATCGCGGTTCAAAGGCAGTGGATCTGGGACAGAGTTCAC<br>TCTCACCATCAGTGACCTGGAGTGTGCCGATGCTGCCACTTAC<br>TACTGTCAAAGTTATTATGGTCTTAGCCGTAATGGTTATGGGA<br>ATGTTTTCGGCGGAGGGACCGAGGTGGTGGTCAAAGGT |
| 203 | mAb B VH (nucleotide) | CAGCAGCAGCTGGAGGAGTCCGGGGGAGGCCTGGTCAAGCCTG<br>GAGGAACCCTGACACTCACCTGCAAAGCCTCTGGAATCGACTT<br>CAGTAGCTACTACTACATGTGCTGGGTCCGCCAGGCTCCAGGG<br>AAGGGGCTGGAGTGGATCGCGTGCATTTATGTTATTGATGATA<br>CTATTTACTGCGCGAACTGGGCGAAAGGCCGATTCACCATCTC<br>CAAAACCTCGTCGACCACGGTGACTCTGCAAATGACCAGTCTG<br>ACAGCCGCGGACACGGCCACGTATTTCTGTGCGAGAGATGGAA<br>GTAGTGGTATTCGTGATTACTTCGACTTGTGGGGCCCAGGCAC<br>CCTGGTCACCGTCTCCTCA |
| 204 | mAb B VL (nucleotide) | GCCTATGATATGACCCAGACTCCAGCCTCTGTGGAGGTAGCTG<br>TGGGAGGCACAGTCACCATCAAGTGCCAGGCCAGTGAGAGCGT<br>TAGCACTTGGTTAGCCTGGTATCAGCAGAAACCAGGGCAGCCT<br>CCCAAGCTCCTGATCTATAAGGCATCCGATCTGGCATCTGGGG<br>TCCCATCGCGGTTCAAAGGCAGTGGATCTGGGACAGAGTTCAC<br>TCTCACCATCAGCGGCGTGGAGTGTGCCGATGCTGCCACTTAC<br>TACTGTCAACAGGGGTATACTTATAATAATGTTGAAAATGTTT<br>TCGGCGGAGGGACCGAGGTGGTGGTCAAAGGT |
| 205 | mAb F VH (nucleotide) | CAGTCGGTGGAGGAGTCCGGAGGAGGCCTGGTAACGCCTGGAG<br>GAACCCTGACACTCACCTGCACAGTCTCTGGAATCGACCTCAG<br>TAGCAATGCAATGAGCTGGGTCCGCCAGGCTCCAGGGGAGGGA<br>CTGGAATGGATCGGAACCATTAGTACTGCTGGTTTCACATATT<br>ACGCGAGCTGGGCGAAAGGCCGATTCACCATCTCCAAAACCTC<br>GACCACGGTGGATCTGAAAATGACCAGTCTGACAGCCGCGGAC<br>ACGGCCACCTATTTCTGTGCCAGACTTCTTTATGGTCCTAACA<br>TCTGGGGCCCAGGCACCCTGGTCACCGTCTCCTTA |
| 206 | mAb F VL (nucleotide) | GACCCTGTGATGACCCAGACTCCAGCCTCCGTGTCTGAACCTG<br>TGGGAGGCACAGTCACCATCAAGTGCCAGGCCAGTCCGAGCAT<br>TAGCAATGAATTATCCTGGTATCAGCAGAAACCAGGGCAGCCT<br>CCCCAGCTCCTGATCTATCTGGCATCTACTCTGGCATCTGGGG<br>TCCCATCGCGGTTCAAAGGCAGTAGATCTGGGACAGAGTTCAC<br>TCTCACCATCAGCGACCTGGAGTGTGCCGATGCTGCCACTTAC<br>TACTGTCAAGGCATTGTTTATGGTCCTGATTATGTTGTTGGTT<br>TCGGCGGAGGGACCGAGGTGGTGGTCAAAGGT |
| 207 | mAb A VH (nucleotide) | CAGTCGTTGGAGGAGTCCGGGGGAGACCTGGTCAAGCCTGGGG<br>CATCCCTGACACTCACCTGCAAAGCCTCTGGATTCGACCTCAG<br>TAGGTTCTACTACATGTGCTGGGTCCGCCAGGCTCCAGGGAAG<br>GGGCTGGAGTGGATCGCATGCATTTATGCTGGTCGTACTGGTA<br>ACACTTACTACGCGAGCTGGGCGAAAGGCCGATTCACCATCTC<br>CAAAACCTCGTCGACCACGGTGACTCTGCAAATGACCAGTCTG<br>ACAGCCGCGGACACGGCCACCTATTTCTGTGCGAGAGCCAGTG<br>GTGATTTTCTTGCTTATACTTATGCTATGGACTTGTGGGGCCC<br>AGGCACCCTGGTCACCGTCTCCTCA |
| 208 | mAb A VL (nucleotide) | GCCGCCGTGCTGACCCAGACTCCAGCCTCCGTGTCTGCAGCTG<br>TGGGAGGCACAGTCACCATCAGTTGCCAGGCCAGTCAGAGTGT<br>TGATAATAACAACTACTTAGCCTGGTATCAGCAGAAACCAGGG<br>CAGCCTCCCAAGCTCCTGATCTACGAAGCATCCAAGCTGGCAT<br>CTGGGGTCCCATCGCGGTTCAGTGGCAGTGGATCTGGGACACA<br>GTTCACTCTCACCATCAGCGACGTGCAGTGTGACGATGCTACC<br>ACTTACTACTGTGCAGGCGGTTATAGTAGTAGTGCTGATGCGA<br>ATGCTTTCGGCGGAGGGACCGAGGTGGTGGTCAAAGGT |

TABLE 19-continued

| Summary of Sequences. | | |
|---|---|---|
| SEQ ID | Description | Sequence |
| 209 | mAb D VH (nucleotide) | CAGGAGCAGCTGGTGGAGTCCGGGGGAGGCCTGGTCCAGCCTG AGGGATCCCTGACACTCACCTGCAAAGCCTCTGGATTCGACTT CAGTAGCTACTGGATGTGCTGGGTCCGCCAGGCTCCAGGGAAG AGGCCTGAGTGGATCGCATGCATTTATGGTGGTGATGGTACTT CATACTTTGCGGGCTGGGCGAAAGGCCGCTTCACCATCTCCAA AACCTCGTCGACCACGGTGACTCTGCAAATGACCAGCCTCACA GCCGCGGACACGGCCACCTATTTCTGTGCGCGAGCCGATTACT ACGTTTATGTTGATGGTGGTTATGGTCATGCTTATGACTTGTG GGGCCCAGGCACCCTGGTCACCGTCTCCTCA |
| 210 | mAb D VL (nucleotide) | GACATTGTGATGACCCAGACTCCAGCCTCCGTGGAGGCAGCTG TGGGAGGCTCAGTCACCATCAAGTGCCAGGCCAGTGACGACAT TTATAGTTACTTGGCCTGGTATCAGCAGAAACCAGGGCAGCCT CCCAAGCTCCTGATCTTTGATGCATCCTCTCTGCCATCTGGGG TCCCATCGCGCTTCAAAGGCAGTGGATCTGGGACACAGTTCAC TCTCACCATCAGCGGCGTGCAGTGTGCCGATGCTGCCACTTAT TACTGTCAAAACTATTATGGTAGTAGTAGTAGTGTTCATGCTT TCGGCGGAGGGACCGAGGTGGTGGTCAAAGGT |
| 211 | mAb H VH (nucleotide) | CAGTCGGTGGAGGAGTCCGGGGGTCGCCTGGTCACGCCTGGGA CACCCCTGACACTCACCTGCACAGTCTCTGGATTCTCCCTCAG TACCTATGCAATGGGCTGGGTCCGCCAGGCTCCAGGGAAGGGG CTGGAGTACATCGGAATCATTTATGGTGGTAGTGGTACATTCT ACGCGAGCTGGGCGAAAGGCCGATTCACCATCTCCAAAACCTC GACCACGGTGGATCTGAAAATCACCAGTCCGACAACCGAGGAC ACGGCCACCTATTTCTGTGCCAGAGATGGTGATGATAGTTATT TCGACTACTTTAACTTGTGGGGCCAAGGCACCCTGGTCACCGT CTCCTCA |
| 212 | mAb H VL (nucleotide) | GCCGCCGTGCTGACCCAGACTCCAGCCTCCGTGTCTGCAGCTG TGGGAGGCACAGTCAGCATCAGTTGCCAGTCCAATGAGAACAT TGGTAGTAATTTAGCCTGGTATCAGCAGAAACCAGGGCAGCCT CCCAAGCTCCTGATTTATGGTGCATCCACTCTGACATCTGGGG TCCCATCGCGGTTCAAAGGCAGTGGGTCTGGGACAGCGTTCAC TCTCACCATCAGCGGCGTGCAGTGTGACGATGCTGCCACTTAC TACTGTCTAGGCGGTTATTTGAGTACTAGTGATACGACTTTCG GCGGAGGGACCGCGGTGGTGGTCAAAGGT |
| 213 | mAb E HC (nucleotide) | CAGTCGGTGGAGGAGTCCGGGGGTCGCCTGGTCACGCCTGGGA CACCCCTGACACTCACCTGCACAGTCTCTGGATTCTCCCTCAG TAGCTATGGAATGGGCTGGGTCCGCCAGGCTCCAGGGAAGGGG CTGGAATACATCGGAATCATTAGTAGTAGTGGTACATACTACG CGAACTGGGCGAAAGGCCGATTCACCATCTCCAGAACCTCGAC CACGGTGGATCTGAAAGTCGCCAGTCCGACAACCGAGGACACG GCCACCTATTTCTGTGCCAGATATTTTGCTGGTGGTGCCTATG ACATCTGGGGCCCAGGCACCCTGGTCACCGTCTCCTTAGGGCA ACCTAAGGCTCCATCAGTGTTCCCACTGGCCCCCTGCTGCGGG GACACACCCAGCTCCACGGTGACCCTGGGCTGCCTGGTCAAAG GCTACCTCCCGGAGCCAGTGACCGTGACCTGGAACTCGGGCAC CCTCACCAATGGGGTACGCACCTTCCCGTCCGTCCGGCAGTCC TCAGGCCTCTACTCGCTGAGCAGCGTGGTGAGCGTGACCTCAA GCAGCCAGCCCGTCACCTGCAACGTGGCCCACCCAGCCACCAA CACCAAAGTGGACAAGACCGTTGCACCCTCGACATGCAGCAAG CCCACGTGCCCACCCCCTGAACTCCTGGGGGGACCGTCTGTGT TCATCTTCCCCCCAAAACCCAAGGACACCCTCATGATCTCACG CACCCCCGAGGTCACATGCGTGGTGGTGGACGTGAGCCAGGAT GACCCCGAGGTGCAGTTCACATGGTACATAAACAACGAGCAGG TGCGCACCGCCCGGCCGCCGCTACGGGAGCAGCAGTTCAACAG CACGATCCGCGTGGTCAGCACCCTCCCCATCACGCACCAGGAC TGGCTGAGGGGCAAGGAGTTCAAGTGCAAAGTCCACAACAAGG CACTCCCGGCCCCCATCGAGAAAACCATCTCCAAAGCCAGAGG GCAGCCCCTGGAGCCGAAGGTCTACACCATGGGCCCTCCCCGG GAGGAACTGAGCAGCAGGTCGGTCAGCCTGACCTGCATGATCA ACGGCTTCTACCCTTCCGACATCTCGGTGGAGTGGGAGAAGAA CGGGAAGGCAGAGGACAACTACAAGACCACGCCGGCCGTGCTG GACAGCGACGGCTCCTACTTCCTCTACAGCAAGCTCTCAGTGC CCACGAGTGAGTGGCAGCGGGGCGACGTGTTCACCTGCTCCGT GATGCACGAGGCCTTGCACAACCACTACACGCAGAAGTCCATC TCCCGCTCTCCGGGTAAATGA |
| 214 | mAb E LC (nucleotide) | GCTCAAGTGCTGACCCAGACTCCATCCTCCGTGTCTGCAGCTG TGGGAGGCACAGTCACCATCAATTGCCAGGCCAGTCAGAGTGT TGTTAGTAACAACTACCTAGCCTGGTTTCAGCAGAAACCAGGG CAGCCTCCCAAGCTCCTGATCTATTTTGCATCCACTCTGGCAT CTGGGGTCCCATCGCGGTTCAAAGGCAGTGGATCTGGGACACA GTTCACTCTCACCATCAGCGACCTGGAGTGTGACGATGCTGCC |

TABLE 19-continued

Summary of Sequences.

| SEQ ID | Description | Sequence |
|---|---|---|
| | | ACTTACTACTGTCTAGGCGTTTATAATAATGTTGATACTTTCG GCGGAGGGACCGAGGTGGTGGTCAAAGGTGATCCAGTTGCACC TACTGTCCTCCTCTTCCCACCAGCTGCTGATCAGGTGGCAACT GGAACAGTCACCATCGTGTGTGTGGCGAATAAATACTTTCCCG ATGTCACCGTCACCTGGGAGGTGGATGGCACCACCCAAACAAC TGGCATCGAGAACAGTAAAACACCGCAGAATTCTGCAGATTGT ACCTACAACCTCAGCAGCACTCTGACACTGACCAGCACACAGT ACAACAGCCACAAAGAGTACACCTGCAAGGTGACCCAGGGCAC GACCTCAGTCGTCCAGAGCTTCAACAGGGGTGACTGCTAG |
| 215 | mAb C HC (nucleotide) | CAGTCGGTGGAGGAGTCCGGGGGTCGCCTGGTCACGCCTGGGA CACCCCTGACACTCACCTGCACAGCCTCTGGATTCTCCCTCAG TAGGTACTATATGAGCTGGGTCCGCCAGGCTCCAGGGAAGGGG CTGGAATGGATCGGAATGATTTATCCTAGTAGTGGCAGTACAT GGTACGCGAGCTGGGTGAAAGGCCGATTCACCATCTCCGCAAC CGCGACCTCGGTGGATTTGAAAATCACCAGTCCGACAACCGAG GACACGGCCACCTATTTCTGTGTCAGAGATCGTTACCCTGGTT ATAATGGTGATTCATTTAATTTGTGGGGCCAGGGCACCCTGGT CACCGTCTCCTCAGGGCAACCTAAGGCTCCATCAGTGTTCCCA CTGGCCCCCTGCTGCGGGGACACACCCAGCTCCACGGTGACCC TGGGCTGCCTGGTCAAAGGCTACCTCCCGGAGCCAGTGACCGT GACCTGGAACTCGGGCACCCTCACCAATGGGGTACGCACCTTC CCGTCCGTCCGGCAGTCCTCAGGCCTCTACTCGCTGAGCAGCG TGGTGAGCGTGACCTCAAGCAGCCAGCCCGTCACCTGCAACGT GGCCCACCCAGCCACCAACACCAAAGTGGACAAGACCGTTGCA CCCTCGACATGCAGCAAGCCCACGTGCCCACCCCCTGAACTCC TGGGGGGACCGTCTGTGTTCATCTTCCCCCCAAAACCCAAGGA CACCCTCATGATCTCACGCACCCCCGAGGTCACATGCGTGGTG GTGGACGTGAGCCAGGATGACCCCGAGGTGCAGTTCACATGGT ACATAAACAACGAGCAGGTGCGCACCGCCCGGCCGCCGCTACG GGAGCAGCAGTTCAACAGCACGATCCGCGTGGTCAGCACCCTC CCCATCACGCACCAGGACTGGCTGAGGGGCAAGGAGTTCAAGT GCAAAGTCCACAACAAGGCACTCCCGGCCCCCATCGAGAAAAC CATCTCCAAAGCCAGAGGGCAGCCCCTGGAGCCGAAGGTCTAC ACCATGGGCCCTCCCCGGGAGGAACTGAGCAGCAGGTCGGTCA GCCTGACCTGCATGATCAACGGCTTCTACCCTTCCGACATCTC GGTGGAGTGGGAGAAGAACGGGAAGGCAGAGGACAACTACAAG ACCACGCCGGCCGTGCTGGACAGCGACGGCTCCTACTTCCTCT ACAGCAAGCTCTCAGTGCCCACGAGTGAGTGGCAGCGGGGCGA CGTGTTCACCTGCTCCGTGATGCACGAGGCCTTGCACAACCAC TACACGCAGAAGTCCATCTCCCGCTCTCCGGGTAAATGA |
| 216 | mAb C LC (nucleotide) | GCCCAAGTGCTGACCCAGACTGCATCGCCCGTGTCTGCAGCTG TGGGAAGCACAGTCACCATCAATTGCCAGGCCAGTCAGAGTGT TTATAATAACAACTACTTAGCCTGGTTTCAGCAGAAACCAGGG CAGCCTCCCAAGCGCCTGATCTACCAGGCATCCAAACTGGCAA TTGGGGTCCCATCGCGGTTCAGTGGCAGTGGATCTGGAACACA GTTCACTCTCACCATCAGCGACGTGCAGTGTGACGATGCTGCC ACTTACTACTGTCTAGGCAGTTATGGTTGTAATAGTGTTGATT GTAATGTTTTCGGCGGAGGGACCGAGGTGGTGGTCAAAGGTGA TCCAGTTGCACCTACTGTCCTCATCTTCCCACCAGCTGCTGAT CAGGTGGCAACTGGAACAGTCACCATCGTGTGTGTGGCGAATA AATACTTTCCCGATGTCACCGTCACCTGGGAGGTGGATGGCAC CACCCAAACAACTGGCATCGAGAACAGTAAAACACCGCAGAAT TCTGCAGATTGTACCTACAACCTCAGCAGCACTCTGACACTGA CCAGCACACAGTACAACAGCCACAAAGAGTACACCTGCAAGGT GACCCAGGGCACGACCTCAGTCGTCCAGAGCTTCAACAGGGGT GACTGCTAG |
| 217 | mAb G HC (nucleotide) | CAGTCGCTGGAGGAGTCCGGGGGTCGCCTGGTCACGCCTGGGA CACTCCTGACACTCACCTGCACCGTCTCTGGATTCTCCCTCAG TAGCAATGCAATGAGCTGGGTCCGCCAGGCTCCAGGGGAGGGG CTGGAGTGGATCGGAACCATTAGTAGTCGTGGTAGCACATACT ACGCGAACTGGGCGAAAGGCCGATTCACCATCTCCAAAACCTC GACCACGGTGGATCTGAAAATCACCAGTCCGACAACCGAGGAC ACGGCCACCTATTTCTGTGCCAGAAGTAGTCTTGCTGGTTATG AGCCTTACTATTTTAAGTTGTGGGGCCAGGGCACCCTGGTCAC CGTCTCCTCAGGGCAACCTAAGGCTCCATCAGTGTTCCCACTG GCCCCCTGCTGCGGGGACACACCCAGCTCCACGGTGACCCTGG GCTGCCTGGTCAAAGGCTACCTCCCGGAGCCAGTGACCGTGAC CTGGAACTCGGGCACCCTCACCAATGGGGTACGCACCTTCCCG TCCGTCCGGCAGTCCTCAGGCCTCTACTCGCTGAGCAGCGTGG TGAGCGTGACCTCAAGCAGCCAGCCCGTCACCTGCAACGTGGC CCACCCAGCCACCAACACCAAAGTGGACAAGACCGTTGCACCC TCGACATGCAGCAAGCCCACGTGCCCACCCCCTGAACTCCTGG GGGGACCGTCTGTGTTCATCTTCCCCCCAAAACCCAAGGACAC |

TABLE 19-continued

Summary of Sequences.

| SEQ ID | Description | Sequence |
|---|---|---|
| | | CCTCATGATCTCACGCACCCCCGAGGTCACATGCGTGGTGGTG<br>GACGTGAGCCAGGATGACCCCGAGGTGCAGTTCACATGGTACA<br>TAAACAACGAGCAGGTGCGCACCGCCCGGCCGCCGCTACGGGA<br>GCAGCAGTTCAACAGCACGATCCGCGTGGTCAGCACCCTCCCC<br>ATCACGCACCAGGACTGGCTGAGGGGCAAGGAGTTCAAGTGCA<br>AAGTCCACAACAAGGCACTCCCGGCCCCCATCGAGAAAACCAT<br>CTCCAAAGCCAGAGGGCAGCCCCTGGAGCCGAAGGTCTACACC<br>ATGGGCCCTCCCCGGGAGGAACTGAGCAGCAGGTCGGTCAGCC<br>TGACCTGCATGATCAACGGCTTCTACCCTTCCGACATCTCGGT<br>GGAGTGGGAGAAGAACGGGAAGGCAGAGGACAACTACAAGACC<br>ACGCCGGCCGTGCTGGACAGCGACGGCTCCTACTTCCTCTACA<br>GCAAGCTCTCAGTGCCCACGAGTGAGTGGCAGCGGGGCGACGT<br>GTTCACCTGCTCCGTGATGCACGAGGCCTTGCACAACCACTAC<br>ACGCAGAAGTCCATCTCCCGCTCTCCGGGTAAATGA |
| 218 | mAb G LC (nucleotide) | GACGTCGTGATGACCCAGACTGCATCCCCCGTGTCTGCAGCTG<br>TGGGAGGCACAGTCACCATCAAGTGCCAGGCCAGTGAGAGCAT<br>TAGTAGCTACTTAGCCTGGTATCAGCAGAAACCAGGGCAGCCT<br>CCCAAGCTCCTGATCTATGGTGCATCCGATCTGGCATCTGGGG<br>TCCCATCGCGGTTCAAAGGCAGTGGATCTGGGACAGAGTTCAC<br>TCTCACCATCAGTGACCTGGAGTGTGCCGATGCTGCCACTTAC<br>TACTGTCAAAGTTATTATGGTCTTAGCCGTAATGGTTATGGGA<br>ATGTTTTCGGCGGAGGGACCGAGGTGGTGGTCAAAGGTGATCC<br>AGTTGCACCTACTGTCCTCATCTTCCCACCAGCTGCTGATCAG<br>GTGGCAACTGGAACAGTCACCATCGTGTGTGTGGCGAATAAAT<br>ACTTTCCCGATGTCACCGTCACCTGGGAGGTGGATGGCACCAC<br>CCAAACAACTGGCATCGAGAACAGTAAAACACCGCAGAATTCT<br>GCAGATTGTACCTACAACCTCAGCAGCACTCTGACACTGACCA<br>GCACACAGTACAACAGCCACAAAGAGTACACCTGCAAGGTGAC<br>CCAGGGCACGACCTCAGTCGTCCAGAGCTTCAACAGGGGTGAC<br>TGCTAG |
| 219 | mAb B HC (nucleotide) | CAGCAGCAGCTGGAGGAGTCCGGGGGAGGCCTGGTCAAGCCTG<br>GAGGAACCCTGACACTCACCTGCAAAGCCTCTGGAATCGACTT<br>CAGTAGCTACTACTACATGTGCTGGGTCCGCCAGGCTCCAGGG<br>AAGGGGCTGGAGTGGATCGCGTGCATTTATGTTATTGATGATA<br>CTATTTACTGCGCGAACTGGGCGAAAGGCCGATTCACCATCTC<br>CAAAACCTCGTCGACCACGGTGACTCTGCAAATGACCAGTCTG<br>ACAGCCGCGGACACGGCCACGTATTTCTGTGCGAGAGATGGAA<br>GTAGTGGTATTCGTGATTACTTCGACTTGTGGGGCCCAGGCAC<br>CCTGGTCACCGTCTCCTCAGGGCAACCTAAGGCTCCATCAGTG<br>TTCCCACTGGCCCCCTGCTGCGGGGACACACCCAGCTCCACGG<br>TGACCCTGGGCTGCCTGGTCAAAGGCTACCTCCCGGAGCCAGT<br>GACCGTGACCTGGAACTCGGGCACCCTCACCAATGGGGTACGC<br>ACCTTCCCGTCCGTCCGGCAGTCCTCAGGCCTCTACTCGCTGA<br>GCAGCGTGGTGAGCGTGACCTCAAGCAGCCAGCCCGTCACCTG<br>CAACGTGGCCCACCCAGCCACCAACACCAAAGTGGACAAGACC<br>GTTGCACCCTCGACATGCAGCAAGCCCACGTGCCCACCCCCTG<br>AACTCCTGGGGGGACCGTCTGTGTTCATCTTCCCCCCAAAACC<br>CAAGGACACCCTCATGATCTCACGCACCCCCGAGGTCACATGC<br>GTGGTGGTGGACGTGAGCCAGGATGACCCCGAGGTGCAGTTCA<br>CATGGTACATAAACAACGAGCAGGTGCGCACCGCCCGGCCGCC<br>GCTACGGGAGCAGCAGTTCAACAGCACGATCCGCGTGGTCAGC<br>ACCCTCCCCATCACGCACCAGGACTGGCTGAGGGGCAAGGAGT<br>TCAAGTGCAAAGTCCACAACAAGGCACTCCCGGCCCCCATCGA<br>GAAAACCATCTCCAAAGCCAGAGGGCAGCCCCTGGAGCCGAAG<br>GTCTACACCATGGGCCCTCCCCGGGAGGAACTGAGCAGCAGGT<br>CGGTCAGCCTGACCTGCATGATCAACGGCTTCTACCCTTCCGA<br>CATCTCGGTGGAGTGGGAGAAGAACGGGAAGGCAGAGGACAAC<br>TACAAGACCACGCCGGCCGTGCTGGACAGCGACGGCTCCTACT<br>TCCTCTACAGCAAGCTCTCAGTGCCCACGAGTGAGTGGCAGCG<br>GGGCGACGTGTTCACCTGCTCCGTGATGCACGAGGCCTTGCAC<br>AACCACTACACGCAGAAGTCCATCTCCCGCTCTCCGGGTAAAT<br>GA |
| 220 | mAb B LC (nucleotide) | GCCTATGATATGACCCAGACTCCAGCCTCTGTGGAGGTAGCTG<br>TGGGAGGCACAGTCACCATCAAGTGCCAGGCCAGTGAGAGCGT<br>TAGCACTTGGTTAGCCTGGTATCAGCAGAAACCAGGGCAGCCT<br>CCCAAGCTCCTGATCTATAAGGCATCCGATCTGGCATCTGGGG<br>TCCCATCGCGGTTCAAAGGCAGTGGATCTGGGACAGAGTTCAC<br>TCTCACCATCAGCGGCGTGGAGTGTGCCGATGCTGCCACTTAC<br>TACTGTCAACAGGGGTATACTTATAATAATGTTGAAAATGTTT<br>TCGGCGGAGGGACCGAGGTGGTGGTCAAAGGTGATCCAGTTGC<br>ACCTACTGTCCTCATCTTCCCACCAGCTGCTGATCAGGTGGCA<br>ACTGGAACAGTCACCATCGTGTGTGTGGCGAATAAATACTTTC<br>CCGATGTCACCGTCACCTGGGAGGTGGATGGCACCACCCAAAC |

TABLE 19-continued

Summary of Sequences.

| SEQ ID | Description | Sequence |
|---|---|---|
| | | AACTGGCATCGAGAACAGTAAAACACCGCAGAATTCTGCAGAT<br>TGTACCTACAACCTCAGCAGCACTCTGACACTGACCAGCACAC<br>AGTACAACAGCCACAAAGAGTACACCTGCAAGGTGACCCAGGG<br>CACGACCTCAGTCGTCCAGAGCTTCAACAGGGGTGACTGCTAG |
| 221 | mAb F HC (nucleotide) | CAGTCGGTGGAGGAGTCCGGAGGAGGCCTGGTAACGCCTGGAG<br>GAACCCTGACACTCACCTGCACAGTCTCTGGAATCGACCTCAG<br>TAGCAATGCAATGAGCTGGGTCCGCCAGGCTCCAGGGGAGGGA<br>CTGGAATGGATCGGAACCATTAGTACTGCTGGTTTCACATATT<br>ACGCGAGCTGGGCGAAAGGCCGATTCACCATCTCCAAAACCTC<br>GACCACGGTGGATCTGAAAATGACCAGTCTGACAGCCGCGGAC<br>ACGGCCACCTATTTCTGTGCCAGACTTCTTTATGGTCCTAACA<br>TCTGGGGCCCAGGCACCCTGGTCACCGTCTCCTTAGGGCAACC<br>TAAGGCTCCATCAGTGTTCCCACTGGCCCCCTGCTGCGGGGAC<br>ACACCCAGCTCCACGGTGACCCTGGGCTGCCTGGTCAAAGGCT<br>ACCTCCCGGAGCCAGTGACCGTGACCTGGAACTCGGGCACCCT<br>CACCAATGGGGTACGCACCTTCCCGTCCGTCCGGCAGTCCTCA<br>GGCCTCTACTCGCTGAGCAGCGTGGTGAGCGTGACCTCAAGCA<br>GCCAGCCCGTCACCTGCAACGTGGCCCACCCAGCCACCAACAC<br>CAAAGTGGACAAGACCGTTGCACCCTCGACATGCAGCAAGCCC<br>ACGTGCCCACCCCCTGAACTCCTGGGGGGACCGTCTGTGTTCA<br>TCTTCCCCCCAAAACCCAAGGACACCCTCATGATCTCACGCAC<br>CCCCGAGGTCACATGCGTGGTGGTGGACGTGAGCCAGGATGAC<br>CCCGAGGTGCAGTTCACATGGTACATAAACAACGAGCAGGTGC<br>GCACCGCCCGGCCGCCGCTACGGGAGCAGCAGTTCAACAGCAC<br>GATCCGCGTGGTCAGCACCCTCCCCATCACGCACCAGGACTGG<br>CTGAGGGGCAAGGAGTTCAAGTGCAAAGTCCACAACAAGGCAC<br>TCCCGGCCCCCATCGAGAAAACCATCTCCAAAGCCAGAGGGCA<br>GCCCCTGGAGCCGAAGGTCTACACCATGGGCCCTCCCCGGGAG<br>GAACTGAGCAGCAGGTCGGTCAGCCTGACCTGCATGATCAACG<br>GCTTCTACCCTTCCGACATCTCGGTGGAGTGGGAGAAGAACGG<br>GAAGGCAGAGGACAACTACAAGACCACGCCGGCCGTGCTGGAC<br>AGCGACGGCTCCTACTTCCTCTACAGCAAGCTCTCAGTGCCCA<br>CGAGTGAGTGGCAGCGGGGCGACGTGTTCACCTGCTCCGTGAT<br>GCACGAGGCCTTGCACAACCACTACACGCAGAAGTCCATCTCC<br>CGCTCTCCGGGTAAATGA |
| 222 | mAb F LC (nucleotide) | GACCCTGTGATGACCCAGACTCCAGCCTCCGTGTCTGAACCTG<br>TGGGAGGCACAGTCACCATCAAGTGCCAGGCCAGTCCGAGCAT<br>TAGCAATGAATTATCCTGGTATCAGCAGAAACCAGGGCAGCCT<br>CCCCAGCTCCTGATCTATCTGGCATCTACTCTGGCATCTGGGG<br>TCCCATCGCGGTTCAAAGGCAGTAGATCTGGGACAGAGTTCAC<br>TCTCACCATCAGCGACCTGGAGTGTGCCGATGCTGCCACTTAC<br>TACTGTCAAGGCATTGTTTATGGTCCTGATTATGTTGTTGGTT<br>TCGGCGGAGGGACCGAGGTGGTGGTCAAAGGTGATCCAGTTGC<br>ACCTACTGTCCTCATCTTCCCACCAGCTGCTGATCAGGTGGCA<br>ACTGGAACAGTCACCATCGTGTGTGTGGCGAATAAATACTTTC<br>CCGATGTCACCGTCACCTGGGAGGTGGATGGCACCACCCAAAC<br>AACTGGCATCGAGAACAGTAAAACACCGCAGAATTCTGCAGAT<br>TGTACCTACAACCTCAGCAGCACTCTGACACTGACCAGCACAC<br>AGTACAACAGCCACAAAGAGTACACCTGCAAGGTGACCCAGGG<br>CACGACCTCAGTCGTCCAGAGCTTCAACAGGGGTGACTGCTAG |
| 223 | mAb A HC (nucleotide) | CAGTCGTTGGAGGAGTCCGGGGGAGACCTGGTCAAGCCTGGGG<br>CATCCCTGACACTCACCTGCAAAGCCTCTGGATTCGACCTCAG<br>TAGGTTCTACTACATGTGCTGGGTCCGCCAGGCTCCAGGGAAG<br>GGGCTGGAGTGGATCGCATGCATTTATGCTGGTCGTACTGGTA<br>ACACTTACTACGCGAGCTGGGCGAAAGGCCGATTCACCATCTC<br>CAAAACCTCGTCGACCACGGTGACTCTGCAAATGACCAGTCTG<br>ACAGCCGCGGACACGGCCACCTATTTCTGTGCGAGAGCCAGTG<br>GTGATTTTCTTGCTTATACTTATGCTATGGACTTGTGGGGCCC<br>AGGCACCCTGGTCACCGTCTCCTCAGGGCAACCTAAGGCTCCA<br>TCAGTGTTCCCACTGGCCCCCTGCTGCGGGGACACACCCAGCT<br>CCACGGTGACCCTGGGCTGCCTGGTCAAAGGCTACCTCCCGGA<br>GCCAGTGACCGTGACCTGGAACTCGGGCACCCTCACCAATGGG<br>GTACGCACCTTCCCGTCCGTCCGGCAGTCCTCAGGCCTCTACT<br>CGCTGAGCAGCGTGGTGAGCGTGACCTCAAGCAGCCAGCCCGT<br>CACCTGCAACGTGGCCCACCCAGCCACCAACACCAAAGTGGAC<br>AAGACCGTTGCACCCTCGACATGCAGCAAGCCCACGTGCCCAC<br>CCCCTGAACTCCTGGGGGGACCGTCTGTGTTCATCTTCCCCCC<br>AAAACCCAAGGACACCCTCATGATCTCACGCACCCCCGAGGTC<br>ACATGCGTGGTGGTGGACGTGAGCCAGGATGACCCCGAGGTGC<br>AGTTCACATGGTACATAAACAACGAGCAGGTGCGCACCGCCCG<br>GCCGCCGCTACGGGAGCAGCAGTTCAACAGCACGATCCGCGTG<br>GTCAGCACCCTCCCCATCACGCACCAGGACTGGCTGAGGGGCA<br>AGGAGTTCAAGTGCAAAGTCCACAACAAGGCACTCCCGGCCCC |

TABLE 19-continued

Summary of Sequences.

| SEQ ID | Description | Sequence |
|---|---|---|
| | | CATCGAGAAAACCATCTCCAAAGCCAGAGGGCAGCCCCTGGAG CCGAAGGTCTACACCATGGGCCCTCCCCGGGAGGAACTGAGCA GCAGGTCGGTCAGCCTGACCTGCATGATCAACGGCTTCTACCC TTCCGACATCTCGGTGGAGTGGGAGAAGAACGGGAAGGCAGAG GACAACTACAAGACCACGCCGGCCGTGCTGGACAGCGACGGCT CCTACTTCCTCTACAGCAAGCTCTCAGTGCCCACGAGTGAGTG GCAGCGGGGCGACGTGTTCACCTGCTCCGTGATGCACGAGGCC TTGCACAACCACTACACGCAGAAGTCCATCTCCCGCTCTCCGG GTAAATGA |
| 224 | mAb A LC (nucleotide) | GCCGCCGTGCTGACCCAGACTCCAGCCTCCGTGTCTGCAGCTG TGGGAGGCACAGTCACCATCAGTTGCCAGGCCAGTCAGAGTGT TGATAATAACAACTACTTAGCCTGGTATCAGCAGAAACCAGGG CAGCCTCCCAAGCTCCTGATCTACGAAGCATCCAAGCTGGCAT CTGGGGTCCCATCGCGGTTCAGTGGCAGTGGATCTGGGACACA GTTCACTCTCACCATCAGCGACGTGCAGTGTGACGATGCTACC ACTTACTACTGTGCAGGCGGTTATAGTAGTAGTGCTGATGCGA ATGCTTTCGGCGGAGGGACCGAGGTGGTGGTCAAAGGTGATCC AGTTGCACCTACTGTCCTCATCTTCCCACCAGCTGCTGATCAG GTGGCAACTGGAACAGTCACCATCGTGTGTGTGGCGAATAAAT ACTTTCCCGATGTCACCGTCACCTGGGAGGTGGATGGCACCAC CCAAACAACTGGCATCGAGAACAGTAAAACACCGCAGAATTCT GCAGATTGTACCTACAACCTCAGCAGCACTCTGACACTGACCA GCACACAGTACAACAGCCACAAAGAGTACACCTGCAAGGTGAC CCAGGGCACGACCTCAGTCGTCCAGAGCTTCAACAGGGGTGAC TGCTAG |
| 225 | mAb D HC (nucleotide) | CAGGAGCAGCTGGTGGAGTCCGGGGGAGGCCTGGTCCAGCCTG AGGGATCCCTGACACTCACCTGCAAAGCCTCTGGATTCGACTT CAGTAGCTACTGGATGTGCTGGGTCCGCCAGGCTCCAGGGAAG AGGCCTGAGTGGATCGCATGCATTTATGGTGGTGATGGTACTT CATACTTTGCGGGCTGGGCGAAAGGCCGCTTCACCATCTCCAA AACCTCGTCGACCACGGTGACTCTGCAAATGACCAGCCTCACA GCCGCGGACACGGCCACCTATTTCTGTGCGCGAGCCGATTACT ACGTTTATGTTGATGGTGGTTATGGTCATGCTTATGACTTGTG GGGCCCAGGCACCCTGGTCACCGTCTCCTCAGGGCAACCTAAG GCTCCATCAGTGTTCCCACTGGCCCCCTGCTGCGGGGACACAC CCAGCTCCACGGTGACCCTGGGCTGCCTGGTCAAAGGCTACCT CCCGGAGCCAGTGACCGTGACCTGGAACTCGGGCACCCTCACC AATGGGGTACGCACCTTCCCGTCCGTCCGGCAGTCCTCAGGCC TCTACTCGCTGAGCAGCGTGGTGAGCGTGACCTCAAGCAGCCA GCCCGTCACCTGCAACGTGGCCCACCCAGCCACCAACACCAAA GTGGACAAGACCGTTGCACCCTCGACATGCAGCAAGCCCACGT GCCCACCCCCTGAACTCCTGGGGGGACCGTCTGTGTTCATCTT CCCCCCAAAACCCAAGGACACCCTCATGATCTCACGCACCCCC GAGGTCACATGCGTGGTGGTGGACGTGAGCCAGGATGACCCCG AGGTGCAGTTCACATGGTACATAAACAACGAGCAGGTGCGCAC CGCCCGGCCGCCGCTACGGGAGCAGCAGTTCAACAGCACGATC CGCGTGGTCAGCACCCTCCCCATCACGCACCAGGACTGGCTGA GGGGCAAGGAGTTCAAGTGCAAAGTCCACAACAAGGCACTCCC GGCCCCCATCGAGAAAACCATCTCCAAAGCCAGAGGGCAGCCC CTGGAGCCGAAGGTCTACACCATGGGCCCTCCCCGGGAGGAAC TGAGCAGCAGGTCGGTCAGCCTGACCTGCATGATCAACGGCTT CTACCCTTCCGACATCTCGGTGGAGTGGGAGAAGAACGGGAAG GCAGAGGACAACTACAAGACCACGCCGGCCGTGCTGGACAGCG ACGGCTCCTACTTCCTCTACAGCAAGCTCTCAGTGCCCACGAG TGAGTGGCAGCGGGGCGACGTGTTCACCTGCTCCGTGATGCAC GAGGCCTTGCACAACCACTACACGCAGAAGTCCATCTCCCGCT CTCCGGGTAAATGA |
| 226 | mAb D LC (nucleotide) | GACATTGTGATGACCCAGACTCCAGCCTCCGTGGAGGCAGCTG TGGGAGGCTCAGTCACCATCAAGTGCCAGGCCAGTGACGACAT TTATAGTTACTTGGCCTGGTATCAGCAGAAACCAGGGCAGCCT CCCAAGCTCCTGATCTTTGATGCATCCTCTCTGCCATCTGGGG TCCCATCGCGCTTCAAAGGCAGTGGATCTGGGACACAGTTCAC TCTCACCATCAGCGGCGTGCAGTGTGCCGATGCTGCCACTTAT TACTGTCAAAACTATTATGGTAGTAGTAGTAGTAGTGTTCATGCTT TCGGCGGAGGGACCGAGGTGGTGGTCAAAGGTGATCCAGTTGC ACCTACTGTCCTCATCTTCCCACCAGCTGCTGATCAGGTGGCA ACTGGAACAGTCACCATCGTGTGTGTGGCGAATAAATACTTTC CCGATGTCACCGTCACCTGGGAGGTGGATGGCACCACCCAAAC AACTGGCATCGAGAACAGTAAAACACCGCAGAATTCTGCAGAT TGTACCTACAACCTCAGCAGCACTCTGACACTGACCAGCACAC AGTACAACAGCCACAAAGAGTACACCTGCAAGGTGACCCAGGG CACGACCTCAGTCGTCCAGAGCTTCAACAGGGGTGACTGCTAG |

TABLE 19-continued

| Summary of Sequences. | | |
|---|---|---|
| SEQ ID | Description | Sequence |
| 227 | mAb H HC (nucleotide) | CAGTCGGTGGAGGAGTCCGGGGGTCGCCTGGTCACGCCTGGGA<br>CACCCCTGACACTCACCTGCACAGTCTCTGGATTCTCCCTCAG<br>TACCTATGCAATGGGCTGGGTCCGCCAGGCTCCAGGGAAGGGG<br>CTGGAGTACATCGGAATCATTTATGGTGGTAGTGGTACATTCT<br>ACGCGAGCTGGGCGAAAGGCCGATTCACCATCTCCAAAACCTC<br>GACCACGGTGGATCTGAAAATCACCAGTCCGACAACCGAGGAC<br>ACGGCCACCTATTTCTGTGCCAGAGATGGTGATGATAGTTATT<br>TCGACTACTTTAACTTGTGGGGCCAAGGCACCCTGGTCACCGT<br>CTCCTCAGGGCAACCTAAGGCTCCATCAGTGTTCCCACTGGCC<br>CCCTGCTGCGGGGACACACCCAGCTCCACGGTGACCCTGGGCT<br>GCCTGGTCAAAGGCTACCTCCCGGAGCCAGTGACCGTGACCTG<br>GAACTCGGGCACCCTCACCAATGGGGTACGCACCTTCCCGTCC<br>GTCCGGCAGTCCTCAGGCCTCTACTCGCTGAGCAGCGTGGTGA<br>GCGTGACCTCAAGCAGCCAGCCCGTCACCTGCAACGTGGCCCA<br>CCCAGCCACCAACACCAAAGTGGACAAGACCGTTGCACCCTCG<br>ACATGCAGCAAGCCCACGTGCCCACCCCCTGAACTCCTGGGGG<br>GACCGTCTGTGTTCATCTTCCCCCCAAAACCCAAGGACACCCT<br>CATGATCTCACGCACCCCCGAGGTCACATGCGTGGTGGTGGAC<br>GTGAGCCAGGATGACCCCGAGGTGCAGTTCACATGGTACATAA<br>ACAACGAGCAGGTGCGCACCGCCCGGCCGCCGCTACGGGAGCA<br>GCAGTTCAACAGCACGATCCGCGTGGTCAGCACCCTCCCCATC<br>ACGCACCAGGACTGGCTGAGGGGCAAGGAGTTCAAGTGCAAAG<br>TCCACAACAAGGCACTCCCGGCCCCCATCGAGAAAACCATCTC<br>CAAAGCCAGAGGGCAGCCCCTGGAGCCGAAGGTCTACACCATG<br>GGCCCTCCCCGGGAGGAACTGAGCAGCAGGTCGGTCAGCCTGA<br>CCTGCATGATCAACGGCTTCTACCCTTCCGACATCTCGGTGGA<br>GTGGGAGAAGAACGGGAAGGCAGAGGACAACTACAAGACCACG<br>CCGGCCGTGCTGGACAGCGACGGCTCCTACTTCCTCTACAGCA<br>AGCTCTCAGTGCCCACGAGTGAGTGGCAGCGGGGCGACGTGTT<br>CACCTGCTCCGTGATGCACGAGGCCTTGCACAACCACTACACG<br>CAGAAGTCCATCTCCCGCTCTCCGGGTAAATGA |
| 228 | mAb H LC (nucleotide) | GCCGCCGTGCTGACCCAGACTCCAGCCTCCGTGTCTGCAGCTG<br>TGGGAGGCACAGTCAGCATCAGTTGCCAGTCCAATGAGAACAT<br>TGGTAGTAATTTAGCCTGGTATCAGCAGAAACCAGGGCAGCCT<br>CCCAAGCTCCTGATTTATGGTGCATCCACTCTGACATCTGGGG<br>TCCCATCGCGGTTCAAAGGCAGTGGGTCTGGGACAGCGTTCAC<br>TCTCACCATCAGCGGCGTGCAGTGTGACGATGCTGCCACTTAC<br>TACTGTCTAGGCGGTTATTTGAGTACTAGTGATACGACTTTCG<br>GCGGAGGGACCGCGGTGGTGGTCAAAGGTGATCCAGTTGCACC<br>TACTGTCCTCATCTTCCCACCAGCTGCTGATCAGGTGGCAACT<br>GGAACAGTCACCATCGTGTGTGTGGCGAATAAATACTTTCCCG<br>ATGTCACCGTCACCTGGGAGGTGGATGGCACCACCCAAACAAC<br>TGGCATCGAGAACAGTAAAACACCGCAGAATTCTGCAGATTGT<br>ACCTACAACCTCAGCAGCACTCTGACACTGACCAGCACACAGT<br>ACAACAGCCACAAAGAGTACACCTGCAAGGTGACCCAGGGCAC<br>GACCTCAGTCGTCCAGAGCTTCAACAGGGGTGACTGCTAG |
| 229 | Rabbit heavy chain constant region | GGGCAACCTAAGGCTCCATCAGTGTTCCCACTGGCCCCCTGCT<br>GCGGGGACACACCCAGCTCCACGGTGACCCTGGGCTGCCTGGT<br>CAAAGGCTACCTCCCGGAGCCAGTGACCGTGACCTGGAACTCG<br>GGCACCCTCACCAATGGGGTACGCACCTTCCCGTCCGTCCGGC<br>AGTCCTCAGGCCTCTACTCGCTGAGCAGCGTGGTGAGCGTGAC<br>CTCAAGCAGCCAGCCCGTCACCTGCAACGTGGCCCACCCAGCC<br>ACCAACACCAAAGTGGACAAGACCGTTGCACCCTCGACATGCA<br>GCAAGCCCACGTGCCCACCCCCTGAACTCCTGGGGGGACCGTC<br>TGTGTTCATCTTCCCCCCAAAACCCAAGGACACCCTCATGATC<br>TCACGCACCCCCGAGGTCACATGCGTGGTGGTGGACGTGAGCC<br>AGGATGACCCCGAGGTGCAGTTCACATGGTACATAAACAACGA<br>GCAGGTGCGCACCGCCCGGCCGCCGCTACGGGAGCAGCAGTTC<br>AACAGCACGATCCGCGTGGTCAGCACCCTCCCCATCACGCACC<br>AGGACTGGCTGAGGGGCAAGGAGTTCAAGTGCAAAGTCCACAA<br>CAAGGCACTCCCGGCCCCCATCGAGAAAACCATCTCCAAAGCC<br>AGAGGGCAGCCCCTGGAGCCGAAGGTCTACACCATGGGCCCTC<br>CCCGGGAGGAACTGAGCAGCAGGTCGGTCAGCCTGACCTGCAT<br>GATCAACGGCTTCTACCCTTCCGACATCTCGGTGGAGTGGGAG<br>AAGAACGGGAAGGCAGAGGACAACTACAAGACCACGCCGGCCG<br>TGCTGGACAGCGACGGCTCCTACTTCCTCTACAGCAAGCTCTC<br>AGTGCCCACGAGTGAGTGGCAGCGGGGCGACGTGTTCACCTGC<br>TCCGTGATGCACGAGGCCTTGCACAACCACTACACGCAGAAGT<br>CCATCTCCCGCTCTCCGGGTAAATGA |
| 230 | Rabbit light chain constant region | GATCCAGTTGCACCTACTGTCCTCATCTTCCCACCAGCTGCTG<br>ATCAGGTGGCAACTGGAACAGTCACCATCGTGTGTGTGGCGAA<br>TAAATACTTTCCCGATGTCACCGTCACCTGGGAGGTGGATGGC<br>ACCACCCAAACAACTGGCATCGAGAACAGTAAAACACCGCAGA |

TABLE 19-continued

| Summary of Sequences. | | |
|---|---|---|
| SEQ ID | Description | Sequence |
| | | ATTCTGCAGATTGTACCTACAACCTCAGCAGCACTCTGACACT GACCAGCACACAGTACAACAGCCACAAAGAGTACACCTGCAAG GTGACCCAGGGCACGACCTCAGTCGTCCAGAGCTTCAACAGGG GTGACTGCTAG |
| 231 | Signature peptide for CP | GAYPLSIEPIGVR |
| 232 | Signature peptide for CP, internal standard spike ($^{13}C_5$, $^{15}N$)Val | GAYPLSIEPIGVR |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. An isolated antibody which binds to human ceruloplasmin having the amino acid sequence set out in SEQ ID NO: 1, comprising:

(a) heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively;

(b) heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively; or (c) heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively.

2. The antibody of claim 1, wherein the antibody comprises heavy and light chain variable regions comprising the amino acid sequences selected from the group consisting of:

(a) SEQ ID NOs: 25 and 26, respectively, (b) SEQ ID NOs: 49 and 50, respectively, and (c) SEQ ID NOs: 73 and 74, respectively.

3. The antibody of claim 1, wherein the antibody comprises heavy and light chains comprising the amino acid sequences selected from the group consisting of:

(a) SEQ ID NOs: 27 and 28, respectively, (b) SEQ ID NOs: 51 and 52, respectively, and (c) SEQ ID NOs: 75 and 76, respectively.

4. A nucleic acid which comprises a nucleotide sequence encoding the heavy and/or light chain variable region of the antibody of claim 1.

5. An expression vector comprising the nucleic acid of claim 4.

6. A cell transformed with the expression vector of claim 5.

7. An antibody mixture comprising two or three antibodies which bind to human ceruloplasmin having the amino acid sequence set out in SEQ ID NO: 1, wherein the two or three antibodies are selected from the group consisting of:

(a) an isolated antibody comprising heavy chain variable region CDR1, CDR2, and CDR3 sequences comprising the amino acid sequences set forth in SEQ ID NOs: 5, 6, and 7, respectively, and light chain variable region CDR1, CDR2, and CDR3 sequences comprising the amino acid sequences set forth in SEQ ID NOs: 8, 9, and 10, respectively;

(b) an isolated antibody heavy chain variable region CDR1, CDR2, and CDR3 sequences comprising the amino acid sequences set forth in SEQ ID NOs: 29, 30, and 31, respectively, and light chain variable region CDR1, CDR2, and CDR3 sequences comprising the amino acid sequences set forth in SEQ ID NOs: 32, 33, and 34, respectively; and (c) an isolated antibody heavy chain variable region CDR1, CDR2, and CDR3 sequences comprising the amino acid sequences set forth in SEQ ID NOs: 53, 54, and 55, respectively, and light chain variable region CDR1, CDR2, and CDR3 sequences comprising the amino acid sequences set forth in SEQ ID NOs: 56, 57, and 58, respectively.

8. The antibody mixture of claim 7, wherein the two or three antibodies comprise heavy and light chain variable regions comprising the amino acid sequences selected from the group consisting of:

(a) SEQ ID NOs: 25 and 26, respectively, (b) SEQ ID NOs: 49 and 50, respectively, and (c) SEQ ID NOs: 73 and 74, respectively.

9. The antibody mixture of claim 7, wherein the two or three antibodies comprise heavy and light chains comprising the amino acid sequences selected from the group consisting of:

(a) SEQ ID NOs: 27 and 28, respectively, (b) SEQ ID NOs: 51 and 52, respectively, and (c) SEQ ID NOs: 75 and 76, respectively.

10. The antibody mixture of claim 7, wherein the antibody mixture comprises two antibodies selected from the group consisting of: subparts (a) and (b), (a) and (c), and (b) and (c).

11. The antibody mixture of claim 10, wherein the two antibodies are present in an (a):(b), (a):(c), (b):(a), (b):(c), (c):(a), or (c):(b) ratio of 2:1.

12. The antibody mixture of claim 7, wherein the antibody mixture comprises the antibodies of subparts (a), (b), and (c).

13. The antibody mixture of claim 12, wherein the antibodies of subparts (a), (b), and (c) are present in an (a):(b):(c), (a):(c):(b), (b):(a):(c), (b):(c):(a), (c):(a):(b), or (c):(b):(a) ratio of 2:1:1.

14. A kit for measuring copper concentration in a biological sample comprising the antibody mixture of claim 7, and instructions for use.

15. A method of measuring non-ceruloplasmin bound copper concentration in a biological sample, the method comprising:

(a) contacting the biological sample with an immunocapture reagent comprising the antibody mixture of claim 7 to form immunocaptured ceruloplasmin, (b) removing the immunocaptured ceruloplasmin to obtain a non-ceruloplasmin sample, and (c) measuring copper concentration in the non-ceruloplasmin sample.

16. A method of measuring labile-bound copper concentration in a biological sample, the method comprising:

(a) contacting the biological sample with an immunocapture reagent comprising the antibody mixture of claim 7 to form immunocaptured ceruloplasmin, (b) removing the immunocaptured ceruloplasmin to obtain a non-ceruloplasmin sample, (c) contacting the non-ceruloplasmin sample with a chelator which binds to labile-bound copper, (d) removing non-labile-bound copper to obtain a labile-bound copper sample, and (e) measuring copper concentration in the labile-bound copper sample.

17. The method of claim 15, wherein the biological sample is from a patient who has or is suspected of having a copper metabolism-associated disease or disorder.

18. A method of identifying a patient as having a copper metabolism associated disease or disorder, the method comprising:

measuring the concentration of non-ceruloplasmin-bound copper or labile-bound copper in a biological sample from the patient according to the method of claim 15;

identifying the patient as having the copper metabolism associated disease or disorder based on the concentration of non-ceruloplasmin-bound copper or labile-bound copper in the biological sample relative to a threshold concentration, and administering to the patient an effective amount of a therapeutic agent to treat the copper metabolism associated disease or disorder.

19. A method of treating a patient who has been diagnosed as having a copper metabolism associated disease or disorder according to the method of claim 18, the method comprising administering to the patient an effective amount of a therapeutic agent to treat the copper metabolism associated disease or disorder.

20. A method of identifying a subject as suited for treatment with bis-choline tetrathiomolybdate, the method comprising:

determining a concentration of non-ceruloplasmin-bound copper or labile-bound copper in a biological sample from the subject according to the method of claim 15;

identifying the subject as suited for treatment with bis-choline tetrathiomolybdate based on the concentration of non-ceruloplasmin-bound copper or labile-bound copper in the biological sample relative to a threshold concentration; and administering an effective amount of bis-choline tetrathiomolybdate to the subject identified as suited for treatment with bis-choline tetrathiomolybdate.

* * * * *